US006992170B2

(12) United States Patent
Prayaga et al.

(10) Patent No.: US 6,992,170 B2
(45) Date of Patent: Jan. 31, 2006

(54) POLYPEPTIDES AND POLYNUCLEOTIDES HOMOLOGOUS TO THYMOSIN, EPHRIN A RECEPTORS, AND FIBROMODULIN

(75) Inventors: Sudhirdas K. Prayaga, O'Fallon, MO (US); Raymond J. Taupier, Jr., East Haven, CT (US); Raj Bandaru, Watertown, MA (US)

(73) Assignee: CuraGen Corporation, New Haven, CT (US)

(*) Notice: Subject to any disclaimer, the term of this patent is extended or adjusted under 35 U.S.C. 154(b) by 351 days.

(21) Appl. No.: 09/973,424

(22) Filed: Oct. 9, 2001

(65) Prior Publication Data

US 2003/0203426 A1 Oct. 30, 2003

Related U.S. Application Data

(63) Continuation-in-part of application No. 09/953,248, filed on Sep. 14, 2001, which is a continuation-in-part of application No. 09/689,486, filed on Oct. 12, 2000, now Pat. No. 6,855,806, and a continuation-in-part of application No. 09/687,276, filed on Oct. 13, 2000.

(60) Provisional application No. 60/159,805, filed on Oct. 15, 1999, provisional application No. 60/159,992, filed on Oct. 18, 1999, provisional application No. 60/086,423, filed on Oct. 18, 1999, and provisional application No. 60/160,952, filed on Oct. 22, 1999.

(51) Int. Cl.
*C07K 14/00* (2006.01)
*C12P 21/06* (2006.01)
*A61K 38/00* (2006.01)

(52) U.S. Cl. ............................ 530/350; 435/69.1; 514/2

(58) Field of Classification Search ................ 530/350; 435/69.1; 514/2

See application file for complete search history.

(56) References Cited

FOREIGN PATENT DOCUMENTS

| WO | WO 96/11016 | 4/1996 |
| WO | WO 99/47674 | 9/1999 |
| WO | WO 01/29217 | 4/2001 |
| WO | WO 00/06190 | 2/2002 |

OTHER PUBLICATIONS

EMBL Database Accession No. AAB39218, submitted by S. Park (Dec. 23, 1996).*
Antonsson, et al. (1993). "Structure and deduced amino acid sequence of the human fibromodulin gene" *Biochemica Et Biophysica Acta* 1174(2):204–206.
Chan, et al. (1991). "Eek and Erk, New Members of the Eph Subclass of Receptor Protein–tyrosine Kinases" *Oncogene, Basingstoke, Hants, GB* 6:1057–1061.

McCreary, et al. (1998). "Sequence of a Human Kidney Complementary DNA clone Encoding Thymosin Beta–10" *Biochemical and Biophysical Research Communications* 152(2):862–866.
International Search Report for PCT/US02/31498. Mailed on Oct. 24, 2002.
Abdollahi et al. (1991). "Sequence and expression of a cDNA encoding MyD118: a novel myeloid differentiation primary response gene induced by multiple cytokines." *Oncogene* 6(1): 165–167.
Aumailley and Gayraud (1998). "Structure and biological activity of the extracellular matrix." *J Mol Med* 76(3–4): 253–265.
Bodey et al. (2000). "Review of thymic hormones in cancer diagnosis and treatment." *Int J Immunopharmacol* 22(4): 261–273.
Bruckner–Tuderman and Bruckner (1998). "Genetic diseases of the extracellular matrix: more than just connective tissue disorders." *J Mol Med* 76(3–4): 226–237.
GenBank Accession No.: X59292 (Jan. 21, 1999).
GenBank Accession No.: NP_065387 (Nov. 2, 2000).
Chan and Watt (1991). "eek and erk, new members of the eph subclass of receptor protein– tyrosine kinases." *Oncogene* 6(6): 1057–1061.
Choi et al. (1999). "Characterization of ephrin–A1 and ephrin–A4 as ligands for the EphA8 receptor protein tyrosine kinase." *Mol Cells* 9(4): 440–445.
Frisen et al. (1999). "Ephrins and their Eph receptors: multitalented directors of embryonic development." *Embo J* 18(19): 5159–5165.
Hall (1995). "Thymosin beta–10 accelerates apoptosis." *Cell Mol Biol Res* 41(3): 167–180.
Lacy et al. (1999). "Identification of FLRT1, FLRT2, and FLRT3: a novel family of transmembrane leucine–rich repeat proteins." *Genomics* 62(3): 417–426.
Lin and Morrison–Bogorad (1991). "Cloning and characterization of a testis–specific thymosin beta 10 cDNA. Expression in post–meiotic male germ cells." *J Biol Chem* 266(34): 23347–23353.
Muallem et al. (1995). "Actin filament disassembly is a sufficient final trigger for exocytosis in nonexcitable cells." *J Cell Biol* 128(4): 589–598.

(Continued)

*Primary Examiner*—Janet Andres
(74) *Attorney, Agent, or Firm*—Mei L. Benni; George M. Yahwak; CuraGen Corporation

(57) ABSTRACT

Disclosed herein are novel human nucleic acid sequences that have homology to thymosin, ephrin A receptors, proteoglycans and fibromodulin. Also disclosed are polypeptides encoded by these nucleic acid sequences, and antibodies which immunospecifically-bind to the polypeptide, as well as derivatives, variants, mutants, or fragments of the aforementioned polypeptide, polynucleotide, or antibody. The invention further discloses therapeutic, diagnostic and research methods for diagnosis, treatment, and prevention of disorders involving these novel nucleic acids and proteins.

4 Claims, 3 Drawing Sheets

OTHER PUBLICATIONS

Genbank Accession No. O09127 May 30, 2000.
Santelli et al. (1999). "Thymosin beta–10 gene overexpression is a general event in human carcinogenesis." *Am J Pathol* 155(3): 799–804.
Sztrolovics et al. (1999). "Resistance of small leucine–rich repeat proteoglycans to proteolytic degradation during interleukin–1–stimulated cartilage catabolism." *Biochem J* 339(Pt 3): 571–577.
Sztrolovics et al. (1994). "Localization of the human fibromodulin gene (FMOD) to Chromosome 1q32 and completion of the cDNA sequence." *Genomics* 23(3): 715–717.
Wang et al. (1998). "Molecular distinction and angiogenic interaction between embryonic arteries and veins revealed by ephrin–B2 and its receptor Eph–B4 [see comments]." *Cell* 93(5): 741–753.

EMBL Database Accession No.: Z93023 (Mar. 19, 1997).
EMBL Database Accession No.: AA758513 (Jan. 26, 1989).
EMBL Database Accession No.: AL035703 (Mar. 12, 1999).
EMBL Database Accession No.: U72207 (Dec. 25, 1996).
EMBL Database Accession No.: AB040892 (May 23, 2000).
EMBL Database Accession No.: AF007139 (Feb. 9, 1998).
EMBL Database Accession No.: AF169675 (Jan. 31, 2000).
EMBL Database Accession No.: AP000597 (Oct. 15, 1999).
Nagase et al. (2000). *DNA Res* 7: 143–150.
Park and Sanchez (1997) *Oncogene* 14: 533–542.
Tureci, et al. (1998). *Proc. Natl. Acad. Sci. USA* 95: 7608–7613.
Weterman, et al. (1993). *Int. J. Cancer* 53: 278–284.
International Search Report for PCT/US 00/28474. Mailed on Jul. 5, 2001.

* cited by examiner

Figure 1. Western blot of a NOV2 polypeptide secreted by 293 cells.
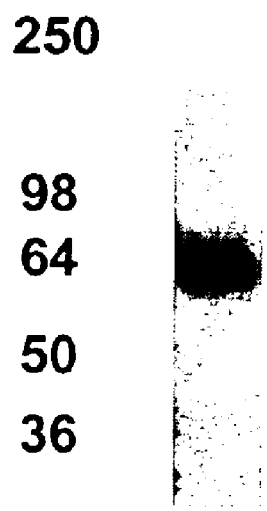

Figure 2. Western blot of a NOV3 polypeptide secreted by 293 cells.
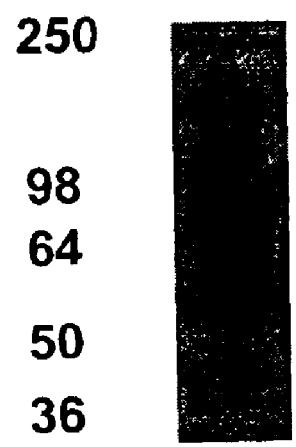

Figure 3. T47D Cell Proliferation in response to NOV4 Monoclonal Antibody Stimulation
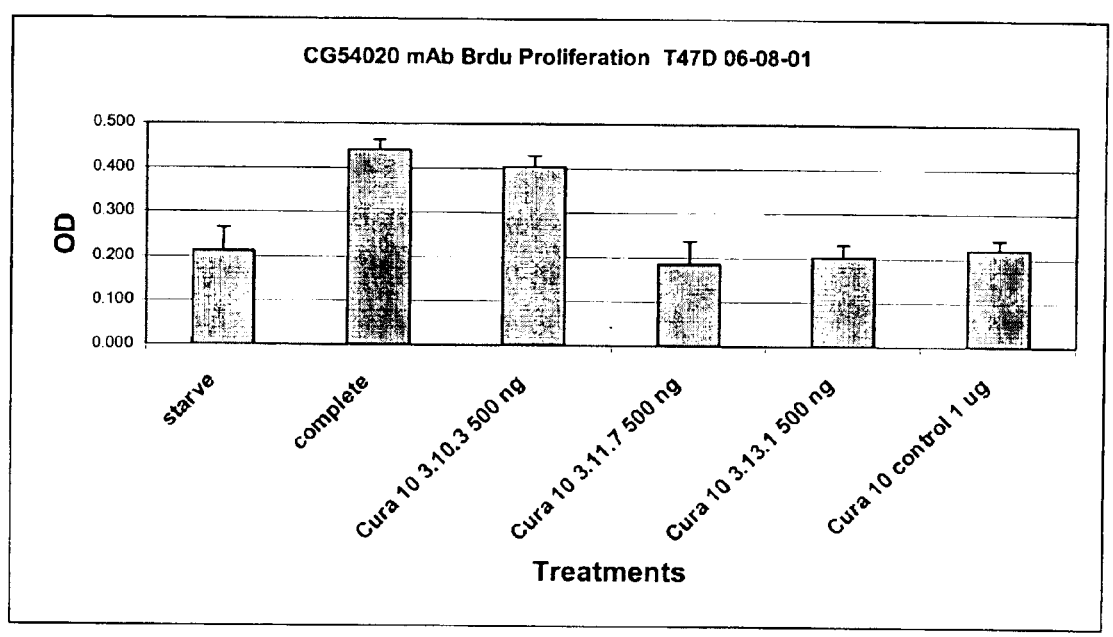

SEQUENCE LISTING

```
<160> NUMBER OF SEQ ID NOS: 84

<210> SEQ ID NO 1
<211> LENGTH: 430
<212> TYPE: DNA
<213> ORGANISM: Homo sapiens
<220> FEATURE:
<221> NAME/KEY: CDS
<222> LOCATION: (61)..(234)

<400> SEQUENCE: 1
gccagcagga gtgccatggt gagaggcact ggcagggaat gctaggattg tttttaagaaa     60 atg gca gac aaa cca gac ata ggg gaa atc gcc agc ttc aat aag gcc      108
Met Ala Asp Lys Pro Asp Ile Gly Glu Ile Ala Ser Phe Asn Lys Ala
  1               5                  10                  15 aag ctg aag aaa aca gag atg cag gag aac acc ctg ctg acc aaa gag      156
Lys Leu Lys Lys Thr Glu Met Gln Glu Asn Thr Leu Leu Thr Lys Glu
             20                  25                  30 gcc att gag cag gag aag cgg gtg aaa ttt cct aag agc ctg gag gat      204
Ala Ile Glu Gln Glu Lys Arg Val Lys Phe Pro Lys Ser Leu Glu Asp
         35                  40                  45 tcc cta ccc ctg tca tct tcg aga ccc cag tagtaatgtg gaggaagaat       254
Ser Leu Pro Leu Ser Ser Ser Arg Pro Gln
     50                  55 caccacaaga tggacacaag ccacaaactg tgacgtgaac ctgggcactc cgtgctgatg    314
ccaccagcct gagggtccct atgggtccaa tcagactgcc aaattctctg gtttgccctg    374
ggatattata gaaaattatt tgcgtgaata atgaaaacac agctcatggc aaaaaa         430
```

```
<210> SEQ ID NO 2
<211> LENGTH: 58
<212> TYPE: PRT
<213> ORGANISM: Homo sapiens

<400> SEQUENCE: 2

Met Ala Asp Lys Pro Asp Ile Gly Glu Ile Ala Ser Phe Asn Lys Ala
 1               5                   10                  15
Lys Leu Lys Lys Thr Glu Met Gln Glu Asn Thr Leu Leu Thr Lys Glu
            20                  25                  30
Ala Ile Glu Gln Glu Lys Arg Val Lys Phe Pro Lys Ser Leu Glu Asp
        35                  40                  45
Ser Leu Pro Leu Ser Ser Ser Arg Pro Gln
    50                  55

<210> SEQ ID NO 3
<211> LENGTH: 13
<212> TYPE: PRT
<213> ORGANISM: Homo sapiens

<400> SEQUENCE: 3

Lys Leu Lys Lys Thr Glu Asn Thr Gln Glu Glu Lys Asn
 1               5                   10

<210> SEQ ID NO 4
<211> LENGTH: 3018
<212> TYPE: DNA
<213> ORGANISM: Homo sapiens

<400> SEQUENCE: 4 atggccccg cccggggccg cctgccccct gcgctctggg tcgtcacggc cgcggcggcg        60
gcggccacct gcgtgtccgc ggcgcgcggc gaagtgaatt tgctggacac gtcgaccatc      120
cacggggact ggggctggct cacgtatccg gctcatgggt gggactccat caacgaggtg      180
gacgagtcct tccagcccat ccacacgtac caggtttgca acgtcatgag ccccaaccag      240
aacaactggc tgcgcacgag ctgggtcccc cgagacggcg cccggcgcgt ctatgctgag      300
atcaagttta ccctgcgcga ctgcaacagc atgcctggtg tgctgggcac ctgcaaggag      360
accttcaacc tctactacct ggagtcggac cgcgacctgg gggccagcac acaagaaagc      420
cagttcctca aaatcgacac cattgcggcc gacgagagct tcacaggtgc cgaccttggt      480
gtgcggcgtc tcaagctcaa cacggaggtg cgcagtgtgg gtcccctcag caagcgcggc      540
ttctacctgg ccttccagga cataggtgcc tgcctggcca tcctctctct ccgcatctac      600
tataagaagt gccctgccat ggtgcgcaat ctggctgcct ctctcggagg cagtgacgggg      660
gccgactcgt cctcactggt ggaggtgagg ggccagtgcg tgcggcactc agaggagcgg      720
gacacaccca agatgtactg cagcgcggag ggcgagtggc tcgtgcccat cggcaaatgc      780
gtgtgcagtg ccggctacga ggagcggcgg gatgcctgtg tggcctgtga gctgggcttc      840
tacaagtcag cccctgggga ccagctgtgt gcccgctgcc ctcccacag ccactccgca      900
gctccagccg cccaagcctg ccactgtgac ctcagctact accgtgcagc cctggacccg      960
ccgtcctcag cctgcacccg gccaccctcg gcaccagtga acctgatctc cagtgtgaat     1020
gggacatcag tgactctgga gtgggccct cccctggacc caggtggccg cagtgacatc     1080
acctacaatg ccgtgtgccg ccgctgcccc tgggcactga ccgctgcga ggcatgtggg     1140
agcggcaccc gctttgtgcc ccagcagaca agcctggtgc aggccagcct gctggtggcc     1200
aacctgctgg cccacatgaa ctactccttc tggatcgagg ccgtcaatgg cgtgtccgac     1260
```

-continued

```
ctgagcccg agcccgccg ggccgctgtg gtcaacatca ccacgaacca ggcagcccg      1320 tcccaggtgg tggtgatccg tcaagagcgg gcggggcaga ccagcgtctc gctgctgtgg   1380
caggagcccg agcagccgaa cggcatcatc ctggagtatg agatcaagta ctacgagaag   1440
gacaaggaga tgcagagcta ctccaccctc aaggccgtca ccaccagagc caccgtctcc   1500
ggcctcaagc cgggcacccg ctacgtgttc caggtccgag cccgcacctc agcaggctgt   1560
ggccgcttca gccaggccat ggaggtggag accgggaaac cccggccccg ctatgacacc   1620
aggaccattg tctggatctg cctgacgctc atcacgggcc tggtggtgct tctgctcctg   1680
ctcatctgca agaagaggca ctgtggctac agcaaggcct tccaggactc ggacgaggag   1740
aagatgcact atcagaatgg acaggcaccc ccacctgtct tcctgcctct gcatcacccc   1800
ccgggaaagc tcccagagcc ccagttctat gcggaacccc acacctacga ggagccaggc   1860
cgggcgggcc gcagtttcac tcgggagatc gaggcctcta ggatccacat cgagaaaatc   1920
atcggctctg gagactccgg ggaagtctgc tacgggaggc tgcgggtgcc agggcagcgg   1980
gatgtgcccg tggccatcaa ggccctcaaa gccggctaca cggagagaca gaggcgggac   2040
ttcctgagcg aggcgtccat catggggcaa ttcgaccatc caacatcat ccgcctcgag    2100 ggtgtcgtca cccgtggccg cctggcaatg attgtgactg agtacatgga gaacggctct   2160
ctggacacct tcctgaggac ccacgacggg cagttcacca tcatgcagct ggtgggcatg   2220
ctgagaggag tgggtgccgg catgcgctac ctctcagacc tgggctatgt ccaccgagac   2280
ctggccgccc gcaacgtcct ggttgacagc aacctggtct gcaaggtgtc tgacttcggg   2340
ctctcacggg tgctggagga cgacccggat gctgcctaca ccaccacggg cgggaagatc   2400
cccatccgct ggacgccc agaggccatc gccttccgca ccttctcctc ggccagcgac     2460
gtgtggagct tcggcgtggt catgtgggag gtgctggcct atggggagcg ccctactgg    2520 aacatgacca accgggatgt gatcagctct gtggaggagg ggtaccgcct gcccgcaccc   2580
atgggctgcc ccacgccct gcaccagctc atgctcgact gttggcacaa ggaccgggcg    2640
cagcggcctc gcttctccca gattgtcagt gtcctcgatg cgctcatccg cagccctgag   2700
agtctcaggg ccaccgccac agtcagcagg tgcccacccc ctgccttcgt ccggagctgc   2760
tttgacctcc gaggggcag cggtggcggt ggggcctca ccgtggggga ctggctggac     2820
tccatccgca tgggccggta ccgagaccac ttcgctgcgg gcggatactc ctctctgggc   2880
atggtgctac gcatgaacgc ccaggacgtg cgcgccctgg gcatcaccct catgggccac   2940
cagaagaaga tcctgggcag cattcagacc atgcgggccc agctgaccag cacccagggg   3000
ccccgccggc acctctga                                                  3018
```

<210> SEQ ID NO 5
<211> LENGTH: 992
<212> TYPE: PRT
<213> ORGANISM: Homo sapiens

<400> SEQUENCE: 5

Met Ala Pro Ala Arg Gly Arg Leu Pro Pro Ala Leu Trp Val Val Thr
 1               5                  10                  15

Ala Ala Ala Ala Ala Thr Cys Val Ser Ala Ala Arg Gly Glu Val
            20                  25                  30

Asn Leu Leu Asp Thr Ser Thr Ile His Gly Asp Trp Gly Trp Leu Thr
         35                  40                  45

Tyr Pro Ala His Gly Trp Asp Ser Ile Asn Glu Val Asp Glu Ser Phe

```
                50                  55                  60
Gln Pro Ile His Thr Tyr Gln Val Cys Asn Val Met Ser Pro Asn Gln
 65                  70                  75                  80

Asn Asn Trp Leu Arg Thr Ser Trp Val Pro Arg Asp Gly Ala Arg Arg
                 85                  90                  95

Val Tyr Ala Glu Ile Lys Phe Thr Leu Arg Asp Cys Asn Ser Met Pro
                100                 105                 110

Gly Val Leu Gly Thr Cys Lys Glu Thr Phe Asn Leu Tyr Tyr Leu Glu
                115                 120                 125

Ser Asp Arg Asp Leu Gly Ala Ser Thr Gln Glu Ser Gln Phe Leu Lys
                130                 135                 140

Ile Asp Thr Ile Ala Ala Asp Glu Ser Phe Thr Gly Ala Asp Leu Gly
145                 150                 155                 160

Val Arg Arg Leu Lys Leu Asn Thr Glu Val Arg Ser Val Gly Pro Leu
                165                 170                 175

Ser Lys Arg Gly Phe Tyr Leu Ala Phe Gln Asp Ile Gly Ala Cys Leu
                180                 185                 190

Ala Ile Leu Ser Leu Arg Ile Tyr Tyr Lys Lys Cys Pro Ala Met Val
                195                 200                 205

Arg Asn Leu Ala Ala Phe Ser Glu Ala Val Thr Gly Ala Asp Ser Ser
                210                 215                 220

Ser Leu Val Glu Val Arg Gly Gln Cys Val Arg His Ser Glu Glu Arg
225                 230                 235                 240

Asp Thr Pro Lys Met Tyr Cys Ser Ala Glu Gly Glu Trp Leu Val Pro
                245                 250                 255

Ile Gly Lys Cys Val Cys Ser Ala Gly Tyr Glu Glu Arg Arg Asp Ala
                260                 265                 270

Cys Val Ala Cys Glu Leu Gly Phe Tyr Lys Ser Ala Pro Gly Asp Gln
                275                 280                 285

Leu Cys Ala Arg Cys Pro Pro His Ser His Ser Ala Ala Pro Ala Ala
                290                 295                 300

Gln Ala Cys His Cys Asp Leu Ser Tyr Tyr Arg Ala Ala Leu Asp Pro
305                 310                 315                 320

Pro Ser Ser Ala Cys Thr Arg Pro Pro Ser Ala Pro Val Asn Leu Ile
                325                 330                 335

Ser Ser Val Asn Gly Thr Ser Val Thr Leu Glu Trp Ala Pro Pro Leu
                340                 345                 350

Asp Pro Gly Gly Arg Ser Asp Ile Thr Tyr Asn Ala Val Cys Arg Arg
                355                 360                 365

Cys Pro Trp Ala Leu Ser Arg Cys Glu Ala Cys Gly Ser Gly Thr Arg
                370                 375                 380

Phe Val Pro Gln Gln Thr Ser Leu Val Gln Ala Ser Leu Leu Val Ala
385                 390                 395                 400

Asn Leu Leu Ala His Met Asn Tyr Ser Phe Trp Ile Glu Ala Val Asn
                405                 410                 415

Gly Val Ser Asp Leu Ser Pro Glu Pro Arg Arg Ala Ala Val Val Asn
                420                 425                 430

Ile Thr Thr Asn Gln Ala Ala Pro Ser Gln Val Val Ile Arg Gln
                435                 440                 445

Glu Arg Ala Gly Gln Thr Ser Val Ser Leu Leu Trp Gln Glu Pro Glu
                450                 455                 460

Gln Pro Asn Gly Ile Ile Leu Glu Tyr Glu Ile Lys Tyr Tyr Glu Lys
465                 470                 475                 480
```

-continued

Asp Lys Glu Met Gln Ser Tyr Ser Thr Leu Lys Ala Val Thr Thr Arg
            485                 490                 495

Ala Thr Val Ser Gly Leu Lys Pro Gly Thr Arg Tyr Val Phe Gln Val
        500                 505                 510

Arg Ala Arg Thr Ser Ala Gly Cys Gly Arg Phe Ser Gln Ala Met Glu
        515                 520                 525

Val Glu Thr Gly Lys Pro Arg Pro Arg Tyr Asp Thr Arg Thr Ile Val
    530                 535                 540

Trp Ile Cys Leu Thr Leu Ile Thr Gly Leu Val Val Leu Leu Leu Leu
545                 550                 555                 560

Leu Ile Cys Lys Lys Arg His Cys Gly Tyr Ser Lys Ala Phe Gln Asp
            565                 570                 575

Ser Asp Glu Glu Lys Met His Tyr Gln Asn Gly Gln Ala Pro Pro Pro
            580                 585                 590

Val Phe Leu Pro Leu His His Pro Gly Lys Leu Pro Glu Pro Gln
        595                 600                 605

Phe Tyr Ala Glu Pro His Thr Tyr Glu Glu Pro Gly Arg Ala Gly Arg
    610                 615                 620

Ser Phe Thr Arg Glu Ile Glu Ala Ser Arg Ile His Ile Glu Lys Ile
625                 630                 635                 640

Ile Gly Ser Gly Asp Ser Gly Glu Val Cys Tyr Gly Arg Leu Arg Val
            645                 650                 655

Pro Gly Gln Arg Asp Val Pro Val Ala Ile Lys Ala Leu Lys Ala Gly
            660                 665                 670

Tyr Thr Glu Arg Gln Arg Arg Asp Phe Leu Ser Glu Ala Ser Ile Met
    675                 680                 685

Gly Gln Phe Asp His Pro Asn Ile Ile Arg Leu Glu Gly Val Val Thr
    690                 695                 700

Arg Gly Arg Leu Ala Met Ile Val Thr Glu Tyr Met Glu Asn Gly Ser
705                 710                 715                 720

Leu Asp Thr Phe Leu Arg Thr His Asp Gly Gln Phe Thr Ile Met Gln
            725                 730                 735

Leu Val Gly Met Leu Arg Gly Val Gly Ala Gly Met Arg Tyr Leu Ser
            740                 745                 750

Asp Leu Gly Tyr Val His Arg Asp Leu Ala Ala Arg Asn Val Leu Val
            755                 760                 765

Asp Ser Asn Leu Val Cys Lys Val Ser Asp Phe Gly Leu Ser Arg Val
770                 775                 780

Leu Glu Asp Asp Pro Asp Ala Ala Tyr Thr Thr Thr Gly Gly Lys Ile
785                 790                 795                 800

Pro Ile Arg Trp Thr Ala Pro Glu Ala Ile Ala Phe Arg Thr Phe Ser
            805                 810                 815

Ser Ala Ser Asp Val Trp Ser Phe Gly Val Val Met Trp Glu Val Leu
            820                 825                 830

Ala Tyr Gly Glu Arg Pro Tyr Trp Asn Met Thr Asn Arg Asp Val Ile
    835                 840                 845

Ser Ser Val Glu Glu Gly Tyr Arg Leu Pro Ala Pro Met Gly Cys Pro
850                 855                 860

His Ala Leu His Gln Leu Met Leu Asp Cys Trp His Lys Asp Arg Ala
865                 870                 875                 880

Gln Arg Pro Arg Phe Ser Gln Ile Val Ser Val Leu Asp Ala Leu Ile
            885                 890                 895

| | | | | | | | | | | |
|---|---|---|---|---|---|---|---|---|---|---|
|Arg|Ser|Pro|Glu|Ser|Leu|Arg|Ala|Thr|Ala|Thr|Val|Ser|Arg|Cys|Pro|
| | | |900| | | |905| | | |910| | | | |

Arg Ser Pro Glu Ser Leu Arg Ala Thr Ala Thr Val Ser Arg Cys Pro
             900                 905                 910

Pro Pro Ala Phe Val Arg Ser Cys Phe Asp Leu Arg Gly Gly Ser Gly
         915                 920                 925

Gly Gly Gly Gly Leu Thr Val Gly Asp Trp Leu Asp Ser Ile Arg Met
         930                 935                 940

Gly Arg Tyr Arg Asp His Phe Ala Ala Gly Tyr Ser Ser Leu Gly
945                 950                 955                 960

Met Val Leu Arg Met Asn Ala Gln Asp Val Arg Ala Leu Gly Ile Thr
             965                 970                 975

Leu Met Gly His Gln Lys Lys Ile Leu Gly Ser Ile Gln Thr Met Arg
             980                 985                 990

<210> SEQ ID NO 6
<211> LENGTH: 2025
<212> TYPE: DNA
<213> ORGANISM: Homo sapiens

<400> SEQUENCE: 6

```
atggtggtgg cacacccac cgccactgcc accaccacgc ccactgccac tgtcacggcc      60
accgttgtga tgaccacggc caccatggac ctgcgggact ggctgttcct ctgctacggg     120
ctcatcgcct tcctgacgga ggtcatcgac agcaccacct gccctcggt gtgccgctgc      180
gacaacggct tcatctactg caacgaccgg ggactcacat ccatccccgc agatatccct     240
gatgatgcca ccaccctcta cctgcagaac aaccagatca caacgccgg catcccccag      300
gacctcaaga ccaaggtcaa cgtgcaggtc atctacctat acgagaatga cctggatgag     360
ttccccatca acctgccccg ctccctccgg gagctgcacc tgcaggacaa caatgtgcgc     420
accattgcca gggactcgct ggcccgcatc ccgctgctgg agaagctgca cctggatgac     480
aactccgtgt ccaccgtcag cattgaggag acgccttcg ccgacagcaa acagctcaag      540
ctgctcttcc tgagccggaa ccacctgagc agcatcccct cggggctgcc gcacacgctg     600
gaggagctgc ggctggatga caaccgcatc tccaccatcc cgctgcatgc cttcaagggc     660
ctcaacagcc tgcggcgcct ggtgctggac ggtaacctgc tggccaacca gcgcatcgcc     720
gacgacacct tcagccgcct acagaacctc acagagctct cgctggtgcg caattcgctg     780
gccgcgccac ccctcaacct gcccagcgcc cacctgcaga agctctacct gcaggacaat     840
gccatcagcc acatcccta caacacgctg gccaagatgc gtgagctgga gcggctggac     900
ctgtccaaca caacctgac cacgctgccc cgcggcctgt tcgacgacct ggggaacctg     960
gcccagctgc tgctcaggaa caaccttgg ttttgtggct gcaacctcat gtggctgcgg     1020
gactgggtga aggcacgggc ggccgtggtc aacgtgcggg gcctcatgtg ccagggcccc    1080
gagaaggtcc ggggcatggc catcaaggac attaccagcg agatggacga gtgttttgag    1140
acggggccga gggcggcgt ggccaatgcg gctgccaaga ccacgccag caaccacgcc    1200
tctgccacca cgccccaggg ttccctgttt accctcaagg ccaaaaggcc agggctgcgc    1260
ctccccgact ccaacattga ctaccccatg gccacgggtg atggcgccaa gaccctggcc   1320
atccacgtga aggccctgac ggcagactcc atccgcatca cgtggaaggc cacgctcccc   1380
gcctcctctt tccggctcag ttggctgcgc ctgggccaca gccagccgt gggctccatc    1440
acggagacct tggtgcaggg ggacaagaca gagtacctgc tgacagccct ggagcccaag   1500
tccacctaca tcatctgcat ggtcaccatg gagaccagca atgcctacgt agctgatgag   1560
acaccgtgt gtgccaaggc agagacagcc gacagctatg ccctaccac cacactcaac    1620
```

-continued

| | |
|---|---|
| caggagcaga acgctggccc catggcgagc ctgcccctgg cgggcatcat cggcggggca | 1680 |
| gtggctctgg tcttcctctt cctggtcctg ggggccatct gctggtacgt gcaccaggct | 1740 |
| ggcgagctgc tgacccggga gagggcctac aaccggggca gcaggaaaaa ggatgactat | 1800 |
| atggagtcag ggaccaagaa ggataactcc atcctggaaa tccgcggccc tgggctgcag | 1860 |
| atgctgccca tcaacccgta ccgcgccaaa gaggagtacg tggtccacac tatcttcccc | 1920 |
| tccaacggca gcagcctctg caaggccaca cacaccattg gctacggcac cacgcggggc | 1980 |
| taccgggacg gcggcatccc cgacatagac tactcctaca catga | 2025 |

<210> SEQ ID NO 7
<211> LENGTH: 674
<212> TYPE: PRT
<213> ORGANISM: Homo sapiens

<400> SEQUENCE: 7

```
Met Val Val Ala His Pro Thr Ala Thr Ala Thr Thr Pro Thr Ala
 1               5                  10                  15

Thr Val Thr Ala Thr Val Val Met Thr Thr Ala Thr Met Asp Leu Arg
             20                  25                  30

Asp Trp Leu Phe Leu Cys Tyr Gly Leu Ile Ala Phe Leu Thr Glu Val
         35                  40                  45

Ile Asp Ser Thr Thr Cys Pro Ser Val Cys Arg Cys Asp Asn Gly Phe
     50                  55                  60

Ile Tyr Cys Asn Asp Arg Gly Leu Thr Ser Ile Pro Ala Asp Ile Pro
 65                  70                  75                  80

Asp Asp Ala Thr Thr Leu Tyr Leu Gln Asn Asn Gln Ile Asn Asn Ala
                 85                  90                  95

Gly Ile Pro Gln Asp Leu Lys Thr Lys Val Asn Val Gln Val Ile Tyr
            100                 105                 110

Leu Tyr Glu Asn Asp Leu Asp Glu Phe Pro Ile Asn Leu Pro Arg Ser
        115                 120                 125

Leu Arg Glu Leu His Leu Gln Asp Asn Asn Val Arg Thr Ile Ala Arg
    130                 135                 140

Asp Ser Leu Ala Arg Ile Pro Leu Leu Glu Lys Leu His Leu Asp Asp
145                 150                 155                 160

Asn Ser Val Ser Thr Val Ser Ile Glu Glu Asp Ala Phe Ala Asp Ser
                165                 170                 175

Lys Gln Leu Lys Leu Leu Phe Leu Ser Arg Asn His Leu Ser Ser Ile
            180                 185                 190

Pro Ser Gly Leu Pro His Thr Leu Glu Glu Leu Arg Leu Asp Asp Asn
        195                 200                 205

Arg Ile Ser Thr Ile Pro Leu His Ala Phe Lys Gly Leu Asn Ser Leu
    210                 215                 220

Arg Arg Leu Val Leu Asp Gly Asn Leu Leu Ala Asn Gln Arg Ile Ala
225                 230                 235                 240

Asp Asp Thr Phe Ser Arg Leu Gln Asn Leu Thr Glu Leu Ser Leu Val
                245                 250                 255

Arg Asn Ser Leu Ala Ala Pro Pro Leu Asn Leu Pro Ser Ala His Leu
            260                 265                 270

Gln Lys Leu Tyr Leu Gln Asp Asn Ala Ile Ser His Ile Pro Tyr Asn
        275                 280                 285

Thr Leu Ala Lys Met Arg Glu Leu Glu Arg Leu Asp Leu Ser Asn Asn
    290                 295                 300
```

```
Asn Leu Thr Thr Leu Pro Arg Gly Leu Phe Asp Asp Leu Gly Asn Leu
305                 310                 315                 320

Ala Gln Leu Leu Leu Arg Asn Asn Pro Trp Phe Cys Gly Cys Asn Leu
            325                 330                 335

Met Trp Leu Arg Asp Trp Val Lys Ala Arg Ala Ala Val Val Asn Val
            340                 345                 350

Arg Gly Leu Met Cys Gln Gly Pro Glu Lys Val Arg Gly Met Ala Ile
            355                 360                 365

Lys Asp Ile Thr Ser Glu Met Asp Glu Cys Phe Glu Thr Gly Pro Gln
370                 375                 380

Gly Gly Val Ala Asn Ala Ala Lys Thr Thr Ala Ser Asn His Ala
385                 390                 395                 400

Ser Ala Thr Thr Pro Gln Gly Ser Leu Phe Thr Leu Lys Ala Lys Arg
            405                 410                 415

Pro Gly Leu Arg Leu Pro Asp Ser Asn Ile Asp Tyr Pro Met Ala Thr
            420                 425                 430

Gly Asp Gly Ala Lys Thr Leu Ala Ile His Val Lys Ala Leu Thr Ala
            435                 440                 445

Asp Ser Ile Arg Ile Thr Trp Lys Ala Thr Leu Pro Ala Ser Ser Phe
450                 455                 460

Arg Leu Ser Trp Leu Arg Leu Gly His Ser Pro Ala Val Gly Ser Ile
465                 470                 475                 480

Thr Glu Thr Leu Val Gln Gly Asp Lys Thr Glu Tyr Leu Leu Thr Ala
            485                 490                 495

Leu Glu Pro Lys Ser Thr Tyr Ile Ile Cys Met Val Thr Met Glu Thr
            500                 505                 510

Ser Asn Ala Tyr Val Ala Asp Glu Thr Pro Val Cys Ala Lys Ala Glu
            515                 520                 525

Thr Ala Asp Ser Tyr Gly Pro Thr Thr Thr Leu Asn Gln Glu Gln Asn
            530                 535                 540

Ala Gly Pro Met Ala Ser Leu Pro Leu Ala Gly Ile Ile Gly Gly Ala
545                 550                 555                 560

Val Ala Leu Val Phe Leu Phe Leu Val Leu Gly Ala Ile Cys Trp Tyr
            565                 570                 575

Val His Gln Ala Gly Glu Leu Leu Thr Arg Glu Arg Ala Tyr Asn Arg
            580                 585                 590

Gly Ser Arg Lys Lys Asp Asp Tyr Met Glu Ser Gly Thr Lys Lys Asp
            595                 600                 605

Asn Ser Ile Leu Glu Ile Arg Gly Pro Gly Leu Gln Met Leu Pro Ile
610                 615                 620

Asn Pro Tyr Arg Ala Lys Glu Glu Tyr Val Val His Thr Ile Phe Pro
625                 630                 635                 640

Ser Asn Gly Ser Ser Leu Cys Lys Ala Thr His Thr Ile Gly Tyr Gly
            645                 650                 655

Thr Thr Arg Gly Tyr Arg Asp Gly Gly Ile Pro Asp Ile Asp Tyr Ser
            660                 665                 670

Tyr Thr

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Ag190
```

-continued

```
          Forward PCR Primer Sequence

<400> SEQUENCE: 8
tggaggaaga atcaccacaa ga                                              22

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Ag190
      Probe PCR Primer Sequence

<400> SEQUENCE: 9
caagccacaa actgtgacgt gaacctg                                         27

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Ag190
      Reverse PCR Primer Sequence

<400> SEQUENCE: 10
gtggcatcag cacggagtg                                                  19

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Ag087
      Forward PCR Primer Sequence

<400> SEQUENCE: 11
cgcagtttca ctcgggagat                                                 20

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Ag087 Probe
      PCR Primer Sequence

<400> SEQUENCE: 12
cctctaggat ccacatcgag aaaatcatcg g                                    31

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Ag087
      Reverse PCR Primer Sequence

<400> SEQUENCE: 13
agcagacttc cccggagtct                                                 20

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: NOV2
      Forward PCR Primer Sequence
```

-continued

<400> SEQUENCE: 14
ggatccgcgc gcggcgaagt gaatttgctg g          31

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: NOV2
      Reverse PCR Primer Sequence

<400> SEQUENCE: 15
ctcgagggtc ctggtgtcat agcggggcc             29

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: NOV2 S1 PCR
      Primer Sequence

<400> SEQUENCE: 16
tacctggagt cggaccgc                         18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: NOV2 S2 PCR
      Primer Sequence

<400> SEQUENCE: 17
gcggtccgac tccaggta                         18

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: NOV2 S3 PCR
      Primer Sequence

<400> SEQUENCE: 18
cagtgcgtgc ggcactcag                        19

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: NOV2 S4 PCR
      Primer Sequence

<400> SEQUENCE: 19
tgagtgccgc acgcactgg                        19

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: NOV2 S5 PCR
      Primer Sequence

```
<400> SEQUENCE: 20
ctggacccag gtggccgc                                                    18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: NOV2 S6 PCR
      Primer Sequence

<400> SEQUENCE: 21
gcggccacct gggtccag                                                    18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: NOV2 S7 PCR
      Primer Sequence

<400> SEQUENCE: 22
cccgagcagc cgaacggc                                                    18

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: NOV2 S8 PCR
      Primer Sequence

<400> SEQUENCE: 23
gccgttcggc tgctcggg                                                    18

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: NOV3
      Forward PCR Primer Sequence

<400> SEQUENCE: 24
ggatccacca cctgcccctc ggtgtgc                                          27

<210> SEQ ID NO 25
<211> LENGTH: 35
<212> TYPE: DNA
<213> ORGANISM: Artificial Sequence
<220> FEATURE:
<223> OTHER INFORMATION: Description of Artificial Sequence: NOV3
      Reverse PCR Primer Sequence

<400> SEQUENCE: 25
ctcgaggcca gcgttctgct cctggttgag tgtgg                                 35

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: NOV3 S1 PCR
      Primer Sequence

<400> SEQUENCE: 26
```

```
cgcaccattg ccagggac                                                    18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: NOV3 S2 PCR
      Primer Sequence

<400> SEQUENCE: 27
gtccctggca atggtgcg                                                    18

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: NOV3 S3 PCR
      Primer Sequence

<400> SEQUENCE: 28
ctggtgcgca attcgctggc c                                                21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: NOV3 S4 PCR
      Primer Sequence

<400> SEQUENCE: 29
ggccagcgaa ttgcgcacca g                                                21

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: NOV3 S5 PCR
      Primer Sequence

<400> SEQUENCE: 30
cacgcctctg ccaccacg                                                    18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: NOV3 S6 PCR
      Primer Sequence

<400> SEQUENCE: 31
cgtggtggca gaggcgtg                                                    18

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: pSec-V5 His
      Forward Oligonucleotide Primer Sequence

<400> SEQUENCE: 32
```

-continued ctcgtcctcg agggtaagcc tatccctaac                                30

<210> SEQ ID NO 33
<211> LENGTH: 31
<212> TYPE: DNA
<213> ORGANISM: Artificial Sequence
<220> FEATURE:
<223> OTHER INFORMATION: Description of Artificial Sequence: pSec-V5 His
      Reverse Oligonucleotide Primer Sequence

<400> SEQUENCE: 33
ctcgtcgggc ccctgatcag cgggtttaaa c                              31

<210> SEQ ID NO 34
<211> LENGTH: 40
<212> TYPE: PRT
<213> ORGANISM: Homo sapiens

<400> SEQUENCE: 34

Met Ala Asp Lys Pro Asp Met Gly Glu Ile Ala Ser Phe Asp Lys Ala
1               5                   10                  15

Lys Leu Lys Lys Thr Glu Thr Gln Glu Lys Asn Thr Leu Pro Thr Lys
            20                  25                  30

Glu Thr Ile Glu Gln Glu Lys Arg
        35                  40

<210> SEQ ID NO 35
<211> LENGTH: 10
<212> TYPE: PRT
<213> ORGANISM: Homo sapiens

<400> SEQUENCE: 35

Lys Leu Lys Lys Thr Glu Thr Gln Glu Asn
1               5                   10

<210> SEQ ID NO 36
<211> LENGTH: 38
<212> TYPE: PRT
<213> ORGANISM: Homo sapiens

<400> SEQUENCE: 36

Ala Asp Lys Pro Asp Met Gly Glu Ile Ala Ser Phe Asp Lys Ala Lys
1               5                   10                  15

Leu Lys Lys Thr Glu Thr Gln Glu Lys Asn Thr Leu Pro Thr Lys Glu
            20                  25                  30

Thr Ile Glu Gln Glu Lys
        35

<210> SEQ ID NO 37
<211> LENGTH: 40
<212> TYPE: PRT
<213> ORGANISM: Bos taurus

<400> SEQUENCE: 37

Ala Asp Lys Pro Asp Leu Gly Glu Ile Asn Ser Phe Asp Lys Ala Lys
1               5                   10                  15

Leu Lys Lys Thr Glu Thr Gln Glu Lys Asn Thr Leu Pro Thr Lys Glu
            20                  25                  30

Thr Ile Glu Gln Glu Lys Gln Ala
        35                  40

<210> SEQ ID NO 38

```
<211> LENGTH: 40
<212> TYPE: PRT
<213> ORGANISM: Sus scrofa

<400> SEQUENCE: 38

Ala Asp Lys Pro Asp Met Gly Glu Ile Asn Ser Phe Asp Lys Ala Lys
 1               5                  10                  15

Leu Lys Lys Thr Glu Thr Gln Glu Lys Asn Thr Leu Pro Thr Lys Glu
             20                  25                  30

Thr Ile Glu Gln Glu Lys Gln Ala
         35                  40

<210> SEQ ID NO 39
<211> LENGTH: 40
<212> TYPE: PRT
<213> ORGANISM: Homo sapiens

<400> SEQUENCE: 39

Ser Asp Lys Pro Asp Met Ala Glu Ile Glu Lys Phe Asp Lys Ser Lys
 1               5                  10                  15

Leu Lys Lys Thr Glu Thr Gln Glu Lys Asn Pro Leu Pro Ser Lys Glu
             20                  25                  30

Thr Ile Glu Gln Glu Lys Gln Ala
         35                  40

<210> SEQ ID NO 40
<211> LENGTH: 41
<212> TYPE: PRT
<213> ORGANISM: Mus musculus

<400> SEQUENCE: 40

Met Ser Asp Lys Pro Asp Met Ala Glu Ile Glu Lys Phe Asp Lys Ser
 1               5                  10                  15

Lys Leu Lys Lys Thr Glu Thr Gln Glu Lys Asn Pro Leu Pro Ser Lys
             20                  25                  30

Glu Thr Ile Glu Gln Glu Lys Gln Ala
         35                  40

<210> SEQ ID NO 41
<211> LENGTH: 40
<212> TYPE: PRT
<213> ORGANISM: Oryctolagus cuniculus

<400> SEQUENCE: 41

Ala Asp Lys Pro Asp Met Ala Glu Ile Glu Lys Phe Asp Lys Ser Lys
 1               5                  10                  15

Leu Lys Lys Thr Glu Thr Gln Glu Lys Asn Pro Leu Pro Ser Lys Glu
             20                  25                  30

Thr Ile Glu Gln Glu Lys Gln Ala
         35                  40

<210> SEQ ID NO 42
<211> LENGTH: 39
<212> TYPE: PRT
<213> ORGANISM: Xenopus laevis

<400> SEQUENCE: 42

Ser Asp Lys Pro Asp Met Ala Glu Ile Glu Lys Phe Asp Lys Ala Lys
 1               5                  10                  15

Leu Lys Thr Glu Thr Gln Glu Lys Asn Pro Leu Pro Ser Lys Glu
             20                  25                  30
```

-continued

Thr Ile Glu Gln Glu Lys Gln
        35

<210> SEQ ID NO 43
<211> LENGTH: 40
<212> TYPE: PRT
<213> ORGANISM: Homo sapiens

<400> SEQUENCE: 43

Ser Asp Lys Pro Gly Met Ala Glu Ile Glu Lys Phe Asp Lys Ser Lys
 1               5                  10                  15

Leu Lys Lys Thr Glu Thr Gln Glu Lys Asn Pro Leu Ser Ser Lys Glu
            20                  25                  30

Thr Ile Glu Gln Glu Arg Gln Ala
        35                  40

<210> SEQ ID NO 44
<211> LENGTH: 40
<212> TYPE: PRT
<213> ORGANISM: Oncorhynchus mykiss

<400> SEQUENCE: 44

Ser Asp Lys Pro Asn Leu Glu Glu Val Ala Ser Phe Asp Lys Thr Lys
 1               5                  10                  15

Leu Lys Lys Thr Glu Thr Gln Glu Lys Asn Pro Leu Pro Thr Lys Glu
            20                  25                  30

Thr Ile Glu Gln Glu Lys Gln Ala
        35                  40

<210> SEQ ID NO 45
<211> LENGTH: 40
<212> TYPE: PRT
<213> ORGANISM: Oncorhynchus mykiss

<400> SEQUENCE: 45

Ser Asp Lys Pro Asp Leu Ala Glu Val Ser Asn Phe Asp Lys Thr Lys
 1               5                  10                  15

Leu Lys Lys Thr Glu Thr Gln Glu Lys Asn Pro Leu Pro Thr Lys Glu
            20                  25                  30

Thr Ile Glu Gln Glu Lys Gln Ala
        35                  40

<210> SEQ ID NO 46
<211> LENGTH: 40
<212> TYPE: PRT
<213> ORGANISM: Lateolabrax japonicus

<400> SEQUENCE: 46

Ser Asp Lys Pro Asp Ile Ser Glu Val Thr Ser Phe Asp Lys Thr Lys
 1               5                  10                  15

Leu Lys Lys Thr Glu Thr Gln Glu Lys Asn Pro Leu Pro Ser Lys Glu
            20                  25                  30

Thr Ile Glu Gln Glu Lys Ala Ala
        35                  40

<210> SEQ ID NO 47
<211> LENGTH: 39
<212> TYPE: PRT
<213> ORGANISM: Rattus norvegicus

<400> SEQUENCE: 47

```
Met Ser Asp Lys Pro Asp Leu Ser Glu Val Glu Thr Phe Asp Lys Ser
 1               5                  10                  15

Lys Leu Lys Lys Thr Asn Thr Glu Glu Lys Asn Thr Leu Pro Ser Lys
                20                  25                  30

Glu Thr Ile Gln Gln Glu Lys
                35

<210> SEQ ID NO 48
<211> LENGTH: 38
<212> TYPE: PRT
<213> ORGANISM: Homo sapiens

<400> SEQUENCE: 48

Ser Asp Lys Pro Asp Leu Ser Glu Val Glu Lys Phe Asp Arg Ser Lys
 1               5                  10                  15

Leu Lys Lys Thr Asn Thr Glu Glu Lys Asn Thr Leu Pro Ser Lys Glu
                20                  25                  30

Thr Ile Gln Gln Glu Lys
                35

<210> SEQ ID NO 49
<211> LENGTH: 35
<212> TYPE: PRT
<213> ORGANISM: Drosophila melanogaster

<400> SEQUENCE: 49

Ile Ala Gly Ile Glu Asn Phe Asp Ala Lys Lys Leu Lys His Thr Glu
 1               5                  10                  15

Thr Asn Glu Lys Asn Val Leu Pro Thr Lys Glu Val Ile Glu Ala Glu
                20                  25                  30

Lys Gln Ala
        35

<210> SEQ ID NO 50
<211> LENGTH: 31
<212> TYPE: PRT
<213> ORGANISM: Drosophila melanogaster

<400> SEQUENCE: 50

Gly Ile Thr Ala Phe Asn Gln Asn Asn Leu Lys His Thr Glu Thr Asn
 1               5                  10                  15

Glu Lys Asn Pro Leu Pro Asp Lys Glu Ala Ile Glu Gln Glu Lys
                20                  25                  30

<210> SEQ ID NO 51
<211> LENGTH: 38
<212> TYPE: PRT
<213> ORGANISM: Homo sapiens

<400> SEQUENCE: 51

Ala Asp Lys Pro Asp Met Gly Glu Ile Ala Ser Phe Asp Lys Ala Lys
 1               5                  10                  15

Leu Lys Lys Thr Glu Thr Gln Glu Lys Asn Thr Leu Pro Thr Lys Glu
                20                  25                  30

Thr Ile Glu Gln Glu Lys
                35

<210> SEQ ID NO 52
<211> LENGTH: 991
<212> TYPE: PRT
```

<213> ORGANISM: Mus musculus

<400> SEQUENCE: 52

```
Met Ala Pro Ala Arg Ala Arg Leu Ser Pro Ala Leu Trp Val Val Thr
 1               5                  10                  15
Ala Ala Ala Ala Ala Thr Cys Val Ser Ala Gly Arg Gly Glu Val Asn
            20                  25                  30
Leu Leu Asp Thr Ser Thr Ile His Gly Asp Trp Gly Trp Leu Thr Tyr
        35                  40                  45
Pro Ala His Gly Trp Asp Ser Ile Asn Glu Val Asp Glu Ser Phe Arg
    50                  55                  60
Pro Ile His Thr Tyr Gln Val Cys Asn Val Met Ser Pro Asn Gln Asn
65                  70                  75                  80
Asn Trp Leu Arg Thr Asn Trp Val Pro Arg Asp Gly Ala Arg Arg Val
                85                  90                  95
Tyr Ala Glu Ile Lys Phe Thr Leu Arg Asp Cys Asn Ser Ile Pro Gly
            100                 105                 110
Val Leu Gly Thr Cys Lys Glu Thr Phe Asn Leu His Tyr Leu Glu Ser
        115                 120                 125
Asp Arg Asp Leu Gly Ala Ser Thr Gln Glu Ser Gln Phe Leu Lys Ile
    130                 135                 140
Asp Thr Ile Ala Ala Asp Glu Ser Phe Thr Gly Ala Asp Leu Gly Val
145                 150                 155                 160
Arg Arg Leu Lys Leu Asn Thr Glu Val Arg Gly Val Gly Pro Leu Ser
                165                 170                 175
Lys Arg Gly Phe Tyr Leu Ala Phe Gln Asp Ile Gly Ala Cys Leu Ala
            180                 185                 190
Ile Leu Ser Leu Arg Ile Tyr Tyr Lys Lys Cys Pro Ala Met Val Arg
        195                 200                 205
Asn Leu Ala Ala Phe Ser Glu Ala Val Thr Gly Ala Asp Ser Ser Ser
    210                 215                 220
Leu Val Glu Val Arg Gly Gln Cys Val Arg His Ser Glu Glu Arg Asp
225                 230                 235                 240
Thr Pro Lys Met Tyr Cys Ser Ala Glu Gly Glu Trp Leu Val Pro Ile
                245                 250                 255
Gly Lys Cys Val Cys Ser Ala Gly Tyr Glu Glu Arg Arg Asp Ala Cys
            260                 265                 270
Met Ala Cys Glu Leu Gly Phe Tyr Lys Ser Ala Pro Gly Asp Gln Leu
        275                 280                 285
Cys Ala Arg Cys Pro Pro His Ser His Ser Ala Thr Pro Ala Ala Gln
    290                 295                 300
Thr Cys Arg Cys Asp Leu Ser Tyr Tyr Arg Ala Ala Leu Asp Pro Pro
305                 310                 315                 320
Ser Ala Ala Cys Thr Arg Pro Pro Ser Ala Pro Val Asn Leu Ile Ser
                325                 330                 335
Ser Val Asn Gly Thr Ser Val Thr Leu Glu Trp Ala Pro Pro Leu Asp
            340                 345                 350
Pro Gly Gly Arg Ser Asp Ile Thr Tyr Asn Ala Val Cys Arg Arg Cys
        355                 360                 365
Pro Trp Ala Leu Ser His Cys Glu Ala Cys Gly Ser Gly Thr Arg Phe
    370                 375                 380
Val Pro Gln Gln Thr Ser Leu Ala Gln Ala Ser Leu Leu Val Ala Asn
385                 390                 395                 400
```

```
Leu Leu Ala His Met Asn Tyr Ser Phe Trp Ile Glu Ala Val Asn Gly
            405                 410                 415

Val Ser Asn Leu Ser Pro Glu Pro Arg Ser Ala Ala Val Val Asn Ile
            420                 425                 430

Thr Thr Asn Gln Ala Ala Pro Ser Gln Val Val Ile Arg Gln Glu
            435                 440                 445

Arg Ala Gly Gln Thr Ser Val Ser Leu Leu Trp Gln Glu Pro Glu Gln
        450                 455                 460

Pro Asn Gly Ile Ile Leu Glu Tyr Glu Ile Lys Tyr Glu Lys Asp
465                 470                 475                 480

Lys Glu Met Gln Ser Tyr Ser Thr Leu Lys Ala Val Thr Thr Arg Ala
                485                 490                 495

Thr Val Ser Gly Leu Lys Pro Gly Thr Arg Tyr Val Phe Gln Val Arg
            500                 505                 510

Ala Arg Thr Ser Ala Gly Cys Gly Arg Phe Ser Gln Ala Met Glu Val
            515                 520                 525

Glu Thr Gly Lys Pro Arg Pro Arg Tyr Asp Thr Arg Thr Ile Val Trp
        530                 535                 540

Ile Cys Leu Thr Leu Ile Thr Gly Leu Val Val Leu Leu Leu Leu Leu
545                 550                 555                 560

Ile Cys Lys Lys Arg His Cys Gly Tyr Ser Lys Ala Phe Gln Asp Ser
                565                 570                 575

Asp Glu Glu Lys Met His Tyr Gln Asn Gly Gln Ala Pro Pro Val
            580                 585                 590

Phe Leu Pro Leu Asn His Pro Gly Lys Phe Pro Glu Thr Gln Phe
        595                 600                 605

Ser Ala Glu Pro His Thr Tyr Glu Glu Pro Gly Arg Ala Gly Arg Ser
    610                 615                 620

Phe Thr Arg Glu Ile Glu Ala Ser Arg Ile His Ile Glu Lys Ile Ile
625                 630                 635                 640

Gly Ser Gly Glu Ser Gly Glu Val Cys Tyr Gly Arg Leu Gln Val Pro
                645                 650                 655

Gly Gln Arg Asp Val Pro Val Ala Ile Lys Ala Leu Lys Ala Gly Tyr
            660                 665                 670

Thr Glu Arg Gln Arg Gln Asp Phe Leu Ser Glu Ala Ala Ile Met Gly
        675                 680                 685

Gln Phe Asp His Pro Asn Ile Ile Arg Leu Glu Gly Val Val Thr Arg
690                 695                 700

Gly Arg Leu Ala Met Ile Val Thr Glu Tyr Met Glu Asn Gly Ser Leu
705                 710                 715                 720

Asp Ala Phe Leu Arg Thr His Asp Gly Gln Phe Thr Ile Val Gln Leu
                725                 730                 735

Val Gly Met Leu Arg Gly Val Gly Ala Gly Met Arg Tyr Leu Ser Asp
            740                 745                 750

Leu Gly Tyr Ile His Arg Asp Leu Ala Ala Arg Asn Val Leu Val Asp
        755                 760                 765

Gly Arg Leu Val Cys Lys Val Ser Asp Phe Gly Leu Ser Arg Ala Leu
770                 775                 780

Glu Asp Asp Pro Glu Ala Ala Tyr Thr Thr Ala Gly Gly Lys Ile Pro
785                 790                 795                 800

Ile Arg Trp Thr Ala Pro Glu Ala Ile Ala Phe Arg Thr Phe Ser Ser
                805                 810                 815

Ala Ser Asp Val Trp Ser Phe Gly Val Val Met Trp Glu Val Leu Ala
```

```
                    820                 825                 830
Tyr Gly Glu Arg Pro Tyr Trp Asn Met Thr Asn Gln Asp Val Ile Ser
            835                 840                 845

Ser Val Glu Glu Gly Tyr Arg Leu Pro Ala Pro Met Gly Cys Pro Arg
850                 855                 860

Ala Leu His Gln Leu Met Leu Asp Cys Trp His Lys Asp Arg Ala Gln
865                 870                 875                 880

Arg Pro Arg Phe Ala His Val Val Ser Val Leu Asp Ala Leu Val His
                885                 890                 895

Ser Pro Glu Ser Leu Arg Ala Thr Ala Thr Val Ser Arg Cys Pro Pro
            900                 905                 910

Pro Ala Phe Ala Arg Ser Cys Phe Asp Leu Arg Ala Gly Gly Ser Gly
            915                 920                 925

Asn Gly Asp Leu Thr Val Gly Asp Trp Leu Asp Ser Ile Arg Met Gly
        930                 935                 940

Arg Tyr Arg Asp His Phe Ala Ala Gly Gly Tyr Ser Ser Leu Gly Met
945                 950                 955                 960

Val Leu Arg Met Asn Ala Gln Asp Val Arg Ala Leu Gly Ile Thr Leu
                965                 970                 975

Met Gly His Gln Lys Lys Ile Leu Gly Ser Ile Gln Thr Met Arg
            980                 985                 990

<210> SEQ ID NO 53
<211> LENGTH: 992
<212> TYPE: PRT
<213> ORGANISM: Homo sapiens

<400> SEQUENCE: 53

Met Ala Pro Ala Arg Gly Arg Leu Pro Pro Ala Leu Trp Val Val Thr
1               5                   10                  15

Ala Ala Ala Ala Ala Thr Cys Val Ser Ala Ala Arg Gly Glu Val
            20                  25                  30

Asn Leu Leu Asp Thr Ser Thr Ile His Gly Asp Trp Gly Trp Leu Thr
        35                  40                  45

Tyr Pro Ala His Gly Trp Asp Ser Ile Asn Glu Val Asp Glu Ser Phe
    50                  55                  60

Gln Pro Ile His Thr Tyr Gln Val Cys Asn Val Met Ser Pro Asn Gln
65                  70                  75                  80

Asn Asn Trp Leu Arg Thr Ser Trp Val Pro Arg Asp Gly Ala Arg Arg
                85                  90                  95

Val Tyr Ala Glu Ile Lys Phe Thr Leu Arg Asp Cys Asn Ser Met Pro
            100                 105                 110

Gly Val Leu Gly Thr Cys Lys Glu Thr Phe Asn Leu Tyr Tyr Leu Glu
        115                 120                 125

Ser Asp Arg Asp Leu Gly Ala Ser Thr Gln Glu Ser Gln Phe Leu Lys
    130                 135                 140

Ile Asp Thr Ile Ala Ala Asp Glu Ser Phe Thr Gly Ala Asp Leu Gly
145                 150                 155                 160

Val Arg Arg Leu Lys Leu Asn Thr Glu Val Arg Ser Val Gly Pro Leu
                165                 170                 175

Ser Lys Arg Gly Phe Tyr Leu Ala Phe Gln Asp Ile Gly Ala Cys Leu
            180                 185                 190

Ala Ile Leu Ser Leu Arg Ile Tyr Tyr Lys Lys Cys Pro Ala Met Val
        195                 200                 205
```

```
Arg Asn Leu Ala Ala Phe Ser Glu Ala Val Thr Gly Ala Asp Ser Ser
    210                 215                 220

Ser Leu Val Glu Val Arg Gly Gln Cys Val Arg His Ser Glu Glu Arg
225                 230                 235                 240

Asp Thr Pro Lys Met Tyr Cys Ser Ala Glu Gly Glu Trp Leu Val Pro
                245                 250                 255

Ile Gly Lys Cys Val Cys Ser Ala Gly Tyr Glu Glu Arg Arg Asp Ala
            260                 265                 270

Cys Val Ala Cys Glu Leu Gly Phe Tyr Lys Ser Ala Pro Gly Asp Gln
        275                 280                 285

Leu Cys Ala Arg Cys Pro Pro His Ser His Ser Ala Ala Pro Ala Ala
    290                 295                 300

Gln Ala Cys His Cys Asp Leu Ser Tyr Arg Ala Ala Leu Asp Pro
305                 310                 315                 320

Pro Ser Ser Ala Cys Thr Arg Pro Pro Ser Ala Pro Val Asn Leu Ile
                325                 330                 335

Ser Ser Val Asn Gly Thr Ser Val Thr Leu Glu Trp Ala Pro Pro Leu
            340                 345                 350

Asp Pro Gly Gly Arg Ser Asp Ile Thr Tyr Asn Ala Val Cys Arg Arg
        355                 360                 365

Cys Pro Trp Ala Leu Ser Arg Cys Glu Ala Cys Gly Ser Gly Thr Arg
    370                 375                 380

Phe Val Pro Gln Gln Thr Ser Leu Val Gln Ala Ser Leu Leu Val Ala
385                 390                 395                 400

Asn Leu Leu Ala His Met Asn Tyr Ser Phe Trp Ile Glu Ala Val Asn
                405                 410                 415

Gly Val Ser Asp Leu Ser Pro Glu Pro Arg Arg Ala Ala Val Val Asn
            420                 425                 430

Ile Thr Thr Asn Gln Ala Ala Pro Ser Gln Val Val Ile Arg Gln
        435                 440                 445

Glu Arg Ala Gly Gln Thr Ser Val Ser Leu Leu Trp Gln Glu Pro Glu
    450                 455                 460

Gln Pro Asn Gly Ile Ile Leu Glu Tyr Glu Ile Lys Tyr Tyr Glu Lys
465                 470                 475                 480

Asp Lys Glu Met Gln Ser Tyr Ser Thr Leu Lys Ala Val Thr Thr Arg
                485                 490                 495

Ala Thr Val Ser Gly Leu Lys Pro Gly Thr Arg Tyr Val Phe Gln Val
            500                 505                 510

Arg Ala Arg Thr Ser Ala Gly Cys Gly Arg Phe Ser Gln Ala Met Glu
        515                 520                 525

Val Glu Thr Gly Lys Pro Arg Pro Arg Tyr Asp Thr Arg Thr Ile Val
    530                 535                 540

Trp Ile Cys Leu Thr Leu Ile Thr Gly Leu Val Val Leu Leu Leu Leu
545                 550                 555                 560

Leu Ile Cys Lys Lys Arg His Cys Gly Tyr Ser Lys Ala Phe Gln Asp
                565                 570                 575

Ser Asp Glu Glu Lys Met His Tyr Gln Asn Gly Gln Ala Pro Pro Pro
            580                 585                 590

Val Phe Leu Pro Leu His His Pro Pro Gly Lys Leu Pro Glu Pro Gln
        595                 600                 605

Phe Tyr Ala Glu Pro His Thr Tyr Glu Glu Pro Gly Arg Ala Gly Arg
    610                 615                 620

Ser Phe Thr Arg Glu Ile Glu Ala Ser Arg Ile His Ile Glu Lys Ile
```

```
                625                 630                 635                 640
     Ile Gly Ser Gly Asp Ser Gly Glu Val Cys Tyr Gly Arg Leu Arg Val
                     645                 650                 655

Pro Gly Gln Arg Asp Val Pro Val Ala Ile Lys Ala Leu Lys Ala Gly
                     660                 665                 670

Tyr Thr Glu Arg Gln Arg Arg Asp Phe Leu Ser Glu Ala Ser Ile Met
                     675                 680                 685

Gly Gln Phe Asp His Pro Asn Ile Ile Arg Leu Glu Gly Val Val Thr
                     690                 695                 700

Arg Gly Arg Leu Ala Met Ile Val Thr Glu Tyr Met Glu Asn Gly Ser
     705                 710                 715                 720

Leu Asp Thr Phe Leu Arg Thr His Asp Gly Gln Phe Thr Ile Met Gln
                     725                 730                 735

Leu Val Gly Met Leu Arg Gly Val Gly Ala Gly Met Arg Tyr Leu Ser
                     740                 745                 750

Asp Leu Gly Tyr Val His Arg Asp Leu Ala Ala Arg Asn Val Leu Val
                     755                 760                 765

Asp Ser Asn Leu Val Cys Lys Val Ser Asp Phe Gly Leu Ser Arg Val
     770                 775                 780

Leu Glu Asp Asp Pro Asp Ala Ala Tyr Thr Thr Thr Gly Gly Lys Ile
     785                 790                 795                 800

Pro Ile Arg Trp Thr Ala Pro Glu Ala Ile Ala Phe Arg Thr Phe Ser
                     805                 810                 815

Ser Ala Ser Asp Val Trp Ser Phe Gly Val Val Met Trp Glu Val Leu
                     820                 825                 830

Ala Tyr Gly Glu Arg Pro Tyr Trp Asn Met Thr Asn Arg Asp Val Ile
                     835                 840                 845

Ser Ser Val Glu Glu Gly Tyr Arg Leu Pro Ala Pro Met Gly Cys Pro
     850                 855                 860

His Ala Leu His Gln Leu Met Leu Asp Cys Trp His Lys Asp Arg Ala
     865                 870                 875                 880

Gln Arg Pro Arg Phe Ser Gln Ile Val Ser Val Leu Asp Ala Leu Ile
                     885                 890                 895

Arg Ser Pro Glu Ser Leu Arg Ala Thr Ala Thr Val Ser Arg Cys Pro
                     900                 905                 910

Pro Pro Ala Phe Val Arg Ser Cys Phe Asp Leu Arg Gly Gly Ser Gly
                     915                 920                 925

Gly Gly Gly Gly Leu Thr Val Gly Asp Trp Leu Asp Ser Ile Arg Met
                     930                 935                 940

Gly Arg Tyr Arg Asp His Phe Ala Ala Gly Gly Tyr Ser Ser Leu Gly
     945                 950                 955                 960

Met Val Leu Arg Met Asn Ala Gln Asp Val Arg Ala Leu Gly Ile Thr
                     965                 970                 975

Leu Met Gly His Gln Lys Lys Ile Leu Gly Ser Ile Gln Thr Met Arg
                     980                 985                 990

<210> SEQ ID NO 54
<211> LENGTH: 450
<212> TYPE: PRT
<213> ORGANISM: Mus musculus

<400> SEQUENCE: 54

Met Ala Pro Ala Arg Ala Arg Leu Ser Pro Ala Leu Trp Val Val Thr
 1               5                   10                  15
```

-continued

```
Ala Ala Ala Ala Ala Thr Cys Val Ser Ala Gly Arg Gly Glu Val Asn
                20                  25                  30

Leu Leu Asp Thr Ser Thr Ile His Gly Asp Trp Gly Trp Leu Thr Tyr
            35                  40                  45

Pro Ala His Gly Trp Asp Ser Ile Asn Glu Val Asp Glu Ser Phe Arg
        50                  55                  60

Pro Ile His Thr Tyr Gln Val Cys Asn Val Met Ser Pro Asn Gln Asn
65                  70                  75                  80

Asn Trp Leu Arg Thr Asn Trp Val Pro Arg Asp Gly Ala Arg Arg Val
                85                  90                  95

Tyr Ala Glu Ile Lys Phe Thr Leu Arg Asp Cys Asn Ser Ile Pro Gly
            100                 105                 110

Val Leu Gly Thr Cys Lys Glu Thr Phe Asn Leu His Tyr Leu Glu Ser
        115                 120                 125

Asp Arg Asp Leu Gly Ala Ser Thr Gln Glu Ser Gln Phe Leu Lys Ile
    130                 135                 140

Asp Thr Ile Ala Ala Asp Glu Ser Phe Thr Gly Ala Asp Leu Gly Val
145                 150                 155                 160

Arg Arg Leu Lys Leu Asn Thr Glu Val Arg Gly Val Gly Pro Leu Ser
                165                 170                 175

Lys Arg Gly Phe Tyr Leu Ala Phe Gln Asp Ile Gly Ala Cys Leu Ala
            180                 185                 190

Ile Leu Ser Leu Arg Ile Tyr Tyr Lys Lys Cys Pro Ala Met Val Arg
        195                 200                 205

Asn Leu Ala Ala Phe Ser Glu Ala Val Thr Gly Ala Asp Ser Ser Ser
    210                 215                 220

Leu Val Glu Val Arg Gly Gln Cys Val Arg His Ser Glu Glu Arg Asp
225                 230                 235                 240

Thr Pro Lys Met Tyr Cys Ser Ala Glu Gly Glu Trp Leu Val Pro Ile
                245                 250                 255

Gly Lys Cys Val Cys Ser Ala Gly Tyr Glu Glu Arg Arg Asp Ala Cys
            260                 265                 270

Met Ala Cys Glu Leu Gly Phe Tyr Lys Ser Ala Pro Gly Asp Gln Leu
        275                 280                 285

Cys Ala Arg Cys Pro Pro His Ser His Ser Ala Thr Pro Ala Ala Gln
    290                 295                 300

Thr Cys Arg Cys Asp Leu Ser Tyr Tyr Arg Ala Ala Leu Asp Pro Pro
305                 310                 315                 320

Ser Ala Ala Cys Thr Arg Pro Pro Ser Ala Pro Val Asn Leu Ile Ser
                325                 330                 335

Ser Val Asn Gly Thr Ser Val Thr Leu Glu Trp Ala Pro Pro Leu Asp
            340                 345                 350

Pro Gly Gly Arg Ser Asp Ile Thr Tyr Asn Ala Val Cys Arg Arg Cys
        355                 360                 365

Pro Trp Ala Leu Ser His Cys Glu Ala Cys Gly Ser Gly Thr Arg Phe
    370                 375                 380

Val Pro Gln Gln Thr Ser Leu Ala Gln Ala Ser Leu Leu Val Ala Asn
385                 390                 395                 400

Leu Leu Ala His Met Asn Tyr Ser Phe Trp Ile Glu Ala Val Asn Gly
                405                 410                 415

Val Ser Asn Leu Ser Pro Glu Pro Arg Ser Ala Ala Val Val Asn Ile
            420                 425                 430

Thr Thr Asn Gln Ala Ala Pro Ser Gln Val Val Val Ile Arg Gln Glu
```

```
            435                 440                 445
Arg Ala
    450

<210> SEQ ID NO 55
<211> LENGTH: 480
<212> TYPE: PRT
<213> ORGANISM: Homo sapiens

<400> SEQUENCE: 55

Met Arg Gly Ser Gly Pro Arg Gly Ala Gly His Arg Arg Pro Pro Ser
  1               5                  10                  15

Gly Gly Gly Asp Thr Pro Ile Thr Pro Ala Ser Leu Ala Gly Cys Tyr
             20                  25                  30

Ser Ala Pro Arg Arg Ala Pro Leu Trp Thr Cys Leu Leu Leu Cys Ala
         35                  40                  45

Ala Leu Arg Thr Leu Leu Ala Ser Pro Ser Asn Glu Val Asn Leu Leu
     50                  55                  60

Asp Ser Arg Thr Val Met Gly Asp Leu Gly Trp Ile Ala Phe Pro Lys
 65                  70                  75                  80

Asn Gly Trp Glu Glu Ile Gly Glu Val Asp Glu Asn Tyr Ala Pro Ile
                 85                  90                  95

His Thr Tyr Gln Val Cys Lys Val Met Glu Gln Asn Gln Asn Asn Trp
            100                 105                 110

Leu Leu Thr Ser Trp Ile Ser Asn Glu Gly Ala Ser Arg Ile Phe Ile
        115                 120                 125

Glu Leu Lys Phe Thr Leu Arg Asp Cys Asn Ser Leu Pro Gly Gly Leu
    130                 135                 140

Gly Thr Cys Lys Glu Thr Phe Asn Met Tyr Tyr Phe Glu Ser Asp Asp
145                 150                 155                 160

Gln Asn Gly Arg Asn Ile Lys Glu Asn Gln Tyr Ile Lys Ile Asp Thr
                165                 170                 175

Ile Ala Ala Asp Glu Ser Phe Thr Glu Leu Asp Leu Gly Asp Arg Val
            180                 185                 190

Met Lys Leu Asn Thr Glu Val Arg Asp Val Gly Pro Leu Ser Lys Lys
        195                 200                 205

Gly Phe Tyr Leu Ala Phe Gln Asp Val Gly Ala Cys Ile Ala Leu Val
    210                 215                 220

Ser Val Arg Val Tyr Tyr Lys Lys Cys Pro Ser Val Val Arg His Leu
225                 230                 235                 240

Ala Val Phe Pro Asp Thr Ile Thr Gly Ala Asp Ser Ser Gln Leu Leu
                245                 250                 255

Glu Val Ser Gly Ser Cys Val Asn His Ser Val Thr Asp Glu Pro Pro
            260                 265                 270

Lys Met His Cys Ser Ala Glu Gly Glu Trp Leu Val Pro Ile Gly Lys
        275                 280                 285

Cys Met Cys Lys Ala Gly Tyr Glu Glu Lys Asn Gly Thr Cys Gln Val
    290                 295                 300

Cys Arg Pro Gly Phe Phe Lys Ala Ser Pro His Ile Gln Ser Cys Gly
305                 310                 315                 320

Lys Cys Pro Pro His Ser Tyr Thr His Glu Glu Ala Ser Thr Ser Cys
                325                 330                 335

Val Cys Glu Lys Asp Tyr Phe Arg Arg Glu Ser Asp Pro Pro Thr Met
            340                 345                 350
```

-continued

```
Ala Cys Thr Arg Pro Pro Ser Ala Pro Arg Asn Ala Ile Ser Asn Val
        355                 360                 365

Asn Glu Thr Ser Val Phe Leu Glu Trp Ile Pro Pro Ala Asp Thr Gly
    370                 375                 380

Gly Arg Lys Asp Val Ser Tyr Tyr Ile Ala Cys Lys Lys Cys Asn Ser
385                 390                 395                 400

His Ala Gly Val Cys Glu Glu Cys Gly Gly His Val Arg Tyr Leu Pro
                405                 410                 415

Arg Gln Ser Gly Leu Lys Asn Thr Ser Val Met Met Val Asp Leu Leu
                420                 425                 430

Ala His Thr Asn Tyr Thr Phe Glu Ile Glu Ala Val Asn Gly Val Ser
            435                 440                 445

Asp Leu Ser Pro Gly Ala Arg Gln Tyr Val Ser Val Asn Val Thr Thr
        450                 455                 460

Asn Gln Ala Ala Pro Ser Pro Val Thr Asn Val Lys Lys Gly Lys Ile
465                 470                 475                 480

<210> SEQ ID NO 56
<211> LENGTH: 456
<212> TYPE: PRT
<213> ORGANISM: Gallus gallus

<400> SEQUENCE: 56

Met Gly Leu Arg Gly Gly Gly Arg Ala Gly Gly Pro Ala Pro Gly
  1               5                  10                  15

Trp Thr Cys Leu Leu Leu Cys Ala Ala Leu Arg Ser Leu Leu Ala Ser
                20                  25                  30

Pro Gly Ser Glu Val Asn Leu Leu Asp Ser Arg Thr Val Met Gly Asp
            35                  40                  45

Leu Gly Trp Ile Ala Tyr Pro Lys Asn Gly Trp Glu Glu Ile Gly Glu
        50                  55                  60

Val Asp Glu Asn Tyr Ala Pro Ile His Thr Tyr Gln Val Cys Lys Val
 65                  70                  75                  80

Met Glu Gln Asn Gln Asn Asn Trp Leu Leu Thr Ser Trp Ile Ser Asn
                85                  90                  95

Glu Gly Arg Pro Ala Ser Ser Phe Glu Leu Lys Phe Thr Leu Arg Asp
            100                 105                 110

Cys Asn Ser Leu Pro Gly Gly Leu Gly Thr Cys Lys Glu Thr Phe Asn
        115                 120                 125

Met Tyr Tyr Phe Glu Ser Asp Glu Asp Gly Arg Asn Ile Arg Glu
    130                 135                 140

Asn Gln Tyr Ile Lys Ile Asp Thr Ile Ala Ala Asp Glu Ser Phe Thr
145                 150                 155                 160

Glu Leu Asp Leu Gly Asp Arg Val Met Lys Leu Asn Thr Glu Val Arg
                165                 170                 175

Asp Val Gly Pro Leu Thr Lys Lys Gly Phe Tyr Leu Ala Phe Gln Asp
            180                 185                 190

Val Gly Ala Cys Ile Ala Leu Val Ser Val Arg Val Tyr Tyr Lys Lys
        195                 200                 205

Cys Pro Ser Val Ile Arg Asn Leu Ala Arg Phe Pro Asp Thr Ile Thr
    210                 215                 220

Gly Ala Asp Ser Ser Gln Leu Leu Glu Val Ser Gly Val Cys Val Asn
225                 230                 235                 240

His Ser Val Thr Asp Glu Ala Pro Lys Met His Cys Ser Ala Glu Gly
                245                 250                 255
```

-continued

Glu Trp Leu Val Pro Ile Gly Lys Cys Leu Cys Lys Ala Gly Tyr Glu
            260                 265                 270

Glu Lys Asn Asn Thr Cys Gln Val Cys Arg Pro Gly Phe Phe Lys Ala
            275                 280                 285

Ser Pro His Ser Pro Ser Cys Ser Lys Cys Pro Pro His Ser Tyr Thr
            290                 295                 300

Leu Asp Glu Ala Ser Thr Ser Cys Leu Cys Glu Glu His Tyr Phe Arg
305                 310                 315                 320

Arg Glu Ser Asp Pro Pro Thr Met Ala Cys Thr Arg Pro Pro Ser Ala
            325                 330                 335

Pro Arg Ser Ala Ile Ser Asn Val Asn Glu Thr Ser Val Phe Leu Glu
            340                 345                 350

Trp Ile Pro Pro Ala Asp Thr Gly Gly Arg Lys Asp Val Ser Tyr Tyr
            355                 360                 365

Ile Ala Cys Lys Lys Cys Asn Ser His Ser Gly Leu Cys Glu Ala Cys
            370                 375                 380

Gly Ser His Val Arg Tyr Leu Pro Gln Gln Thr Gly Leu Lys Asn Thr
385                 390                 395                 400

Ser Val Met Met Val Asp Leu Leu Ala His Thr Asn Tyr Thr Phe Glu
            405                 410                 415

Ile Glu Ala Val Asn Gly Val Ser Asp Gln Asn Pro Gly Ala Arg Gln
            420                 425                 430

Phe Val Ser Val Asn Val Thr Thr Asn Gln Ala Ala Pro Ser Pro Val
            435                 440                 445

Ser Ser Val Lys Lys Gly Lys Ile
    450                 455

<210> SEQ ID NO 57
<211> LENGTH: 649
<212> TYPE: PRT
<213> ORGANISM: Homo sapiens

<400> SEQUENCE: 57

Met Ile Ser Ala Ala Trp Ser Ile Phe Leu Ile Gly Thr Lys Ile Gly
1               5                   10                  15

Leu Phe Leu Gln Val Ala Pro Leu Ser Val Met Ala Lys Ser Cys Pro
            20                  25                  30

Ser Val Cys Arg Cys Asp Ala Gly Phe Ile Tyr Cys Asn Asp Arg Phe
            35                  40                  45

Leu Thr Ser Ile Pro Thr Gly Ile Pro Glu Asp Ala Thr Thr Leu Tyr
        50                  55                  60

Leu Gln Asn Asn Gln Ile Asn Asn Ala Gly Ile Pro Ser Asp Leu Lys
65                  70                  75                  80

Asn Leu Leu Lys Val Glu Arg Ile Tyr Leu Tyr His Asn Ser Leu Asp
                85                  90                  95

Glu Phe Pro Thr Asn Leu Pro Lys Tyr Val Lys Glu Leu His Leu Gln
            100                 105                 110

Glu Asn Asn Ile Arg Thr Ile Thr Tyr Asp Ser Leu Ser Lys Ile Pro
            115                 120                 125

Tyr Leu Glu Glu Leu His Leu Asp Asp Asn Ser Val Ser Ala Val Ser
        130                 135                 140

Ile Glu Glu Gly Ala Phe Arg Asp Ser Asn Tyr Leu Arg Leu Leu Phe
145                 150                 155                 160

Leu Ser Arg Asn His Leu Ser Thr Ile Pro Trp Gly Leu Pro Arg Thr

-continued

```
                165                 170                 175
Ile Glu Glu Leu Arg Leu Asp Asp Asn Arg Ile Ser Thr Ile Ser Ser
            180                 185                 190
Pro Ser Leu Gln Gly Leu Thr Ser Leu Lys Arg Leu Val Leu Asp Gly
            195                 200                 205
Asn Leu Leu Asn Asn His Gly Leu Gly Asp Lys Val Phe Phe Asn Leu
            210                 215                 220
Val Asn Leu Thr Glu Leu Ser Leu Val Arg Asn Ser Leu Thr Ala Ala
225                 230                 235                 240
Pro Val Asn Leu Pro Gly Thr Asn Leu Arg Lys Leu Tyr Leu Gln Asp
            245                 250                 255
Asn His Ile Asn Arg Val Pro Pro Asn Ala Phe Ser Tyr Leu Arg Gln
            260                 265                 270
Leu Tyr Arg Leu Asp Met Ser Asn Asn Asn Leu Ser Asn Leu Pro Gln
            275                 280                 285
Gly Ile Phe Asp Asp Leu Asp Asn Ile Thr Gln Ile Leu Arg Asn
            290                 295                 300
Asn Pro Trp Tyr Cys Gly Cys Lys Met Lys Trp Val Arg Asp Trp Leu
305                 310                 315                 320
Gln Ser Leu Pro Val Lys Val Asn Val Arg Gly Leu Met Cys Gln Ala
            325                 330                 335
Pro Glu Lys Val Arg Gly Met Ala Ile Lys Asp Leu Asn Ala Glu Leu
            340                 345                 350
Phe Asp Cys Lys Asp Ser Gly Ile Val Ser Thr Ile Gln Ile Thr Thr
            355                 360                 365
Ala Ile Pro Asn Thr Val Tyr Pro Ala Gln Gly Gln Trp Pro Ala Pro
            370                 375                 380
Val Thr Lys Gln Pro Asp Ile Lys Asn Pro Lys Leu Thr Lys Asp His
385                 390                 395                 400
Gln Thr Thr Gly Ser Pro Ser Arg Lys Thr Ile Thr Ile Thr Val Lys
            405                 410                 415
Ser Val Thr Ser Asp Thr Ile His Ile Ser Trp Lys Leu Ala Leu Pro
            420                 425                 430
Met Thr Ala Leu Arg Leu Ser Trp Leu Lys Leu Gly His Ser Pro Ala
            435                 440                 445
Phe Gly Ser Ile Thr Glu Thr Ile Val Thr Gly Glu Arg Ser Glu Tyr
            450                 455                 460
Leu Val Thr Ala Leu Glu Pro Asp Ser Pro Tyr Lys Val Cys Met Val
465                 470                 475                 480
Pro Met Glu Thr Ser Asn Leu Tyr Leu Phe Asp Glu Thr Pro Val Cys
            485                 490                 495
Ile Glu Thr Glu Thr Ala Pro Leu Arg Met Tyr Asn Pro Thr Thr Thr
            500                 505                 510
Leu Asn Arg Glu Gln Glu Lys Glu Pro Tyr Lys Asn Pro Asn Leu Pro
            515                 520                 525
Leu Ala Ala Ile Ile Gly Gly Ala Val Ala Leu Val Thr Ile Ala Leu
            530                 535                 540
Leu Ala Leu Val Cys Trp Tyr Val His Arg Asn Gly Ser Leu Phe Ser
545                 550                 555                 560
Arg Asn Cys Ala Tyr Ser Lys Gly Arg Arg Lys Asp Asp Tyr Ala
            565                 570                 575
Glu Ala Gly Thr Lys Lys Asp Asn Ser Ile Leu Glu Ile Arg Glu Thr
            580                 585                 590
```

```
Ser Phe Gln Met Leu Pro Ile Ser Asn Glu Pro Ile Ser Lys Glu Glu
            595                 600                 605

Phe Val Ile His Thr Ile Phe Pro Pro Asn Gly Met Asn Leu Tyr Lys
            610                 615                 620

Asn Asn His Ser Glu Ser Ser Ser Asn Arg Ser Tyr Arg Asp Ser Gly
625                 630                 635                 640

Ile Pro Asp Ser Asp His Ser His Ser
                645

<210> SEQ ID NO 58
<211> LENGTH: 660
<212> TYPE: PRT
<213> ORGANISM: Homo sapiens

<400> SEQUENCE: 58

Met Gly Leu Gln Thr Thr Lys Trp Pro Ser His Gly Ala Phe Phe Leu
  1               5                  10                  15

Lys Ser Trp Leu Ile Ile Ser Leu Gly Leu Tyr Ser Gln Val Ser Lys
             20                  25                  30

Leu Leu Ala Cys Pro Ser Val Cys Arg Cys Asp Arg Asn Phe Val Tyr
         35                  40                  45

Cys Asn Glu Arg Ser Leu Thr Ser Val Pro Leu Gly Ile Pro Glu Gly
     50                  55                  60

Val Thr Val Leu Tyr Leu His Asn Asn Gln Ile Asn Asn Ala Gly Phe
 65                  70                  75                  80

Pro Ala Glu Leu His Asn Val Gln Ser Val His Thr Val Tyr Leu Tyr
                 85                  90                  95

Gly Asn Gln Leu Asp Glu Phe Pro Met Asn Leu Pro Lys Asn Val Arg
            100                 105                 110

Val Leu His Leu Gln Glu Asn Asn Ile Gln Thr Ile Ser Arg Ala Ala
            115                 120                 125

Leu Ala Gln Leu Leu Lys Leu Glu Glu Leu His Leu Asp Asp Asn Ser
        130                 135                 140

Ile Ser Thr Val Gly Val Glu Asp Gly Ala Phe Arg Glu Ala Ile Ser
145                 150                 155                 160

Leu Lys Leu Leu Phe Leu Ser Lys Asn His Leu Ser Ser Val Pro Val
                165                 170                 175

Gly Leu Pro Val Asp Leu Gln Glu Leu Arg Val Asp Glu Asn Arg Ile
            180                 185                 190

Ala Val Ile Ser Asp Met Ala Phe Gln Asn Leu Thr Ser Leu Glu Arg
        195                 200                 205

Leu Ile Val Asp Gly Asn Leu Leu Thr Asn Lys Gly Ile Ala Glu Gly
    210                 215                 220

Thr Phe Ser His Leu Thr Lys Leu Lys Glu Phe Ser Ile Val Arg Asn
225                 230                 235                 240

Ser Leu Ser His Pro Pro Asp Leu Pro Gly Thr His Leu Ile Arg
                245                 250                 255

Leu Tyr Leu Gln Asp Asn Gln Ile Asn His Ile Pro Leu Thr Ala Phe
            260                 265                 270

Ser Asn Leu Arg Lys Leu Glu Arg Leu Asp Ile Ser Asn Asn Gln Leu
        275                 280                 285

Arg Met Leu Thr Gln Gly Val Phe Asp Asn Leu Ser Asn Leu Lys Gln
    290                 295                 300

Leu Thr Ala Arg Asn Asn Pro Trp Phe Cys Asp Cys Ser Ile Lys Trp
```

```
                305                 310                 315                 320
Val Thr Glu Trp Leu Lys Tyr Ile Pro Ser Ser Leu Asn Val Arg Gly
                325                 330                 335

Phe Met Cys Gln Gly Pro Glu Gln Val Arg Gly Met Ala Val Arg Glu
                340                 345                 350

Leu Asn Met Asn Leu Leu Ser Cys Pro Thr Thr Pro Gly Leu Pro
                355                 360             365

Leu Phe Thr Pro Ala Pro Ser Thr Ala Ser Pro Thr Thr Gln Pro Pro
            370                 375                 380

Thr Leu Ser Ile Pro Asn Pro Ser Arg Ser Tyr Thr Pro Pro Thr Pro
385                 390                 395                 400

Thr Thr Ser Lys Leu Pro Thr Ile Pro Asp Trp Asp Gly Arg Glu Arg
                405                 410                 415

Val Thr Pro Pro Ile Ser Glu Arg Ile Gln Leu Ser Ile His Phe Val
                420                 425                 430

Asn Asp Thr Ser Ile Gln Val Ser Trp Leu Ser Leu Phe Thr Val Met
            435                 440                 445

Ala Tyr Lys Leu Thr Trp Val Lys Met Gly His Ser Leu Val Gly Gly
            450                 455                 460

Ile Val Gln Glu Arg Ile Val Ser Gly Glu Lys Gln His Leu Ser Leu
465                 470                 475                 480

Val Asn Leu Glu Pro Arg Ser Thr Tyr Arg Ile Cys Leu Val Pro Leu
                485                 490                 495

Asp Ala Phe Asn Tyr Arg Ala Val Glu Asp Thr Ile Cys Ser Glu Ala
                500                 505                 510

Thr Thr His Ala Ser Tyr Leu Asn Asn Gly Ser Asn Thr Ala Ser Ser
            515                 520                 525

His Glu Gln Thr Thr Ser His Ser Met Gly Ser Pro Phe Leu Leu Ala
            530                 535                 540

Gly Leu Ile Gly Gly Ala Val Ile Phe Val Leu Val Val Leu Leu Ser
545                 550                 555                 560

Val Phe Cys Trp His Met His Lys Lys Gly Arg Tyr Thr Ser Gln Lys
                565                 570                 575

Trp Lys Tyr Asn Arg Gly Arg Arg Lys Asp Asp Tyr Cys Glu Ala Gly
                580                 585                 590

Thr Lys Lys Asp Asn Ser Ile Leu Glu Met Thr Glu Thr Ser Phe Gln
            595                 600                 605

Ile Val Ser Leu Asn Asn Asp Gln Leu Leu Lys Gly Asp Phe Arg Leu
            610                 615                 620

Gln Pro Ile Tyr Thr Pro Asn Gly Gly Ile Asn Tyr Thr Asp Cys His
625                 630                 635                 640

Ile Pro Asn Asn Met Arg Tyr Cys Asn Ser Ser Val Pro Asp Leu Glu
                645                 650                 655

His Cys His Thr
            660

<210> SEQ ID NO 59
<211> LENGTH: 674
<212> TYPE: PRT
<213> ORGANISM: Homo sapiens

<400> SEQUENCE: 59

Met Val Val Ala His Pro Thr Ala Thr Thr Thr Pro Thr Ala
1               5                   10                  15
```

-continued

```
Thr Val Thr Ala Thr Val Val Met Thr Thr Ala Thr Met Asp Leu Arg
            20                  25                  30

Asp Trp Leu Phe Leu Cys Tyr Gly Leu Ile Ala Phe Leu Thr Glu Val
        35                  40                  45

Ile Asp Ser Thr Thr Cys Pro Ser Val Cys Arg Cys Asp Asn Gly Phe
    50                  55                  60

Ile Tyr Cys Asn Asp Arg Gly Leu Thr Ser Ile Pro Ala Asp Ile Pro
65                  70                  75                  80

Asp Asp Ala Thr Thr Leu Tyr Leu Gln Asn Asn Gln Ile Asn Asn Ala
                85                  90                  95

Gly Ile Pro Gln Asp Leu Lys Thr Lys Val Asn Val Gln Val Ile Tyr
            100                 105                 110

Leu Tyr Glu Asn Asp Leu Asp Glu Phe Pro Ile Asn Leu Pro Arg Ser
        115                 120                 125

Leu Arg Glu Leu His Leu Gln Asp Asn Asn Val Arg Thr Ile Ala Arg
    130                 135                 140

Asp Ser Leu Ala Arg Ile Pro Leu Leu Glu Lys Leu His Leu Asp Asp
145                 150                 155                 160

Asn Ser Val Ser Thr Val Ser Ile Glu Glu Asp Ala Phe Ala Asp Ser
                165                 170                 175

Lys Gln Leu Lys Leu Leu Phe Leu Ser Arg Asn His Leu Ser Ser Ile
            180                 185                 190

Pro Ser Gly Leu Pro His Thr Leu Glu Glu Leu Arg Leu Asp Asp Asn
        195                 200                 205

Arg Ile Ser Thr Ile Pro Leu His Ala Phe Lys Gly Leu Asn Ser Leu
    210                 215                 220

Arg Arg Leu Val Leu Asp Gly Asn Leu Leu Ala Asn Gln Arg Ile Ala
225                 230                 235                 240

Asp Asp Thr Phe Ser Arg Leu Gln Asn Leu Thr Glu Leu Ser Leu Val
                245                 250                 255

Arg Asn Ser Leu Ala Ala Pro Pro Leu Asn Leu Pro Ser Ala His Leu
            260                 265                 270

Gln Lys Leu Tyr Leu Gln Asp Asn Ala Ile Ser His Ile Pro Tyr Asn
        275                 280                 285

Thr Leu Ala Lys Met Arg Glu Leu Glu Arg Leu Asp Leu Ser Asn Asn
    290                 295                 300

Asn Leu Thr Thr Leu Pro Arg Gly Leu Phe Asp Asp Leu Gly Asn Leu
305                 310                 315                 320

Ala Gln Leu Leu Leu Arg Asn Asn Pro Trp Phe Cys Gly Cys Asn Leu
                325                 330                 335

Met Trp Leu Arg Asp Trp Val Lys Ala Arg Ala Ala Val Val Asn Val
            340                 345                 350

Arg Gly Leu Met Cys Gln Gly Pro Glu Lys Val Arg Gly Met Ala Ile
        355                 360                 365

Lys Asp Ile Thr Ser Glu Met Asp Glu Cys Phe Glu Thr Gly Pro Gln
    370                 375                 380

Gly Gly Val Ala Asn Ala Ala Lys Thr Thr Ala Ser Asn His Ala
385                 390                 395                 400

Ser Ala Thr Thr Pro Gln Gly Ser Leu Phe Thr Leu Lys Ala Lys Arg
                405                 410                 415

Pro Gly Leu Arg Leu Pro Asp Ser Asn Ile Asp Tyr Pro Met Ala Thr
            420                 425                 430

Gly Asp Gly Ala Lys Thr Leu Ala Ile His Val Lys Ala Leu Thr Ala
```

```
                435                 440                 445
Asp Ser Ile Arg Ile Thr Trp Lys Ala Thr Leu Pro Ala Ser Ser Phe
    450                 455                 460

Arg Leu Ser Trp Leu Arg Leu Gly His Ser Pro Ala Val Gly Ser Ile
465                 470                 475                 480

Thr Glu Thr Leu Val Gln Gly Asp Lys Thr Glu Tyr Leu Leu Thr Ala
                485                 490                 495

Leu Glu Pro Lys Ser Thr Tyr Ile Ile Cys Met Val Thr Met Glu Thr
            500                 505                 510

Ser Asn Ala Tyr Val Ala Asp Glu Thr Pro Val Cys Ala Lys Ala Glu
            515                 520                 525

Thr Ala Asp Ser Tyr Gly Pro Thr Thr Thr Leu Asn Gln Glu Gln Asn
    530                 535                 540

Ala Gly Pro Met Ala Ser Leu Pro Leu Ala Gly Ile Ile Gly Gly Ala
545                 550                 555                 560

Val Ala Leu Val Phe Leu Phe Leu Val Leu Gly Ala Ile Cys Trp Tyr
                565                 570                 575

Val His Gln Ala Gly Glu Leu Leu Thr Arg Glu Arg Ala Tyr Asn Arg
            580                 585                 590

Gly Ser Arg Glu Lys Asp Asp Tyr Met Glu Ser Gly Thr Lys Lys Asp
            595                 600                 605

Asn Ser Ile Leu Glu Ile Arg Gly Pro Gly Leu Gln Met Leu Pro Ile
    610                 615                 620

Asn Pro Tyr Arg Ala Lys Glu Glu Tyr Val Val His Thr Ile Phe Pro
625                 630                 635                 640

Ser Asn Gly Ser Ser Leu Cys Lys Ala Thr His Thr Ile Gly Tyr Gly
                645                 650                 655

Thr Thr Arg Gly Tyr Arg Asp Gly Gly Ile Pro Asp Ile Asp Tyr Ser
            660                 665                 670

Tyr Thr

<210> SEQ ID NO 60
<211> LENGTH: 674
<212> TYPE: PRT
<213> ORGANISM: Homo sapiens

<400> SEQUENCE: 60

Met Val Val Ala His Pro Thr Ala Thr Ala Thr Thr Pro Thr Ala
  1               5                  10                  15

Thr Val Thr Ala Thr Val Val Met Thr Thr Ala Thr Met Asp Leu Arg
                20                  25                  30

Asp Trp Leu Phe Leu Cys Tyr Gly Leu Ile Ala Phe Leu Thr Glu Val
            35                  40                  45

Ile Asp Ser Thr Thr Cys Pro Ser Val Cys Arg Cys Asp Asn Gly Phe
    50                  55                  60

Ile Tyr Cys Asn Asp Arg Gly Leu Thr Ser Ile Pro Ala Asp Ile Pro
65                  70                  75                  80

Asp Asp Ala Thr Thr Leu Tyr Leu Gln Asn Asn Gln Ile Asn Asn Ala
                85                  90                  95

Gly Ile Pro Gln Asp Leu Lys Thr Lys Val Asn Val Gln Val Ile Tyr
            100                 105                 110

Leu Tyr Glu Asn Asp Leu Asp Glu Phe Pro Ile Asn Leu Pro Arg Ser
        115                 120                 125

Leu Arg Glu Leu His Leu Gln Asp Asn Asn Val Arg Thr Ile Ala Arg
```

-continued

```
            130                 135                 140
Asp Ser Leu Ala Arg Ile Pro Leu Leu Glu Lys Leu His Leu Asp Asp
145                 150                 155                 160

Asn Ser Val Ser Thr Val Ser Ile Glu Glu Asp Ala Phe Ala Asp Ser
                165                 170                 175

Lys Gln Leu Lys Leu Leu Phe Leu Ser Arg Asn His Leu Ser Ser Ile
                180                 185                 190

Pro Ser Gly Leu Pro His Thr Leu Glu Glu Leu Arg Leu Asp Asp Asn
                195                 200                 205

Arg Ile Ser Thr Ile Pro Leu His Ala Phe Lys Gly Leu Asn Ser Leu
210                 215                 220

Arg Arg Leu Val Leu Asp Gly Asn Leu Ala Asn Gln Arg Ile Ala
225                 230                 235                 240

Asp Asp Thr Phe Ser Arg Leu Gln Asn Leu Thr Glu Leu Ser Leu Val
                245                 250                 255

Arg Asn Ser Leu Ala Ala Pro Pro Leu Asn Leu Pro Ser Ala His Leu
                260                 265                 270

Gln Lys Leu Tyr Leu Gln Asp Asn Ala Ile Ser His Ile Pro Tyr Asn
                275                 280                 285

Thr Leu Ala Lys Met Arg Glu Leu Glu Arg Leu Asp Leu Ser Asn Asn
                290                 295                 300

Asn Leu Thr Thr Leu Pro Arg Gly Leu Phe Asp Asp Leu Gly Asn Leu
305                 310                 315                 320

Ala Gln Leu Leu Leu Arg Asn Asn Pro Trp Phe Cys Gly Cys Asn Leu
                325                 330                 335

Met Trp Leu Arg Asp Trp Val Lys Ala Arg Ala Ala Val Val Asn Val
                340                 345                 350

Arg Gly Leu Met Cys Gln Gly Pro Glu Lys Val Arg Gly Met Ala Ile
                355                 360                 365

Lys Asp Ile Thr Ser Glu Met Asp Glu Cys Phe Glu Thr Gly Pro Gln
                370                 375                 380

Gly Gly Val Ala Asn Ala Ala Lys Thr Thr Ala Ser Asn His Ala
385                 390                 395                 400

Ser Ala Thr Thr Pro Gln Gly Ser Leu Phe Thr Leu Lys Ala Lys Arg
                405                 410                 415

Pro Gly Leu Arg Leu Pro Asp Ser Asn Ile Asp Tyr Pro Met Ala Thr
                420                 425                 430

Gly Asp Gly Ala Lys Thr Leu Ala Ile His Val Lys Ala Leu Thr Ala
                435                 440                 445

Asp Ser Ile Arg Ile Thr Trp Lys Ala Thr Leu Pro Ala Ser Ser Phe
450                 455                 460

Arg Leu Ser Trp Leu Arg Leu Gly His Ser Pro Ala Val Gly Ser Ile
465                 470                 475                 480

Thr Glu Thr Leu Val Gln Gly Asp Lys Thr Glu Tyr Leu Leu Thr Ala
                485                 490                 495

Leu Glu Pro Lys Ser Thr Tyr Ile Ile Cys Met Val Thr Met Glu Thr
                500                 505                 510

Ser Asn Ala Tyr Val Ala Asp Glu Thr Pro Val Cys Ala Lys Ala Glu
                515                 520                 525

Thr Ala Asp Ser Tyr Gly Pro Thr Thr Leu Asn Gln Glu Gln Asn
                530                 535                 540

Ala Gly Pro Met Ala Ser Leu Pro Leu Ala Gly Ile Ile Gly Gly Ala
545                 550                 555                 560
```

-continued

```
Val Ala Leu Val Phe Leu Phe Leu Val Leu Gly Ala Ile Cys Trp Tyr
                565                 570                 575

Val His Gln Ala Gly Glu Leu Leu Thr Arg Glu Arg Ala Tyr Asn Arg
                580                 585                 590

Gly Ser Arg Glu Lys Asp Asp Tyr Met Glu Ser Gly Thr Lys Lys Asp
                595                 600                 605

Asn Ser Ile Leu Glu Ile Arg Gly Pro Gly Leu Gln Met Leu Pro Ile
                610                 615                 620

Asn Pro Tyr Arg Ala Lys Glu Glu Tyr Val Val His Thr Ile Phe Pro
625                 630                 635                 640

Ser Asn Gly Ser Ser Leu Cys Lys Ala Thr His Thr Ile Gly Tyr Gly
                645                 650                 655

Thr Thr Arg Gly Tyr Arg Asp Gly Gly Ile Pro Asp Ile Asp Tyr Ser
                660                 665                 670

Tyr Thr

<210> SEQ ID NO 61
<211> LENGTH: 246
<212> TYPE: PRT
<213> ORGANISM: Homo sapiens

<400> SEQUENCE: 61

Pro Met Ala Thr Gly Asp Gly Ala Lys Thr Leu Ala Ile His Val Lys
  1               5                  10                  15

Ala Leu Thr Ala Asp Ser Ile Arg Ile Thr Trp Lys Ala Thr Leu Pro
                 20                  25                  30

Ala Ser Ser Phe Arg Leu Ser Trp Leu Arg Leu Gly His Ser Pro Ala
                 35                  40                  45

Val Gly Ser Ile Thr Glu Thr Leu Val Gln Gly Asp Lys Thr Glu Tyr
     50                  55                  60

Leu Leu Thr Ala Leu Glu Pro Lys Ser Thr Tyr Ile Ile Cys Met Val
 65                  70                  75                  80

Thr Met Glu Thr Ser Asn Ala Tyr Val Ala Asp Glu Thr Pro Val Cys
                 85                  90                  95

Ala Lys Ala Glu Thr Ala Asp Ser Tyr Gly Pro Thr Thr Thr Leu Asn
                100                 105                 110

Gln Glu Gln Asn Ala Gly Pro Met Ala Ser Leu Pro Leu Ala Gly Ile
                115                 120                 125

Ile Gly Gly Ala Val Ala Leu Val Phe Leu Phe Leu Val Leu Gly Ala
            130                 135                 140

Ile Cys Trp Tyr Val His Gln Ala Gly Glu Leu Leu Thr Arg Glu Arg
145                 150                 155                 160

Ala Tyr Asn Arg Gly Ser Arg Lys Lys Asp Asp Tyr Met Glu Ser Gly
                165                 170                 175

Thr Lys Lys Asp Asn Ser Ile Leu Glu Ile Arg Gly Pro Gly Leu Gln
                180                 185                 190

Met Leu Pro Ile Asn Pro Tyr Arg Ala Lys Glu Glu Tyr Val Val His
                195                 200                 205

Thr Ile Phe Pro Ser Asn Gly Ser Ser Leu Cys Lys Ala Thr His Thr
                210                 215                 220

Ile Gly Tyr Gly Thr Thr Arg Gly Tyr Arg Asp Gly Gly Ile Pro Asp
225                 230                 235                 240

Ile Asp Tyr Ser Tyr Thr
                245
```

<210> SEQ ID NO 62
<211> LENGTH: 378
<212> TYPE: PRT
<213> ORGANISM: Homo sapiens

<400> SEQUENCE: 62

```
Ile Ser Asn Asn Gln Leu Arg Met Leu Thr Gln Gly Val Phe Asp Asn
  1               5                  10                  15

Leu Ser Asn Leu Lys Gln Leu Thr Ala Arg Asn Asn Pro Trp Phe Cys
             20                  25                  30

Asp Cys Ser Ile Lys Trp Val Thr Glu Trp Leu Lys Tyr Ile Pro Ser
         35                  40                  45

Ser Leu Asn Val Arg Gly Phe Met Cys Gln Gly Pro Glu Gln Val Arg
     50                  55                  60

Gly Met Ala Val Arg Glu Leu Asn Met Asn Leu Leu Ser Cys Pro Thr
 65                  70                  75                  80

Thr Thr Pro Gly Leu Pro Leu Phe Thr Pro Ala Pro Ser Thr Ala Ser
                 85                  90                  95

Pro Thr Thr Gln Pro Pro Thr Leu Ser Ile Pro Asn Pro Ser Arg Ser
            100                 105                 110

Tyr Thr Pro Pro Thr Pro Thr Thr Ser Lys Leu Pro Thr Ile Pro Asp
        115                 120                 125

Trp Asp Gly Arg Glu Arg Val Thr Pro Pro Ile Ser Glu Arg Ile Gln
130                 135                 140

Leu Ser Ile His Phe Val Asn Asp Thr Ser Ile Gln Val Ser Trp Leu
145                 150                 155                 160

Ser Leu Phe Thr Val Met Ala Tyr Lys Leu Thr Trp Val Lys Met Gly
                165                 170                 175

His Ser Leu Val Gly Gly Ile Val Gln Glu Arg Ile Val Ser Gly Glu
            180                 185                 190

Lys Gln His Leu Ser Leu Val Asn Leu Glu Pro Arg Ser Thr Tyr Arg
        195                 200                 205

Ile Cys Leu Val Pro Leu Asp Ala Phe Asn Tyr Arg Ala Val Glu Asp
    210                 215                 220

Thr Ile Cys Ser Glu Ala Thr Thr His Ala Ser Tyr Leu Asn Asn Gly
225                 230                 235                 240

Ser Asn Thr Ala Ser Ser His Glu Gln Thr Thr Ser His Ser Met Gly
                245                 250                 255

Ser Pro Phe Leu Leu Ala Gly Leu Ile Gly Gly Ala Val Ile Phe Val
            260                 265                 270

Leu Val Val Leu Leu Ser Val Phe Cys Trp His Met His Lys Lys Gly
        275                 280                 285

Arg Tyr Thr Ser Gln Lys Trp Lys Tyr Asn Arg Gly Arg Arg Lys Asp
    290                 295                 300

Asp Tyr Cys Glu Ala Gly Thr Lys Lys Asp Asn Ser Ile Leu Glu Met
305                 310                 315                 320

Thr Glu Thr Ser Phe Gln Ile Val Ser Leu Asn Asn Asp Gln Leu Leu
                325                 330                 335

Lys Gly Asp Phe Arg Leu Gln Pro Ile Tyr Thr Pro Asn Gly Gly Ile
            340                 345                 350

Asn Tyr Thr Asp Cys His Ile Pro Asn Asn Met Arg Tyr Cys Asn Ser
        355                 360                 365

Ser Val Pro Asp Leu Glu His Cys His Thr
```

-continued

```
            370                 375
```

<210> SEQ ID NO 63
<211> LENGTH: 338
<212> TYPE: PRT
<213> ORGANISM: Gallus gallus

<400> SEQUENCE: 63

```
Val His Ser Val Trp Thr Arg Thr Val Arg Gln Val Tyr Asn Glu Leu
  1               5                  10                  15

Asp Pro Glu His Trp Ser His Tyr Thr Phe Glu Cys Pro Gln Glu Cys
             20                  25                  30

Phe Cys Pro Pro Ser Phe Pro Asn Ala Leu Tyr Cys Asp Asn Lys Gly
         35                  40                  45

Leu Lys Glu Ile Pro Ala Ile Pro Ala Arg Ile Trp Tyr Leu Tyr Leu
     50                  55                  60

Gln Asn Asn Leu Ile Glu Thr Ile Ser Glu Lys Pro Phe Val Asn Ala
 65                  70                  75                  80

Thr His Leu Arg Trp Ile Asn Leu Asn Lys Asn Lys Ile Thr Asn Asn
                 85                  90                  95

Gly Ile Glu Ser Gly Val Leu Ser Lys Leu Lys Arg Leu Leu Tyr Leu
            100                 105                 110

Phe Leu Glu Asp Asn Glu Leu Glu Glu Val Pro Ala Pro Leu Pro Val
        115                 120                 125

Gly Leu Glu Gln Leu Arg Leu Ala Arg Asn Lys Ile Ser Arg Ile Pro
    130                 135                 140

Glu Gly Val Phe Ser Asn Leu Glu Asn Leu Thr Met Leu Asp Leu His
145                 150                 155                 160

Gln Asn Asn Leu Leu Asp Ser Ala Leu Gln Ser Asp Thr Phe Gln Gly
                165                 170                 175

Leu Asn Ser Leu Met Gln Leu Asn Ile Ala Lys Asn Ser Leu Lys Lys
            180                 185                 190

Met Pro Leu Ser Ile Pro Ala Asn Thr Leu Gln Leu Phe Leu Asp Asn
        195                 200                 205

Asn Ser Ile Glu Val Ile Pro Glu Asn Tyr Phe Ser Ala Ile Pro Lys
    210                 215                 220

Val Thr Phe Leu Arg Leu Asn Tyr Asn Lys Leu Ser Asp Asp Gly Ile
225                 230                 235                 240

Pro Pro Asn Gly Phe Asn Val Ser Ser Ile Leu Asp Leu Gln Leu Ser
                245                 250                 255

His Asn Gln Leu Thr Lys Ile Pro Pro Ile Asn Ala His Leu Glu His
            260                 265                 270

Leu His Leu Asp His Asn Arg Ile Lys Ser Val Asn Gly Thr Gln Ile
        275                 280                 285

Cys Pro Val Ser Ile Ala Val Ala Glu Asp Tyr Gly Leu Tyr Gly Asn
    290                 295                 300

Ile Pro Arg Leu Arg Tyr Leu Arg Leu Asp Gly Asn Glu Ile Gln Pro
305                 310                 315                 320

Pro Ile Pro Leu Asp Ile Met Ile Cys Phe Gln Leu Leu Gln Ala Val
                325                 330                 335

Val Ile
```

<210> SEQ ID NO 64
<211> LENGTH: 326
<212> TYPE: PRT

<213> ORGANISM: Bos taurus

<400> SEQUENCE: 64

```
Pro Tyr Glu Pro Tyr Pro Thr Gly Glu Glu Gly Pro Ala Tyr Ala Tyr
 1               5                  10                  15
Gly Ser Pro Pro Gln Pro Glu Pro Arg Asp Cys Pro Gln Glu Cys Asp
             20                  25                  30
Cys Pro Pro Asn Phe Pro Thr Ala Met Tyr Cys Asp Asn Arg Asn Leu
         35                  40                  45
Lys Tyr Leu Pro Phe Val Pro Ser Arg Met Lys Tyr Val Tyr Phe Gln
     50                  55                  60
Asn Asn Gln Ile Ser Ser Ile Gln Glu Gly Val Phe Asp Asn Ala Thr
 65                  70                  75                  80
Gly Leu Leu Trp Ile Ala Leu His Gly Asn Gln Ile Thr Ser Asp Lys
                 85                  90                  95
Val Gly Lys Lys Val Phe Ser Lys Leu Arg His Leu Glu Arg Leu Tyr
            100                 105                 110
Leu Asp His Asn His Leu Thr Arg Ile Pro Ser Pro Leu Pro Arg Ser
        115                 120                 125
Leu Arg Glu Leu His Leu Asp His Asn Gln Ile Ser Arg Val Pro Asn
    130                 135                 140
Asn Ala Leu Glu Gly Leu Glu Asn Leu Thr Ala Leu Tyr Leu His His
145                 150                 155                 160
Glu Ile Gln Glu Val Gly Ser Ser Met Lys Gly Leu Arg Ser Leu Ile
                165                 170                 175
Leu Leu Asp Leu Ser Tyr Asn His Leu Arg Lys Val Pro Asp Gly Leu
            180                 185                 190
Pro Ser Ala Leu Glu Gln Leu Tyr Leu Glu His Asn Asn Val Phe Ser
        195                 200                 205
Val Pro Asp Ser Tyr Phe Arg Gly Ser Pro Lys Leu Leu Tyr Val Arg
    210                 215                 220
Leu Ser His Asn Ser Leu Thr Asn Asn Gly Leu Ala Ser Asn Thr Phe
225                 230                 235                 240
Asn Ser Ser Ser Leu Leu Glu Leu Asp Leu Ser Tyr Asn Gln Leu Gln
                245                 250                 255
Lys Ile Pro Pro Val Ser Thr Asn Leu Glu Asn Leu Tyr Leu Gln Gly
            260                 265                 270
Asn Arg Ile Asn Glu Phe Ser Ile Ser Ser Phe Cys Thr Val Val Asp
        275                 280                 285
Val Met Asn Phe Ser Lys Leu Gln Val Gln Arg Leu Asp Gly Asn Glu
    290                 295                 300
Ile Lys Arg Ser Ala Met Pro Ala Asp Ala Pro Leu Cys Leu Arg Leu
305                 310                 315                 320
Ala Ser Leu Ile Glu Ile
                325
```

<210> SEQ ID NO 65
<211> LENGTH: 1020
<212> TYPE: DNA
<213> ORGANISM: Homo sapiens

<400> SEQUENCE: 65

```
gcgcgcggcg aagtgaattt gctggacacg tcgaccatcc acggggactg gggctggctc    60
acgtatccgg ctcatgggtg ggactccatc aacgaggtgg acgagtcctt ccagcccatc   120
```

-continued

```
cacacgtacc aggtttgcaa cgtcatgagc cccaaccaga caactggct gcgcacgagc      180 tgggtccccc gagacggcgc ccggcgcgtc tatgctgaga tcaagtttac cctgcgcgac      240
tgcaacagca tgcctggtgt gctgggcacc tgcaaggaga ccttcaacct ctactacctg      300
gagtcggacc gcgacctggg ggccagcaca caagaaagcc agttcctcaa aatcgacacc      360
attgcggccg acgagagctt cacaggtgcc gaccttggtg tgcggcgtct caagctcaac      420
acggaggtgc gcagtgtggg tcccctcagc aagcgcggct tctacctggc cttccaggac      480
ataggtgcct gcctggccat cctctctctc cgcatctact ataagaagtg ccctgccatg      540
gtgcgcaatc tggctgcctt ctcggaggca gtgacggggg ccgactcgtc ctcactggtg      600
gaggtgaggg gccagtgcgt gcggcactca gaggagcggg acacacccaa gatgtactgc      660
agcgcggagg gcgagtggct cgtgcccatc ggcaaatgcg tgtgcagtgc cggctacgag      720
gagcggcggg atgcctgtgt ggcctgtgag ctgggcttct acaagtcagc ccctggggac      780
cagctgtgtg cccgctgccc tccccacagc cactccgcag ctccagccgc caagcctgc       840 cactgtgacc tcagctacta ccgtgcagcc ctggaccgc cgtcctcagc ctgcacccgg       900
ccaccctcgg caccagtgaa cctgatctcc agtgtgaatg ggacatcagt gactctggag      960
tgggcccctc ccctggaccc aggtggccgc agtgacatca cctacaatgc cgtgtgccgc     1020
```

<210> SEQ ID NO 66
<211> LENGTH: 515
<212> TYPE: PRT
<213> ORGANISM: Homo sapiens

<400> SEQUENCE: 66

```
Ala Arg Gly Glu Val Asn Leu Leu Asp Thr Ser Thr Ile His Gly Asp
 1               5                  10                  15

Trp Gly Trp Leu Thr Tyr Pro Ala His Gly Trp Asp Ser Ile Asn Glu
            20                  25                  30

Val Asp Glu Ser Phe Gln Pro Ile His Thr Tyr Gln Val Cys Asn Val
        35                  40                  45

Met Ser Pro Asn Gln Asn Asn Trp Leu Arg Thr Ser Trp Val Pro Arg
    50                  55                  60

Asp Gly Ala Arg Arg Val Tyr Ala Glu Ile Lys Phe Thr Leu Arg Asp
65                  70                  75                  80

Cys Asn Ser Met Pro Gly Val Leu Gly Thr Cys Lys Glu Thr Phe Asn
                85                  90                  95

Leu Tyr Tyr Leu Glu Ser Asp Arg Asp Leu Gly Ala Ser Thr Gln Glu
            100                 105                 110

Ser Gln Phe Leu Lys Ile Asp Thr Ile Ala Ala Asp Glu Ser Phe Thr
        115                 120                 125

Gly Ala Asp Leu Gly Val Arg Arg Leu Lys Leu Asn Thr Glu Val Arg
    130                 135                 140

Ser Val Gly Pro Leu Ser Lys Arg Gly Phe Tyr Leu Ala Phe Gln Asp
145                 150                 155                 160

Ile Gly Ala Cys Leu Ala Ile Leu Ser Leu Arg Ile Tyr Tyr Lys Lys
                165                 170                 175

Cys Pro Ala Met Val Arg Asn Leu Ala Ala Phe Ser Glu Ala Val Thr
            180                 185                 190

Gly Ala Asp Ser Ser Ser Leu Val Glu Val Arg Gly Gln Cys Val Arg
        195                 200                 205

His Ser Glu Glu Arg Asp Thr Pro Lys Met Tyr Cys Ser Ala Glu Gly
    210                 215                 220
```

```
Glu Trp Leu Val Pro Ile Gly Lys Cys Val Cys Ser Ala Gly Tyr Glu
225                 230                 235                 240

Glu Arg Arg Asp Ala Cys Val Ala Cys Glu Leu Gly Phe Tyr Lys Ser
                245                 250                 255

Ala Pro Gly Asp Gln Leu Cys Ala Arg Cys Pro His Ser His Ser
            260                 265                 270

Ala Ala Pro Ala Ala Gln Ala Cys His Cys Asp Leu Ser Tyr Tyr Arg
            275                 280                 285

Ala Ala Leu Asp Pro Pro Ser Ser Ala Cys Thr Arg Pro Pro Ser Ala
            290                 295                 300

Pro Val Asn Leu Ile Ser Ser Val Asn Gly Thr Ser Val Thr Leu Glu
305                 310                 315                 320

Trp Ala Pro Pro Leu Asp Pro Gly Gly Arg Ser Asp Ile Thr Tyr Asn
                325                 330                 335

Ala Val Cys Arg Arg Cys Pro Trp Ala Leu Ser Arg Cys Glu Ala Cys
                340                 345                 350

Gly Ser Gly Thr Arg Phe Val Pro Gln Gln Thr Ser Leu Val Gln Ala
                355                 360                 365

Ser Leu Leu Val Ala Asn Leu Leu Ala His Met Asn Tyr Ser Phe Trp
370                 375                 380

Ile Glu Ala Val Asn Gly Val Ser Asp Leu Ser Pro Glu Pro Arg Arg
385                 390                 395                 400

Ala Ala Val Val Asn Ile Thr Thr Asn Gln Ala Ala Pro Ser Gln Val
                405                 410                 415

Val Val Ile Arg Gln Glu Arg Ala Gly Gln Thr Ser Val Ser Leu Leu
                420                 425                 430

Trp Gln Glu Pro Glu Gln Pro Asn Gly Ile Ile Leu Glu Tyr Glu Ile
                435                 440                 445

Lys Tyr Tyr Glu Lys Asp Lys Glu Met Gln Ser Tyr Ser Thr Leu Lys
450                 455                 460

Ala Val Thr Thr Arg Ala Thr Val Ser Gly Leu Lys Pro Gly Thr Arg
465                 470                 475                 480

Tyr Val Phe Gln Val Arg Ala Arg Thr Ser Ala Gly Cys Gly Arg Phe
                485                 490                 495

Ser Gln Ala Met Glu Val Glu Thr Gly Lys Pro Arg Pro Arg Tyr Asp
                500                 505                 510

Thr Arg Thr
        515

<210> SEQ ID NO 67
<211> LENGTH: 1992
<212> TYPE: DNA
<213> ORGANISM: Homo sapiens

<400> SEQUENCE: 67
atggtggtgg cacaccccac cgccactgcc accaccacgc ccactgccac tgtcacggcc      60
accgttgtga tgaccacggc caccatggac ctgcgggact ggctgttcct ctgctacggg     120
ctcatcgcct tcctgacgga ggtcatcgac agcaccacct gccctcggt gtgccgctgc      180 gacaacggct tcatctactg caacgaccgg ggactcacat ccatcccgc agatatccct      240 gatgatgcca ccaccctcta cctgcagaac aaccagatca caacgccgg catcccccag      300 gacctcaaga ccaaggtcaa cgtgcaggtc atctacctat acgagaatga cctggatgag     360
ttccccatca acctgccccg ctccctccgg gagctgcacc tgcaggacaa caatgtgcgc     420
```

-continued

```
accattgcca gggactcgct ggcccgcatc ccgctgctgg agaagctgca cctggatgac        480
aactccgtgt ccaccgtcag cattgaggag gacgccttcg ccgacagcaa acagctcaag        540
ctgctcttcc tgagccggaa ccacctgagc agcatcccct cggggctgcc gcacacgctg        600
gaggagctgc ggctggatga caaccgcatc tccaccatcc cgctgcatgc cttcaagggc        660
ctcaacagcc tgcggcgcct ggtgctggac ggtaacctgc tggccaacca gcgcatcgcc        720
gacgacacct tcagccgcct acagaacctc acagagctct cgctggtgcg caattcgctg        780
gccgcgccac ccctctacct gcaggacaat gccatcagcc acatccccta caacacgctg        840
gccaagatgc gtgagctgga gcggctggac ctgtccaaca caacctgac cacgctgccc         900 cgcggcctgt tcgacgacct ggggaacctg gcccagctgc tgctcaggaa caacccttgg        960
ttttgtggct gcaacctcat gtggctgcgg gactgggtga aggcacgggc ggccgtggtc       1020
aacgtgcggg gcctcatgtg ccagggccct gagaaggtcc ggggcatggc catcaaggac       1080
attaccagcg aggtggagag tgttttgaga cgggcgccgc agggcggcgt ggccaatgcg       1140
gctgccaaga ccacggccag caaccacgcc tctgccacca cgcccagggg ttccctgttt       1200
accctcaagg ccaaaaggcc agggctgcgc ctccccgact ccaacattga ctaccccatg       1260
gccacgggtg atggcgccaa gaccctggcc atccacgtga aggccctgac ggcagactcc       1320
atccgcatca cgtggaaggc cacgctcccc gcctcctctt tccggctcag ttggctgcgc       1380
ctgggccaca gcccagccgt gggctccatc acggagacct tggtgcaggg ggacaagaca       1440
gagtacctgc tgacagccct ggagcccaag tccacctaca tcatctgcat ggtcaccatg       1500
gagaccagca atgcctacgt agctgatgag acacccgtgt gtgccaaggc agagacagcc       1560
gacagctatg cccctaccac cacactcaac caggagcaga acgctggccc catggcgagc       1620
ctgcccctgg cgggcatcat cggcggggca gtggctctgg tcttcctctt cctggtcctg       1680
ggggccatct gctggtacgt gcaccaggct ggcgagctgc tgacccggga gagggcctac       1740
aaccggggca gcaggaaaaa ggatgactat atggagtcag ggaccaagaa ggataactcc       1800
atcctggaaa tccgcggccc tgggctgcag atgctgccca tcaacccgta ccgcgccaaa       1860
gaagagtacg tggtccacac tatcttcccc tccaacggca gcagcctctg caaggccaca       1920
cacaccattg ctacggcac cacgcggggc taccggacg gcggcatccc cgacatagac         1980
tactcctaca ca                                                            1992
```

<210> SEQ ID NO 68
<211> LENGTH: 664
<212> TYPE: PRT
<213> ORGANISM: Homo sapiens

<400> SEQUENCE: 68

```
Met Val Val Ala His Pro Thr Ala Thr Ala Thr Thr Thr Pro Thr Ala
  1               5                  10                  15

Thr Val Thr Ala Thr Val Val Met Thr Thr Ala Thr Met Asp Leu Arg
             20                  25                  30

Asp Trp Leu Phe Leu Cys Tyr Gly Leu Ile Ala Phe Leu Thr Glu Val
         35                  40                  45

Ile Asp Ser Thr Thr Cys Pro Ser Val Cys Arg Cys Asp Asn Gly Phe
     50                  55                  60

Ile Tyr Cys Asn Asp Arg Gly Leu Thr Ser Ile Pro Ala Asp Ile Pro
 65                  70                  75                  80

Asp Asp Ala Thr Thr Leu Tyr Leu Gln Asn Asn Gln Ile Asn Asn Ala
```

-continued

```
                    85                  90                  95
Gly Ile Pro Gln Asp Leu Lys Thr Lys Val Asn Val Gln Val Ile Tyr
                100                 105                 110
Leu Tyr Glu Asn Asp Leu Asp Glu Phe Pro Ile Asn Leu Pro Arg Ser
                115                 120                 125
Leu Arg Glu Leu His Leu Gln Asp Asn Asn Val Arg Thr Ile Ala Arg
                130                 135                 140
Asp Ser Leu Ala Arg Ile Pro Leu Leu Glu Lys Leu His Leu Asp Asp
145                 150                 155                 160
Asn Ser Val Ser Thr Val Ser Ile Glu Glu Asp Ala Phe Ala Asp Ser
                165                 170                 175
Lys Gln Leu Lys Leu Leu Phe Leu Ser Arg Asn His Leu Ser Ser Ile
                180                 185                 190
Pro Ser Gly Leu Pro His Thr Leu Glu Glu Leu Arg Leu Asp Asp Asn
                195                 200                 205
Arg Ile Ser Thr Ile Pro Leu His Ala Phe Lys Gly Leu Asn Ser Leu
                210                 215                 220
Arg Arg Leu Val Leu Asp Gly Asn Leu Leu Ala Asn Gln Arg Ile Ala
225                 230                 235                 240
Asp Asp Thr Phe Ser Arg Leu Gln Asn Leu Thr Glu Leu Ser Leu Val
                245                 250                 255
Arg Asn Ser Leu Ala Ala Pro Pro Leu Tyr Leu Gln Asp Asn Ala Ile
                260                 265                 270
Ser His Ile Pro Tyr Asn Thr Leu Ala Lys Met Arg Glu Leu Glu Arg
                275                 280                 285
Leu Asp Leu Ser Asn Asn Asn Leu Thr Thr Leu Pro Arg Gly Leu Phe
                290                 295                 300
Asp Asp Leu Gly Asn Leu Ala Gln Leu Leu Leu Arg Asn Asn Pro Trp
305                 310                 315                 320
Phe Cys Gly Cys Asn Leu Met Trp Leu Arg Asp Trp Val Lys Ala Arg
                325                 330                 335
Ala Ala Val Val Asn Val Arg Gly Leu Met Cys Gln Gly Pro Glu Lys
                340                 345                 350
Val Arg Gly Met Ala Ile Lys Asp Ile Thr Ser Glu Val Glu Ser Val
                355                 360                 365
Leu Arg Arg Ala Pro Gln Gly Gly Val Ala Asn Ala Ala Lys Thr
                370                 375                 380
Thr Ala Ser Asn His Ala Ser Ala Thr Thr Pro Gln Gly Ser Leu Phe
385                 390                 395                 400
Thr Leu Lys Ala Lys Arg Pro Gly Leu Arg Leu Pro Asp Ser Asn Ile
                405                 410                 415
Asp Tyr Pro Met Ala Thr Gly Asp Gly Ala Lys Thr Leu Ala Ile His
                420                 425                 430
Val Lys Ala Leu Thr Ala Asp Ser Ile Arg Ile Thr Trp Lys Ala Thr
                435                 440                 445
Leu Pro Ala Ser Ser Phe Arg Leu Ser Trp Leu Arg Leu Gly His Ser
                450                 455                 460
Pro Ala Val Gly Ser Ile Thr Glu Thr Leu Val Gln Gly Asp Lys Thr
465                 470                 475                 480
Glu Tyr Leu Leu Thr Ala Leu Glu Pro Lys Ser Thr Tyr Ile Ile Cys
                485                 490                 495
Met Val Thr Met Glu Thr Ser Asn Ala Tyr Val Ala Asp Glu Thr Pro
                500                 505                 510
```

-continued

```
Val Cys Ala Lys Ala Glu Thr Ala Asp Ser Tyr Gly Pro Thr Thr Thr
            515                 520                 525
Leu Asn Gln Glu Gln Asn Ala Gly Pro Met Ala Ser Leu Pro Leu Ala
        530                 535                 540
Gly Ile Ile Gly Gly Ala Val Ala Leu Val Phe Leu Phe Leu Val Leu
545                 550                 555                 560
Gly Ala Ile Cys Trp Tyr Val His Gln Ala Gly Glu Leu Leu Thr Arg
                565                 570                 575
Glu Arg Ala Tyr Asn Arg Gly Ser Arg Lys Lys Asp Asp Tyr Met Glu
            580                 585                 590
Ser Gly Thr Lys Lys Asp Asn Ser Ile Leu Glu Ile Arg Gly Pro Gly
        595                 600                 605
Leu Gln Met Leu Pro Ile Asn Pro Tyr Arg Ala Lys Glu Glu Tyr Val
    610                 615                 620
Val His Thr Ile Phe Pro Ser Asn Gly Ser Ser Leu Cys Lys Ala Thr
625                 630                 635                 640
His Thr Ile Gly Tyr Gly Thr Thr Arg Gly Tyr Arg Asp Gly Gly Ile
                645                 650                 655
Pro Asp Ile Asp Tyr Ser Tyr Thr
            660
```

```
<210> SEQ ID NO 69
<211> LENGTH: 26
<212> TYPE: DNA
<213> ORGANISM: Homo sapiens

<400> SEQUENCE: 69
caacgtgcag gtcatctacc tatacg                                          26

<210> SEQ ID NO 70
<211> LENGTH: 25
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 70
gcccgtctca aaacactctc catct                                           25

<210> SEQ ID NO 71
<211> LENGTH: 54
<212> TYPE: PRT
<213> ORGANISM: Artificial Sequence
<220> FEATURE:
<223> OTHER INFORMATION: Description of Artificial Sequence:
      oligonucleotide primer

<400> SEQUENCE: 71

Asn Pro Phe Asn Cys Asp Cys Glu Leu Arg Trp Leu Leu Arg Trp Leu
  1               5                  10                  15
Arg Glu Thr Asn Pro Arg Arg Leu Glu Asp Gln Glu Asp Leu Arg Cys
             20                  25                  30
Ala Ser Pro Glu Ser Leu Arg Gly Gln Pro Leu Leu Glu Leu Leu Pro
         35                  40                  45
Ser Asp Phe Ser Cys Pro
     50

<210> SEQ ID NO 72
```

-continued

```
<211> LENGTH: 84
<212> TYPE: PRT
<213> ORGANISM: Artificial Sequence
<220> FEATURE:
<223> OTHER INFORMATION: Description of Artificial Sequence:consensus
      sequence

<400> SEQUENCE: 72

Pro Ser Ala Pro Thr Asn Leu Thr Val Thr Asp Val Thr Ser Thr Ser
 1               5                  10                  15

Leu Thr Leu Ser Trp Ser Pro Pro Thr Gly Asn Gly Pro Ile Thr Gly
             20                  25                  30

Tyr Glu Val Thr Tyr Arg Gln Pro Lys Asn Gly Gly Glu Trp Asn Glu
         35                  40                  45

Leu Thr Val Pro Gly Thr Thr Thr Ser Tyr Thr Leu Thr Gly Leu Lys
     50                  55                  60

Pro Gly Thr Glu Tyr Glu Val Arg Val Gln Ala Val Asn Gly Gly Gly
 65                  70                  75                  80

Gly Pro Glu Ser

<210> SEQ ID NO 73
<211> LENGTH: 23
<212> TYPE: PRT
<213> ORGANISM: Artificial Sequence
<220> FEATURE:
<223> OTHER INFORMATION: Description of Artificial Sequence:consensus
      sequence

<400> SEQUENCE: 73

Asn Leu Glu Glu Leu Asp Leu Ser Asn Asn Leu Thr Ser Leu Pro Pro
 1               5                  10                  15

Gly Leu Phe Ser Asn Leu Pro
             20

<210> SEQ ID NO 74
<211> LENGTH: 949
<212> TYPE: DNA
<213> ORGANISM: Homo sapiens

<400> SEQUENCE: 74
atggtggtgg cacacccac cgccactgcc accaccacgc ccactgccac tgtcacggcc      60
accgttgtga tgaccacggc caccatggac ctgcgggact ggctgttcct ctgctacggg    120
ctcatcgcct tcctgacgga ggtcatcgac agcaccacct gccctcggt gtgccgctgc    180
gacaacggct tcatctactg caacgaccgg ggactcacat ccatcccgc agatatccct    240
gatgacgcca ccaccctcta tctgcagaac aaccagatca caacgctgg catccccag    300
gacctcaaga ccaaggtcaa cgtgcaggtc atctacctat acgagaatga cctggatgag    360
ttccccatca acctgccccg ctccctccgg gagctgcacc tgcaggacaa caatgtgcgc    420
accattgcca gggactcgct ggcccgcatc ccgctgctgg agaagctgca cctggatgac    480
aactccgtgt ccaccgtcag cattgaggag acgccttcg ccgacagcaa acagctcaag    540
ctgctcttcc tgagccggaa ccacctgagc agcatcccct cggggctgcc gcacacgctg    600
gaggagctgc ggctggatga caaccgcatc tccaccatcc cgctgcatgc cttcaagggc    660
ctcaacagcc tgcggcgcct ggtgctggac ggtaacctgc tggccaacca gcgcatcgcc    720
gacgacacct tcagccgcct acagaacctc acagagctct cgctggtgcg caattcgctg    780
gccgcgccac ccctcaacct gcccagcgcc cacctgcaga aactctacct gcaggacaat    840
```

```
gccatcagcc acatccccta caacacgctg gccaagatgc gtgagctgga gcggctggac    900
ctgtccaaca caacctgac cacgctgccc cgcggcctgt cgacgacc                  949
```

<210> SEQ ID NO 75
<211> LENGTH: 674
<212> TYPE: PRT
<213> ORGANISM: Homo sapiens

<400> SEQUENCE: 75

```
Met Val Val Ala His Pro Thr Ala Thr Thr Pro Thr Ala
  1               5                  10                  15

Thr Val Thr Ala Thr Val Val Met Thr Thr Ala Thr Met Asp Leu Arg
                 20                  25                  30

Asp Trp Leu Phe Leu Cys Tyr Gly Leu Ile Ala Phe Leu Thr Glu Val
             35                  40                  45

Ile Asp Ser Thr Thr Cys Pro Ser Val Cys Arg Cys Asp Asn Gly Phe
         50                  55                  60

Ile Tyr Cys Asn Asp Arg Gly Leu Thr Ser Ile Pro Ala Asp Ile Pro
 65                  70                  75                  80

Asp Asp Ala Thr Thr Leu Tyr Leu Gln Asn Asn Gln Ile Asn Asn Ala
                 85                  90                  95

Gly Ile Pro Gln Asp Leu Lys Thr Lys Val Asn Val Gln Val Ile Tyr
            100                 105                 110

Leu Tyr Glu Asn Asp Leu Asp Glu Phe Pro Ile Asn Leu Pro Arg Ser
        115                 120                 125

Leu Arg Glu Leu His Leu Gln Asp Asn Asn Val Arg Thr Ile Ala Arg
    130                 135                 140

Asp Ser Leu Ala Arg Ile Pro Leu Leu Glu Lys Leu His Leu Asp Asp
145                 150                 155                 160

Asn Ser Val Ser Thr Val Ser Ile Glu Glu Asp Ala Phe Ala Asp Ser
                165                 170                 175

Lys Gln Leu Lys Leu Leu Phe Leu Ser Arg Asn His Leu Ser Ser Ile
            180                 185                 190

Pro Ser Gly Leu Pro His Thr Leu Glu Glu Leu Arg Leu Asp Asp Asn
        195                 200                 205

Arg Ile Ser Thr Ile Pro Leu His Ala Phe Lys Gly Leu Asn Ser Leu
    210                 215                 220

Arg Arg Leu Val Leu Asp Gly Asn Leu Leu Ala Asn Gln Arg Ile Ala
225                 230                 235                 240

Asp Asp Thr Phe Ser Arg Leu Gln Asn Leu Thr Glu Leu Ser Leu Val
                245                 250                 255

Arg Asn Ser Leu Ala Ala Pro Pro Leu Asn Leu Pro Ser Ala His Leu
            260                 265                 270

Gln Lys Leu Tyr Leu Gln Asp Asn Ala Ile Ser His Ile Pro Tyr Asn
        275                 280                 285

Thr Leu Ala Lys Met Arg Glu Leu Glu Arg Leu Asp Leu Ser Asn Asn
    290                 295                 300

Asn Leu Thr Thr Leu Pro Arg Gly Leu Phe Asp Leu Gly Asn Leu
305                 310                 315                 320

Ala Gln Leu Leu Leu Arg Asn Asn Pro Trp Phe Cys Gly Cys Asn Leu
                325                 330                 335

Met Trp Leu Arg Asp Trp Val Lys Ala Arg Ala Val Val Asn Val
            340                 345                 350

Arg Gly Leu Met Cys Gln Gly Pro Glu Lys Val Arg Gly Met Ala Ile
```

```
                    355                 360                 365
Lys Asp Ile Thr Ser Glu Met Asp Glu Cys Phe Glu Thr Gly Pro Gln
            370                 375                 380
Gly Gly Val Ala Asn Ala Ala Lys Thr Thr Ala Ser Asn His Ala
385                 390                 395                 400
Ser Ala Thr Thr Pro Gln Gly Ser Leu Phe Thr Leu Lys Ala Lys Arg
                405                 410                 415
Pro Gly Leu Arg Leu Pro Asp Ser Asn Ile Asp Tyr Pro Met Ala Thr
            420                 425                 430
Gly Asp Gly Ala Lys Thr Leu Ala Ile His Val Lys Ala Leu Thr Ala
            435                 440                 445
Asp Ser Ile Arg Ile Thr Trp Lys Ala Thr Leu Pro Ala Ser Ser Phe
        450                 455                 460
Arg Leu Ser Trp Leu Arg Leu Gly His Ser Pro Ala Val Gly Ser Ile
465                 470                 475                 480
Thr Glu Thr Leu Val Gln Gly Asp Lys Thr Glu Tyr Leu Leu Thr Ala
                485                 490                 495
Leu Glu Pro Lys Ser Thr Tyr Ile Ile Cys Met Val Thr Met Glu Thr
            500                 505                 510
Ser Asn Ala Tyr Val Ala Asp Glu Thr Pro Val Cys Ala Lys Ala Glu
            515                 520                 525
Thr Ala Asp Ser Tyr Gly Pro Thr Thr Thr Leu Asn Gln Glu Gln Asn
        530                 535                 540
Ala Gly Pro Met Ala Ser Leu Pro Leu Ala Gly Ile Ile Gly Ala
545                 550                 555                 560
Val Ala Leu Val Phe Leu Phe Leu Val Leu Gly Ala Ile Cys Trp Tyr
                565                 570                 575
Val His Gln Ala Gly Glu Leu Leu Thr Arg Glu Arg Ala Tyr Asn Arg
            580                 585                 590
Gly Ser Arg Glu Lys Asp Asp Tyr Met Glu Ser Gly Thr Lys Lys Asp
            595                 600                 605
Asn Ser Ile Leu Glu Ile Arg Gly Pro Gly Leu Gln Met Leu Pro Ile
        610                 615                 620
Asn Pro Tyr Arg Ala Lys Glu Glu Tyr Val Val His Thr Ile Phe Pro
625                 630                 635                 640
Ser Asn Gly Ser Ser Leu Cys Lys Ala Thr His Thr Ile Gly Tyr Gly
                645                 650                 655
Thr Thr Arg Gly Tyr Arg Asp Gly Gly Ile Pro Asp Ile Asp Tyr Ser
            660                 665                 670
Tyr Thr

<210> SEQ ID NO 76
<211> LENGTH: 31
<212> TYPE: PRT
<213> ORGANISM: Artificial Sequence
<220> FEATURE:
<223> OTHER INFORMATION: Description of Artificial Sequence:consensus
      sequence

<400> SEQUENCE: 76

Ala Cys Pro Arg Glu Cys Thr Cys Ser Pro Phe Gly Leu Val Val Asp
1               5                   10                  15
Cys Ser Gly Arg Gly Leu Thr Leu Glu Val Pro Arg Asp Leu Pro
                20                  25                  30
```

-continued

```
<210> SEQ ID NO 77
<211> LENGTH: 23
<212> TYPE: PRT
<213> ORGANISM: Artificial Sequence
<220> FEATURE:
<223> OTHER INFORMATION: Description of Artificial Sequence:consensus
      sequence

<400> SEQUENCE: 77

Asn Leu Glu Glu Leu Asp Leu Ser Asn Asn Leu Thr Ser Leu Pro Pro
 1               5                  10                  15

Gly Leu Phe Ser Asn Leu Pro
            20

<210> SEQ ID NO 78
<211> LENGTH: 23
<212> TYPE: PRT
<213> ORGANISM: Artificial Sequence
<220> FEATURE:
<223> OTHER INFORMATION: Description of Artificial Sequence:consensus
      sequence

<400> SEQUENCE: 78

Asn Leu Glu Glu Leu Asp Leu Ser Asn Asn Leu Thr Ser Leu Pro Pro
 1               5                  10                  15

Gly Leu Phe Ser Asn Leu Pro
            20

<210> SEQ ID NO 79
<211> LENGTH: 23
<212> TYPE: PRT
<213> ORGANISM: Artificial Sequence
<220> FEATURE:
<223> OTHER INFORMATION: Description of Artificial Sequence:consensus
      sequence

<400> SEQUENCE: 79

Asn Leu Glu Glu Leu Asp Leu Ser Asn Asn Leu Thr Ser Leu Pro Pro
 1               5                  10                  15

Gly Leu Phe Ser Asn Leu Pro
            20

<210> SEQ ID NO 80
<211> LENGTH: 23
<212> TYPE: PRT
<213> ORGANISM: Artificial Sequence
<220> FEATURE:
<223> OTHER INFORMATION: Description of Artificial Sequence:consensus
      sequence

<400> SEQUENCE: 80

Asn Leu Glu Glu Leu Asp Leu Ser Asn Asn Leu Thr Ser Leu Pro Pro
 1               5                  10                  15

Gly Leu Phe Ser Asn Leu Pro
            20

<210> SEQ ID NO 81
<211> LENGTH: 23
<212> TYPE: PRT
<213> ORGANISM: Artificial Sequence
<220> FEATURE:
<223> OTHER INFORMATION: Description of Artificial Sequence:consensus
      sequence

<400> SEQUENCE: 81

Asn Leu Glu Glu Leu Asp Leu Ser Asn Asn Leu Thr Ser Leu Pro Pro
```

```
                1               5              10              15
Gly Leu Phe Ser Asn Leu Pro
                20

<210> SEQ ID NO 82
<211> LENGTH: 23
<212> TYPE: PRT
<213> ORGANISM: Artificial Sequence
<220> FEATURE:
<223> OTHER INFORMATION: Description of Artificial Sequence:consensus
      sequence

<400> SEQUENCE: 82

Asn Leu Glu Glu Leu Asp Leu Ser Asn Asn Leu Thr Ser Leu Pro Pro
  1               5                  10                  15

Gly Leu Phe Ser Asn Leu Pro
                20

<210> SEQ ID NO 83
<211> LENGTH: 23
<212> TYPE: PRT
<213> ORGANISM: Artificial Sequence
<220> FEATURE:
<223> OTHER INFORMATION: Description of Artificial Sequence:consensus
      sequence

<400> SEQUENCE: 83

Asn Leu Glu Glu Leu Asp Leu Ser Asn Asn Leu Thr Ser Leu Pro Pro
  1               5                  10                  15

Gly Leu Phe Ser Asn Leu Pro
                20

<210> SEQ ID NO 84
<211> LENGTH: 23
<212> TYPE: PRT
<213> ORGANISM: Artificial Sequence
<220> FEATURE:
<223> OTHER INFORMATION: Description of Artificial Sequence:consensus
      sequence

<400> SEQUENCE: 84

Asn Leu Glu Glu Leu Asp Leu Ser Asn Asn Leu Thr Ser Leu Pro Pro
  1               5                  10                  15

Gly Leu Phe Ser Asn Leu Pro
                20
```

POLYPEPTIDES AND POLYNUCLEOTIDES HOMOLOGOUS TO THYMOSIN, EPHRIN A RECEPTORS, AND FIBROMODULIN

RELATED APPLICATIONS

This application is a Continuation-in-part of U.S. Ser. No. 09/953,248, filed Sep. 14, 2001, which is a Continuation-in-part of U.S. Ser. No. 09/689,486 filed Oct. 12, 2000 now U.S. Pat. No. 6,855,806, and U.S. Ser. No. 09/687,276 filed Oct. 13, 2000, both of which claim priority to U.S. Ser. No. 60/159,805, filed Oct. 15, 1999; U.S. Ser. No. 60/159,992, filed Oct. 18, 1999; U.S. Ser. No. 60/086,423, filed Oct. 18, 1999; and U.S. Ser. No. 60/160,952 filed Oct. 22, 1999. The contents of these applications are incorporated herein by reference in their entireties.

BACKGROUND OF THE INVENTION

The invention generally relates to nucleic acids and polypeptides encoded therefrom. More specifically, the invention relates to nucleic acids encoding membrane bound and secreted polypeptides that are homologous to thymosin, fibromodulin and ephrin-type A receptors, as well as vectors, host cells, antibodies, and recombinant methods for producing these nucleic acids and polypeptides.

Beta-thymosins are a family of related peptides that were first isolated from calf thymus, but are known to be present in a wide variety of mammalian and other vertebrate cells and tissues. Thymosin-beta-4 (TMSB4) was the first member of the family to be characterized, and was proposed to be a thymic hormone acting at early stages of T-cell maturation. However, the high concentration of the protein and presence of its mRNA in a number of other tissues and cells, in addition to the lack of an identifiable secretory signal sequence, suggested a more generalized function in many cell types. This was confirmed by findings that TMSB4 forms a 1:1 complex with G-actin in blood platelets (A. Weber et al., "Interaction of thymosin beta 4 with muscle and platelet actin: implications for actin sequestration in resting platelets," 31(27) *Biochemistry* 6179–85 (1992)).

Thymosin-beta-10 is related closely to TMSB4 in sequence and is also an actin-sequestering protein. mRNA species of similar molecular weights encoding TMSB10 are found in most tissues of rats, although Lin and Morrison-Bogorad (1991) identified TMSB10 mRNA of higher molecular weight in the testes of sexually mature rats. The latter differs from the more ubiquitous form only in its 5'-untranslated region, beginning 14 nucleotides upstream of the translation initiation codon. This finding, together with primer extension experiments, suggested that the two mRNA types are transcribed from the same gene through a combination of differential promoter utilization and alternative splicing. Both mRNAs are found in pachytene spermatocytes; only testes-specific mRNA is detected in postmeiotic haploid spermatids. Immunohistochemical analysis shows that the protein was present in differentiating spermatids, which suggests that testes-specific TMSB10 mRNA is translated in haploid male germ cells. Immunoblot analysis using specific antibodies indicates that TMSB10 synthesized in adult testes is identical in size to that made in the brain (S. C. Lin et al., "Cloning and characterization of a testis-specific thymosin beta 10 cDNA. Expression in post-meiotic male germ cells," 266(34) *J. Biol. Chem.* 23347–53 (1991)).

Ephrin receptors comprise the largest known family of receptor protein tyrosine kinases. They have been implicated in mediating developmental events, particularly in the nervous system. Receptors in the ephrin subfamily typically have a single kinase domain and an extracellular region containing a Cys-rich domain and two fibronectin type III repeats. Along with their ligands, called ephrins, they play important roles in neural development, angiogenesis, and vascular network assembly (9(4) *Mol. Cells*, 440–5 (1999 Aug. 31)).

Fibromodulin is a member of a family of small interstitial proteoglycans that also includes decorin, biglycan and lumican. The proteoglycans bind to other matrix macromolecules and thereby help to stabilize the matrix. (Buckwalter et al., 47 *Instr. Course Lect* 477–86 (1998)). It is speculated that they may influence the function of chondrocytes and bind growth factors. Proteoglycan protein cores are structurally related and consist of a central region of leucine-rich repeats flanked by disulfide-bonded terminal domains. Fibromodulin has up to 4 keratin sulfate chains within its leucine-rich domain. It enjoys wide tissue distribution and is most abundant in articular cartilage, tendon and ligament. It has been suggested that fibromodulin participates in the assembly of the extracellular matrix by virtue of its ability to interact with type I and type II collagen fibrils and to inhibit fribrillogenesis in vitro. Sztrolovics et al. cloned the 3'-untranslated region of fibromodulin cDNA, and used it to map the gene by fluorescence in situ hybridization (FISH) to 1q32 (Sztrolovics et al., 23 *Genomics* 715–7 (1994)). This localization to chromosome 1 has since been confirmed by PCR analysis of somatic cell hybrids.

SUMMARY OF THE INVENTION

The invention is based in part upon the discovery of novel nucleic acid sequences encoding polypeptides. Nucleic acids encoding these polypeptides and derivatives and fragments thereof, will hereinafter be collectively designated as "NOV."

In one aspect, the invention provides an isolated NOV1 nucleic acid molecule encoding a NOV1 polypeptide that has identity to the polypeptide sequence for the small actin-sequestering peptide thymosin-beta-10. In another aspect, the invention provides an isolated NOV2 nucleic acid molecule encoding a NOV2 polypeptide that has identity to ephrin type-A receptor 8. In yet another aspect, the invention provides an isolated NOV3 nucleic acid molecule encoding a NOV3 polypeptide that has homology to a family of proteoglycans. In still another aspect, the invention provides an isolated NOV4 nucleic acid molecule encoding a NOV4 polypeptide that has identity to mature extracellular ephrin type-A receptor 8. In still another aspect, the invention provides an isolated NOV5 nucleic acid molecule encoding a NOV5 polypeptide that has homology to the proteoglycan, fibromodulin.

In some embodiments, the NOV nucleic acid molecule can hybridize under stringent conditions to a nucleic acid sequence complementary to a nucleic acid molecule that includes a protein-coding sequence of the nucleic acid sequence. A preferred embodiment of the invention is an oligonucleotide, e.g., an oligonucleotide which includes at least 6 contiguous nucleotides of a NOV nucleic acid (e.g., SEQ ID NO: 1, 4, 6, 65, or 67) or a complement of said oligonucleotide.

Also included in the invention are substantially purified NOV polypeptides (SEQ ID NO: 2, 5, 7, 66 or 68), and polypeptides having conservative amino acid substitutions to these NOV polypeptides. The invention also features antibodies that immunoselectively-bind to NOV polypeptides.

In another aspect, the invention includes pharmaceutical compositions that include therapeutically- or prophylactically-effective amounts of a therapeutic and a pharmaceutically-acceptable carrier. The therapeutic can be, e.g., a NOV nucleic acid, a NOV polypeptide, or an antibody specific for a NOV polypeptide. In a further aspect, the invention includes, in one or more containers, a therapeutically- or prophylactically-effective amount of this pharmaceutical composition.

In a further aspect, the invention includes a method of producing a polypeptide by culturing a cell that includes a NOV nucleic acid, under conditions allowing for expression of the NOV polypeptide encoded by the DNA. If desired, the NOV polypeptide can then be recovered.

In another aspect, the invention includes a method of detecting the presence of a NOV polypeptide in a sample. In the method, a sample is contacted with a compound that selectively binds to the polypeptide under conditions allowing for formation of a complex between the polypeptide and the compound. The complex is detected, if present, thereby identifying the NOV polypeptide within the sample.

Also included in the invention is a method of detecting the presence of a NOV nucleic acid molecule in a sample by contacting the sample with a NOV nucleic acid probe or primer, and detecting whether the nucleic acid probe or primer bound to a NOV nucleic acid molecule in the sample.

In a further aspect, the invention provides a method for modulating the activity of a NOV polypeptide by contacting a cell sample that includes the NOV polypeptide with a compound that binds to the NOV polypeptide in an amount sufficient to modulate the activity of said polypeptide. The compound can be, e.g., a small molecule, such as a nucleic acid, peptide, polypeptide, peptidomimetic, carbohydrate, lipid or other organic (carbon containing) or inorganic molecule, as further described herein.

Also within the scope of the invention is the use of a therapeutic in the manufacture of a medicament for treating or preventing disorders or syndromes outlined in the preferred embodiment below. The therapeutic can be, e.g., a NOV nucleic acid, a NOV polypeptide, or a NOV-specific antibody, or biologically-active derivatives or fragments thereof.

In the preferred embodiments, the invention further includes methods for screening for a modulator of disorders or syndromes including, e.g., those involving development, differentiation, and activation of thymic immune cells; methods for diagnosing and treating disorders, and/or for screening for a modulator of disorders or syndromes including, e.g., diagnosis of several human neoplasias; rheumatoid arthritis; congenital muscular dystrophies; various muscle disorders; fixed deformities (arthrogryposis); small cell lung cancer NCI-H23; prostate cancer; atopy; dysprothrombinemia; hypoprothrombinemia; Smith-Lemli-Opitz syndrome, type I; Smith-Lemli-Opitz syndrome, type II; xeroderma pigmentosum, group E, subtype 2; high bone mass; Bardet-Biedl syndrome 1; CPT deficiency, hepatic, type I; carcinoid tumor of lung; centrocytic lymphoma; cervical carcinoma; hyperparathyroidism, AD; hypokalemic periodic paralysi; Leigh syndrome; acute promyelocytic leukemia, NUMA/RARA type; macular dystrophy, vitelliform type; McArdle disease; Meckel syndrome, type 2; multiple endocrine neoplasia I; multiple myeloma; parathyroid adenomatosis 1; prolactinoma; hyperparathyroidism; carcinoid syndrome; digenic retinitis pigmentosa; somatotrophinoma; neovascular inflammatory vitreoretinopathy; arthritis; and tendonitis, in addition to other diseases, disorders and conditions associated with fibromodulin deficiency or disorder; in pathologies related to spermatogenesis and male infertility; diagnosis of several human neoplasias; in diseases or pathologies of cells in blood circulation such as red blood cells and platelets; neurological, cardiac and vascular pathologies; rheumatoid arthritis; congenital muscular dystrophies; various muscle disorders; fixed deformities (arthrogryposis); small cell lung cancer NCI-H23; prostate cancer; and abnormal white matter. The method includes contacting a test compound with a NOV polypeptide and determining if the test compound binds to said NOV polypeptide. Binding of the test compound to the NOV polypeptide indicates the test compound is a modulator of activity, or of latency or predisposition to the aforementioned disorders or syndromes. In addition, these materials are further useful in the generation of antibodies that bind immunospecifically to the novel substances of the invention for use in diagnostic and/or therapeutic methods.

Also within the scope of the invention is a method for screening for a modulator of activity, or of latency or predisposition to disorders or syndromes listed above by administering a test compound to a test animal at increased risk for the aforementioned disorders or syndromes. The test animal expresses a recombinant polypeptide encoded by a NOV nucleic acid. Expression or activity of NOV polypeptide is then measured in the test animal, as is expression or activity of the protein in a control animal which recombinantly-expresses NOV polypeptide and is not at increased risk for the disorder or syndrome. Next, the expression of NOV polypeptide in both the test animal and the control animal is compared. A change in the activity of NOV polypeptide in the test animal relative to the control animal indicates the test compound is a modulator of latency of the disorder or syndrome.

In yet another aspect, the invention includes a method for determining the presence of or predisposition to a disease associated with altered levels of a NOV polypeptide, a NOV nucleic acid, or both, in a subject (e.g., a human subject). The method includes measuring the amount of the NOV polypeptide in a test sample from the subject and comparing the amount of the polypeptide in the test sample to the amount of the NOV polypeptide present in a control sample. An alteration in the level of the NOV polypeptide in the test sample as compared to the control sample indicates the presence of or predisposition to a disease in the subject. Preferably, the predisposition including those listed in the preferred embodiment above.

In a further aspect, the invention includes a method of treating or preventing a pathological condition associated with a disorder in a mammal by administering to the subject a NOV polypeptide, a NOV nucleic acid, or a NOV-specific antibody to a subject (e.g., a human subject), in an amount sufficient to alleviate or prevent the pathological condition.

Unless otherwise defined, all technical and scientific terms used herein have the same meaning as commonly understood by one of ordinary skill in the art to which the invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative purposes only, and not intended to be limiting in any manner. Other features and advantages of the invention will be apparent from the following detailed description and claims.

BRIEF DESCRIPTION OF THE FIGURES

FIG. 1. Western blot of a NOV2 polypeptide secreted by 293 cells.

FIG. 2. Western blot of a NOV3 polypeptide secreted by 293 cells.

FIG. 3. Monoclonal antibody proliferation assay of T47D cells in response to NOV4.

DETAILED DESCRIPTION OF THE INVENTION

The present invention provides novel nucleotides and polypeptides encoded thereby. Included in the invention are the novel nucleic acid sequences and their polypeptides. The sequences are collectively referred to as "NOV nucleic acids" or "NOV polynucleotides" and the corresponding encoded polypeptides are referred to as "NOV polypeptides" or "NOV proteins." Unless indicated otherwise, "NOV" is meant to refer to any of the novel sequences disclosed herein. Table 14 provides a summary of the NOV nucleic acids and their encoded polypeptides.

NOV nucleic acids and their encoded polypeptides are useful in a variety of applications and contexts. The various NOV nucleic acids and polypeptides according to the invention are useful as novel members of the protein families according to the presence of domains and sequence relatedness to previously described proteins.

For example, NOV1 is homologous to members of the thymosin beta 10 family of proteins. As a result, NOV1 has various marker utilities as described herein. Also, NOV1 has efficacy in treatment of conditions involving development, differentiation, and activation of thymic immune cells; in pathologies related to spermatogenesis and male infertility; diagnosis of several human neoplasias; in diseases or pathologies of cells in blood circulation such as red blood cells and platelets; and detection of small cell lung cancer.

NOV2 and NOV4 are homologous to members of the ephrin A receptor family. As a result, NOV2 and NOV4 have various marker utilities as described herein. NOV2 and NOV4 also have roles in the treatment of conditions involving neurological, cardiac and vascular pathologies, as well as in the detection of prostate and breast cancers. For example, tests for clone NOV2 on a panel of tissue lines show highest percentage of expression in prostate cancer with bone metastasis and a prostate cancer tissue line (tissue 87073, OD04720-01), small cell lung cancer and certain breast cancer tissue lines (GENPAK 064006 and Clontech 9100266), but negligible expression in prostate cancer tissue, benign prostate tissue (tissue 84141, OD04410), large cell and non-small cell lung cancers, and non-cancerous breast tissue immediately adjacent to cancer tissue (see Tables 16 and 17). Likewise, tests for clone NOV4 on panels of tissue lines show high percentage levels of expression in testis, certain breast cancers, single-stranded central nervous system tissue 94909-XF-498 and dermal fibroblast line 93771-IL-4; however, normal prostate and prostate cancer tissue, other breast cancer cell lines (MDA-N, BT-249 and MCF-7, for example), spinal cord and certain other dermal fibroblast tissue lines (IFN-gamma, CCD1070-IL-1-beta and CCD1070-TNF alpha, as examples) show little or no level of expression.

NOV3 and NOV5 are homologous to members of the proteoglycan family. As a result, NOV3 and NOV5 have various marker utilities as described herein, and function in the treatment of conditions involving rheumatoid arthritis; congenital muscular dystrophies; various muscle disorders; fixed deformities (arthrogryposis); and abnormal white matter. Multiple sequence and BLAST alignment of NOV3 polypeptide and human fibronectin leucine-rich repeat transmembrane protein FLRT1 shows approximately 99% identity. This indicates that NOV3 functions in the same manner as the FLRT1 transmembrane protein. Multiple sequence and BLAST alignments for NOV5 homo sapiens leucine-rich repeat transmembrane protein messenger RNA and polypeptide show 89% and 97% respectively. As with NOV3, this degree of sequence identity with fibronectin, a known proteoglycan, indicates that NOV5 has utility both in targeting and treating connective tissue disorders. Additional utilities for NOV nucleic acids and polypeptides according to the invention are also discussed herein.

NOV1

A NOV1 nucleic acid sequence according to the invention includes nucleic acids encoding a polypeptide related to the small actin-sequestering peptide thymosin-beta-10. An example of this nucleic acid and its encoded polypeptide is presented in Table 1. The disclosed nucleic acid (SEQ ID NO: 1) is 430 nucleotides in length and contains an open reading frame (ORF) that begins with an ATG initiation codon at nucleotides 61–63 and ends with a TAG stop codon at nucleotides 235–237.

The representative ORF includes a 58 amino acid polypeptide (SEQ ID NO: 2) and is flanked by putative upstream and downstream untranslated regions that are underlined in Table 1. The encoded polypeptide has a high degree of homology (approximately 85 percent identity) with thymosin beta 10 from human (Table 2). A search of the PROSITE database of protein families and domains confirmed that a NOV1 polypeptide is a member of the thymosin beta family, which is defined by polypeptides containing a stretch of 11 highly conserved amino acid residues K-L-K-K-T-[E or N]-T-[Q or E]-E-K-N (SEQ ID NO: 3) located in the central part of the thymosin beta proteins (Table 2). The PROSITE database consists of biologically significant sites, patterns and profiles that help to reliably identify to which known protein family a new sequence belongs.

Furthermore, a search of the PFAM database reveals that a NOV1 polypeptide conforms to the sequence profile of thymosin beta family of proteins (Table 3). The query sequence in the table is a NOV1 polypeptide and the subject is a consensus sequence formed from the thymosin beta family of proteins. The presently disclosed NOV1 polypeptide has 84 percent identity across its entire length to the consensus thymosin beta sequence (Table 4). The NOV1 polypeptide bears more homology to the consensus thymosin beta sequence than do many other members of the family. Also, this degree of homology between a NOV1 polypeptide and the thymosin beta consensus (both in terms of length and complexity) is very unlikely to have occurred by change alone (Expect value in Table 3 less than 1 in $5*10^{10}$ by chance). Pfam is a large collection of multiple sequence alignments and profile hidden Markov models covering many common protein domain families. It is designed to be both an accurate and comprehensive method to determine homology. A multiple alignment of the thymosin-beta family is presented in Table 3. Based on its relatedness to the thymosin-beta-10 protein, the NOV1 protein is a novel member of the actin-sequestering protein family.

The thymosin-betas comprise a family of structurally related, highly conserved acidic polypeptides that sequester actin and regulate actin dynamics within cells. During embryogenesis the control of actin polymerization is essential in processes such as cell migration, angiogenesis and neurogenesis. Direct visualization and quantitation of actin filaments has shown that thymosin-betas, like agonists, induced actin depolymerization at the apical membrane where exocytosis occurs (S. Muallem et al., 128(4) *J. Cell Biol* 589–98 (1995)). Thymosin-beta-10 is widely distributed in mammalian tissues including the nervous system, and the presence of this transcript in different regions of the rat forebrain, including hippocampus, neocortex and several brain nuclei, provides evidence for the participation of thymosin-beta-10 in the control of the actin dynamics that takes place in neurons. Thymosin-beta-10 is expressed at relatively high levels in embryonic and developing tissues (A. K. Hall, 41(3) *Cell Mol. Biol. Res.* 167–80 (1995)), and given that it is involved in the inhibition of actin polymerization, the thymosin-beta-10 protein-like proteins can play an important role in early development.

Messenger RNA species of similar molecular weights encoding thymosin beta-10 are found in most tissues of the rat; however, Lin and Morrison-Bogorad identified an additional thymosin-beta-10 mRNA of higher molecular weight in the testis of sexually mature rats (Lin et al., "Cloning and characterization of a testis-specific thymosin beta 10 cDNA. Expression in post-meiotic male germ cells," 266(34) *J. Biol. Chem.*, 23347–53 (1991)). The latter mRNA differs from the ubiquitous form only in its 5-prime untranslated region, beginning 14 nucleotides upstream of the translation initiation codon. This finding, together with primer extension experiments, suggested that the two mRNA types are transcribed from the same gene through a combination of differential promoter utilization and alternative splicing. Both mRNAs were present in pachytene spermatocytes; only the testis-specific mRNA was detected in postmeiotic haploid spermatids. Immunohistochemical analysis showed that the protein was present in differentiating spermatids, suggesting that the testis-specific thymosin-beta-10 mRNA is translated in haploid male germ cells. Immunoblot analysis using specific antibodies showed that the thymosin-beta-10 protein synthesized in adult testis was identical in size to that synthesized in brain.

Thymosin-beta-10-like proteins also influence several properties of lymphocytes including cyclic nucleotide levels, migration inhibitory factor production, T-dependent antibody production, as well as the expression of various cell surface maturation/differentiation markers (Bodey et al., 22(4) *Int. J. Immunopharmacology* 261–73 (2000)). These and other observations suggest that thymosin beta-10 (a) plays a significant and possibly obligatory role in cellular processes controlling apoptosis possibly by acting as an actin-mediated tumor suppressor, (b) functions as a neoapoptotic influence during embryogenesis, and (c) can mediate some of the pro-apoptotic anticancer actions of retinoids. Thymosin-beta-10 mRNA is also abundant in a variety of tumors and tumor cell lines.

Thymosin-beta-10 gene overexpression is a general event in human carcinogenesis. Analysis of thymosin-beta-10 mRNA levels in human colon carcinomas, germ cell tumors of different histological types, breast carcinomas, ovarian carcinomas, uterine carcinomas, colon and esophageal carcinoma cell lines all indicated thymosin-beta-10 was over expressed in all of the neoplastic tissues and cell lines compared to the respective normal tissues. Therefore, detection of thymosin-beta-10-like expression can be considered a potential tool for the diagnosis of several human neoplasias. (Santelli et al., 155(3) *Annals of Am. J. Pathol.* 799–804 (1999)). Not only can thymosins like thymosin beta-10 be used for early detection and diagnosis of neoplasms, but also in recent clinical trials derivatives of thymic hormones, mostly of thymosins, have been used to help treat neoplasms (Bodey et al., 22(4) *Int. J. Immunopharmacol.* 261–73 (2000)). Thymic hormones strengthen the effects of immunomodulators in immunodeficiencies, autoimmune diseases, and neoplastic malignancies. Combined chemo-immunotherapeutical anti-cancer treatment seems to be more efficacious than chemotherapy alone, and the significant hematopoietic toxicity associated with most chemotherapeutical clinical trials can be reduced significantly by the addition of immunotherapy.

Based on its relatedness to the thymosin-beta-10 protein, the NOV1 protein is a novel member of the actin-sequestering protein family. The discovery of molecules related to thymosin-beta-10 satisfies a need in the art by providing new diagnostic or therapeutic compositions useful in the treatment of disorders associated with alterations in the expression of members of thymosin-beta-10-like proteins. Nucleic acids, polypeptides, antibodies, and other compositions of the present invention are useful in a variety of diseases and pathologies, including by way of nonlimiting example, those involving development, differentiation and activation of thymic immune cells, pathologies related to spermatogenesis and male infertility, diagnosis of several human neoplasias, and diseases or pathologies of cells in blood circulation such as red blood cells and platelets.

A NOV1 nucleic acid is useful for detecting specific cell-types. For example a variant splice form of a NOV1 nucleic acid according to the invention can be present in different levels in postmeiotic haploid spermatids. Also, according to the invention the expression of a NOV1 nucleic acid has utility in identifying developing and embryonic tissues from other tissue types. Thymosin-beta-10 mRNA is overexpressed in a variety of tumors and tumor cell lines. Expression levels of thymosin-beta-10 like nucleic acids such as NOV1 are also useful in distinguishing T cell types given that expression of various cell surface/differentiation markers is influenced by thymosin-beta-10 like proteins such as a NOV1 polypeptide. A NOV1 nucleic acid has enhanced expression in certain cancer cell lines, especially non-small cell lung cancer NCI-H23, but not in cell lines from the corresponding normal tissue; therefore, NOV1 nucleic acids are useful as a cancer specific marker in such tissues (Example 1).

Given that thymosin-beta-10 related proteins can sequester actin and regulate actin dynamics within cells, proteins related to the NOV1 polypeptide are useful in screens for test compounds that can modulate actin polymerization or the formation or stability of actin-thymosin beta-10 complexes. Finally, since thymic hormones strengthen the effects of immunomodulators in immunodeficiencies, autoimmune diseases, and neoplastic malignancies, NOV1 related proteins can be used in combined chemo-immunotherapeutical anti-cancer treatments.

TABLE 1

A representative cDNA sequence encoding the thymosin-beta-10-like protein according to the invention
Putative untranslated regions are underlined. The start and stop codons are in bold type.

(SEQ ID NO:1)

<u>GCCAGCAGGAGTGCCATGGTGAGAGGCACTGGCAGGGAATGCTAGGATTGTTTTAAGAAA</u>ATGGCAGACAAACCAGACATAGGGGA

AATCGCCAGCTTCAATAAGGCCAAGCTGAAGAAAACAGAGATGCAGGAGAACACCCTGCTGACCAAAGAGGCCATTGAGCAGGAGA

AGCGGGTGAAATTTCCTAAGAGCCTGGAGGATTCCCTACCCCTGTCATCTTCGAGACCCCAGTAG<u>TAATGTGGAGGAAGAATCACC</u>

<u>ACAAGATGGACACAAGCCACAAACTGTGACGTGAACCTGGGCACTCCGTGCTGATGCCACCAGCCTGAGGGTCCCTATGGGTCCAA</u>

<u>TCAGACTGCCAAATTCTCTGGTTTGCCCTGGGATATTATAGAAAATTATTTGCGTGAATAATGAAAACACAGCTCATGGCAAAAAA</u>

A representative amino acid sequence of the thymosin-beta-10-like protein according to the invention (SEQ ID NO:2)

MADKPDIGEIASFNKAKLKKTEMQENTLLTKEAIEQEKRVKFPKSLEDSLPLSSSRPQ

TABLE 2

Comparison between a NOV1 polypeptide and thymosin beta-10 from human

```
>gb|AAA36746.1|(M92383) thymosin beta-10 [Homo sapiens]
Length = 49
Score = 84.5 bits (192), Expect = 3e-16
Identities = 34/40 (85%), Positives 36/40 (90%), Gaps = 1/40 (2%)

NOV1:   1 MADKPDIGEIASFNKAKLKKTEMQE-NTLLTKEAIEQEKR  39 (SEQ ID NO: 2)
          |||||+|||||+|||||||| || ||| ||| ||||||
Sbjct:  6 MADKPDMGEIASFDKAKLKKTETQEKNTLPTKETIEQEKR  45 (SEQ ID NO: 34)
```

TABLE 3

Multiple Sequence alignment of a NOV1 polypeptide and the thymosin beta family
(Black outlined amino acids indicate potential regions of conserved sequence;
grayed amino acids represent amino acids conservatively substituted; and non-
highlighted amino acids indicate positions in which mutations to a broad range
of alternative amino acid residues occurs. Sequences may be referenced by the
SWISSPROT or TREMBL ID.)

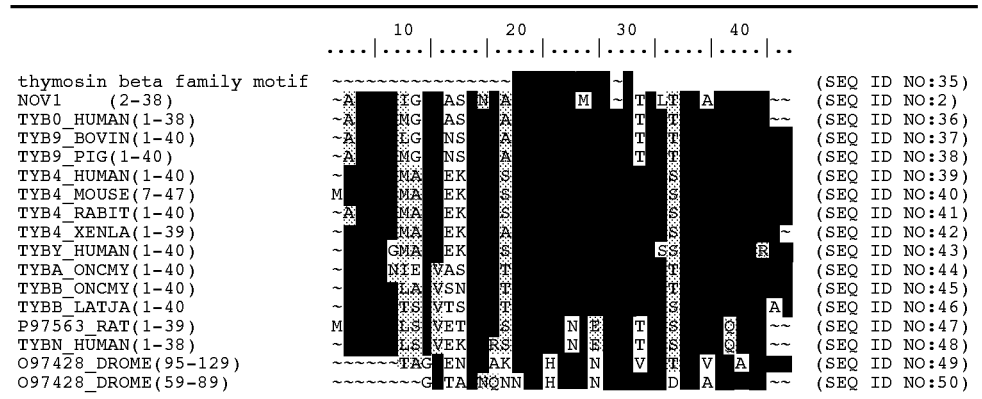

| | |
|---|---|
| thymosin beta family motif | (SEQ ID NO:35) |
| NOV1 (2-38) | (SEQ ID NO:2) |
| TYB0_HUMAN(1-38) | (SEQ ID NO:36) |
| TYB9_BOVIN(1-40) | (SEQ ID NO:37) |
| TYB9_PIG(1-40) | (SEQ ID NO:38) |
| TYB4_HUMAN(1-40) | (SEQ ID NO:39) |
| TYB4_MOUSE(7-47) | (SEQ ID NO:40) |
| TYB4_RABIT(1-40) | (SEQ ID NO:41) |
| TYB4_XENLA(1-39) | (SEQ ID NO:42) |
| TYBY_HUMAN(1-40) | (SEQ ID NO:43) |
| TYBA_ONCMY(1-40) | (SEQ ID NO:44) |
| TYBB_ONCMY(1-40) | (SEQ ID NO:45) |
| TYBB_LATJA(1-40) | (SEQ ID NO:46) |
| P97563_RAT(1-39) | (SEQ ID NO:47) |
| TYBN_HUMAN(1-38) | (SEQ ID NO:48) |
| O97428_DROME(95-129) | (SEQ ID NO:49) |
| O97428_DROME(59-89) | (SEQ ID NO:50) |

TABLE 4

PFAM alignment of a NOV1 polypeptide to the consensus sequence of the thymosin beta family >PD005116 (Closest domain: TYB0_HUMAN 1-38)
Number of sequences in family: 16

TABLE 4-continued

PFAM alignment of a NOV1 polypeptide to the consensus sequence of the thymosin beta family Most frequent protein names: TYB4(4) TYB9(2) TYBB(2)
Commentary (automatic):
      THYMOSIN ACETYLATION T-CELL DIFFERENTIATION
      IMMUNOPOTENTIATION THYMUS BETA-4 ACTIN-BINDING PROTEIN
      BETA
      Length = 38
Score = 145 (60.9 bits), Expect = 5e-10
Identities = 32/38 (84%), Positives = 34/38 (89%), Gaps = 1/38 (2%)

```
NOV1:  2 ADKPDIGEIASFNKAKLKKTEMQE-NTLLTKEAIEQEK 38 (SEQ ID NO: 2)
         |||||+||||||+|||||||| || ||| ||| |||||
Sbjct: 1 ADKPDMGEIASFDKAKLKKTETQEKNTLPTKETIEQEK 38 (SEQ ID NO: 51)
```

NOV2

A NOV2 nucleic acid according to the invention includes nucleic acids encoding a polypeptide related to ephrin type-A receptors. An example of nucleic acid and its encoded polypeptide is presented in Table 5. The disclosed nucleic acid (SEQ ID NO: 4) is 3018 nucleotides in length and contains an open reading frame that begins with an ATG initiation codon at nucleotide 1–3 and ends at nucleotides 2974–2976.

The representative ORF includes a 992 amino acid polypeptide (SEQ ID NO: 5). The encoded polypeptide has a high degree of homology (approximately 95 percent identity) with mouse ephrin type-A receptor 8 precursor (Table 6) (SWISSPROT ACC: O09127, 956 out of 1005 residues). The NOV2 polypeptide also has an even higher degree of homology (100 percent identity) to a human eph- and elk-related kinase known as ephrin receptor EphA8 (Table 6A, partial sequence disclosed in Chan et al., 6 Oncogene 1057–1061 (1991); the full length human ephrin receptor EphA8 full length sequence was deposited in Genbank Sept. 14, 2000 as accession number NP_065387.1.) A multiple alignment with similar proteins showed comparable degrees of similarity to ephrin receptors from mouse (EPA8_mouse), human (EPA5_human), and chicken (EPA5_chick) (Table 7). In the predicted extracellular domain, a cysteine-rich region and tandem fibronectin type III repeats are present while a catalytic domain is present in the intracellular domain. These features are consistent with other members of the Eph family. Based on its relatedness, the NOV2 protein is a member of the ephrin type-A receptor tyrosine-protein kinase family.

The Eph receptors constitute the largest known family of receptor protein tyrosine kinases. They have been implicated in mediating developmental events, particularly in the nervous system. Receptors in the Eph subfamily typically have a single kinase domain and an extracellular region containing a Cys-rich domain and two fibronectin type III repeats. These receptors play important roles along with their ligands, called ephrins, in neural development, angiogenesis, and vascular network assembly. (S. Choi et al., 9(4) Mol. Cells 440–45 (1999)).

The ephrin type-A receptor 8 (EC 2.7.1.112) (tyrosine-protein kinase receptor eek) (eph- and elk-related kinase) (fragment) is designated as the gene product of the gene: epha8 or eek. It is a Type I membrane bound receptor, and its function is to serve as a receptor for members of the ephrin-a family. Its catalytic activity is as a protein tyrosine kinase, phosphorylating tyrosine in appropriate target proteins. It is similar to other protein-tyrosine kinases in the catalytic domain and belongs to the ephrin receptor family.

Eph receptors have tyrosine-kinase activity, and, together with their ephrin ligands, mediate contact-dependent cell interactions that are implicated in the repulsion mechanisms that guide migrating cells and neuronal growth cones to specific destinations. Since Eph receptors and ephrins have complementary expression in many tissues during embryogenesis, bidirectional activation of Eph receptors may occur at interfaces of their expression domains, for example, at segment boundaries in the vertebrate hindbrain. Indeed, Eph receptors play key roles in development of the nervous system and angiogenesis. In the nervous system, they provide positional information by empolying mechanisms that involve repulsion of migrating cells and growing axons (Frisen et al., 18(19)EMBO J. 5159–5165 (1999)). Also, an important function of Eph receptors and ephrins is to mediate cell-contact-dependent repulsion.

A NOV2 sequence according to the invention is useful for detecting cells that express GPI-anchored ephrin-A ligands. For example, cells expressing either a NOV2 nucleic acid or a NOV2 protein have utility in screening for other cells that express GPI-anchored ephrin-A ligands or mimics therefore. As a result, a NOV2 sequence is useful for screening for new ephrin-A ligands expressed on cells. NOV2 is highly expressed in many surgical tumor samples, especially prostate cancer, but minimally or not detectably in the immediate normal adjacent tissue; therefore, the NOV2 expression can be used as a marker for certain cancers, especially prostate cancer (Example 1).

Also, a NOV2 sequence according to the invention is useful to direct the development of the nervous system and angiogenesis by modulating the boundaries between arteries and veins. For example, mice expressing defective Eph receptors similar to a NOV2 sequence have been shown to be defective in angiogenesis and die in mid-gestation (Wang et al., 93 Cell 741–753 (1998)). The protein of the present invention will be useful in a variety of diseases and pathologies, including by way of nonlimiting example, those involving neurological, cardiac and vascular pathologies.

TABLE 5

A representative DNA sequence encoding the ephrin type-A receptor 8-like protein of the invention (SEQ ID NO:4)

ATGGCCCCGCCCGGGGCCGCCTGCCCCCTGCGCTCTGGGTCGTCACGGCCGCGGCGGCGGCGGCCACCT

GCGTGTCCGCGGCGCGCGGCGAAGTGAATTTGCTGGACACGTCGACCATCCACGGGACTGGGGCTGGCT

CACGTATCCGGCTCATGGGTGGGACTCCATCAACGAGGTGGACGAGTCCTTCCAGCCCATCCACACGTAC

CAGGTTTGCAACGTCATGAGCCCCAACCAGAACAACTGGCTGCGCACGAGCTGGGTCCCCCGAGACGGCG

CCCGGCGCGTCTATGCTGAGATCAAGTTTACCCTGCGCGACTGCAACAGCATGCCTGGTGTGCTGGGCAC

CTGCAAGGAGACCTTCAACCTCTACTACCTGGAGTCGGACCGCGACCTGGGGGCCAGCACACAAGAAAGC

CAGTTCCTCAAAATCGACACCATTGCGGCCGACGAGAGCTTCACAGGTGCCGACCTTGGTGTGCGGCGTC

TCAAGCTCAACACGGAGGTGCGCAGTGTGGGTCCCCTCAGCAAGCGCGGCTTCTACCTGGCCTTCCAGGA

CATAGGTGCCTGCCTGGCCATCCTCTCTCCGCATCTACTATAAGAAGTGCCCTGCCATGGTGCGCAAT

CTGGCTGCCTTCTCGGAGGCAGTGACGGGGGCCGACTCGTCCTCACTGGTGGAGGTGAGGGGCCAGTGCG

TGCGGCACTCAGAGGAGCGGGACACACCCAAGATGTACTGCAGCGCGGAGGGCGAGTGGCTCGTGCCCAT

CGGCAAATGCGTGTGCAGTGCCGGCTACGAGGAGCGGCGGGATGCCTGTGTGGCCTGTGAGCTGGGCTTC

TACAAGTCAGCCCCTGGGGACCAGCTGTGTGCCCGCTGCCCTCCCCACAGCCACTCCGCAGCTCCAGCCG

CCCAAGCCTGCCACTGTGACCTCAGCTACTACCGTGCAGCCCTGGACCCGCCGTCCTCAGCCTGCACCCG

GCCACCCTCGGCACCAGTGAACCTGATCTCCAGTGTGAATGGGACATCAGTGACTCTGGAGTGGCCCCT

CCCCTGGACCCAGGTGGCCGCAGTGACATCACCTACAATGCCGTGTGCCGCCGCTGCCCTGGGCACTGA

GCCGCTGCGAGGCATGTGGGAGCGGCACCCGCTTTGTGCCCCAGCAGACAAGCCTGGTGCAGGCCAGCCT

GCTGGTGGCCAACCTGCTGGCCCACATGAACTACTCCTTCTGGATCGAGGCCGTCAATGGCGTGTCCGAC

CTGAGCCCCGAGCCCCGCCGGGCCGCTGTGGTCAACATCACCACGAACCAGGCAGCCCCGTCCCAGGTGG

TGGTGATCCGTCAAGAGCCGGCGGGGCAGACCAGCGTCTCGCTGCTGTGGCAGGAGCCCGAGCAGCCGAA

CGGCATCATCCTGGAGTATGAGATCAAGTACTACGAGAAGGACAAGGAGATGCAGAGCTACTCCACCCTC

AAGGCCGTCACCACCAGAGCCACCGTCTCCGGCCTCAAGCCGGGCACCCGCTACGTGTTCCAGGTCCGAG

CCCGCACCTCAGCAGGCTGTGGCCGCTTCAGCCAGGCCATGGAGGTGGAGACCGGGAAACCCCGGCCCCG

CTATGACACCAGGACCATTGTCTGGATCTGCCTGACGCTCATCACGGGCCTGGTGGTGCTTCTGCTCCTG

CTCATCTGCAAGAAGAGGCACTGTGGCTACAGCAAGGCCTTCCAGGACTCGGACGAGGAGAAGATGCACT

ATCAGAATGGACAGGCACCCCCACCTGTCTTCCTGCCTCTGCATCACCCCCCGGGAAAGCTCCCAGAGCC

CCAGTTCTATGCGGAACCCCACACCTACGAGGAGCCAGGCCGGGCGGGCCGCAGTTTCACTCGGGAGATC

GAGGCCTCTAGGATCCACATCGAGAAAATCATCGGCTCTGGAGACTCCGGGGAAGTCTGCTACGGGAGGC

TGCGGGTGCCAGGGCAGCGGGATGTGCCCGTGGCCATCAAGGCCCTCAAAGCCGGCTACACGGAGAGACA

GAGGCGGGACTTCCTGAGCGAGGCGTCCATCATGGGGCAATTCGACCATCCCAACATCATCCGCCTCGAG

GGTGTCGTCACCCGTGGCCGCCTGGCAATGATTGTGACTGAGTACATGGAGAACGGCTCTCTGGACACCT

TCCTGAGGACCCACGACGGGCAGTTCACCATCATGCAGCTGGTGGGCATGCTGAGAGGAGTGGGTGCCGG

CATGCGCTACCTCTCAGACCTGGGCTATGTCCACCGAGACCTGGCCGCCCGCAACGTCCTGGTTGACAGC

AACCTGGTCTGCAAGGTGTCTGACTTCGGGCTCTCACGGGTGCTGGAGGACGACCCGGATGCTGCCTACA

CCACCACGGGCGGGAAGATCCCCATCCGCTGGACGGCCCCAGAGGCCATCGCCTTCCGCACCTTCTCCTC

GGCCAGCGACGTGTGGAGCTTCGGCGTGGTCATGTGGGAGGTGCTGGCCTATGGGGAGCGGCCCTACTGG

AACATGACCAACCGGGATGTGATCAGCTCTGTGGAGGAGGCGTACCGCCTGCCCGCACCCATGGGCTGCC

CCCACGCCCTGCACCAGCTCATGCTCGACTGTTGGCACAAGGACCGGGCGCAGCGGCCTCGCTTCTCCCA

TABLE 5-continued

```
GATTGTCAGTGTCCTCGATGCGCTCATCCGCAGCCCTGAGAGTCTCAGGGCCACCGCCACAGTCAGCAGG

TGCCCACCCCTGCCTTCGTCCGGAGCTGCTTTGACCTCCGAGGGGCAGCGGTGGCGGTGGGQGCCTCA

CCGTGGGGGACTGGCTGGACTCCATCCGCATGGGCCGGTACCGAGACCACTTCGCTGCGGGCGGATACTC

CTCTCTGGGCATGGTGCTACGCATGAACGCCCAGGACGTGCGCGCCCTGGGCATCACCCTCATGGGCCAC

CAGAAGAAGATCCTGGGCAGCATTCAGACCATGCGGGCCCAGCTGACCAGCACCCAGGGGCCCCGCCGGC

ACCTCTGA
```

A representative amino acid sequence of the ephrin type-A receptor 8-like protein of the invention (SEQ ID NO:5)

```
MAPARGRLPPALWVVTAAAAAATCVSAARGEVNLLDTSTIHGDWGWLTYPAHGWDSINEVDESFQPIHTYQVCNVMSPNQNNWLRT

SWVPRDGARRVYAEIKFTLRDCNSMPGVLGTCKETFNLYYLESDRDLGASTQESQFLKIDTIAADESFTGADLGVRRLKLNTEVRS

VGPLSKRGFYLAFQDIGACLAILSLRIYYKKCPAMVRNLAAFSEAVTGADSSSLVEVRGQCVRHSEERDTPKMYCSAEGEWLVPIG

KCVCSAGYEERRDACVACELGFYKSAPGDQLCARCPPHSHSAAPAAQACHCDLSYYRAALDPPSSACTRPPSAPVNLISSVNGTSV

TLEWAPPLDPGGRSDITYNAVCRRCPWALSRCEACGSGTRFVPQQTSLVQASLLVANLLAHMNYSFWIEAVNGVSDLSPEPRRAAV

VNITTNQAAPSQVVVIRQERAGQTSVSLLWQEPEQPNGIILEYEIKYYEKDKEMQSYSTLKAVTTRATVSGLKPGTRYVFQVRART

SAGCGRFSQAMEVETGKPRPRYDTRTIVWICLTLTTGLVVLLLLLICKKRHCGYSKAFQDSDEEKMHYQNGQAPPPVFLPLHHPPG

KLPEPQFYAEPHTYEEPGRAGRSFTREIEASRIHIEKIIGSGDSGEVCYGRLRVPGQRDVPVAIKALKAGYTERQRRDFLSEASIM

GQFDHPNIIRLEGVVTRGRLAMIVTEYMENGSLDTFLRTHDGQFTIMQLVGMLRGVGAGMRYLSDLGYVHRDLAARNVLVDSNLVC

KVSDFGLSRVLEDDPDAAYTTTGGKIPIRWTAPEAIAFRTFSSASDVWSFGVVMWEVLAYGERPYWNMTNRDVISSVEEGYRLPAP

MGCPHALHQLMLDCWHKDRAQRPRFSQIVSVLDALIRSPESLRATATVSRCPPPAFVRSCFDLRGGSGGGGLTVGDWLDSIRMGR

YRDHFAAGGYSSLGMVLRMNAQDVRALGITLMGHQKKILGSIQTMR
```

TABLE 6

Comparison between a NOV2 polypeptide and mouse ephrin type-A receptor 8 precursor

```
>ref|NP_031965.1| Eph receptor A8
sp|O09127|EPA8_MOUSE EPHRIN TYPR-A RECEPTOR 8 PRECURSOR (TYROSINE-PROTEIN KINASE
RECEPTOR EEK) (EPH-AND ELK-RELATED KINASE)
gb|AAB39218.1| (U72207) Eph-and Elk_related kinase [Mus musculus]
Length = 1004
Score = 3036 bits (7128), Expected = 0.0
Identities = 945/992 (95%), Positives = 964/992 (96%), Gaps = 1/992 (0%)

NOV2:    1 MAPARGRLPPALWVVTAAAAAATCVSAARGEVNLLDTSTIHGDWGWLTYPAHGWDSINEV    60 (SEQ ID NO: 5)
           |||||  || |||||||||||| |||||  |||||||||||||||||||||||||||||
Sbjct:   1 MAPARARLSPALWVVTAAAAA-TCVSAGRGEVNLLDTSTIHGDWGWLTYPAHGWDSINEV    59 (SEQ ID NO: 52)

NOV2:   61 DESFQPIHTYQVCNVMSPNQNNWLRTSWVPRDGARRVYAEIKFTLRDCNSMPGVLGTCKE   120
           ||||+||||||||||||||||||||+||||||||||||||||||||||||+||||||||
Sbjct:  60 DESFRPIHTYQVCNVMSPNQNNWLRTNWVPRDGARRVYAEIKFTLRDCNSIPGVLGTCKE   119

NOV2:  121 TFNLYYLESDRDLGASTQESQFLKIDTIAADESFTGADLGVRRLKLNTEVRSVGPLSKRG   180
           ||||+||||||||||||||||||||||||||||||||||||||||||||| ||||||||
Sbjct: 120 TFNLHYLESDRDLGASTQESQFLKIDTIAADESFTGADLGVRRLKLNTEVRGVGPLSKRG   179

NOV2:  181 FYLAFQDIGACLAILSLRTYYKKCPAMVRNLAAFSEAVTGADSSSLVEVRGQCVRHSEER   240
           ||||||||||||||||||||||||||||||||||||||||||||||||||||||||||||
Sbjct: 180 FYLAFQDIGACLAILSLRIYYKKCPAMVRNLAAFSEAVTGADSSSLVEVRGQCVRHSEER   239

NOV2:  241 DTPKMYCSAEGEWLVPIGKCVCSAGYEERRDACVACELGFYKSAPGDQLCARCPPHSHSA   300
           |||||||||||||||||||||||||||||||||+|||||||||||||||||||||||||
Sbjct: 240 DTPKMYCSAEGEWLVPIGKCVCSAGYEERRDACMACELGFYKSAPGDQLCARCPPHSHSA   299
```

TABLE 6-continued

Comparison between a NOV2 polypeptide and mouse ephrin type-A receptor 8 precursor

```
NOV2:   301 APAAQACHCDLSYYRAALDPPSSACTRPPSAPVNLISSVNGTSVTLEWAPPLDPGGRSDI 360
            |||| | ||||||||||||+||||||||||||||||||||||||||||||||||||||||
Sbjct:  300 TPAAQTCRCDLSYYRAALDPPSAACTRPPSAPVNLISSVNGTSVTLEWAPPLDPGGRSDI 359

NOV2:   361 TYNAVCRRCPWALSRCEACGSGTRFVPQQTSLVQASLLVANLLAHMNYSFWIEAVNGVSD 420
            ||||||||||||| |||||||||||||||||| |||||||||||||||||||||||||+
Sbjct:  360 TYNAVCRRCPWALSHCEACGSGTRFVPQQTSLAQASLLVANLLAHMNYSFWIEAVNGVSN 419

NOV2:   421 LSPEPRRAAVVNITTNQAAPSQVVVIRQERAGQTSVSLLWQEPEQPNGIILEYEIKYYEK 480
            ||||||  |||||||||||||||||||||||||||||||||||||||||||||||||||
Sbjct:  420 LSPEPRSAAVVNITTNQAAPSQVVVIRQERAGQTSVSLLWQEPEQPNGIILEYEIKYYEK 479

NOV2:   481 DKEMQSYSTLKAVTTRATVSGLKPGTRYVFQVRARTSAGCGRFSQAMEVETGKPRPRYDT 540
            ||||||||||||||||||||||||||||||||||||||||||||||||||||||||||||
Sbjct:  480 DKEMQSYSTLKAVTTRATVSGLKPGTRYVFQVRARTSAGCGRFSQAMEVETGKPRPRYDT 539

NOV2:   541 RTIVWICLTLITGLVVLLLLICKKRHCGYSKAFQDSDEEKMHYQNGQAPPPVFLPHHP 600
            ||||||||||||||||||||||||||||||||||||||||||||||||||||||+||
Sbjct:  540 RTIVWICLTLITGLVVLLLLICKKRHCGYSKAFQDSDEEKMHYQNGQAPPPVFLPLNHP 599

NOV2:   601 PGKLPEPQFYAEPHTYEEPGRAGRSFTREIEASRIHIEKIIGSGDSGEVCYGRLRVPGQR 660
            ||| || || ||||||||||||||||||||||||||||||||+||||||||+|||||
Sbjct:  600 PGKFPETQFSAEPHTYEEPGRAGRSFTREIEASRIHIEKIIGSGESGEVCYGRLQVPGQR 659

NOV2:   661 DVPVAIKALKAGYTERQRRDFLSEASIMGQFDHPNIIRLEGVVTRGRLAMIVTEYMENGS 720
            ||||||||||||||||||+|||||+|||||||||||||||||||||||||||||||||
Sbjct:  660 DVPVAIKALKAGYTERQRQDFLSEAAIMGQFDHPNIIRLEGVVTRGRLAMIVTEYMENGS 719

NOV2:   721 LDTFLRTHDGQFTIMQLVGMLRGVGAGMRYLSDLGYVHRDLAARNVLVDSNLVCKVSDFG 780
            || ||||||||||+||||||||||||||||||||+|||||||||||||  ||||||||
Sbjct:  720 LDAFLRTHDGQFTIVQLVGMLRGVGAGMRYLSDLGYIHRDLAARNVLVDGRLVCKVSDFG 779

NOV2:   781 LSRVLEDDPDAAYTTTGGKIPIRWTAPEAIAFRTFSSASDVWSFGVVMWEVLAYGERPYW 840
            ||| |||||+||||  ||||||||||||||||||||||||||||||||||||||||||
Sbjct:  780 LSRALEDDPEAAYTTAGGKIPIRWTAPEAIAFRTFSSASDVWSFGVVMWEVLAYGERPYW 839

NOV2:   841 NMTNRDVISSVEEGYRLPAPMGCPHALHQLMLDCWHKDRAQRPRFSQIVSVLDALIRSPE 900
            ||||+||||||||||||||||||| |||||||||||||||||||+ +||||||+ |||
Sbjct:  840 NMTNQDVISSVEEGYRLPAPMGCPRALHQLMLDCWHKDRAQRPRFAHVVSVLDALVHSPE 899

NOV2:   901 SLRATATVSRCPPPAFVRSCFDLRGGSGGGGLTVGDWLDSIRMGRYRDHFAAGGYSSLG 960
            |||||||||||||||| |||||||||| |  | |||||||||||||||||||||||||
Sbjct:  900 SLRATATVSRCPPPAFARSCFDLRAGGSGNGDLTVGDWLDSIRMGRYRDHFAAGGYSSLG 959

NOV2:   961 MVLRMNAQDVRALGITLMGHQKKILGSIQTMR 992
            ||||||||||||||||||||||||||||||||
Sbjct:  960 MVLRMNAQDVRALGITLMGHQKKILGSIQTMR 991
```

TABLE 6A

Comparison between a NOV2 polypeptide and human ephrin receptor EphA8

>ref|NP_065387.1|EphA8; Ephrin receptor EphA8 (eph- and eld-related kinase); Hek3:
    eph-, elk-related tyrosine kinase; ephrin receptor EphA8
emb|CAB81612.1|(AL035703) dJ61A9.1 (tyrosine kinase) [Homo sapiens]
        Length = 1005
Score = 2054 bits (5262), Expect = 0.0
Identities = 992/992 (100%), Positives = 992/992 (100%)

```
NOV2 :    1 MAPARGRLPPALWVVTAAAAAATCVSAARGEVNLLDTSTIHGDWGWLTYPAHGWDSINEV  60 (SEQ ID NO: 5)
            ||||||||||||||||||||||||||||||||||||||||||||||||||||||||||||
Sbjct:    1 MAPARGRLPPALWVVTAAAAAATCVSAARGEVNLLDTSTIHGDWGWLTYPAHGWDSINEV  60 (SEQ ID NO: 53)

NOV2 :   61 DESFQPIHTYQVCNVMSPNQNNWLRTSWVPRDGARRVYAEIKFTLRDCNSMPGVLGTCKE 120
            ||||||||||||||||||||||||||||||||||||||||||||||||||||||||||||
Sbjct:   61 DESFQPIHTYQVCNVMSPNQNNWLRTSWVPRDGARRVYAEIKFTLRDCNSMPGVLGTCKE 120
```

TABLE 6A-continued

Comparison between a NOV2 polypeptide and human ephrin receptor EphA8

```
NOV2  : 121 TFNLYYLESDRDLGASTQESQFLKIDTIAADESFTGADLGVRRLKLNTEVRSVGPLSKRG 180
            TFNLYYLESDRDLGASTQESQFLKIDTIAADESFTGADLGVRRLKLNTEVRSVGPLSKRG
Sbjct : 121 TFNLYYLESDRDLGASTQESQFLKIDTIAADESFTGADLGVRRLKLNTEVRSVGPLSKRG 180

NOV2  : 181 FYLAFQDIGACLAILSLRIYYKKCPAMVRNLAAFSEAVTGADSSSLVEVRGQCVRHSEER 240
            ||||||||||||||||||||||||||||||||||||||||||||||||||||||||||||
Sbjct : 181 FYLAFQDIGACLAILSLRIYYKKCPAMVRNLAAFSEAVTGADSSSLVEVRGQCVRHSEER 240

NOV2  : 241 DTPKMYCSAEGEWLVPIGKCVCSAGYEERRDACVACELGFYKSAPGDQLCAPCPPHSHSA 300
            |||||||||||||||||||||||||||||||||||||||||||||||||| |||||||||
Sbjct : 241 DTPKMYCSAEGEWLVPIGKCVCSAGYEERRDACVACELGFYKSAPGDQLCARCPPHSHSA 300

NOV2  : 301 APAAQACHCDLSYYRAALDPPSSACTRPPSAPVNLISSVNGTSVTLEWAPPLDPGGRSDI 360
            APAAQACHCDLSYYRAALDPPSSACTRPPSAPVNLISSVNGTSVTLEWAPPLDPGGRSDI
Sbjct : 301 APAAQACHCDLSYYRAALDPPSSACTRPPSAPVNLISSVNGTSVTLEWAPPLDPGGRSDI 360

NOV2  : 361 TYNAVCRRCPWALSRCEACGSGTRFVPQQTSLVQASLLVANLLAHMNYSFWIEAVNGVSD 420
            ||||||||||||||||||||||||||||||||||||||||||||||||||||||||||||
Sbjct : 361 TYNAVCRRCPWALSRCEACGSGTRFVPQQTSLVQASLLVANLLAHMNYSFWIEAVNGVSD 420

NOV2  : 421 LSPEPRRAAVVNITTNQAAPSQVVVIRQERAGQTSVSLLWQEPEQPNGIILEYEIKYYEK 480
            ||||||||||||||||||||||||||||||||||||||||||||||||||||||||||||
Sbjct : 421 LSPEPRRAAVVNITTNQAAPSQVVVIRQERAGQTSVSLLWQEPEQPNGIILEYEIKYYEK 480

NOV2  : 481 DKEMQSYSTLKAVTTRATVSGLKPGTRYVFQVRARTSAGCGRFSQAMEVETGKPRPRYDT 540
            DKEMQSYSTLKAVTTRATVSGLKPGTRYVFQVRARTSAGCGRFSQA EVETGKPRPRYDT
Sbjct : 481 DKEMQSYSTLKAVTTRATVSGLKPGTRYVFQVPARTSAGCGRFSQANEVETGKPRPRYDT 540

NOV2  : 541 RTIVWICLTLITGLVVLLLLLICKKRHCGYSKAFQDSDEEKMHYQNGQAPPPVFLPLHHP 600
            ||||||||||||||||||||||||||||||||||||||||||||||||||||||||||||
Sbjct : 541 RTIVWICLTLITGLVVLLLLLICKKRHCGYSKAFQDSDEEKMHYQNGQAPPPVFLPLHHP 600

NOV2  : 601 PGKLPEPQFYAEPHTYEEPGRAGRSFTREIEASRIHIEKIIGSGDSGEVCYGRLRVPGQR 660
            ||||||||||||||||||||||||||||||||||||||||||||||||||||||||||||
Sbjct : 601 PGKLPEPQFYAEPHTYEEPGRAGRSFTREIEASRIHIEKIIGSGDSGEVCYGRLRVPGQR 660

NOV2  : 661 DVPVAIKALKAGYTERQRRDFLSEASIMGQFDHPNIIRLEGVVTRGRLAMIVTEYMENGS 720
            ||||||||||||||||||||||||||||||||||||||||||||||||||||||||||||
Sbjct : 661 DVPVAIKALKAGYTERQRRDFLSEASIMGQFDHPNIIRLEGVVTRGRLAMIVTEYMENGS 720

NOV2  : 721 LDTFLRTHDGQFTIMQLVGMLRGVGAGMRYLSDLGYVHRDLAARNVLVDSNLVCKVSDFG 780
            |||||||| |||||||||||||||||||||||||||||||||||||||||||||||||||
Sbjct : 721 LDTFLRTUDGQFTIMQLVGMLRGVGAGMRYLSDLGYVHRDLAARNVLVDSNLVCKVSDFG 780

NOV2  : 781 LSRVLEDDPDAAYTTTGGKIPIRWTAPEAIAFRTFSSASDVWSFGVVMWEVLAYGERPYW 840
            ||||||||||||||| ||||||||||||||||||||||||||||||||||||||||||||
Sbjct : 781 LSRVLEDDPDAAYTTTCGKIPIRWTAPEAIAFRTFSSASDVWSFGVVMWEVLAYGERPYW 840

NOV2  : 841 NMTNRDVISSVEEGYRLPAPMGCPHALHQLMLDCWHKDRAQRPRFSQIVSVLDALIRSPE 900
            ||||||||||||||||||||| |||||||||||||| |||||||||||||||||||||||
Sbjct : 841 NMTNRDVISSVEEGYRLPAPMOCPHALHQLMLDCWEKDRAQRPRFSQIVSVLDALIRSPE 900
```

TABLE 6A-continued

Comparison between a NOV2 polypeptide and human ephrin receptor EphA8

```
NOV2 :  901  SLRATATVSRCPPPAFVRSCFDLRGGSGGGGGLTVGDWLDSIRMGRYRDHFAAGGYSSLG  960
             ||||||||||||||||||||||||||||||||||||||||||||||||||||||||||||
Sbjct:  901  SLRATATVSRCPPPAFVRSCFDLRGGSGGGGGLTVGDWLDSIRMORYRDHFAAGGYSSLG  960

NOV2 :  961  MVLRMNAQDVRALGITLMGHQKKILGSIQTMR  992
             ||||||| ||||||||||||||||||||||||
Sbjct:  961  MVLRNNAQDVRALGITLMGHQKKILGSIQTMR  992
```

TABLE 7

Multiple alignment of the NOV2 ephrin type-A receptor 8-like protein of the invention, shown as AL035703 Spliced2, with similiar proteins
Table 7 shows multiple sequence alignment of the NOV2 ephrim type-A receptor 8-like protein of the invention, shown as AL035703 Spliced2, with simuliar proteins. The various aligned proteins are as follows: AL035703 Spliced2 (SEQ ID NO:5) with several proteins: EPA8 Mouse (SEQ ID NO:54), EPA5 Human (SEQ ID NO:55) and EPA5 Chick (SEQ ID NO:56). (Black outlined amino acids indicate potential regions of conserved sequence; greyed amino acids represent amino acids conservatively substituted; and non-highlighted amino acids indicate positions in which mutations to a broad range of alternative amino acid residues occurs)

```
AL035703_Spliced2    -----MAPARGRLP----------------------PALWVVTAAAAATCVSAARC-E
EPA8_MOUSE           -----MAPARARLS----------------------PALWVVT-AAAATCVSAGRC-P
EPA5_HUMAN           MRGSCPRGAGHRREPSGGGDTPITPASLAGCYSAPRRAPLWTCLLLCAALRTILASPSNE
EPA5_CHICK           ---MGLRGGGGR---AGG---------------P---APGWTCLLLCAALRSLLASPGSE AL035703_Spliced2    VNLLDTSLIHGDWGWLTYEAHGWDSINEVDESFQPIHTYQVCNVMSPNQNNWLRTSWVPR
EPA8_MOUSE           VNLLDTSLIHGDWGWLTYEAHGWDSINEVDESFRPIHTYQVCNVMSPNQNNWLRINWVPR
EPA5_HUMAN           VNLLDSRIVMGDLGWIAFPKNGWEEIGEVDENYAPIHTYQVCKVMEQNQNNWLLTSWISN
EPA5_CHICK           VNLLDSRIVMGDLGWIAYPKNGWEEIGEVDENYAPIHTYQVCKVMEQNQNNWLLTSWISN AL035703_Spliced2    DGARRVYAEIKFTLRDCNSMPGVLGTCKETFNLYYLESDRDLGASTQESQFLKIDTIAAD
EPA8_MOUSE           DGARRVYAEIKFTLRDCNSLPGVLGTCKETFNLHYLESDRDLGASTQESQFLKIDTIAAD
EPA5_HUMAN           EGASRIFIELKFTLRDCNSLPGGLGTCKETFNMYYFESDDQNGRNIKENQYIKIDTIAAD
EPA5_CHICK           EGRPASSFELKFTLRDCNSLPGGLGTCKETFNMYYFESDDEDGRNIRENQYIKIDTIAAD AL035703_Spliced2    ESFTGADLGVRRLKLNTEVRSVGPLSKRGFYLAFQDIGACLAILSLRIYYKKCPAMVRNL
EPA8_MOUSE           ESFTGADLGVRRLKLNTEVRGVGPLSKRGFYLAFQDIGACLATESLRIYYKKCPAMVRNL
EPA5_HUMAN           ESFTELDLGDRVMKLNTEVRDVGPLSKKGFYLAFQDVGACLALVSVRMYYKKCPSVVRHL
EPA5_CHICK           ESFTELDLGDRVMKLNTEVRDVGPLIKKGFYLAFQDVGACLALVSVRMYYKKCPSVLRNL AL035703_Spliced2    AAFSLAVTGADSSSLVEVRGQCVRHSEERDTPKMYCSAEGEWLVPIGKCVCSAGYEERRD
EPA8_MOUSE           AAFSLAVTGADSSSLVEVRGQCVRHSEERDTPKMYCSAEGEWLVPIGKCVCSAGYEERRD
EPA5_HUMAN           AVEPDTITGADSSQLLEVSGSCVNHSVTDEPPKMHCSAEGEWLVPIGKCMCKAGYEEKNG
EPA5_CHICK           AREPDTITGADSSQLLEVSGVCVNHSVTDEAPKMHCSAEGEWLVPIGKCLCKAGYEEKNN AL035703_Spliced2    PVNLISSVNGTSVTLEWAPPLDPGGRSDITYNAVCRRCPWALSRCEACGSGTRVPQQTS
EPA8_MOUSE           PVNLISSVNGTSVTLEWAPPLDPGGRSDITYNAVCRRCPWALSHCEACGSGTRVPQQTS
EPA5_HUMAN           PRNAISNVNETSVFLEWIPPADTGGRKDVSYYIACKKCNSHAGVCEECGHVRYLPRQSG
EPA5_CHICK           PRSAISNVNETSVFLEWIPPADTGGRKDVSYYIACKKCNSHSGLCEACGSHVRYLPQQTG AL035703_Spliced2    LVQASLLVANLLAHMNYSEWIEAVNGVSDLSPEPRRAAVVNITTNQAAPSQVVVIRQERA
EPA8_MOUSE           LAQASLLVANLLAHMNYSEWIEAVNGVSNLSPEPRSAAVVNITTNQAAPSQVVVIRQERA
EPA5_HUMAN           LKNTSVMMVDLLAHTNYTFEIEAVNGVSDLSPGARQYVSVNVTTNQAAPSPVTNVKKGKI
EPA5_CHICK           LKNTSVMMVDLLAHTNYTFEIEAVNGVSDQNEGARQFVSVNVTTNQAAPSPVSSVKKGKI
```

NOV3

A

NOV3 nucleic acid sequence according to the invention includes nucleic acids encoding a polypeptide related to proteoglycans such as fibromodulin and fibronectin. An example of this nucleic acid and its encoded polypeptide is presented in Table 8. The disclosed nucleic acid sequence (SEQ ID NO:6) is 2025 nucleotides in length and contains an open reading frame that begins with an ATG initiation codon at nucleotides 1–3 and ends with a TGA stop codon at nucleotides 2023–2025.

The representative ORE includes a 674 amino acid polypeptide (SEQ ID NO: 7). The encoded polypeptide has a high degree of homology to several leucine-rich repeat members of the proteogylcan family found in the extracellular matrix including fibronectin (Table 9 human fibronectin like proteins, 99 percent to AAF28459.1 (Lacy et al., "Identification of FLRT1, FLRT2, and FLRT3: a novel family of transmembrane leucine-rich repeat proteins," 62(3) *Genomics* 417–426 (1999)) and fibromodulin (Table 10, various fibromodulin or fibromodulin-like proteins).

The extracellular matrix (ECM) is composed of collagens, protoglycans, and noncollagenous glycoproteins that provide cells and tissues with a mechanical scaffold for adhesion, migration, and signal transduction (Aumailley and Gayruad, 76(3–4) *J. Mol. Med.* 253–265 (1998)). These varied and complex functions depend on interactions between ECM components and cellular receptors such as protoglycans that are located on the cell surface. Fibronectins and fibromodulins are both protoglycans that comprise the extracellular matrix. Disruption of the cell-matrix interactions due to mutations in the genes of the matrix proteins can result in functional failures in all tissues (Bruckner-Tuderman and Bruckner, 76(3–4) *J. Mol. Med.* 76(3–4) 226–237(1998)). Included in these disorders are the congenital muscular dystrophies, various muscle disorders, fixed deformities (arthrogryposis), and abnormal white matter by cranial MRI.

Fibronectins are glycoproteins with 2 chains each linked by disulphide bonds that occur in insoluble fibrillar form in the extracellular matrix of animal tissues and soluble in plasma, the latter previously known as cold insoluble globulin. The various slightly different forms of fibronectin appear to be generated by tissue specific differential splicing of fibronectin mRNA, transcribed from a single gene. Fibronectins have multiple domains that confer the ability to interact with many extracellular substances such as collagen, fibrin and heparin and also with specific membrane receptors on responsive cells. Notable is the RGD domain recognized by integrins and two repeats of the EGF like domain. Interaction of a cell's fibronectin receptors (members of the integrin family) with fibronectin adsorbed to a surface results in adhesion and spreading of the cell.

Fibromodulin is collagen-binding protein component of the proteoglycan found in the extracellular matrix. It is mainly expressed in articular cartilage, tendon, and ligament, and is a member of a group of proteins having leucine-rich repeat (LRR) domains; fibromodulin includes as many as ten such motifs. Other components of this family include decorin, biglycan, and lumican. Proteins of this family bind to other matrix macromolecules and thereby help to stabilize the matrix. These proteins may also influence the function of the chondrocytes and bind growth factors.

The core proteins of these proteoglycans are structurally related, consisting of a central region composed of leucine-rich repeats flanked by disulfide-bonded terminal domains. Fibromodulin's central region possesses up to 4 keratan sulfate chains within its leucine-rich domain. Fibromodulin exhibits a wide tissue distribution, with the highest abundance observed in articular cartilage, tendon, and ligament. It has been suggested that fibromodulin participates in the assembly of the extracellular matrix by virtue of its ability to interact with type I and type II collagen fibrils and to inhibit fibrillogenesis in vitro. The 3-prime untranslated region of the fibromodulin cDNA has previously been cloned and used to map the gene by fluorescence in situ hybridization to 1q32. (Sztrolovics et al., 23 *Genomics* 715–717 (1994)). In that study, secondary signals were detected at 9q34.1; however, PCR analysis of somatic cell hybrids confirmed the localization to chromosome 1.

Small proteoglycans, including decorin, biglycan, and fibromodulin, bind to other matrix macromolecules and thereby help to stabilize the matrix. They may also influence the function of the chondrocytes and bind growth factors.

In a bovine nasal-cartilage culture system, it was found that interleukin-1 stimulated cartilage catabolism included the effect that the small leucine-rich repeat proteoglycans decorin, biglycan and lumican showed a resistance to both proteolytic cleavage and release throughout the culture period. In contrast, fibromodulin exhibited a marked decrease in size after day 4, presumably due to proteolytic modification (Sztrolovics R, et al., 339 (Pt 3) *Biochem. J.*, 571–577 (1999)).

The nucleic acids and proteins of the invention are useful in potential therapeutic applications implicated in various orthopedic disorders and/or injuries. They are potentially of use in aiding repair of damage to cartilage and ligaments, and in therapeutic applications to joint repair. Additionally they may be used in treatment of inflammatory diseases of connective tissue, including by way of nonlimiting example, rheumatoid arthritis, congenital muscular dystrophies, various muscle disorders, fixed deformities (arthrogryposis), and abnormal white matter. For example, a cDNA encoding the proteoglycan-like protein may be useful in gene therapy, and the proteoglycan-like protein may be useful when administered to a subject in need thereof. The novel nucleic acid encoding proteoglycan-like protein, and the proteoglycan-like protein of the invention, or fragments thereof, may further be useful in diagnostic applications, wherein the presence or amount of the nucleic acid or the protein are to be assessed. For example in identifying tissue from kidney or brain. These materials are further useful in the generation of antibodies that bind immunospecifically to the novel substances of the invention for use in therapeutic or diagnostic methods.

TABLE 8

A representative DNA sequence of the proteoglycan-like protein of the invention (SEQ ID NO:6)
ATGGTGGTGGCACACCCCACCGCCACTGCCACCACCACGCCCACTGCCACTGTCACGGCCACCGTTGTGA

TGACCACGGCCACCATGGACCTGCGGGACTGGCTGTTCCTCTGCTACGGGCTCATCGCCTTCCTGACGGA

GGTCATCGACAGCACCACCTGCCCCTCGGTGTGCCGCTGCGACAACGGCTTCATCTACTGCAACGACCGG

GGACTCACATCCATCCCCGCAGATATCCCTGATGATGCCACCACCCTCTACCTGCAGAACAACCAGATCA

ACAACGCCGGCATCCCCCAGGACCTCAAGACCAAGGTCAACGTGCAGGTCATCTACCTATACGAGAATGA

CCTGGATGAGTTCCCCATCAACCTGCCCCGCTCCCTCCGGGAGCTGCACCTGCAGGACAACAATGTGCGC

ACCATTGCCAGGGACTCGCTGGCCCGCATCCCGCTGCTGGAGAAGCTGCACCTGGATGACAACTCCGTGT

TABLE 8-continued

```
CCACCGTCAGCATTGAGGAGGACGCCTTCGCCGACAGCAAACAGCTCAAGCTGCTCTTCCTGAGCCGGAA

CCACCTGAGCAGCATCCCCTCGGGGCTGCCGCACACGCTGGAGGAGCTGCGGCTGGATGACAACCGCATC

TCCACCATCCCGCTGCATGCCTTCAAGGGCCTCAACAGCCTGCGGCGCCTGGTGCTGGACGGTAACCTGC

TGGCCAACCAGCGCATCGCCGACGACACCTTCAGCCGCCTACAGAACCTCACAGAGCTCTCGCTGGTGCG

CAATTCGCTGGCCGCGCCACCCCTCAACCTGCCCAGCGCCCACCTGCAGAAGCTCTACCTGCAGGACAAT

GCCATCAGCCACATCCCCTACAACACGCTGGCCAAGATGCGTGAGCTGGAGCGGCTGGACCTGTCCAACA

ACAACCTGACCACGCTGCCCCCCGGCCTGTTCGACGACCTGGGGAACCTGGCCCAGCTGCTGCTCAGGAA

CAACCCTTGGTTTTGTGGCTGCAACCTCATGTGGCTGCGGGACTGGGTGAAGGCACGGGCGGCCGTGGTC

AACGTGCGGGGCCTCATGTGCCAGGGCCCTGAGAAGGTCCGGGGCATGGCCATCAAGGACATTACCAGCG

AGATGGACGAGTGTTTTGAGACGGGGCCGCAGGGCGGCGTGGCCAATGCGGCTGCCAAGACCACGGCCAG

CAACCACGCCTCTGCCACCACGCCCCAGGGTTCCCTGTTTACCCTCAAGGCCAAAAGGCCAGGGCTGCGC

CTCCCCGACTCCAACATTGACTACCCCATGGCCACGGGTGATGGCGCCAAGACCCTGGCCATCCACGTGA

AGGCCCTGACCGCAGACTCCATCCGCATCACGTGGAAGGCCACGCTCCCCGCCTCCTCTTTCCGGCTCAG

TTGGCTGCGCCTGGGCCACAGCCCAGCCGTGGCTCCATCACGGAGACCTTGGTGCAGGGGGACAAGACA

GAGTACCTGCTGACAGCCCTGGAGCCCAAGTCCACCTACATCATCTGCATGGTCACCATGGAGACCAGCA

ATGCCTACGTAGCTGATGAGACACCCGTGTGTGCCAAGGCAGAGACAGCCGACAGCTATGGCCCTACCAC

CACACTCAACCAGGAGCAGAACGCTGGCCCCATGGCGAGCCTGCCCCTGGCGGGCATCATCGGCGGCGCA

GTGGCTCTGGTCTTCCTCTTCCTGGTCCTGGGGGCCATCTGCTGGTACGTGCACCAGGCTGGCGAGCTGC

TGACCCGGGAGAGGGCCTACAACCGGGGCAGCAGGAAAAAGGATGACTATATGGAGTCAGGGACCAAGAA

GGATAACTCCATCCTGGAAATCCGCGGCCCTGGGCTGCAGATGCTGCCCATCAACCCGTACCGCGCCAAA

GAGGAGTACGTGGTCCACACTATCTTCCCCTCCAACGGCAGCAGCCTCTGCAAGGCCACACACACCATTG

GCTACGGCACCACGCGGGGCTACCGGGACGGCGGCATCCCCGACATAGACTACTCCTACACATGA
```

A representative amino acid sequence of the proteoglycan-like protein of the invention (SEQ ID NO: 7)
MVVAHPTATATTTPTATVTATVVMTTATMDLRDWLFLCYGLIAFLTEVIDSTTCPSVCRCDNGFIYCNDR

GLTSIPADIPDDATTLYLQNNQINNAGIPQDLKTKVNVQVIYLYENDLDEFPINLPRSLRELHLQDNNVR

TIARDSLARIPLLEKLHLDDNSVSTVSIEEDAFADSKQLKLLFLSRNHLSSIPSGLPHTLEELRLDDNRI

STIPLHAFKGLNSLRRLVLDGNLLANQRIADDTFSRLQNLTELSLVRNSLAAPPLNLPSAHLQKLYLQDN

AISHIPYNTLAKMRELERLDLSNNNLTTLPRGLFDDLGNLAQLLLRNNPWFCGCNLMWLRDWVKARAAVV

NVRGLMCQGPEKVRGMAIKDITSEMDECFETGPQGGVANAAAKTTASNHASATTPQGSLFTLKAKRPGLR

LPDSNIDYPMATGDGAKTLAIHVKALTADSIRITWKATLPASSFRLSWLRLGHSPAVGSITETLVQGDKT

EYLLTALEPKSTYIICMVTMETSNAYVADETPVCAKAETADSYGPTTTLNQEQNAGPMASLPLAGIIGGA

VALVFLFLVLGAICWYVHQAGELLTRERAYNRGSRKKDDYMESGTKKDNSILEIRGPGLQMLPINPYRAK

EEYVVHTIFPSNGSSLCKATHTIGYGTTRGYRDGGIPDIDYSYT

TABLE 9

Multiple sequence and BLAST alignment of a NOV3 polypeptide and the human fibronectin leucine repeat transmembrane family.

Table 9 shows sequence alignment between a NOV3 polypeptide with several members of the human fibronectin leucine repeat transmembrane family: AAF28461.1|AF169 (SEQ ID NO:57), AAF28460.1|AF169 (SEQ ID NO:58) and AAF28459.1|AF169 (SEQ ID NO:59). (Black outlined amino acids indicate potential regions of conserved sequence; greyed amino acids represent amino acids conservatively substituted; and non-highlighted amino acids indicate positions in which mutations to a broad range of alternative amino acid residues occurs).

TABLE 9-continued

Multiple Sequence and BLAST alignment of a NOV3 polypeptide and the human fibronectin leucine repeat transmembrane family.

Table 9 shows sequence alignment between a NOV3 polypeptide with several members of the human fibronectin leucine repeat transmembrane family: AAF28461.1|AF169 (SEQ ID NO:57), AAF28460.1|AF169 (SEQ ID NO:58) and AAF28459.1|AF169 (SEQ ID NO:59). (Black outlined amino acids indicate potential regions of conserved sequence; greyed amino acids represent amino acids conservatively substituted; and non-highlighted amino acids indicate positions in which mutations to a broad range of alternative amino acid residues occurs).

```
          390       400       410       420       430       440       450       460       470       480
          ....|....|....|....|....|....|....|....|....|....|....|....|....|....|....|....|....|....|....|....|
AAF28461.1|AF169  277           SN       D  H  H       KM      QSH VK     A                   A  FE KDS ------
AAF28460.1|AF169  367 ---IVSTIQI
AAF28460.1|AF169  282 H  QRM  T  V  N S  K TA     D SH   TH   YH SSL   F    Q          MRE  MN LS PH T GLPLFTPAPSH SP
AAF28459.1|AF169  300                                                                                        381
NOV3              300                                                                          395

490       500       510       520       530       540       550       560       570       580
          ....|....|....|....|....|....|....|....|....|....|....|....|....|....|....|....|....|....|....|....|
AAF28461.1|AF169  368                                                                      F       H RS      V  467
TAIPNTVYPA  QWPA VT Q DEKN KLTK HQTPGS SR   H S S H    LA MT L
AAF28460.1|AF169  382                                                                                        481
QPPTL  EPN SR YTP PTIPDWDGRERV P LSER Q SIHF NDT QV LSLFTYM KK H V M LVG  I Q R S    QHLS V
AAF28459.1|AF169  396                                                                                        495
NOV3              396                                                                                        495

590       600
          ....|....|....|....|....|....|....|....|....|....|....|....|....|....|....|....|....|....|....|....|
AAF28461.1|AF169  468           D P KY      LLF    HT  PLRM - N    R  EKE  YKNPN      A         TTA A-
LV     RNN S F NC 565
AAF28460.1|AF169  482 N   R    R   H  LDAF - R V DTH S  THA YNN SN AS H   T SHSMGSPFL    IF LVV S-
VF  HM KK RYT QKWK 579
AAF28459.1|AF169  496                                                        590
NOV3              496                                                        590
```

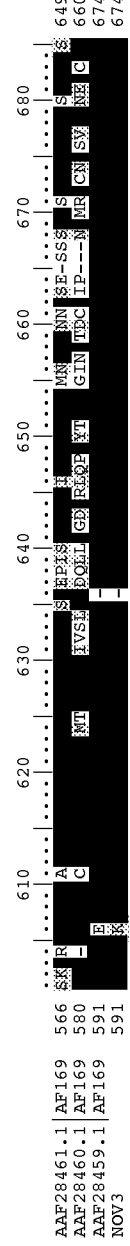

TABLE 9-continued

Multiple sequence and BLAST alignment of a NOV3 polypeptide and the human fibronectin leucine repeat transmembrane family.

Table 9 shows sequence alignment between a NOV3 polypeptide with several members of the human fibronectin leucine repeat transmembrane family: AAF28461.1|AF169 (SEQ ID NO:57), AAF28460.1|AF169 (SEQ ID NO:58) and AAF28459.1|AF169 (SEQ ID NO:59). (Black outlined amino acids indicate potential regions of conserved sequence; greyed amino acids represent amino acids conservatively substituted; and non-highlighted amino acids indicate positions in which mutations to a broad range of alternative amino acid residues occurs).

```
NOV3:   361  EKVRGMAIKDITSEMDECFETGPQGGVANAAAKTTASNHASATTPQGSLFTLKAKRPGLR   420
             ||||||||||||||||||||||||||||||||||||||||||||||||||||||||||||
Sbjct:  361  EKVRGMAIKDITSEMDECFETGPQGGVANAAAKTTASNHASATTPQGSLFTLKAKRPGLR   420

NOV3:   421  LPDSNIDYPMATGDGAKTLAIHVKALTADSIRITWKATLPASSFRLSWLRLGHSPAVGSI   480
             |||||||||||||||||||||||||||||||||||||||||||| |||||||||||||||
Sbjct:  421  LPDSNIDYPMATGDGAKTLAIHVKALTADSIRITWKATLPASSFPWSWLRLGHSPAVGSI   480

NOV3:   481  TETLVQGDKTEYLLTALEPKSTYIICMVTMETSNAVVADETPVCAKAETADSYGPTTTLN   540
             ||||||||||||||||||||||||||||||||||||||||||||||||||||||||||||
Sbjct:  481  TETLVQGDKTEYLLTALEPKSTYIICMVTMETSNAVVADETPVCAKAETADSYGPTTTLN   540

NOV3:   541  QEQNAGPMASLPLAGIIGGAVALVFLFLVLGAICWVHQAGELLITRERAYNRGSRKKDDY   600
             ||||||||||||||||||||||||||||||||||||||||||||||+|||
Sbjct:  541  QEQNAGPMASLPLAGIIGGAVALVFLFLVLGAICWVHQAGELLITRERAYNRGSREKDDY   600

NOV3:   601  MESGTKKDNSILEIRGPGLQMLPINPYRAKEYVVHTIFPSNGSSLCKATHTIGYGTTRG   660
             ||||||||||||||||||||||||||||||||||||||||||||||||||||||||||||
Sbjct:  601  MESGTKKDNSILEIRGPGLQMLPINPYRAKEYVVHTIFPSNGSSLCKATHTIGYGTTRG   660

NOV3:   661  YRDGGIPDIDYISYT   674
             |||| ||||||||||
Sbjct:  661  YRDCGIPDIDYISYT   674
```

TABLE 10

Multiple Sequence alignment between NOV3 polypeptide and various fibromodulins
(NOV3 is denoted AP000597_GENSCAN_3)
Table 10 shows sequence alignment between a NOV3 polypeptide with various fribromodu-
lins: ACC NO: O43408 (SEQ ID NO:61), ACC NO: AP000597 (SEQ ID NO:7), ACC NO: O43155
(SEQ ID NO:62), ACC NO: O42235 (SEQ ID NO:63) and FMOD Bovin FM (SEQ ID NO:64). (Black
outlined amino acids indicate potential regions of conserved sequence; greyed amino
acids represent amino acids conservatively substituted; and non-highlighted amino
acids indicate positions in which mutations to a broad range of alternative amino
acid residues occurs)

```
O43408_Human_Hypothetical  ------------------------------------------------------------
AP000597_GENSCAN_3         LSNNNLTHLPRGLFPDLGNLAQLLLRNNEWFCGCNLMWLRDWVKARAAVVNVRGLMCQGP
O43155_Human_KIA           ISNNQLRMLTQGVFDNLSNLKQLTARNNEWFCDCSIKWVTEWLKYIPDDLNVRGFMCQGP
O42235_Chicken_KSP         VHSVWTRIVRQVYNELDPEHWSHYTFECEQECFCPPSFPNALYCDNKGLKEIP----AIP
FMOD_BOVIN_FM              PYEP-YPIGEEGPAYAYGSPPQPEPRDCEQECDCPPNFPTAMYCDNRNLKYLP----FVE O43408_Human_Hypothetical  ------------------------------------------------------------
AP000597_GENSCAN_3         EKVRGMAIKDITSEMDECFETGP----QGGVANAAAKTTASNHASATTPQGSLFTLKAKR
O43155_Human_KIA           EQVRGMAVRELNMNLLSCPTTTPGLPLTTPAPSTASPTTQPPTLSIPNPSRSYTPPTPTT
O42235_Chicken_KSP         ARIW---YLYLQNNLIETISEKP----FVNATHLRWINLNKNKITNNGIESGVLSKLKRL
FMOD_BOVIN_FM              SRMK---YVYFQNNQISSIQEGV----EDNATGLLWIALHGNQITSDKVGKKVFSKLRHL O43408_Human_Hypothetical  ------------PMAIGDGAKTLAIHVKALTADSIRTIWKATLPASSFRLSWLRLGHSPA
AP000597_GENSCAN_3         PGLRLPDSNIDYPMAIGDGAKTLAIHVKALTADSIRITWKATLPASSFRLSWLRLGHSPA
O43155_Human_KIA           SKLPTIPDWDGRERVIPEISERIQLSIHFVNDTSLQVSWLSLFTVMAYKLTWVKMGHSLV
O42235_Chicken_KSP         LYLFLEDN----ELEEVPAPLPVGIEQLRLARNKISRIPEGVFSNLENLTMLDLHQNNLL
FMOD_BOVIN_FM              ERLYLDHN----NLTRIESPLPRSLRELHLDHNQLSRVPNNALEGLENLTALYLHHNEIQ O43408_Human_Hypothetical  VGSITETILVQGDKTEYLLTALEPKSTYIICMVTMETSNAYVADETPVCAKAETADSY---
AP000597_GENSCAN_3         VGSITETILVQGDKTEYLLTALEPKSTYIICMVTMETSNAYVADETPVCAKAETADSY---
O43155_Human_KIA           GGIVQDRIVSGEKQHLSLVNLEPRSTYRICLVPLDAFN-YRAVEDTICSEATTHASYLNN
O42235_Chicken_KSP         DSALQSDTFQGLNSLMQLNIAKNSLKKMPLSIPANTLQ-LFLDNNSIEVIPENYFSA--I
FMOD_BOVIN_FM              E---VGSSMKGLRSLILLDLSYNHLRKVPDGLPSALEQ-LYLEHNNVFSVPDSYFRG--S O43408_Human_Hypothetical  GPTITLNQEQNAGPMASLP--LAGIIGGAVALVFLFLVLGAICWYVHQAGELLIRERAYN
AP000597_GENSCAN_3         GPTITLNQEQNAGPMASLP--LAGIIGGAVALVFLFLVLGAICWYVHQAGELLIRERAYN
O43155_Human_KIA           GSNIASSHEQTTSHSMGSPFLLAGKIGGAVIFVLVVLLS-VFCWHMHKKCRYTSQKWKYN
O42235_Chicken_KSP         PKVLFLRLNYNKLSDDGIP-----PNGFNVSSLIDLQLS--------HN--QITKIPPINA
FMOD_BOVIN_FM              PKLLYVRLSHNSLTNNGIA-----SNTFNSSSILELDLS--------YN--QLQKIPPVST O43408_Human_Hypothetical  RGSRKKDDYMESGTKKDNSILEIRGPGLQMLPIN-PYRAKELYVVHTIFPSNGSSLCKAT
AP000597_GENSCAN_3         RGSRKKDDYMESGTKKDNSILEIRGPGLQMLPIN-PYRAKELYVVHTIFPSNGSSLCKAT
O43155_Human_KIA           RG-RRKDDYCEAGTKKDNSILEMTETSPQIVSLNNDQLLKGDIRLQPIYTPNGGINYTDC
O42235_Chicken_KSP         HLEHLHLDHNRIKSVNGTQICPVS------IAVAEDYGLYGNIPRLRYLRLDG--NEIQP
FMOD_BOVIN_FM              NLENLYLQGNRINEFSISSFCTVVD---------------VMNFSKLQVQRLDGN-EIKRS O43408_Human_Hypothetical  HTIGYGTTRGYRDGGIPDIDYSYT
AP000597_GENSCAN_3         HTIGYGTTRGYRDGGIPDIDYSYT
O43155_Human_KIA           HIP---NNMRYCNSSVPDLEHCHT
O42235_Chicken_KSP         PIP---LDIMICFQLLQAVVI---
FMOD_BOVIN_FM              AMP---ADAPLCLRLASLIEI---
```

NOV4

A NOV4 nucleic acid according to the invention includes nucleic acids encoding a polypeptide related to ephrin type-A receptors. An example of nucleic acid and its encoded polypeptide is presented in Table 11. The disclosed nucleic acid (SEQ ID NO: 65) is 1545 nucleotides in length.

The representative ORF includes a 515 amino acid polypeptide (SEQ ID NO: 66). The encoded polypeptide has a high degree of homology (approximately 95 percent identity) with mouse ephrin type-A receptor 8. NOV4 is a sequence variant of NOV2 and, as such, is a member of the ephrin type-A receptor tyrosine-protein kinase family.

The Eph receptors constitute the largest known family of receptor protein tyrosine kinases. They have been implicated in mediating developmental events, particularly in the nervous system. Receptors in the Eph subfamily typically have a single kinase domain and an extracellular region containing a Cys-rich domain and two fibronectin type III repeats. These receptors play important roles along with their ligands, called ephrins, in neural development, angiogenesis, and vascular network assembly. (S. Choi et al., 9(4) *Mol. Cells* 440–45 (1999)).

The ephrin type-A receptor 8 (EC 2.7.1.112) (tyrosine-protein kinase receptor eek) (eph- and elk-related kinase) (fragment) is designated as the gene product of the gene: epha8 or eek. It is a Type I membrane bound receptor, and its function is to serve as a receptor for members of the ephrin-a family. Its catalytic activity is as a protein tyrosine kinase, phosphorylating tyrosine in appropriate target proteins. It is similar to other protein-tyrosine kinases in the catalytic domain and belongs to the ephrin receptor family.

Eph receptors have tyrosine-kinase activity, and, together with their ephrin ligands, mediate contact-dependent cell interactions that are implicated in the repulsion mechanisms that guide migrating cells and neuronal growth cones to specific destinations. Since Eph receptors and ephrins have complementary expression in many tissues during embryogenesis, bidirectional activation of Eph receptors may occur at interfaces of their expression domains, for example, at segment boundaries in the vertebrate hindbrain. Indeed, Eph receptors play key roles in development of the nervous system and angiogenesis. In the nervous system, they provide positional information by empolying mechanisms that involve repulsion of migrating cells and growing axons (Frisen et al., 18(19) *EMBO J.* 5159–5165 (1999)). Also, an important function of Eph receptors and ephrins is to mediate cell-contact-dependent repulsion.

A NOV4 sequence according to the invention is useful for detecting cells that express GPI-anchored ephrin-A ligands. For example, cells expressing either a NOV4 nucleic acid or a NOV4 protein have utility in screening for other cells that express GPI-anchored ephrin-A ligands or mimics therefore. As a result, a NOV4 sequence is useful for screening for new ephrin-A ligands expressed on cells. NOV4 is highly expressed in many surgical tumor samples; therefore, the NOV4 expression can be used as a marker for certain cancers.

Also, a NOV4 sequence according to the invention is useful to direct the development of the nervous system and angiogenesis by modulating the boundaries between arteries and veins. For example, mice expressing defective Eph receptors similar to a NOV4 sequence have been shown to be defective in angiogensis and die in mid-gestation (Wang et al., 93 Cell 741–753 (1998)). The protein of the present invention will be useful in a variety of diseases and pathologies, including by way of nonlimiting example, those involving neurological, cardiac and vascular pathologies.

NOV4 exhibited highest levels of expression in TAQ-MAN$^R$ Reverse Transcription runs in testis (100%), 85976 Breast Cancer Mets (100%), breast cancer Res. Gen. (90%), 94909-XF-498-CNS-ssDNA (100%) and dermal fibroblast-IL-4 (100%) cell lines. Lower but consistent levels of expression were obtained in breast cancer (pl. effusion) T47D cells (15%), melanoma UACC-62 (10%), breast cancer Clontech 9100266 (38%), 94925-NCI-H1155-large cell lung cancer/neuroendocrine-ss cDNA (21%), 94923-NCI-H82-small cell lung cancer/neuroendocrine-ss cDNA (18%), 94918-DMS-79-small cell lung cancer/neuroendocrine-ss cDNA (19%) and normal prostate clontech A+ 6546-1 (20%) cell lines. These results differ to some degree from the parent clone, NOV2, which did not exhibit high levels of expression in central nervous system, testis and fibroblast tissue, but did exhibit positive levels of expression in cancer cell lines. Such differences in expression reflect the distinction among variants. It is noteworthy that clone NOV4 is minimally or not detectably found in the immediate normal tissue adjacent to breast and lung tissue.

TABLE 11

A representative DNA sequence encoding the ephrin type-A receptor 8-like protein of the invention.

(SEQ ID NO: 65)

GCGCGCGGCGAAGTGAATTTGCTGGACACGTCGACCATCCACGGGGACTGGGGCTGGCTC

ACGTATCCGGCTCATGGGTGGGACTCCATCAACGAGGTGGACGAGTCCTTCCAGCCCATC

CACACGTACCAGGTTTGCAACGTCATGAGCCCCAACCAGAACAACTGGCTGCGCACGAGC

TGGGTCCCCCGAGACGGCGCCCGGCGCGTCTATGCTGAGATCAAGTTTACCCTGCGCGAC

TGCAACAGCATGCCTGGTGTGCTGGGCACCTGCAAGGAGACCTTCAACCTCTACTACCTG

GAGTCGGACCGCGACCTGGGGGCCAGCACACAAGAAAGCCAGTTCCTCAAAATCGACACC

ATTGCGGCCGACGAGAGCTTCACAGGTGCCGACCTTGGTGTGCGGCGTCTCAAGCTCAAC

ACGGAGGTGCGCAGTGTGGGTCCCCTCAGCAAGCGCGGCTTCTACCTGGCCTTCCAGGAC

ATAGGTGCCTGCCTGGCCATCCTCTCTCTCCGCATCTACTATAAGAAGTGCCCTGCCATG

GTGCGCAATCTGGCTGCCTTCTCGGAGGCAGTGACGGGGCCGACTCGTCCTCACTGGTG

GAGGTGAGGGGCCAGTGCGTGCGGCACTCAGAGGAGCGGGACACACCCAAGATGTACTGC

AGCGCGGAGGGCGAGTGGCTCGTGCCCATCGGCAAATGCGTGTGCAGTGCCGGCTACGAG

GAGCGGCGGGATGCCTGTGTGGCCTGTGAGCTGGGCTTCTACAAGTCAGCCCCTGGGGAC

CAGCTGTGTGCCCGCTGCCCTCCCCACAGCCACTCCGCAGCTCCAGCCGCCCAAGCCTGC

CACTGTGACCTCAGCTACTACCGTGCAGCCCTQGACCCGCCGTCCTCAGCCTGCACCCGG

CCACCCTCGGCACCAGTGAACCTGATCTCCAGTGTGAATGGGACATCAGTGACTCTGGAG

TGGGCCCCTCCCCTGGACCCAGGTGGCCGCAGTGACATCACCTACAATGCCGTGTGCCGC

A representative amino acid sequence encoding the ephrin type-A receptor 8-like protein of the invention (SEQ ID NO: 66)

ARGEVNLLDTSTIHGDWGWLTYPAHGWDSJNEVDESFQPIHTYQVCNVMSPNQNNWLRTS

WVPRDGARRVYAEIKFTLRDCNSMPGVLGTCKETFNLYYLESDRDLGASTQESQFLKIDT

IAADESFTGADLGVRRLKLNTEVRSVGPLSKRGFYLAFQDIGACLAILSLRIYYKKCPAM

VRNLAAFSEAVTGADSSSLVEVRGQCVRHSEERDTPKMYCSAEGEWLVPIGKCVCSAGYE

ERRDACVACELGFYKSAPGDQLCARCPPHSHSAAPAAQACHCDLSYYRAALDPPSSACTR

PPSAPVNLISSVNGTSVTLEWAPPLDPGGRSDITYNAVCRRCPWALSRCEACGSGTRFVP

TABLE 11-continued

```
QQTSLVQASLLVANLLAHMNYSFWIEAVNGVSDLSPEPRRAAVVNITTNQAAPSQVVVIR

QERAGQTSVSLLWQEPEQPNGIILEYEIKYYEKDKEMQSYSTLKAVTTRATVSGLKPGTR

YVFQVRARTSAGCGRFSQAMEVETGKPRLPRYDTRT
```

NOV5

A NOV5 nucleic acid sequence according to the invention includes nucleic acids encoding a polypeptide related to members of the proteoglycan family and specifically to fibromodulin. An example of this nucleic acid and its encoded polypeptide is presented in Tables 12 and 13. The disclosed nucleic acid sequence (SEQ ID NO: 67) is 2660 nucleotides in length and contains an open reading frame (ORF) that begins with an ATG initiation codon at nucleotides 1–3 and ends with an ATG stop codon at nucleotides 1993–1995. The representative ORF includes a 664 amino acid polypeptide (SEQ ID NO: 68) and is flanked by putative untranslated regions, if any, upstream from the initiation codon and downstream from the termination codon. The encoded polypeptide has a high degree of homology to several leucine-rich repeat members of the proteoglycan family found in the extracellular matrix including fibronectin.

The extracellular matrix (ECM) is composed of collagens, protoglycans, and noncollagenous glycoproteins that provide cells and tissues with a mechanical scaffold for adhesion, migration, and signal transduction (Aumailley and Gayruad 76(3–4) *J. Mol. Med.* 253–265). These varied and complex functions depend on interactions between ECM components and cellular receptors such as protoglycans that are located on the cell surface. The fibromodulin-like gene disclosed in this invention is expressed in at least cartilage, tendon and ligament tissues. Fibronectins and fibromodulins are both protoglycans that comprise the extracellular matrix. Disruption of the cell-matrix interactions due to mutations in the genes of the matrix proteins can result in functional failures in all tissues (Bruckner-Tuderman and Bruckner 76(3–4) *J. Mol. Med.* 226–237(1998)). Included in these disorders are the congenital muscular dystrophies, various muscle disorders, fixed deformities (arthrogryposis), and abnormal white matter by cranial MRI.

Fibronectins are glycoproteins with 2 chains each linked by disulphide bonds that occur in insoluble fibrillar form in the extracellular matrix of animal tissues and soluble in plasma, the latter previously known as cold insoluble globulin. The various slightly different forms of fibronectin appear to be generated by tissue specific differential splicing of fibronectin mRNA, transcribed from a single gene. Fibronectins have multiple domains that confer the ability to interact with many extracellular substances such as collagen, fibrin and heparin and also with specific membrane receptors on responsive cells. Notable is the RGD domain recognized by integrins and two repeats of the EGF like domain. Interaction of a cell's fibronectin receptors (members of the integrin family) with fibronectin adsorbed to a surface results in adhesion and spreading of the cell.

Fibromodulin is collagen-binding protein component of the proteoglycan found in the extracellular matrix. It is mainly expressed in articular cartilage, tendon, and ligament, and is a member of a group of proteins having leucine-rich repeat (LRR) domains; fibromodulin includes as many as ten such motifs. Other components of this family include decorin, biglycan, and lumican. Proteins of this family bind to other matrix macromolecules and thereby help to stabilize the matrix. These proteins may also influence the function of the chondrocytes and bind growth factors.

The core proteins of these proteoglycans are structurally related, consisting of a central region composed of leucine-rich repeats flanked by disulfide-bonded terminal domains. Fibromodulin's central region possesses up to 4 keratan sulfate chains within its leucine-rich domain. Fibromodulin exhibits a wide tissue distribution, with the highest abundance observed in articular cartilage, tendon, and ligament. It has been suggested that fibromodulin participates in the assembly of the extracellular matrix by virtue of its ability to interact with type I and type II collagen fibrils and to inhibit fibrillogenesis in vitro. The 3-prime untranslated region of the fibromodulin cDNA has previously been cloned and used to map the gene by fluorescence in situ hybridization to 1q32. (Sztrolovics et al., 23 *Genomics* 715–717(1994)). In that study, secondary signals were detected at 9q34.1; however, PCR analysis of somatic cell hybrids confirmed the localization to chromosome 1.

Small proteoglycans, including decorin, biglycan, and fibromodulin, bind to other matrix macromolecules and thereby help to stabilize the matrix. They may also influence the function of the chondrocytes and bind growth factors.

In a bovine nasal-cartilage culture system, it was found that interleukin-1 stimulated cartilage catabolism included the effect that the small leucine-rich repeat proteoglycans decorin, biglycan and lumican showed a resistance to both proteolytic cleavage and release throughout the culture period. In contrast, fibromodulin exhibited a marked decrease in size after day 4, presumably due to proteolytic modification (Sztrolovics et al.,339(Pt3) *Biochem. J.,* 571–577, (1999)).

The nucleic acids and proteins of the invention are useful in potential therapeutic applications implicated in various orthopedic disorders and/or injuries. They are potentially of use in aiding repair of damage to cartilage and ligaments, and in therapeutic applications to joint repair. Additionally they may be used in treatment of inflammatory diseases of connective tissue, including by way of nonlimiting example, rheumatoid arthritis, congenital muscular dystrophies, various muscle disorders, fixed deformities (arthrogryposis), and abnormal white matter. NOV5 has utility similar to that of NOV3, and may be found in skeletal tissue, carcinoid lung tumors, arthritis and tendonitis as examples. Thus, a cDNA encoding the proteoglycan-like protein may be useful in gene therapy, and the proteoglycan-like protein may be useful when administered to a subject in need thereof. The novel nucleic acid encoding proteoglycan-like protein, and the proteoglycan-like protein of the invention, or fragments thereof, may further be useful in diagnostic applications, wherein the presence or amount of the nucleic acid or the protein are to be assessed as for example, in identifying tissue from kidney or brain. These materials are further useful in the generation of antibodies that bind immunospecifically to the novel substances of the invention for use in therapeutic or diagnostic methods.

NOV5 maps to chromosome 11q12–13. This assignment was made using mapping information associated with genomic clones, public genes and ESTs sharing sequence identity with the disclosed sequence and CuraGen Corporation's Electronic Northern bioinformatic tool.

NOV5 is expressed in at least the following tissues: cartilage, tendon, and ligament. Expression information was derived from the tissue sources of the sequences that were included in the derivation of the sequence of NOV5.

The disclosed NOV5 nucleic acid of 1992 nucleotides encoding a novel Fibromodulin-like protein is shown in Table 12. An open reading frame was identified beginning at nucleotides 1–3, which results in a polypeptide that is a novel functional Fibromodulin-like protein. The start codon of the open reading frame is highlighted in bold type. Putative untranslated regions (underlined), if any, are found upstream from the initiation codon and downstream from the termination codon. The encoded protein having 664 amino acid residues is presented using the one-letter code in Table 13.

TABLE 12

A representative nucleotide sequence encoding the fibromodulin-like protein of the invention.

>CG54254_02 (SEQ ID NO:67)
ATGGTGGTGGCACACCCCACCGCCACTGCCACCACCACGCCCACTGCCACTGTCACGGCCACCGTTGT

GATGACCACGGCCACCATGGACCTGCGGGACTGGCTGTTCCTCTGCTACGGGCTCATCGCCTTCCTGAC

GGAGGTCATCGACAGCACCACCTGCCCCTCGGTGTGCCGCTGCGACAACGGCTTCATCTACTGCAACG

ACCGGGACTCACATCCATCCCCGCAGATATCCCTGATGATGCCACCACCCTCTACCTGCAGAACAAC

CAGATCAACAACGCCGGCATCCCCCAGGACCTCAAGACCAAGGTCAACGTGCAGGTCATCTACCTATA

CGAGAATGACCTGGATGAGTTCCCCATCAACCTGCCCCGCTCCCTCCGGGAGCTGCACCTGCAGGACA

ACAATGTGCGCACCATTGCCAGGGACTCGCTGGCCCGCATCCCGCTGCTGGAGAAGCTQCACCTGGAT

GACAACTCCGTGTCCACCGTCAGCATTGAGGAGGACGCCTTCGCCGACAGCAAACAGCTCAAGCTGCT

CTTCCTGAGCCGGAACCACCTGAGCAGCATCCCCTCGGGGCTGCCGCACACGCTGGAGGAGCTGCGGC

TGGATGACAACCGCATCTCCACCATCCCGCTGCATGCCTTCAAGGGCCTCAACAGCCTGCGGCGCCTG

GTGCTGGACGGTAACCTGCTGGCCAACCAGCGCATCGCCGACGACACCTTCAGCCGCCTACAGAACCT

CACAGAGCTCTCGCTGGTGCGCAATTCGCTGGCCGCGCCACCCCTCTACCTGCAGGACAATGCCATCA

GCCACATCCCCTACAACACGCTGGCCAAGATGCGTGAGCTGGAGCGGCTGGACCTGTGCAACAACAAC

CTGACCACGCTGCCCCGCGGCCTGTTCGACGACCTGGGGAACCTGGCCCAGCTGCTGCTCAGGAACAA

CCCTTGGTTTTGTGGCTGCAACCTCATGTGGCTGCGGGACTGGGTGAAGGCACGGGCGGCCGTGGTCA

ACGTGCGGGGCCTCATGTGCCAGGGCCCTGAGAAGGTCCGGGGCATGGCCATCAAGGACATTACCAG

CGAGGTGGAGAGTGTTTTGAGACGGGCGCCGCAGGGCGGCGTGGCCAATGCGGCTGCCAAGACCACG

GCCAGCAACCACGCCTCTGCCAGCACGCCCCAGGGTTCCCTGTTTACCCTCAAGGCCAAAAGGCCAGG

GCTGCGCCTCCCCGACTCCAACATTGACTACCCCATGGCCACGGGTGATGGCGCCAAGACCCTGGCCA

TCCACGTGAAGGCCCTGACGGCAGACTCCATCCGCATCACGTGGAAGGCCACGCTCCCCGCCTCCTCT

TTCCGGCTCAGTTGGCTGCGCCTGGGCCACAGCCCAGCCGTGGGCTCCATCACGGAGACCTTGGTGCA

GGGGGACAAGACAGAGTACCTGCTGACAGCCCTGGAGCCCAAGTCCACCTACATCATCTGCATGGTCA

CCATGGAGACCAGCAATGCCTACGTAGCTGATGAGACACCCGTGTGTGCCAAGGCAGAGACAGCCGA

CAGCTATGGCCCTACCACCACACTCAACCAGGAGCAGAACGCTGGCCCCATGGCGAGCCTGCCCCTGG

CGGGCATCATCGGCGGGGCAGTGGCTCTGGTCTTCCTCTTCCTGGTCCTGGGGGCCATCTGCTGGTACG

TGCACCAGGCTGGCGAGCTGCTGACCCGGGAGAGGGCCTACAACCGGGGCAGCAGGAAAAAGGATGA

CTATATGGAGTCAGGGACCAAGAAGGATAACTCCATCCTGGAAATCCGCGGCCCTGGGCTGCAGATGC

TGCCCATCAACCCGTACCGCGCCAAAGAAGAGTACGTGGTCCACACTATCTTCCCCTCCAACGGCAGC

AGCCTCTGCAAGGCCACACACACCATTGGCTACGGCACCACGCGGGGCTACCGGGACGGCGGCATCC

CCGACATAGACTACTCCTACACA

TABLE 13

Representative amino acid sequence of the fibromodulin-like protein of the invention.

>CG54254_02 (SEQ ID NO:68)
MVVAHPTATATTTPTATVTATVVMTTATMDLRDWLFLCYGLIAFLTEVIDSTTCPSVCRC

DNGFIYCNDRGLTSIPADIPDDATTLYLQNNQINNAGIPQDLKTKVNVQVIYLYENDLDE

FPINLPRSLRELHLQDNNVRTIARDSLARIPLLEKLHLDDNSVSTVSIEEDAFADSKQLK

LLFLSRNHLSSIPSGLPHTLEELRLDDNRISTIPLHAFKGLNSLRRLVLDGNLLANQRIA

DDTFSRLQNLTELSLVRNSLAAPPLYLQDNAISHIPYNTLAKMRELERLDLSNNNLTTLP

RGLFDDLGNLAQLLLRNNPWFCGCNLMWLRDWVKARAAVVNVRGLMCQGPEKVRGMAIKD

ITSEVESVLRRAPQGGVANAAAKTTASNHASATTPQGSLFTLKAKRPGLRLPDSNIDYPM

ATGDGAKTLAIHVKALTADSIRITWKATLPASSFRLSWLRLGHSPAVGSITETLVQGDKT

EYLLTALEPKSTYIICMVTMETSNAYVADETPVCAKAETADSYGPTTTLNQEQNAGPMAS

LPLAGIIGGAVALVFLFLVLGAICWYVHQAGELLTRERAYNRGSRKKDDYMESGTKKDNS

ILEIRGPGLQMLPINPYRAKEEYVVHTIFPSNGSSLCKATHTIGYGTTRGYRDGGIPDID

YSYT

PSORT predicts presence of the sequence within the plasma membrane with a certainty of 0.46 and integral likelihood of transmembrane presence between positions 51 and 52 of SEQ ID NO: 68. Signal P Predicts that NOV5 has a signal peptide that cleaves between positions 51 and 52 of SEQ ID NO: 68.

In a search of sequence databases, it was found, for example, that the nucleic acid sequence of this invention has 882 of 951 bases (92%) identical to a human leucine-rich repeat transmembrane protein FLRT1 (FLRT1) mRNA, (Accession No. gb: GENBANK-ID:AF169675|acc:AF169675.1) (FLRT1; Table 22). The full amino acid sequence of the protein of the invention was found to have 655 of 674 amino acid residues (97%) identical to, and 658 of 674 amino acid residues (97%) similar to, the 674 amino acid protein from a human leucine-rich repeat transmembrane protein FLRT1 (Accession No: ptnr: SPTREMBL-ACC:Q9NZU1) (FLRT1; Table 23).

TABLE 22

BLASTN search using NOV5 (CuraGen Acc. No. CG554254-02).

```
>gb:GENBANK-ID:AF169675|acc:AF169675.1 Homo sapiens leucine-rich repeat
transmembrane protein FLRT1 (FLRT1) mRNA, complete cds-Homo
sapiens, 2660 bp.
Length = 2660
Score = 3978 (596.9 bits), Expect = 4.0e-174, P = 4.0e-174
Identities = 882/951 (92%), Positives = 882/951 (92%), Strand = Plus/Plus NOV5:    1 ATGGTGGTGGCACACCCCACCGCCACTGCCACCACCACGCCCACTGCCACTGTCACGGCC   60 (SEQ ID NO: 67)
           ||||||||||||||||||||||||||||||||||||||||||||||||||||||||||||
FLRT1:   1 ATGGTGGTGGCACACCCCACCGCCACTGCCACCACCACGCCCACTGCCACTGTCACGGCC   60 (SEQ ID NO: 74)

NOV5:   61 ACCGTTGTGATGACCACGGCCACCATGGACCTGCGGGACTGGCTGTTCCTCTGCTACGGG  120
           ||||||||||||||||||||||||||||||||||||||||||||||||||||||||||||
FLRT1:  61 ACCGTTGTGATGACCACGGCCACCATGGACCTGCGGGACTGGCTGTTCCTCTGCTACGGG  120

NOV5:  121 CTCATCGCCTTCCTGACGGAGGTCATCGACAGCACCACCTGCCCCTCGGTGTGCCGCTGC  180
           ||||||||||||||||||||||||||||||||||||||||||||||||||||||||||||
FLRT1: 121 CTCATCGCCTTCCTGACGGAGGTCATCGACAGCACCACCTGCCCCTCGGTGTGCCGCTGC  180

NOV5:  181 GACAACGGCTTCATCTACTGCAACGACCGGGACTCACATCCATCCCCGCAGATATCCCT  240
           ||||||||||||||||||||||||||||||||||||||||||||||||||||||||||||
FLRT1: 181 GACAACGGCTTCATCTACTGCAACGACCGGGACTCACATCCATCCCCGCAGATATCCCT  240

NOV5:  241 GATGATGCCACCACCCTCTACCTGCAGAACAACCAGATCAACAACGCCGGCATCCCCCAG  300
           |||| ||||||||||||||| ||| |||||||||||||||||||| |||||||||||||
FLRT1: 241 GATGACGCCACCACCCTCTATCTGCAGAACAACCAGATCAACAACGCTGGCATCCCCCAG  300

NOV5:  301 GACCTCAAGACCAAGGTCAACGTGCAGGTCATCTACCTATACGAGAATGACCTGGATGAG  360
           ||||||||||||||||||||||||||||||||| ||||||||||||||||||||||||||
FLRT1: 301 GACCTCAAGACCAACGTCAACGTGCAGGTCATCTACCTATACGAGAATGACCTGGATGAG  360
```

TABLE 22-continued

BLASTN search using NOV5 (CuraGen Acc. No. CG554254-02).

```
NOV5:  361 TTCCCCATCAACCTGCCCCGCTCCCTCCGGGAGCTGCACCTGCAGGACAACAATGTGCGC 420
           ||||||||||||||||||||||||||||||||||||||||||||||||||||||||||||
FLRT1  361 TTCCCCATCAACCTGCCCCGCTCCCTCCGGGAGCTGCACCTGCAGGACAACAATGTGCGC 420

NOV5:  421 ACCATTGCCAGGGACTCGCTGGCCCGCATCCCGCTGCTGGAGAAGCTGCACCTGGATGAC 480
           ||||||||||||||||||||||||||||||||||||||||||||||||||||||||||||
FLRT1  421 ACCATTGCCAGGGACTCGCTGGCCCGCATCCCGCTGCTGGAGAAGCTGCACCTGGATGAC 480

NOV5:  481 AACTCCGTGTCCACCGTCAGCATTGAGGAGGACGCCTTCGCCGACAGCAAACAGCTCAAG 540
           ||||||||||||||||||||||||||||||||||||||||||||||||||||||||||||
FLRT1  481 AACTCCGTGTCCACCGTCAGCATTGAGGAGGACGCCTTCGCCGACAGCAAACAGCTCAAG 540

NOV5:  541 CTGCTCTTCCTGAGCCGGAACCACCTGAGCAGCATCCCTCGGGGCTGCCGCACACGCTG 600
           ||||||||||||||||||||||||||||||||||||||||||||||||||||||||||||
FLRT1  541 CTGCTCTTCCTGAGCCGGAACCACCTGAGCAGCATCCCTCGGGGCTGCCGCACACGCTG 600

NOV5:  601 GAGGAGCTGCGGCTGGATGACAACCGCATCTCCACCATCCCGCTGCATGCCTTCAAGGGC 660
           ||||||||||||||||||||||||||||||||||||||||||||||||||||||||||||
FLRT1  601 GAGGAGCTGCGGCTGGATGACAACCGCATCTCCACCATCCCGCTGCATGCCTTCAAGGGC 660

NOV5:  661 CTCAACAGCCTGCGGCGCCTGGTGCTGGACGGTAACCTGCTGGCCAACCAGCGCATCGCC 720
           ||||||||||||||||||||||||||||||||||||||||||||||||||| ||||||||
FLRT1  661 CTCAACAGCCTGCGGCGCCTGGTGCTGGACGGTAACCTGCTCGCCAACCAGCGCATCGCC 720

NOV5:  721 GACGACACCTTCAGCCGCCTACAGAACCTCACAGAGCTCTCGCTGGTGCGCAATTCGCTG 780
           ||||||||||||||||||||||| |||||||||||||||||||| ||||||||||||||
FLRT1  721 GACGACACCTTCAGCCGCCTACACAACCTCACAGAGCTCTCGCTGCTGCGCAATTCGCTG 780

NOV5:  781 GCCGCGCCACCCCTCTACCTGCAGGACAATGCC-ATCAGCCACATCCCCTACAACACGCT 839
           ||||||||||||||||||| ||    |||||||||    |||||    |    ||
FLRT1  781 GCCGCGCCACCCCTCAACCTGCC---CAGCGCCCACCTGC-AGAAACTCTAC--CT-GCA 833

NOV5:  840 GGCCAAGATGCG-TGAGCTGGAGCGGCTGGACCTGTCCAAC-AACAACC-TGACCACGCT 896
           ||||| ||| |||| || || |  |||| |||||  |
FLRT1  834 GGACAA--TGCCATCAGCCACATCCCCTACAACACGCTGGCCAAGATGCGTGAGCTGGA- 890

NOV5:  897 GCCCCGCGGCCTGTTCGACGACCTGGGGA--AC-CTGGCCCAGCTGC-TGCTC-AGGAAC 951
           ||  |  ||||||||||||   ||  ||||||||||||||||||
FLRT1  891 GCGGCTGGACCTGTCCAACAACAACCTGACCACGCTGCCCC-GCGGCCTGTTCGACGACC 949
```

TABLE 23

BLASTP search using the protein of NOV5 (CuraGen Acc. No. CG554254-02).

>ptnr:SPTREMBL-ACC:Q9NZU1 LEUCINE-RICH REPEAT TRANSMEMBRANE PROTEIN FLRT1-Homo
sapiens (Human), 674 aa.
Length=674
Score = 3370 (1186.3 bits), Expect=0.0, P = 0.0
Identities = 655/674 (97%), Positives = 658/674 (97%)

```
NOV5:    1 MVVAHPTATATTTPTATVTATVVMTTATMDLRDWLFLCYGLIAFLTEVIDSTTCPSVCRC  60 (SEQ ID NO: 68)
           ************************************************************
FLET1    1 MVVAHPTATATTTPTATVTATVVMTTATMDLRDWLFLCYGLIAFLTEVIDSTTCPSVCRC  60 (SEQ ID NO: 75)

NOV5:   61 DNGFIYCNDRGLTSIPADIPDDATTLYLQNNQINNAGIPQDLKTKVNVQVIYLYENDLDE 120
           ************************************************************
FLET1   61 DNGFIYCNDRGLTSIPADIPDDATTLYLQNNQINNAGIPQDLKTKVNVQVIYLYENDLDE 120

NOV5:  121 FPINLPRSLRELHLQDNNVRTIARDSLARIPLLEKLHLDDNSVSTVSIEEDAFADSKQLK 180
           ************************************************************
FLRT1  121 FPINLPRSLRELHLQDNNVRTIARDSLARIPLLEKLHLDDNSVSTVSIEEDAFADSKQLK 180

NOV5:  181 LLFLSPNHLSSIPSGLPHTLEELRLDDNRISTIPLHAFKGLNSLRRLVLDGNLLANQRIA 240
           *****  *****************************************************
FLET1  181 LLFLSRNHLSSIPSGLPHTLEELRLDDNRISTIPLHAFKGLNSLRRLVLDGNLLANQRIA 240

NOV5:  241 DDTFSRLQNLTELSLVRNSLAAPPL----------YLQDNAISHIPYNTLAKMRELERLD 290
           *************************          *****************************
FLRT1  241 DDTFSRLQNLTELSLVRNSLAAPPLNLPSAHLQKLYLQDNAISHIPYNTLAKMRELERLD 300

NOV5:  291 LSNNNLTTLPRGLFDDLGNLAQLLLRNNPWFCGCNLMWLRDWVKARAAVVNVRGLMCQGP 350
           *********************************  ************************
FLRT1  301 LSNNNLTTLPRGLFDDLGNLAQLLLRNNPWFCCCNLMWLRDWVKARAAVVNVRGLMCQGPLTCQGP 360
```

TABLE 23-continued

BLASTP search using the protein of NOV5 (CuraGen Acc. No. CG554254-02).

```
NOV5:  351 EKVRGMAIKDITSEVESVLRRAPQGGVANAAAKTTASNHASATTPQGSLFTLKAKRPGLR 410
           ***************++******************************************
FLRT1: 361 EKVRGMAIKDITSEMDECFETGPQGGVANAAAKTTASNHASATTPQGSLFTLKAKRPGLR 420

NOV5:  411 LPDSNIDYPMATGDGAKTLAIHVKALTADSIRITWKATLPASSFRLSWLRLGHSPAVGSI 470
           ************************************************************
FLRT1: 421 LPDSNIDYPMATGDGAKTLAIHVKALTADSIRITWKATLPASSFRLSWLRLGHSPAVGSI 480

NOV5:  471 TETLVQGDKTEYLLTALEPKSTYIICMVTMETSNAYVADETPVCAKAETADSYGPTTTLN 530
           ************************************************************
FLRT1: 481 TETLVQGDKTEYLLTALEPKSTYIICMVTMETSNAYVADETPVCAKAETADSYGPTTTLN 540

NOV5:  531 QEQNAGPMASLPLAGIIGGAVALVFLFLVLGATCWYVHQAGELLTRERAYNRGSRKKDDY 590
           **********************************************************+****
FLRT1: 541 QEQNAGPMASLPLAGIIGGAVALVFLFLVLGATCWYVHQAGELLTRERAYNRGSREKDDY 600

NOV5:  591 MESGTKKDNSILEIRGPGLQMLPINPYRAKEEYVVHTIFPSNGSSLCKATHTIGYGTTRG 650
           ************************************************************
FLRT1: 601 MESGTKKDNSILEIRGPGLQMLPINPYRAKEEYVVHTIFPSNGSSLCKATHTIGYGTTRG 660

NOV5:  651 YRDGGIPDIDYSYT 664
           **************
FLRT1: 661 YRDGGIPDIDYSYT 674
```

Where * indicates identity and + indicates similarity.

The presence of identifiable domains in the protein disclosed herein was determined by searches versus domain databases such as PFAM, PROSITE, PRODOM, BLOCKS or PRINTS and then identified by the Interpro domain accession number. Significant domains are summarized in the Table 24 below:

TABLE 24

Significant domains of NOV5.

Scores for sequence family classification (score includes all domains):

| Model | Description | Score | E-value | N |
|---|---|---|---|---|
| LRR | Leucine Rich Repeat | 105.5 | 1e-27 | 9 |
| LRRCT | Leucine rich repeat C-terminal domain | 48.0 | 2.1e-10 | 1 |
| LRRNT | Leucine rich repeat N-terminal domain | 33.4 | 5.3e-06 | 1 |
| fn3 | Fibronectin type III domain | 13.8 | 0.12 | 1 |

Parsed for domains:

| Model | Domain | seq-f | seq-t | hnm-f | hmm-t | score | E-value |
|---|---|---|---|---|---|---|---|
| LRRNT | 1/1 | 53 | 80 ... | 1 | 31 [] | 33.4 | 5.3e-06 |
| LRR | 1/9 | 82 | 106 ... | 1 | 23 [] | 5.4 | 1.7e+02 |
| LRR | 2/9 | 107 | 126 ... | 1 | 23 [] | 5.6 | 1.5e+02 |
| LRR | 3/9 | 128 | 151 ... | 1 | 23 [] | 16.2 | 0.81 |
| LRR | 4/9 | 152 | 177 ... | 1 | 23 [] | 13.7 | 4.4 |
| LRR | 5/9 | 178 | 197 ... | 1 | 23 [] | 14.4 | 2.7 |
| LRR | 6/9 | 199 | 222 ... | 1 | 23 [] | 25.0 | 0.0018 |
| LRR | 7/9 | 223 | 248 ... | 1 | 23 [] | 12.8 | 8.5 |
| LRR | 8/9 | 249 | 276 ... | 1 | 23 [] | 9.7 | 38 |
| LRR | 9/9 | 285 | 308 ... | 1 | 23 [] | 28.1 | 0.00021 |
| LRRCT | 1/1 | 318 | 369 ... | 1 | 54 [] | 48.0 | 2.1e-10 |
| fn3 | 1/1 | 425 | 503 ... | 1 | 84 [] | 13.8 | 0.12 |

Alignments of top-scoring domains:
LRRNT: domain 1 of 1, from 53 to 80: score 33.4, E = 5.3e-06
```
      *->aCpreCtCspfglvVdCsgrgLtlevPrdlP<-*        (SEQ ID NO: 76)
         Cp  C+C     ++C +rgLt ++P d+P
   53 TCPSVCRCD--NOFIYCNDRGLT-SIPADIP        80 SEQ ID NO: 68
```

LEE: domain 1 of 9, from 82 to 106: score 5.4, E = 1.7e+02
```
      *->nLeeLdLsnN.Lt..slppylfsnLp<-*        (SEQ ID NO: 77)
         ++L+L+nN+++++p++++
   82 DATTLYLQNNqINnaGIPQD-LKTKV       106 SEQ ID NO: 68
```

LEE: domain 2 of 9, from 107 to 126: score 5.6, E = 1.5e+30 02
```
      *->nLeeLdLsnN.Ltslppglfsnlp<-*        (SEQ ID NO: 78)
          n ++++L  N+L ++p    nLp
```

TABLE 24-continued

Significant domains of NOV5.

```
  107 NVQVIYLYENdLDEFPI----NLP                                    126 SEQ ID NO: 68

LEE: domain 3 of 9, from 128 to 151: score 16.2, E = 0.81
     *->nLeeLdLsnN.LtslppglfsnLp<-*                               (SEQ ID NO: 79)
         +L+eL+L++N++++  ++++  p
  128 SLRELHLQDNnVRTIARDSLARIP                                    151 SEQ ID NO: 68

LEE: domain 4 of 9, from 152 to 177: score 13.7, E = 4.4
     *->nLeeLdLsnN.Lt..slppglfsnLp<-*                             (SEQ ID NO: 80)
         Le+L+L++N+++s+++++f+++
  152 LLEKLHLDDNsVStvSIEEDAFADSK                                  177 SEQ ID NO: 68

LEE: domain 5 of 9, from 178 to 197: score 14.4, E = 2.7
     *->nLeeLdLsnN.LtslppglfsnLp<-*                               (SEQ ID NO: 81)
         +L+L Ls+N+L+s+p+   +Lp
  178 QLKLLFLSENhLSSIPS----GLP                                    197 SEQ ID NO: 68

LEE: domain 6 of 9, from 199 to 222: score 25.0, E = 0.0018
     *->nLeeLdLsnN.LtslppglfsnLp<-*                               (SEQ ID NO: 82)
         LeeL+L++N+++++p ++f++L+
  199 TLEELRLDDNrISTIPLHAFKGLN                                    222 SEQ ID NO: 68

LRR: domain 7 of 9, from 223 to 248: score 12.8, E = 8.5
     *->nLeeLdLsnN.Lt..slppglfsnLp<-*                             (SEQ ID NO: 83)
         +L++L L++N L ++++++fs Le
  223 SLRRLVLDGNlLAnqRIADDTFSRLQ                                  248 SEQ ID NO: 68

LRR: domain 8 of 9, from 249 to 276: score 9.7, E = 38
     *->nLeeLdLsnN.Lt....slppglfsnLp<-*                           (SEQ ID NO: 84)
         nL+eL+L +N+L ++L ++++s+p
  249 NLTELSLVENsLAapplYLQDNAISHIP                                276 SEQ ID NO: 68

LEE: domain 9 of 9, from 285 to 308: score 28.1, E = 0.00021
     *->nLeeLdLsnN.LtslppglfsnLp<-*                               (SEQ ID NO: 73)
         Le+LdLsnN+Lt+lp glf++L
  285 ELERLDLSNNnLTTLPRGLFDDLG                                    308 SEQ ID NO: 68

LRRCT: domain 1 of 1, from 318 to 369: score 48.0, E = 2.1e-10
     *->NpfnCDCeLrwLlrWlretnprrledqedlrCasPeslrGqpllellpsdfsCp<-* (SEQ ID NO: 71)
         NP+C C+L+wL++W++++++++++  l+C++Pe++rG+++++++++*
  318 NPWFCGCNLMWLRDWVKA-RAAVVNVR-GLMCQGPEKVRGMAIKDITSEVESVL       362 (SEQ ID NO: 68)

fn3: domain 1 of 1, from 42S to S03: score 13.8, E = 0.12
     *->PsaPtnltvtdvtstsltlsWspptgngpitgYevtyRqpkngge..           
         +   ++V+++t++s++++W++     p +++++++   +++
  425 GAKTLAIHVKALTADSIRITWKAT---LPASSFRLSW-LRLGNSPav              467 (SEQ ID NO: 68)

. . . wneltvpgtttsytltgLkPgteYevrVqAvnggGGpeS<-*             (SEQ ID NO: 87)
         +++e  v g++t+y lt L+P ++Y +++   +   +S
  468 gsITETLVQGDKTEYLLTALEPKSTYIICMV---TM--ETS                   503 (SEQ ID NO: 68)
```

Leucine-rich repeats (LRRs) are relatively short motifs (22–28 residues in length) found in a variety of cytoplasmic, membrane and extracellular proteins. Although these proteins are associated with widely different functions, a common property involves protein-protein interaction. Little is known about the 3D structure of LRRs, although it is believed that they can form amphipathic structures with hydrophobic surfaces capable of interacting with membranes. In vitro studies of a synthetic LRR from Drosophila Toll protein have indicated that the peptides form gels by adopting beta-sheet structures that form extended filaments. These results are consistent with the idea that LRRs mediate protein-protein interactions and cellular adhesion. Other functions of LRR-containing proteins include, for example, binding to enzymes and vascular repair. The 3-D structure of ribonuclease inhibitor, a protein containing 15 LRRs, has been determined, revealing LRRs to be a new class of alpha/beta fold. LRRs form elongated non-globular structures and are often flanked by cysteine rich domains.

This indicates that the sequence of the invention has properties similar to those of other proteins known to contain this/these domain(s) and similar to the properties of these domains.

The protein similarity information, expression pattern, cellular localization, and map location for the NOV5 protein and nucleic acid disclosed herein suggest that this fibromodulin-like protein may have important structural and/or physiological functions characteristic of the fibromodulin family. Therefore, NOV5 nucleic acids and proteins of the invention are useful in potential diagnostic and therapeutic applications and as a research tool. These include serving as a specific or selective nucleic acid or protein diagnostic and/or prognostic marker, wherein the presence or amount of the nucleic acid or the protein are to be assessed. These also include potential therapeutic applications such as the following: (i) a protein therapeutic, (ii) a small molecule drug target, (iii) an antibody target (therapeutic, diagnostic, drug targeting/cytotoxic antibody), (iv) a nucleic acid useful in gene therapy (gene delivery/gene ablation), (v) an agent promoting tissue regeneration in vitro and in vivo, and (vi) a biological defense weapon.

The nucleic acids and proteins of the invention have applications in the diagnosis and/or treatment of various diseases and disorders. For example, the compositions of the present invention will have efficacy for the treatment of patients suffering from: atopy; Dysprothrombinemia; Hypoprothrombinemia; Smith-Lemli-Opitz syndrome, type I; Smith-Lemli-Opitz syndrome, type II; Xeroderma pigmentosum, group E, subtype 2; High bone mass; Bardet-Biedl syndrome 1; CPT deficiency, hepatic, type I; Carcinoid tumor of lung; Centrocytic lymphoma; Cervical carcinoma; Hyperparathyroidism, AD; Hypokalemic periodic paralysi; Leigh syndrome; Leukemia, acute promyelocytic, NUMA/RARA type; Macular dystrophy, vitelliform type; McArdle disease; Meckel syndrome, type 2; Multiple endocrine neoplasia I; Multiple myeloma; Parathyroid adenomatosis 1; Prolactinoma, hyperparathyroidism, carcinoid syndrome; Retinitis pigmentosa, digenic; Somatotrophinoma; Vitreoretinopathy, neovascular inflammatory; arthritis, tendinitis; as well as other diseases, disorders and conditions.

These materials are further useful in the generation of antibodies that bind immunospecifically to the novel substances of the invention for use in diagnostic and/or therapeutic methods.

TABLE 14

Sequences and Corresponding SEQ ID Numbers

| NOV number | clone | SEQ ID number of nucleic acid sequence | SEQ ID number of encoded amino acid sequence | homology | ORF of nucleic acid |
|---|---|---|---|---|---|
| 1 | AL109798_A | 1 | 2 | thymosin beta 10 | 61-237 |
| 2 | AL035703_A | 4 | 5 | ephrin A receptor | 1-2976 |
| 3 | AP000597_A | 6 | 7 | proteoglycan | 1-2025 |
| 4 | AL035703_A | 65 | 66 | ephrin A receptor | 1-1545 |
| 5 | CG54254-02 | 67 | 68 | fibromodulin | 1-1995 |

NOV Nucleic Acids and Polypeptides

One aspect of the invention pertains to isolated nucleic acid molecules that encode NOV polypeptides or biologically-active portions thereof. Also included in the invention are nucleic acid fragments sufficient for use as hybridization probes to identify NOV-encoding nucleic acids (e.g., NOV mRNAs) and fragments for use as PCR primers for the amplification and/or mutation of NOV nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but preferably is comprised double-stranded DNA.

A NOV nucleic acid can encode a mature NOV polypeptide. As used herein, a "mature" form of a polypeptide or protein disclosed in the present invention is the product of a naturally occurring polypeptide or precursor form or proprotein. The naturally occurring polypeptide, precursor or proprotein includes, by way of nonlimiting example, the full length gene product, encoded by the corresponding gene. Alternatively, it can be defined as the polypeptide, precursor or proprotein encoded by an open reading frame described herein. The product "mature" form arises, again by way of nonlimiting example, as a result of one or more naturally occurring processing steps as they may take place within the cell, or host cell, in which the gene product arises. Examples of such processing steps leading to a "mature" form of a polypeptide or protein include the cleavage of the N-terminal methionine residue encoded by the initiation codon of an open reading frame, or the proteolytic cleavage of a signal peptide or leader sequence. Thus a mature form arising from a precursor polypeptide or protein that has residues 1 to N, where residue 1 is the N-terminal methionine, would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Further as used herein, a "mature" form of a polypeptide or protein may arise from a step of post-translational modification other than a proteolytic cleavage event. Such additional processes include, by way of non-limiting example, glycosylation, myristoylation or phosphorylation. In general, a mature polypeptide or protein may result from the operation of only one of these processes, or a combination of any of them.

The term "probes", as utilized herein, refers to nucleic acid sequences of variable length, preferably between at least about 10 nucleotides (nt), 100 nt, or as many as approximately, e.g., 6,000 nt, depending upon the specific use. Probes are used in the detection of identical, similar, or complementary nucleic acid sequences. Longer length probes are generally obtained from a natural or recombinant source, are highly specific, and much slower to hybridize than shorter-length oligomer probes. Probes can be single- or double-stranded and designed to have specificity in PCR, membrane-based hybridization technologies, or ELISA-like technologies.

The term "isolated" nucleic acid molecule, as utilized herein, is one which is separated from other nucleic acid molecules which are present in the natural source of the nucleic acid. Preferably, an "isolated" nucleic acid is free of sequences which naturally flank the nucleic acid (i.e., sequences located at the 5'- and 3'-termini of the nucleic acid) in the genomic DNA of the organism from which the nucleic acid is derived. For example, in various embodiments, the isolated NOV nucleic acid molecules can contain less than about 5 kb, 4 kb, 3 kb, 2 kb, 1 kb, 0.5 kb or 0.1 kb of nucleotide sequences which naturally flank the nucleic acid molecule in genomic DNA of the cell/tissue from which the nucleic acid is derived (e.g., brain, heart, liver, spleen, etc.). Moreover, an "isolated" nucleic acid molecule, such as a cDNA molecule, can be substantially free of other cellular material or culture medium when produced by recombinant techniques, or of chemical precursors or other chemicals when chemically synthesized. A nucleic acid molecules of the invention, e.g., a nucleic acid molecule having the nucleotide sequence of SEQ ID NO: 1, 4, 6, 65 or 67, or a complement of this aforementioned nucleotide sequence, can be isolated using standard molecular biology techniques and the sequence information provided herein. Using all or a portion of the nucleic acid sequence of SEQ ID NO: 1, 4, 6, 65 or 67 as a hybridization probe, NOV molecules can be isolated using standard hybridization and cloning techniques (e.g., as described in Sambrook, et al., (eds.), MOLECULAR CLONING: A LABORATORY MANUAL 2nd Ed., Cold Spring Harbor Laboratory Press, Cold Spring Harbor, N.Y., (1989); and Ausubel, et al., (eds.), CURRENT PROTOCOLS IN MOLECULAR BIOLOGY, John Wiley & Sons, New York, N.Y., (1993). A nucleic acids of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to NOV nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence can be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. In one embodiment of the invention, an oligonucleotide comprising a nucleic acid molecule less than 100 nt in length would further comprise at least 6 contiguous nucleotides of SEQ ID NO: 1, 4, 6, 65 or 67 or a complement thereof. Oligonucleotides can be chemically synthesized and may also be used as probes.

In another embodiment, an isolated nucleic acid molecule of the invention comprises a nucleic acid molecule that is a complement of the nucleotide sequence shown in SEQ ID NO: 1, 4, 6, 65 or 67 or a portion of this nucleotide sequence (e.g., a fragment that can be used as a probe or primer or a fragment encoding a biologically-active portion of a NOV polypeptide). A nucleic acid molecule that is complementary to the nucleotide sequence shown in SEQ ID NO: 1, 4, 6, 65 or 67, is one that is sufficiently complementary to the nucleotide sequence shown in SEQ ID NO: 1, 4, 6, 65 or 67 that it can hydrogen bond with little or no mismatches to the nucleotide sequence shown in SEQ ID NO: 1, 4, 6, 65 or 67, thereby forming a stable duplex.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, van der Waals, hydrophobic interactions, and the like. A physical interaction can be either direct or indirect. Indirect interactions can be through or due to the effects of another polypeptide or compound. Direct binding refers to interactions that do not take place through, or due to, the effect of another polypeptide or compound, but instead are without other substantial chemical intermediates.

Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments can be derived from any contiguous portion of a nucleic acid or amino acid sequence of choice.

Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs can be synthetic or from a different evolutionary origin and may have a similar or opposite metabolic activity compared to wild type. Homologs are nucleic acid sequences or amino acid sequences of a particular gene that are derived from different species.

Derivatives and analogs can be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 30%, 50%, 70%, 80%, or 95% identity (with a preferred identity of 80–95%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., CURRENT PROTOCOLS IN MOLECULAR BIOLOGY, John Wiley & Sons, New York, N.Y., (1993), and below.

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of NOV polypeptides. Isoforms can be expressed in different tissues of the same organism as a result of, for example, alternative splicing of RNA. Alternatively, isoforms can be encoded by different genes. In the invention, homologous nucleotide sequences include nucleotide sequences encoding for a NOV polypeptide of species other than humans, including, but not limited to: vertebrates, and thus can include, e.g., frog, mouse, rat, rabbit, dog, cat, cow, horse, and other organisms. Homologous nucleotide sequences also include, but are not limited to, naturally occurring allelic variations and mutations of the nucleotide sequences set forth herein. A homologous nucleotide sequence does not, however, include the exact nucleotide sequence encoding human NOV protein. Homologous nucleic acid sequences include those nucleic acid sequences that encode conservative amino acid substitutions (see below) in SEQ ID NO: 2, 5, 7, 66 or 68, as well as a polypeptide possessing NOV biological activity. Various biological activities of the NOV proteins are described below.

An ORF corresponds to a nucleotide sequence that could potentially be translated into a polypeptide. A stretch of nucleic acids comprising an ORF is uninterrupted by a stop codon. An ORF that represents the coding sequence for a full protein begins with an ATG "start" codon and terminates with one of the three "stop" codons, namely, TAA, TAG, or TGA. For the purposes of this invention, an ORF can be any part of a coding sequence, with or without a start codon, a stop codon, or both. For an ORF to be considered as a good candidate for coding for a bona fide cellular protein, a minimum size requirement is often set, e.g., a stretch of DNA that would encode a protein of 50 amino acids or more.

The nucleotide sequences determined from the cloning of the NOV genes allows for the generation of probes and primers designed for use in identifying and/or cloning NOV homologues in other cell types, e.g. from other tissues, as well as NOV homologues from other vertebrates. The probe/primer typically comprises substantially purified oligonucleotide. The oligonucleotide typically comprises a region of nucleotide sequence that hybridizes under stringent conditions to at least about 12, 25, 50, 100, 150, 200, 250, 300, 350 or 400 consecutive sense strand nucleotide sequence of SEQ ID NO: 1, 4, 6, 65 or 67; or an anti-sense strand nucleotide sequence of SEQ ID NO: 1, 4, 6, 65 or 67; or of a naturally occurring mutant of SEQ ID NO: 1, 4, 6, 65 or 67.

Probes based on the NOV nucleotide sequences can be used to detect transcripts or genomic sequences encoding the same or homologous proteins. In various embodiments, the probe further comprises a label group attached thereto, e.g. the label group can be a radioisotope, a fluorescent compound, an enzyme, or an enzyme co-factor. Such probes can be used as a part of a diagnostic test kit for identifying cells or tissues which mis-express a NOV protein, such as by measuring a level of a NOV-encoding nucleic acid in a sample of cells from a subject e.g., detecting NOV mRNA levels or determining whether a genomic NOV gene has been mutated or deleted.

"A polypeptide having a biologically-active portion of a NOV polypeptide" refers to polypeptides exhibiting activity similar, but not necessarily identical to, an activity of a polypeptide of the invention, including mature forms, as measured in a particular biological assay, with or without dose dependency. A nucleic acid fragment encoding a "biologically-active portion of NOV" can be prepared by isolating a portion of SEQ ID NO: 1, 4, 6, 65 or 67 that encodes a polypeptide having a NOV biological activity (the biological activities of the NOV proteins are described below), expressing the encoded portion of NOV protein (e.g., by recombinant expression in vitro) and assessing the activity of the encoded portion of NOV.

NOV Nucleic Acid and Polypeptide Variants

The invention further encompasses nucleic acid molecules that differ from the nucleotide sequences shown in SEQ ID NO: 1, 4, 6, 65 or 67, due to degeneracy of the genetic code and thus encode the same NOV proteins as that encoded by the nucleotide sequences shown in SEQ ID NO: 1, 4, 6, 65 or 67. In another embodiment, an isolated nucleic acid molecule of the invention has a nucleotide sequence encoding a protein having an amino acid sequence shown in SEQ ID NO: 2, 5, 7, 66 or 68.

In addition to the NOV nucleotide sequences shown in SEQ ID NO: 1, 4, 6, 65 or 67, it will be appreciated by those skilled in the art that DNA sequence polymorphisms that lead to changes in the amino acid sequences of the NOV polypeptides may exist within a population (e.g., the human population). Such genetic polymorphism in the NOV genes may exist among individuals within a population due to natural allelic variation. As used herein, the terms "gene" and "recombinant gene" refer to nucleic acid molecules comprising an open reading frame (ORF) encoding a NOV protein, preferably a vertebrate NOV protein. Such natural allelic variations can typically result in 1–5% variance in the nucleotide sequence of the NOV genes. Any and all such nucleotide variations and resulting amino acid polymorphisms in the NOV polypeptides, which are the result of natural allelic variation and that do not alter the functional activity of the NOV polypeptides, are intended to be within the scope of the invention.

Moreover, nucleic acid molecules encoding NOV proteins from other species, and thus that have a nucleotide sequence that differs from the human sequence of SEQ ID NO: 1, 4, 6, 65 or 67 are intended to be within the scope of the invention. Nucleic acid molecules corresponding to natural allelic variants and homologues of the NOV cDNAs of the invention can be isolated based on their homology to the human NOV nucleic acids disclosed herein using the human cDNAs, or a portion thereof, as a hybridization probe according to standard hybridization techniques under stringent hybridization conditions.

Accordingly, in another embodiment, an isolated nucleic acid molecule of the invention is at least 6 nucleotides in length and hybridizes under stringent conditions to the nucleic acid molecule comprising the nucleotide sequence of SEQ ID NO: 1, 4, 6, 65 or 67. In another embodiment, the nucleic acid is at least 10, 25, 50, 100, 250, 500, 750, 1000, 1500, or 2000 or more nucleotides in length. In yet another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding NOV proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in Ausubel, et al., (eds.), CURRENT PROTOCOLS IN MOLECULAR BIOLOGY, John Wiley & Sons, N.Y. (1989), 6.3.1–6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions are hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C., followed by one or more washes in 0.2×SSC, 0.01% BSA at 50° C. An isolated nucleic acid molecule of the invention that hybridizes under stringent conditions to the sequences of SEQ ID NO: 1, 4, 6, 65 or 67, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that can hybridize to the nucleic acid molecule comprising the nucleotide sequence of SEQ ID NO: 1, 4, 6, 65 or 67, or fragments, analogs or derivatives thereof, under conditions of moderate stringency is provided. A non-limiting example of moderate stringency hybridization conditions are hybridization in 6×SSC, 5×Denhardt's solution, 0.5% SDS and 100 mg/ml denatured salmon sperm DNA at 55° C., followed by one or more washes in 1×SSC, 0.1% SDS at 37° C. Other conditions of moderate stringency that can be used are well-known within the art. See, e.g., Ausubel, et al. (eds.), CURRENT PROTOCOLS IN MOLECULAR BIOLOGY, John Wiley & Sons, NY (1993), and Kriegler, GENE TRANSFER AND EXPRESSION, A LABORATORY MANUAL, Stockton Press, NY (1990).

In a third embodiment, a nucleic acid that can hybridize to the nucleic acid molecule comprising the nucleotide sequences of SEQ ID NO: 1, 4, 6, 65 or 67, or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that can be used are well known in the art (e.g., as employed for cross-species hybridizations). See, e.g., Ausubel, et al. (eds.), CURRENT PROTOCOLS IN MOLECULAR BIOLOGY, John Wiley & Sons, NY (1993), and Kriegler, GENE TRANSFER AND EXPRESSION, A LABORATORY MANUAL, Stockton Press, NY (1990); Shilo et al., 78 Proc. Natl. Acad. Sci. USA 78: 6789–6792 (1981).

Conservative Mutations

In addition to naturally-occurring allelic variants of NOV sequences that may exist in the population, the skilled artisan will further appreciate that changes can be introduced by mutation into the nucleotide sequences of SEQ ID NO: 1, 4, 6, 65 or 67 thereby leading to changes in the amino acid sequences of the encoded NOV proteins, without altering the functional ability of said NOV proteins. For example, nucleotide substitutions leading to amino acid substitutions at "non-essential" amino acid residues can be made in the sequence of SEQ ID NO: 2, 5, 7, 66 or 68. A "non-essential" amino acid residue is a residue that can be altered from the wild-type sequences of the NOV proteins without altering their biological activity, whereas an "essential" amino acid residue is required for such biological activity. For example, amino acid residues that are conserved among the NOV proteins of the invention are predicted to be particularly non-amenable to alteration. Amino acids for which conservative substitutions can be made are well-known within the art.

Another aspect of the invention pertains to nucleic acid molecules encoding NOV proteins that contain changes in amino acid residues that are not essential for activity. Such NOV proteins differ in amino acid sequence from SEQ ID NO: 2, 5, 7, 66 or 68 yet retain biological activity. In one embodiment, the isolated nucleic acid molecule comprises a nucleotide sequence encoding a protein, wherein the protein comprises an amino acid sequence at least about 45% homologous to the amino acid sequences of SEQ ID NO: 2, 5, 7, 66 or 68. Preferably, the protein encoded by the nucleic acid molecule is at least about 60% homologous to SEQ ID NO: 2, 5, 7, 66 or 68; more preferably at least about 70% homologous to SEQ ID NO: 2, 5, 7, 66 or 68; still more preferably at least about 80% homologous to SEQ ID NO: 2, 5, 7, 66 or 68; even more preferably at least about 90% homologous to SEQ ID NO: 2, 5, 7, 66 or 68; and most preferably at least about 95% homologous to SEQ ID NO: 2, 5, 7, 66 or 68.

An isolated nucleic acid molecule encoding a NOV protein homologous to the protein of SEQ ID NO: 2, 5, 7, 66 or 68, can be created by introducing one or more nucleotide substitutions, additions or deletions into the nucleotide sequence of SEQ ID NO: 1, 4, 6, 65 or 67, such that one or more amino acid substitutions, additions or deletions are introduced into the encoded protein.

Mutations can be introduced into the coding region of amino acid SEQ ID NOS: 2, 5, 7, 9 or 11 by standard techniques, such as site-directed mutagenesis and PCR-mediated mutagenesis. Preferably, these mutations result in conservative amino acid substitutions which are made at one or more predicted, non-essential amino acid residues. A "conservative amino acid substitution" is one in which the amino acid residue is replaced with an amino acid residue having a similar side chain. Families of amino acid residues having similar side chains have been defined within the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in the NOV protein is replaced with another amino acid residue from the same side chain family. Alternatively, in another embodiment, mutations can be introduced randomly along all or part of a NOV coding sequence, such as by saturation mutagenesis, and the resultant mutants can be screened for NOV biological activity to identify mutants that retain activity. Following mutagenesis of SEQ ID NO: 2, 5, 7, 66 or 68, the encoded protein can be expressed by any recombinant technology known in the art and the activity of the protein can be determined.

In one embodiment, a mutant NOV protein can be assayed for (i) the ability to form protein:protein interactions with other NOV proteins, other cell-surface proteins, or biologically-active portions thereof, (ii) complex formation between a mutant NOV protein and a NOV ligand; or (iii) the ability of a mutant NOV protein to bind to an intracellular target protein or biologically-active portion thereof, (e.g. avidin proteins). In yet another embodiment, a mutant NOV protein can be assayed for the ability to regulate a specific biological function (e.g., regulation of insulin release).

Antisense Nucleic Acids

Another aspect of the invention pertains to isolated antisense nucleic acid molecules that can hybridize to or complementary to the nucleic acid molecule comprising the nucleotide sequence of SEQ ID NO: 1, 4, 6, 65 or 67 or fragments, analogs or derivatives thereof. An "antisense" nucleic acid comprises a nucleotide sequence that is complementary to a "sense" nucleic acid encoding a protein (e.g., complementary to the coding strand of a double-stranded cDNA molecule or complementary to an mRNA sequence). In specific aspects, antisense nucleic acid molecules are provided that comprise a sequence complementary to at least about 10, 25, 50, 100, 250 or 500 nucleotides or an entire NOV coding strand, or to only a portion thereof. Nucleic acid molecules encoding fragments, homologs, derivatives and analogs of a NOV protein of SEQ ID NO: 2, 5, 7, 66 or 68; or antisense nucleic acids complementary to a NOV nucleic acid sequence of SEQ ID NO: 1, 4, 6, 65 or 67, are additionally provided. In one embodiment, an antisense nucleic acid molecule is antisense to a "coding region" of the coding strand of a nucleotide sequence encoding a NOV protein. The term "coding region" refers to the region of the nucleotide sequence comprising codons that are translated into amino acid residues. In another embodiment, the antisense nucleic acid molecule is antisense to a "noncoding region" of the coding strand of a nucleotide sequence encoding the NOV protein. The term "noncoding region" refers to 5' and 3' sequences that flank the coding region that are not translated into amino acids (i.e., also referred to as 5' and 3' untranslated regions).

Given the coding strand sequences encoding the NOV protein disclosed herein, antisense nucleic acids of the invention can be designed according to the rules of Watson and Crick or Hoogsteen base pairing. The antisense nucleic acid molecule can be complementary to the entire coding region of NOV mRNA, but more preferably is an oligonucleotide that is antisense to only a portion of the coding or noncoding region of NOV mRNA. For example, the antisense oligonucleotide can be complementary to the region surrounding the translation start site of NOV mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally-occurring nucleotides or variously modified nucleotides designed to increase the biological stability of the molecules or to increase the physical stability of the duplex formed between the antisense and sense nucleic acids (e.g., phosphorothioate derivatives and acridine substituted nucleotides can be used).

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a NOV protein to thereby inhibit expression of the protein (e.g., by inhibiting transcription and/or translation). The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface (e.g., by linking the antisense nucleic acid molecules to peptides or antibodies that bind to cell surface receptors or antigens). The antisense nucleic acid molecules can also be delivered to cells using the vectors described herein. To achieve sufficient nucleic acid molecules, vector constructs in which the antisense nucleic acid molecule is placed under the control of a strong pol II or pol III promoter are preferred.

In yet another embodiment, the antisense nucleic acid molecule of the invention is an alpha-anomeric nucleic acid molecule. An alpha-anomeric nucleic acid molecule forms specific double-stranded hybrids with complementary RNA in which, contrary to the usual alpha-units, the strands run parallel to each other. See, e.g., Gaultier, et al., 1987. Nucl. Acids Res. 15: 6625–6641. The antisense nucleic acid molecule can also comprise a 2'-o-methylribonucleotide (see, e.g., Inoue, et al. 1987. Nucl. Acids Res. 15: 6131–6148) or a chimeric RNA-DNA analogue (see, e.g., Inoue, et al., 1987. FEBS Lett. 215: 327–330.

Ribozymes and PNA Moieties

Nucleic acid modifications include, by way of non-limiting example, modified bases, and nucleic acids whose sugar phosphate backbones are modified or derivatized. These modifications are carried out at least in part to enhance the chemical stability of the modified nucleic acid, such that they can be used, for example, as antisense binding nucleic acids in therapeutic applications in a subject.

In one embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes as described in Haseloff and Gerlach 1988. Nature 334: 585–591) can be used to catalytically cleave NOV mRNA transcripts to thereby inhibit translation of NOV mRNA. A ribozyme having specificity for a NOV-encoding nucleic acid can be designed based upon the nucleotide sequence of a NOV cDNA disclosed herein (i.e., SEQ ID NO: 1, 4, 6, 8, 9 or 10). For example, a derivative of a Tetrahymena L-19 IVS RNA can be constructed in which the nucleotide sequence of the active site is complementary to the nucleotide sequence to be cleaved in a NOV-encoding mRNA. See, e.g., U.S. Pat. No. 4,987,071 to Cech, et al. and U.S. Pat. No. 5,116,742 to Cech, et al. NOV mRNA can also be used to select a catalytic RNA having a specific ribonuclease activity from a pool of RNA molecules. See, e.g., Bartel et al., (1993) Science 261:1411–1418.

Alternatively, NOV gene expression can be inhibited by targeting nucleotide sequences complementary to the regulatory region of the NOV nucleic acid (e.g., the NOV promoter and/or enhancers) to form triple helical structures that prevent transcription of the NOV gene in target cells. See, e.g., Helene, 1991. Anticancer Drug Des. 6: 569–84; Helene, et al. 1992. Ann. N.Y. Acad. Sci. 660: 27–36; Maher, 1992. Bioassays 14: 807–15.

In various embodiments, the NOV nucleic acids can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids. See, e.g., Hyrup, et al., 1996. Bioorg Med Chem 4: 5–23. As used herein, the terms "peptide nucleic acids" or "PNAs" refer to nucleic acid mimics (e.g., DNA mimics) in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup, et al., 1996. supra; Perry-O'Keefe, et al., 1996. Proc. Natl. Acad. Sci. USA 93: 14670–14675.

PNAs of NOV can be used in therapeutic and diagnostic applications. For example, PNAs can be used as antisense or antigene agents for sequence-specific modulation of gene expression by, e.g., inducing transcription or translation arrest or inhibiting replication. PNAs of NOV can also be used, for example, in the analysis of single base pair mutations in a gene (e.g., PNA directed PCR clamping; as artificial restriction enzymes when used in combination with other enzymes, e.g., S1 nucleases (see, Hyrup, et al., 1996. supra); or as probes or primers for DNA sequence and hybridization (see, Hyrup, et al., 1996, supra; Perry-O'Keefe, et al., 1996. supra).

In another embodiment, PNAs of NOV can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of NOV can be generated that may combine the advantageous properties of PNA and DNA. Such chimeras allow DNA recognition enzymes (e.g., RNase H and DNA polymerases) to interact with the DNA portion while the PNA portion would provide high binding affinity and specificity. PNA-DNA chimeras can be linked using linkers of appropriate lengths selected in terms of base stacking, number of bonds between the nucleobases, and orientation (see, Hyrup, et al., 1996. supra). The synthesis of PNA-DNA chimeras can be performed as described in Hyrup, et al., 1996. supra and Finn, et al., 1996. Nucl Acids Res 24: 3357–3363. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA. See, e.g., Mag, et al., 1989. Nucl Acid Res 17: 5973–5988. PNA monomers are then coupled in a stepwise manner to produce a chimeric molecule with a 5' PNA segment and a 3' DNA segment. See, e.g., Finn, et al., 1996. supra. Alternatively, chimeric molecules can be synthesized with a 5' DNA segment and a 3' PNA segment. See, e.g., Petersen, et al., 1975. Bioorg. Med. Chem. Lett. 5: 1119–11124.

In other embodiments, the oligonucleotide may include other appended groups such as peptides (e.g., for targeting host cell receptors in vivo), or agents facilitating transport across the cell membrane (see, e.g., Letsinger, et al., 1989. Proc. Natl. Acad. Sci. U.S.A. 86: 6553–6556; Lemaitre, et al., 1987. Proc. Natl. Acad. Sci. 84: 648–652; PCT Publication No. WO88/09810) or the blood-brain barrier (see, e.g., PCT Publication No. WO 89/10134). In addition, oligonucleotides can be modified with hybridization triggered cleavage agents (see, e.g., Krol, et al., 1988. BioTechniques 6:958–976) or intercalating agents (see, e.g., Zon, 1988. Pharm. Res. 5: 539–549). To this end, the oligonucleotide can be conjugated to another molecule, e.g., a peptide, a hybridization triggered cross-linking agent, a transport agent, a hybridization-triggered cleavage agent, and the like.

NOV Polypeptides

A polypeptide according to the invention includes a polypeptide including the amino acid sequence of NOV polypeptides whose sequences are provided in SEQ ID NO: 2, 5, 7, 66 or 68. The invention also includes a mutant or variant protein any of whose residues can be changed from the corresponding residues shown in SEQ ID NO: 2, 5, 7, 66 or 68 while still encoding a protein that maintains its NOV activities and physiological functions, or a functional fragment thereof.

In general, a NOV variant that preserves NOV-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

One aspect of the invention pertains to isolated NOV proteins, and biologically-active portions thereof, or derivatives, fragments, analogs or homologs thereof. Also provided are polypeptide fragments suitable for use as immunogens to raise anti-NOV antibodies. In one embodiment, native NOV proteins can be isolated from cells or tissue sources by an appropriate purification scheme using standard protein purification techniques. In another embodiment, NOV proteins are produced by recombinant DNA techniques. Alternative to recombinant expression, a NOV protein or polypeptide can be synthesized chemically using standard peptide synthesis techniques.

An "isolated" or "purified" polypeptide or protein or biologically-active portion thereof is substantially free of cellular material or other contaminating proteins from the cell or tissue source from which the NOV protein is derived, or substantially free from chemical precursors or other chemicals when chemically synthesized. The language "substantially free of cellular material" includes preparations of NOV proteins in which the protein is separated from cellular components of the cells from which it is isolated or recombinantly-produced. In one embodiment, the language "substantially free of cellular material" includes preparations of NOV proteins having less than about 30% (by dry weight) of non-NOV proteins (also referred to herein as a "contaminating protein"), more preferably less than about 20% of non-NOV proteins, still more preferably less than about 10% of non-NOV proteins, and most preferably less than about 5% of non-NOV proteins. When the NOV protein or biologically-active portion thereof is recombinantly-produced, it is also preferably substantially free of culture medium, i.e., culture medium represents less than about 20%, more preferably less than about 10%, and most preferably less than about 5% of the volume of the NOV protein preparation.

The language "substantially free of chemical precursors or other chemicals" includes preparations of NOV proteins in which the protein is separated from chemical precursors or other chemicals that are involved in the synthesis of the protein. In one embodiment, the language "substantially free of chemical precursors or other chemicals" includes preparations of NOV proteins having less than about 30% (by dry weight) of chemical precursors or non-NOV chemicals, more preferably less than about 20% chemical precursors or non-NOV chemicals, still more preferably less than about 10% chemical precursors or non-NOV chemicals, and most preferably less than about 5% chemical precursors or non-NOV chemicals.

Biologically-active portions of NOV proteins include peptides comprising amino acid sequences sufficiently homologous to or derived from the amino acid sequences of the NOV proteins (e.g., the amino acid sequence shown in SEQ ID NO: 2, 5, 7, 66 or 68) that include fewer amino acids than the full-length NOV proteins, and exhibit at least one activity of a NOV protein. Typically, biologically-active portions comprise a domain or motif with at least one activity of the NOV protein. A biologically-active portion of a NOV protein can be a polypeptide which is, for example, 10, 25, 50, 100 or more amino acid residues in length. Moreover, other biologically-active portions, in which other regions of the protein are deleted, can be prepared by recombinant techniques and evaluated for one or more of the functional activities of a native NOV protein.

In an embodiment, the NOV protein has an amino acid sequence shown in SEQ ID NO: 2, 5, 7, 66 or 68. In other embodiments, the NOV protein is substantially homologous to SEQ ID NO: 2, 5, 7, 66 or 68, and retains the functional activity of the protein of SEQ ID NO: 2, 5, 7, 9 or 11, yet differs in amino acid sequence due to natural allelic variation or mutagenesis, as described in detail, below. Accordingly, in another embodiment, the NOV protein is a protein that comprises an amino acid sequence at least about 45% homologous to the amino acid sequence of SEQ ID NO: 2, 5, 7, 66 or 68 and retains the functional activity of the NOV proteins of SEQ ID NO: 2, 5, 7, 66 or 68.

Determining Homology Between Two or More Sequences

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology can be determined as the degree of identity between two sequences. The homology can be determined using computer programs known in the art, such as GAP software provided in the GCG program package. See, Needleman and Wunsch, 1970. J Mol Biol 48: 443–453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in SEQ ID NO: 1, 4, 6, 65 or 67.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

Chimeric and Fusion Proteins

The invention also provides NOV chimeric or fusion proteins. As used herein, a NOV "chimeric protein" or "fusion protein" comprises a NOV polypeptide operatively-linked to a non-NOV polypeptide. An "NOV polypeptide" refers to a polypeptide having an amino acid sequence corresponding to a NOV protein (SEQ ID NO: 2, 5, 7, 66 or 68), whereas a "non-NOV polypeptide" refers to a polypeptide having an amino acid sequence corresponding to a protein that is not substantially homologous to the NOV protein, e.g., a protein that is different from the NOV protein and that is derived from the same or a different organism. Within a NOV fusion protein the NOV polypeptide can correspond to all or a portion of a NOV protein. In one embodiment, a NOV fusion protein comprises at least one biologically-active portion of a NOV protein. In another embodiment, a NOV fusion protein comprises at least two biologically-active portions of a NOV protein. In yet another embodiment, a NOV fusion protein comprises at least three biologically-active portions of a NOV protein. Within the fusion protein, the term "operatively-linked" is intended to indicate that the NOV polypeptide and the non-NOV polypeptide are fused in-frame with one another. The non-NOV polypeptide can be fused to the N-terminus or C-terminus of the NOV polypeptide.

In one embodiment, the fusion protein is a GST-NOV fusion protein in which the NOV sequences are fused to the C-terminus of the GST (glutathione S-transferase) sequences. Such fusion proteins can facilitate the purification of recombinant NOV polypeptides. In another embodiment, the fusion protein is a NOV protein containing a heterologous signal sequence at its N-terminus. In certain host cells (e.g., mammalian host cells), expression and/or secretion of NOV can be increased through use of a heterologous signal sequence.

In yet another embodiment, the fusion protein is a NOV-immunoglobulin fusion protein in which the NOV sequences are fused to sequences derived from a member of the immunoglobulin protein family. The NOV-immunoglobulin fusion proteins of the invention can be incorporated into pharmaceutical compositions and administered to a subject to inhibit an interaction between a NOV ligand and a NOV protein on the surface of a cell, to thereby suppress NOV-mediated signal transduction in vivo. The NOV-immunoglobulin fusion proteins can be used to affect the bioavailability of a NOV cognate ligand. Inhibition of the NOV ligand/NOV interaction can be useful therapeutically for both the treatment of proliferative and differentiative disorders, as well as modulating (e.g. promoting or inhibiting) cell survival. Moreover, the NOV-immunoglobulin fusion proteins of the invention can be used as immunogens to produce anti-NOV antibodies in a subject, to purify NOV ligands, and in screening assays to identify molecules that inhibit the interaction of NOV with a NOV ligand.

A NOV chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g., Ausubel, et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). A NOV-encoding nucleic acid can be cloned into such an expression vector such that the fusion moiety is linked in-frame to the NOV protein.

NOV Agonists and Antagonists

The invention also pertains to variants of the NOV proteins that function as either NOV agonists (i.e., mimetics) or as NOV antagonists. Variants of the NOV protein can be generated by mutagenesis (e.g., discrete point mutation or truncation of the NOV protein). An agonist of the NOV protein can retain substantially the same, or a subset of, the biological activities of the naturally occurring form of the NOV protein. An antagonist of the NOV protein can inhibit one or more of the activities of the naturally occurring form of the NOV protein by, for example, competitively binding to a downstream or upstream member of a cellular signaling cascade which includes the NOV protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the NOV proteins.

Variants of the NOV proteins that function as either NOV agonists (i.e., mimetics) or as NOV antagonists can be identified by screening combinatorial libraries of mutants (e.g., truncation mutants) of the NOV proteins for NOV protein agonist or antagonist activity. In one embodiment, a variegated library of NOV variants is generated by combinatorial mutagenesis at the nucleic acid level and is encoded by a variegated gene library. A variegated library of NOV variants can be produced by, for example, enzymatically ligating a mixture of synthetic oligonucleotides into gene sequences such that a degenerate set of potential NOV sequences is expressible as individual polypeptides, or alternatively, as a set of larger fusion proteins (e.g., for phage display) containing the set of NOV sequences therein. There are a variety of methods which can be used to produce libraries of potential NOV variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential NOV sequences. Methods for synthesizing degenerate oligonucleotides are well-known within the art. See, e.g., Narang, 1983. Tetrahedron 39: 3; Itakura, et al., 1984. Annu. Rev. Biochem. 53: 323; Itakura, et al., 1984. Science 198: 1056; Ike, et al., 1983. Nucl. Acids Res. 11: 477.

Polypeptide Libraries

In addition, libraries of fragments of the NOV protein coding sequences can be used to generate a variegated population of NOV fragments for screening and subsequent selection of variants of a NOV protein. In one embodiment, a library of coding sequence fragments can be generated by treating a double stranded PCR fragment of a NOV coding sequence with a nuclease under conditions wherein nicking occurs only about once per molecule, denaturing the double stranded DNA, renaturing the DNA to form double-stranded DNA that can include sense/antisense pairs from different nicked products, removing single stranded portions from reformed duplexes by treatment with S1 nuclease, and ligating the resulting fragment library into an expression vector. By this method, expression libraries can be derived which encodes N-terminal and internal fragments of various sizes of the NOV proteins.

Various techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of NOV proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify NOV variants. See, e.g., Arkin and Yourvan, 1992. Proc. Natl. Acad. Sci. USA 89: 7811–7815; Delgrave, et al., 1993. Protein Engineering 6:327–331.

Anti-NOV Antibodies

The invention encompasses antibodies and antibody fragments, such as Fab or $(Fab)_2$, that bind immunospecifically to any of the NOV polypeptides of said invention.

An isolated NOV protein, or a portion or fragment thereof, can be used as an immunogen to generate antibodies that bind to NOV polypeptides using standard techniques for polyclonal and monoclonal antibody preparation. The full-length NOV proteins can be used or, alternatively, the invention provides antigenic peptide fragments of NOV proteins for use as immunogens. The antigenic NOV peptides comprises at least 4 amino acid residues of the amino acid sequence shown in SEQ ID NO: 2, 5, 7, 66 or 68, and encompasses an epitope of NOV such that an antibody raised against the peptide forms a specific immune complex with NOV. Preferably, the antigenic peptide comprises at least 6, 8, 10, 15, 20, or 30 amino acid residues. Longer antigenic peptides are sometimes preferable over shorter antigenic peptides, depending on use and according to methods well known to someone skilled in the art.

In certain embodiments of the invention, at least one epitope encompassed by the antigenic peptide is a region of NOV that is located on the surface of the protein (e.g., a hydrophilic region). As a means for targeting antibody production, hydropathy plots showing regions of hydrophilicity and hydrophobicity can be generated by any method well known in the art, including, for example, the Kyte Doolittle or the Hopp Woods methods, either with or without Fourier transformation (see, e.g., Hopp and Woods, 1981. Proc. Nat. Acad. Sci. USA 78: 3824–3828; Kyte and Doolittle, 1982. J. Mol. Biol. 157: 105–142, each incorporated herein by reference in their entirety).

As disclosed herein, NOV protein sequences of SEQ ID NO: 2, 5, 7, 66 or 68, or derivatives, fragments, analogs or homologs thereof, can be utilized as immunogens in the generation of antibodies that immunospecifically-bind these protein components. The term "antibody" as used herein refers to immunoglobulin molecules and immunologically-active portions of immunoglobulin molecules, i.e., molecules that contain an antigen binding site that specifically-binds (immunoreacts with) an antigen, such as NOV. Such antibodies include, but are not limited to, polyclonal, monoclonal, chimeric, single chain, Fab and F(ab')$_2$ fragments, and an Fab expression library. In a specific embodiment, antibodies to human NOV proteins are disclosed. Various procedures known within the art can be used for the production of polyclonal or monoclonal antibodies to a NOV protein sequence of SEQ ID NO: 2, 5, 7, 66 or 68, or a derivative, fragment, analog or homolog thereof. Some of these proteins are discussed below.

For the production of polyclonal antibodies, various suitable host animals (e.g., rabbit, goat, mouse or other mammal) can be immunized by injection with the native protein, or a synthetic variant thereof, or a derivative of the foregoing. An appropriate immunogenic preparation can contain, for example, recombinantly-expressed NOV protein or a chemically-synthesized NOV polypeptide. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as Bacille Calmette-Guerin and *Corynebacterium parvum*, or similar immunostimulatory agents. If desired, the antibody molecules directed against NOV can be isolated from the mammal (e.g., from the blood) and further purified by well known techniques, such as protein A chromatography to obtain the IgG fraction.

The term "monoclonal antibody" or "monoclonal antibody composition", as used herein, refers to a population of antibody molecules that contain only one species of an antigen binding site capable of immunoreacting with a particular epitope of NOV. A monoclonal antibody composition thus typically displays a single binding affinity for a particular NOV protein with which it immunoreacts. For preparation of monoclonal antibodies directed towards a particular NOV protein, or derivatives, fragments, analogs or homologs thereof, any technique that provides for the production of antibody molecules by continuous cell line culture can be utilized. Such techniques include, but are not limited to, the hybridoma technique (see, e.g., Kohler & Milstein, 1975. Nature 256: 495–497); the trioma technique; the human B-cell hybridoma technique (see, e.g., Kozbor, et al., 1983. Immunol. Today 4: 72) and the EBV hybridoma technique to produce human monoclonal antibodies (see, e.g., Cole, et al., 1985. In: MONOCLONAL ANTIBODIES AND CANCER THERAPY, Alan R. Liss, Inc., pp. 77–96). Human monoclonal antibodies can be utilized in the practice of the invention and can be produced by using human hybridomas (see, e.g., Cote, et al., 1983. Proc Natl Acad Sci USA 80: 2026–2030) or by transforming human B-cells with Epstein Barr Virus in vitro (see, e.g., Cole, et al., 1985. In: MONOCLONAL ANTIBODIES AND CANCER THERAPY, Alan R. Liss, Inc., pp. 77–96). Each of the above citations is incorporated herein by reference in their entirety.

According to the invention, techniques can be adapted for the production of single-chain antibodies specific to a NOV protein (see, e.g., U.S. Pat. No. 4,946,778). In addition, methods can be adapted for the construction of Fab expression libraries (see, e.g., Huse, et al., 1989. Science 246: 1275–1281) to allow rapid and effective identification of monoclonal Fab fragments with the desired specificity for a NOV protein or derivatives, fragments, analogs or homologs thereof. Non-human antibodies can be "humanized" by techniques well known in the art. See, e.g., U.S. Pat. No. 5,225,539. Antibody fragments that contain the idiotypes to a NOV protein can be produced by techniques known in the art including, but not limited to: (i) an F(ab')$_2$ fragment produced by pepsin digestion of an antibody molecule; (ii) an Fab fragment generated by reducing the disulfide bridges of an F(ab')$_2$ fragment; (iii) an Fab fragment generated by the treatment of the antibody molecule with papain and a reducing agent; and (iv) Fv fragments.

Additionally, recombinant anti-NOV antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in International Application No. PCT/US86/02269; European Patent Application No. 184,187; European Patent Application No. 171,496; European Patent Application No. 173,494; PCT International Publication No. WO 86/01533; U.S. Pat. No. 4,816,567; U.S. Pat. No. 5,225,539; European Patent Application No. 125,023; Better, et al., 1988. Science 240: 1041–1043; Liu, et al., 1987. Proc. Natl. Acad. Sci. USA 84: 3439–3443; Liu, et al., 1987. J. Immunol. 139: 3521–3526; Sun, et al., 1987. Proc. Natl. Acad. Sci. USA 84: 214–218; Nishimura, et al., 1987. Cancer Res. 47: 999–1005; Wood, et al., 1985. Nature 314: 446–449; Shaw, et al., 1988. J. Natl. Cancer Inst. 80: 1553–1559); Morrison (1985) Science 229:1202–1207; Oi, et al. (1986) BioTechniques 4:214; Jones, et al., 1986. Nature 321: 552–525; Verhoeyan, et al., 1988. Science 239: 1534; and Beidler, et al., 1988. J. Immunol. 141: 4053–4060. Each of the above citations are incorporated herein by reference in their entirety.

In one embodiment, methods for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of a NOV protein is facilitated by generation of hybridomas that bind to the fragment of a NOV protein possessing such a domain. Thus, antibodies that are specific for a desired domain within a NOV protein, or derivatives, fragments, analogs or homologs thereof, are also provided herein.

Anti-NOV antibodies can be used in methods known within the art relating to the localization and/or quantitation of a NOV protein (e.g., for use in measuring levels of the NOV protein within appropriate physiological samples, for use in diagnostic methods, for use in imaging the protein, and the like). In a given embodiment, antibodies for NOV proteins, or derivatives, fragments, analogs or homologs thereof, that contain the antibody derived binding domain, are utilized as pharmacologically-active compounds (hereinafter "Therapeutics"). An anti-NOV antibody (e.g., monoclonal antibody) can be used to isolate a NOV polypeptide by standard techniques, such as affinity chromatography or immunoprecipitation. An anti-NOV antibody can facilitate the purification of natural NOV polypeptide from cells and of recombinantly-produced NOV polypeptide expressed in host cells. Moreover, an anti-NOV antibody can be used to detect NOV protein (e.g., in a cellular lysate or cell supernatant) in order to evaluate the abundance and pattern of expression of the NOV protein. Anti-NOV antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

NOV Recombinant Expression Vectors and Host Cells

Another aspect of the invention pertains to vectors, preferably expression vectors, containing a nucleic acid encoding a NOV protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., NOV proteins, mutant forms of NOV proteins, fusion proteins, etc.).

The recombinant expression vectors of the invention can be designed for expression of NOV proteins in prokaryotic or eukaryotic cells. For example, NOV proteins can be expressed in bacterial cells such as *Escherichia coli*, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. Gene 67: 31–40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein. Examples of suitable inducible non-fusion *E. coli* expression vectors include pTrc (Amrann et al., (1988) Gene 69:301–315) and pET 11d (Studier et al., GENE EXPRESSION TECHNOLOGY: METHODS IN ENZYMOLOGY 185, Academic Press, San Diego, Calif. (1990) 60–89).

One strategy to maximize recombinant protein expression in *E. coli* is to express the protein in a host bacteria with an impaired capacity to proteolytically cleave the recombinant protein. See, e.g., Gottesman, GENE EXPRESSION TECHNOLOGY: METHODS IN ENZYMOLOGY 185, Academic Press, San Diego, Calif. (1990) 119–128. Another strategy is to alter the nucleic acid sequence of the nucleic acid to be inserted into an expression vector so that the individual codons for each amino acid are those preferentially utilized in *E. coli* (see, e.g., Wada, et al., 1992. Nucl. Acids Res. 20: 2111–2118). Such alteration of nucleic acid sequences of the invention can be carried out by standard DNA synthesis techniques. In another embodiment, the NOV expression vector is a yeast expression vector. Examples of vectors for expression in yeast *Saccharomyces cerivisae* include pYepSec1 (Baldari, et al., 1987. EMBO J. 6: 229–234), pMFa (Kurjan and Herskowitz, 1982. Cell 30: 933–943), pJRY88 (Schultz et al., 1987. Gene 54: 113–123), pYES2 (Invitrogen Corporation, San Diego, Calif.), and picZ (InVitrogen Corp, San Diego, Calif.). Alternatively, NOV can be expressed in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156–2165) and the pVL series (Lucklow and Summers, 1989. Virology 170: 31–39).

In yet another embodiment, a nucleic acid of the invention is expressed in mammalian cells using a mammalian expression vector. Examples of mammalian expression vectors include pCDM8 (Seed, 1987. Nature 329: 840) and pMT2PC (Kaufman, et al., 1987. EMBO J. 6: 187–195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268–277), lymphoid-specific promoters (Calame and Eaton, 1988. Adv. Immunol. 43: 235–275), in particular promoters of T cell receptors (Winoto and Baltimore, 1989. EMBO J. 8: 729–733) and immunoglobulins (Banerji, et al., 1983. Cell 33: 729–740; Queen and Baltimore, 1983. Cell 33: 741–748), neuron-specific promoters (e.g., the neurofilament promoter; Byrne and Ruddle, 1989. Proc. Natl. Acad. Sci. USA 86: 5473–5477), pancreas-specific promoters (Edlund, et al., 1985. Science 230: 912–916), and mammary gland-specific promoters (e.g., milk whey promoter; U.S. Pat. No. 4,873, 316 and European Application Publication No. 264,166). Developmentally-regulated promoters are also encompassed, e.g., the murine hox promoters (Kessel and Gruss, 1990. Science 249: 374–379) and the α-fetoprotein promoter (Campes and Tilghman, 1989. Genes Dev. 3: 537–546).

The invention further provides a recombinant expression vector comprising a DNA molecule of the invention cloned into the expression vector in an antisense orientation. That is, the DNA molecule is operatively-linked to a regulatory sequence in a manner that allows for expression (by transcription of the DNA molecule) of an RNA molecule that is antisense to NOV mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA.

The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, e.g., Weintraub, et al., "Antisense RNA as a molecular tool for genetic analysis," Reviews-Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, NOV protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding NOV or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) NOV protein. Accordingly, the invention further provides methods for producing NOV protein using the host cells of the invention. In one embodiment, the method comprises culturing the host cell of invention (into which a recombinant expression vector encoding NOV protein has been introduced) in a suitable medium such that NOV protein is produced. In another embodiment, the method further comprises isolating NOV protein from the medium or the host cell.

Transgenic NOV Animals

The host cells of the invention can also be used to produce non-human transgenic animals. For example, in one embodiment, a host cell of the invention is a fertilized oocyte or an embryonic stem cell into which NOV protein-coding sequences have been introduced. Such host cells can then be used to create non-human transgenic animals in which exogenous NOV sequences have been introduced into their genome or homologous recombinant animals in which endogenous NOV sequences have been altered. Such animals are useful for studying the function and/or activity of NOV protein and for identifying and/or evaluating modulators of NOV protein activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous NOV gene has been altered by homologous recombination between the endogenous gene and an exogenous DNA molecule introduced into a cell of the animal, e.g., an embryonic cell of the animal, prior to development of the animal. A transgenic animal of the invention can be created by introducing NOV-encoding nucleic acid into the male pronuclei of a fertilized oocyte (e.g., by microinjection, retroviral infection) and allowing the oocyte to develop in a pseudopregnant female foster animal. The human NOV cDNA sequences of SEQ ID NO:1, 4, 6, 65 or 67 can be introduced as a transgene into the genome of a non-human animal. Alternatively, a non-human homologue of the human NOV gene, such as a mouse NOV gene, can be isolated based on hybridization to the human NOV cDNA (described further supra) and used as a transgene. Intronic sequences and polyadenylation signals can also be included in the transgene to increase the efficiency of expression of the transgene. A tissue-specific regulatory sequence(s) can be operably-linked to the NOV transgene to direct expression of NOV protein to particular cells. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan, 1986. In: MANIPULATING THE MOUSE EMBRYO, Cold Spring Harbor Laboratory Press, Cold Spring Harbor, N.Y. Similar methods are used for production of other transgenic animals. A transgenic founder animal can be identified based upon the presence of the NOV transgene in its genome and/or expression of NOV mRNA in tissues or cells of the animals. A transgenic founder animal can then be used to breed additional animals carrying the transgene. Moreover, transgenic animals carrying a transgene-encoding NOV protein can further be bred to other transgenic animals carrying other transgenes.

To create a homologous recombinant animal, a vector is prepared which contains at least a portion of a NOV gene into which a deletion, addition or substitution has been introduced to thereby alter, e.g., functionally disrupt, the NOV gene. The NOV gene can be a human gene (e.g., the cDNA of SEQ ID NO: 1, 4, 6, 65 or 67), but more preferably, is a non-human homologue of a human NOV gene. For example, a mouse homologue of human NOV gene of SEQ ID NO: 1, 4, 6, 8 or 10 can be used to construct a homologous recombination vector suitable for altering an endogenous NOV gene in the mouse genome. In one embodiment, the vector is designed such that, upon homologous recombination, the endogenous NOV gene is functionally disrupted (i.e., no longer encodes a functional protein; also referred to as a "knock out" vector).

Alternatively, the vector can be designed such that, upon homologous recombination, the At endogenous NOV gene is mutated or otherwise altered but still encodes functional protein (e.g., the upstream regulatory region can be altered to thereby alter the expression of the endogenous NOV protein). In the homologous recombination vector, the altered portion of the NOV gene is flanked at its 5'- and 3'-termini by additional nucleic acid of the NOV gene to allow for homologous recombination to occur between the exogenous NOV gene carried by the vector and an endogenous NOV gene in an embryonic stem cell. The additional flanking NOV nucleic acid is of sufficient length for successful homologous recombination with the endogenous gene. Typically, several kilobases of flanking DNA (both at the 5'- and 3'-termini) are included in the vector. See, e.g., Thomas, et al., 1987. Cell 51: 503 for a description of homologous recombination vectors. The vector is then introduced into an embryonic stem cell line (e.g., by electroporation) and cells in which the introduced NOV gene has homologously-recombined with the endogenous NOV gene are selected. See, e.g., Li, et al., 1992. Cell 69: 915. The selected cells are then injected into a blastocyst of an animal (e.g., a mouse) to form aggregation chimeras. See, e.g., Bradley, 1987. In: TERATOCARCINOMAS AND EMBRYONIC STEM CELLS: A PRACTICAL APPROACH, Robertson, ed. IRL, Oxford, pp. 113–152. A chimeric embryo can then be implanted into a suitable pseudopregnant female foster animal and the embryo brought to term. Progeny harboring the homologously-recombined DNA in their germ cells can be used to breed animals in which all cells of the animal contain the homologously-recombined DNA by germline transmission of the transgene. Methods for constructing homologous recombination vectors and homologous recombinant animals are described further in Bradley, 1991. Curr. Opin. Biotechnol. 2: 823–829; PCT International Publication Nos.: WO 90/11354; WO 91/01140; WO 92/0968; and WO 93/04169.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system, See, e.g., Lakso, et al., 1992. Proc. Natl. Acad. Sci. USA 89: 6232–6236. Another example of a recombinase system is the FLP recombinase system of Saccharomyces cerevisiae. See, O'Gorman, et al., 1991. Science 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, et al., 1997. Nature 385: 810–813. In brief, a cell (e.g., a somatic cell) from the transgenic animal can be isolated and induced to exit the growth cycle and enter G0 phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell (e.g., the somatic cell) is isolated.

Pharmaceutical Compositions

The NOV nucleic acid molecules, NOV proteins, and anti-NOV antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a NOV protein or anti-NOV antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. Proc. Natl. Acad. Sci. USA 91: 3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system. The pharmaceutical compositions can be included in a container, pack, or dispenser together with instructions for administration.

Screening and Detection Methods

The isolated nucleic acid molecules of the invention can be used to express NOV protein (e.g., via a recombinant expression vector in a host cell in gene therapy applications), to detect NOV mRNA (e.g., in a biological sample) or a genetic lesion in a NOV gene, and to modulate NOV activity, as described further, below. In addition, the NOV proteins can be used to screen drugs or compounds that modulate the NOV protein activity or expression as well as to treat disorders characterized by insufficient or excessive production of NOV protein or production of NOV protein forms that have decreased or aberrant activity compared to NOV wild-type protein. In addition, the anti-NOV antibodies of the invention can be used to detect and isolate NOV proteins and modulate NOV activity.

The invention further pertains to novel agents identified by the screening assays described herein and uses thereof for treatments as described, supra.

Screening Assays

The invention provides a method (also referred to herein as a "screening assay") for identifying modulators, i.e., candidate or test compounds or agents (e.g., peptides, peptidomimetics, small molecules or other drugs) that bind to NOV proteins or have a stimulatory or inhibitory effect on, e.g., NOV protein expression or NOV protein activity. The invention also includes compounds identified in the screening assays described herein. In one embodiment, the invention provides assays for screening candidate or test compounds which bind to or modulate the activity of the membrane-bound form of a NOV protein or polypeptide or biologically-active portion thereof. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. See, e.g., Lam, 1997. Anticancer Drug Design 12: 145.

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. Proc. Natl. Acad. Sci. U.S.A. 90: 6909; Erb, et al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37: 1233.

Libraries of compounds can be presented in solution (e.g., Houghten, 1992. Biotechniques 13: 412–421), or on beads (Lam, 1991. Nature 354: 82–84), on chips (Fodor, 1993. Nature 364: 555–556), bacteria (Ladner, U.S. Pat. No. 5,223,409), spores (Ladner, U.S. Pat. No. 5,233,409), plasmids (Cull, et al., 1992. Proc. Natl. Acad. Sci. USA 89: 1865–1869) or on phage (Scott and Smith, 1990. Science 249: 386–390; Devlin, 1990. Science 249: 404–406; Cwirla, et al., 1990. Proc. Natl. Acad. Sci. U.S.A. 87: 6378–6382; Felici, 1991. J. Mol. Biol. 222: 301–310; Ladner, U.S. Pat. No. 5,233,409.).

In one embodiment, an assay is a cell-based assay in which a cell which expresses a membrane-bound form of NOV protein, or a biologically-active portion thereof, on the cell surface is contacted with a test compound and the ability of the test compound to bind to a NOV protein determined. The cell, for example, can of mammalian origin or a yeast cell. Determining the ability of the test compound to bind to the NOV protein can be accomplished, for example, by coupling the test compound with a radioisotope or enzymatic label such that binding of the test compound to the NOV protein or biologically-active portion thereof can be determined by detecting the labeled compound in a complex. For example, test compounds can be labeled with $^{125}$I, $^{35}$S, $^{14}$C, or $^{3}$H, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of NOV protein, or a biologically-active portion thereof, on the cell surface with a known compound which binds NOV to form an assay mixture, contacting the assay mixture with a test compound, and determining the ability of the test compound to interact with a NOV protein, wherein determining the ability of the test compound to interact with a NOV protein comprises determining the ability of the test compound to preferentially bind to NOV protein or a biologically-active portion thereof as compared to the known compound. In another embodiment, an assay is a cell-based assay comprising contacting a cell expressing a membrane-bound form of NOV protein, or a biologically-active portion thereof, on the cell surface with a test compound and determining the ability of the test compound to modulate (e.g., stimulate or inhibit) the activity of the NOV protein or biologically-active portion thereof.

Determining the ability of the test compound to modulate the activity of NOV or a biologically-active portion thereof can be accomplished, for example, by determining the ability of the NOV protein to bind to or interact with a NOV target molecule. As used herein, a "target molecule" is a molecule with which a NOV protein binds or interacts in nature, for example, a molecule on the surface of a cell which expresses a NOV interacting protein, a molecule on the surface of a second cell, a molecule in the extracellular milieu, a molecule associated with the internal surface of a cell membrane or a cytoplasmic molecule. A NOV target molecule can be a non-NOV molecule or a NOV protein or polypeptide of the invention. In one embodiment, a NOV target molecule is a component of a signal transduction pathway that facilitates transduction of an extracellular signal (e.g. a signal generated by binding of a compound to a membrane-bound NOV molecule) through the cell membrane and into the cell. The target, for example, can be a second intercellular protein that has catalytic activity or a protein that facilitates the association of downstream signaling molecules with NOV.

Determining the ability of the NOV protein to bind to or interact with a NOV target molecule can be accomplished by one of the methods described above for determining direct binding. In one embodiment, determining the ability of the NOV protein to bind to or interact with a NOV target molecule can be accomplished by determining the activity of the target molecule. For example, the activity of the target molecule can be determined by detecting induction of a cellular second messenger of the target (i.e. intracellular $Ca^{2+}$, diacylglycerol, IP3, etc.), detecting catalytic/enzymatic activity of the target an appropriate substrate, detecting the induction of a reporter gene (comprising a NOV-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the invention is a cell-free assay comprising contacting a NOV protein or biologically-active portion thereof with a test compound and determining the ability of the test compound to bind to the NOV protein or biologically-active portion thereof. Binding of the test compound to the NOV protein can be determined either directly or indirectly as described above. In one such embodiment, the assay comprises contacting the NOV protein or biologically-active portion thereof with a known compound which binds NOV to form an assay mixture, contacting the assay mixture with a test compound, and determining the ability of the test compound to interact with a NOV protein, wherein determining the ability of the test compound to interact with a NOV protein comprises determining the ability of the test compound to preferentially bind to NOV or biologically-active portion thereof as compared to the known compound.

In still another embodiment, an assay is a cell-free assay comprising contacting NOV protein or biologically-active portion thereof with a test compound and determining the ability of the test compound to modulate (e.g. stimulate or inhibit) the activity of the NOV protein or biologically-active portion thereof. Determining the ability of the test compound to modulate the activity of NOV can be accomplished, for example, by determining the ability of the NOV protein to bind to a NOV target molecule by one of the methods described above for determining direct binding. In an alternative embodiment, determining the ability of the test compound to modulate the activity of NOV protein can be accomplished by determining the ability of the NOV protein to further modulate a NOV target molecule. For example, the catalytic/enzymatic activity of the target molecule on an appropriate substrate can be determined as described, supra.

In yet another embodiment, the cell-free assay comprises contacting the NOV protein or biologically-active portion thereof with a known compound which binds NOV protein to form an assay mixture, contacting the assay mixture with a test compound, and determining the ability of the test compound to interact with a NOV protein, wherein determining the ability of the test compound to interact with a NOV protein comprises determining the ability of the NOV protein to preferentially bind to or modulate the activity of a NOV target molecule.

The cell-free assays of the invention are amenable to use of both the soluble form or the membrane-bound form of NOV protein. In the case of cell-free assays comprising the membrane-bound form of NOV protein, it can be desirable to utilize a solubilizing agent such that the membrane-bound form of NOV protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl) dimethylamminiol-2-hydroxy-1-propane sulfonate (CHAPSO).

In more than one embodiment of the above assay methods of the invention, it can be desirable to immobilize either NOV protein or its target molecule to facilitate separation of complexed from uncomplexed forms of one or both of the proteins, as well as to accommodate automation of the assay. Binding of a test compound to NOV protein, or interaction of NOV protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, GST-NOV fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or NOV protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described, supra. Alternatively, the complexes can be dissociated from the matrix, and the level of NOV protein binding or activity determined using standard techniques.

Other techniques for immobilizing proteins on matrices can also be used in the screening assays of the invention. For example, either the NOV protein or its target molecule can be immobilized utilizing conjugation of biotin and streptavidin. Biotinylated NOV protein or target molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, antibodies reactive with NOV protein or target molecules, but which do not interfere with binding of the NOV protein to its target molecule, can be derivatized to the wells of the plate, and unbound target or NOV protein trapped in the wells by antibody conjugation. Methods for detecting such complexes, in addition to those described above for the GST-immobilized complexes, include immunodetection of complexes using antibodies reactive with the NOV protein or target molecule, as well as enzyme-linked assays that rely on detecting an enzymatic activity associated with the NOV protein or target molecule.

In another embodiment, modulators of NOV protein expression are identified in a method wherein a cell is contacted with a candidate compound and the expression of NOV mRNA or protein in the cell is determined. The level of expression of NOV mRNA or protein in the presence of the candidate compound is compared to the level of expression of NOV mRNA or protein in the absence of the candidate compound. The candidate compound can then be identified as a modulator of NOV mRNA or protein expression based upon this comparison. For example, when expression of NOV mRNA or protein is greater (i.e., statistically significantly greater) in the presence of the candidate compound than in its absence, the candidate compound is identified as a stimulator of NOV mRNA or protein expression. Alternatively, when expression of NOV mRNA or protein is less (statistically significantly less) in the presence of the candidate compound than in its absence, the candidate compound is identified as an inhibitor of NOV mRNA or protein expression. The level of NOV mRNA or protein expression in the cells can be determined by methods described herein for detecting NOV mRNA or protein.

In yet another aspect of the invention, the NOV proteins can be used as "bait proteins" in a two-hybrid assay or three hybrid assay (see, e.g., U.S. Pat. No. 5,283,317; Zervos, et al., 1993. Cell 72: 223–232; Madura, et al., 1993. J. Biol. Chem. 268: 12046–12054; Bartel, et al., 1993. Biotechniques 14: 920–924; Iwabuchi, et al., 1993. Oncogene 8: 1693–1696; and Brent WO 94/10300), to identify other proteins that bind to or interact with NOV ("NOV-binding proteins" or "NOV-bp") and modulate NOV activity. Such NOV-binding proteins are also likely to be involved in the propagation of signals by the NOV proteins as, for example, upstream or downstream elements of the NOV pathway.

The two-hybrid system is based on the modular nature of most transcription factors, which consist of separable DNA-binding and activation domains. Briefly, the assay utilizes two different DNA constructs. In one construct, the gene that codes for NOV is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a NOV-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with NOV.

The invention further pertains to novel agents identified by the aforementioned screening assays and uses thereof for treatments as described herein.

Detection Assays

Portions or fragments of the cDNA sequences identified herein (and the corresponding complete gene sequences) can be used in numerous ways as polynucleotide reagents. By way of example, and not of limitation, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. Some of these applications are described in the subsections, below.

Chromosome Mapping

Once the sequence (or a portion of the sequence) of a gene has been isolated, this sequence can be used to map the location of the gene on a chromosome. This process is called chromosome mapping. Accordingly, portions or fragments of the NOV sequences, SEQ ID NO: 1, 4, 6, 65 or 67, or fragments or derivatives thereof, can be used to map the location of the NOV genes, respectively, on a chromosome. The mapping of the NOV sequences to chromosomes is an important first step in correlating these sequences with genes associated with disease.

Briefly, NOV genes can be mapped to chromosomes by preparing PCR primers (preferably 15–25 bp in length) from the NOV sequences. Computer analysis of the NOV, sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the NOV sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. See, e.g., D'Eustachio, et al., 1983. Science 220: 919–924. Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the NOV sequences to design oligonucleotide primers, sub-localization can be achieved with panels of fragments from specific chromosomes. Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases, will suffice to get good results at a reasonable amount of time. For a review of this technique, see, Verma, et al., HUMAN CHROMOSOMES: A MANUAL OF BASIC TECHNIQUES (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. Such data are found, e.g., in McKusick, MENDELIAN INHERITANCE IN MAN, available on-line through Johns Hopkins University Welch Medical Library). The relationship between genes and disease, mapped to the same chromosomal region, can then be identified through linkage analysis (co-inheritance of physically adjacent genes), described in, e.g., Egeland, et al., 1987. Nature, 325: 783–787.

Moreover, differences in the DNA sequences between individuals affected and unaffected with a disease associated with the NOV gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing

The NOV sequences of the invention can also be used to identify individuals from minute biological samples. In this technique, an individual's genomic DNA is digested with one or more restriction enzymes, and probed on a Southern blot to yield unique bands for identification. The sequences of the invention are useful as additional DNA markers for RFLP ("restriction fragment length polymorphisms," described in U.S. Pat. No. 5,272,057).

Furthermore, the sequences of the invention can be used to provide an alternative technique that determines the actual base-by-base DNA sequence of selected portions of an individual's genome. Thus, the NOV sequences described herein can be used to prepare two PCR primers from the 5'- and 3'-termini of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the invention can be used to obtain such identification sequences from individuals and from tissue. The NOV sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Much of the allelic variation is due to single nucleotide polymorphisms (SNPs), which include restriction fragment length polymorphisms (RFLPs).

Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences can comfortably provide positive individual identification with a panel of perhaps 10 to 1,000 primers that each yield a noncoding amplified sequence of 100 bases. If predicted coding sequences, such as those in SEQ ID NO: 1, 4, 6, 65 or 67 are used, a more appropriate number of primers for positive individual identification would be 500–2,000.

Predictive Medicine

The invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the invention relates to diagnostic assays for determining NOV protein and/or nucleic acid expression as well as NOV activity, in the context of a biological sample (e.g., blood, serum, cells, tissue) to thereby determine whether an individual is afflicted with a disease or disorder, or is at risk of developing a disorder, associated with aberrant NOV expression or activity. The invention also provides for prognostic (or predictive) assays for determining whether an individual is at risk of developing a disorder associated with NOV protein, nucleic acid expression or activity. For example, mutations in a NOV gene can be assayed in a biological sample. Such assays can be used for prognostic or predictive purpose to thereby prophylactically treat an individual prior to the onset of a disorder characterized by or associated with NOV protein, nucleic acid expression, or biological activity.

Another aspect of the invention provides methods for determining NOV protein, nucleic acid expression or activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.) Yet another aspect of the invention pertains to monitoring the influence of agents (e.g., drugs, compounds) on the expression or activity of NOV in clinical trials.

These and other agents are described in further detail in the following sections.

Diagnostic Assays

An exemplary method for detecting the presence or absence of NOV in a biological sample involves obtaining a biological sample from a test subject and contacting the biological sample with a compound or an agent capable of detecting NOV protein or nucleic acid (e.g., mRNA, genomic DNA) that encodes NOV protein such that the presence of NOV is detected in the biological sample. An agent for detecting NOV mRNA or genomic DNA is a labeled nucleic acid probe capable of hybridizing to NOV mRNA or genomic DNA. The nucleic acid probe can be, for example, a full-length NOV nucleic acid, such as the nucleic acid of SEQ ID NO: 1, 4, 6, 65 or 67 or a portion thereof, such as an oligonucleotide of at least 15, 30, 50, 100, 250 or 500 nucleotides in length and sufficient to specifically hybridize under stringent conditions to NOV mRNA or genomic DNA. Other suitable probes for use in the diagnostic assays of the invention are described herein.

An agent for detecting NOV protein is an antibody capable of binding to NOV protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the invention can be used to detect NOV mRNA, protein, or genomic DNA in a biological sample in vitro as well as in vivo. For example, in vitro techniques for detection of NOV mRNA include Northern hybridizations and in situ hybridizations. In vitro techniques for detection of NOV protein include enzyme linked immunosorbent assays (ELISAs), Western blots, immunoprecipitations, and immunofluorescence. In vitro techniques for detection of NOV genomic DNA include Southern hybridizations. Furthermore, in vivo techniques for detection of NOV protein include introducing into a subject a labeled anti-NOV antibody. For example, the antibody can be labeled with a radioactive marker whose presence and location in a subject can be detected by standard imaging techniques. In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting NOV protein, mRNA, or genomic DNA, such that the presence of NOV protein, mRNA or genomic DNA is detected in the biological sample, and comparing the presence of NOV protein, mRNA or genomic DNA in the control sample with the presence of NOV protein, mRNA or genomic DNA in the test sample.

The invention also encompasses kits for detecting the presence of NOV in a biological sample. For example, the kit can comprise: a labeled compound or agent capable of detecting NOV protein or mRNA in a biological sample; means for determining the amount of NOV in the sample; and means for comparing the amount of NOV in the sample with a standard. The compound or agent can be packaged in a suitable container. The kit can further comprise instructions for using the kit to detect NOV protein or nucleic acid.

Prognostic Assays

The diagnostic methods described herein can furthermore be utilized to identify subjects having or at risk of developing a disease or disorder associated with aberrant NOV expression or activity. For example, the assays described herein, such as the preceding diagnostic assays or the following assays, can be utilized to identify a subject having or at risk of developing a disorder associated with NOV protein, nucleic acid expression or activity. For example, those involving development, differentiation, and activation of thymic immune cells; in pathologies related to spermatogenesis and male infertility; diagnosis of several human neoplasias; in diseases or pathologies of cells in blood circulation such as red blood cells and platelets; neurological, cardiac and vascular pathologies; rheumatoid arthritis; congenital muscular dystrophies; various muscle disorders; fixed deformities (arthrogryposis); small cell lung cancer NCI-H23; prostate cancer; and abnormal white matter. Alternatively, the prognostic assays can be utilized to identify a subject having or at risk for developing a disease or disorder. Thus, the invention provides a method for identifying a disease or disorder associated with aberrant NOV expression or activity in which a test sample is obtained from a subject and NOV protein or nucleic acid (e.g., mRNA, genomic DNA) is detected, wherein the presence of NOV protein or nucleic acid is diagnostic for a subject having or at risk of developing a disease or disorder associated with aberrant NOV expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant NOV expression or activity. For example, such methods can be used to determine whether a subject can be effectively treated with an agent for a disorder. Thus, the invention provides methods for determining whether a subject can be effectively treated with an agent for a disorder associated with aberrant NOV expression or activity in which a test sample is obtained and NOV protein or nucleic acid is detected (e.g., wherein the presence of NOV protein or nucleic acid is diagnostic for a subject that can be administered the agent to treat a disorder associated with aberrant NOV expression or activity).

The methods of the invention can also be used to detect genetic lesions in a NOV gene, thereby determining if a subject with the lesioned gene is at risk for a disorder characterized by aberrant cell proliferation and/or differentiation. In various embodiments, the methods include detecting, in a sample of cells from the subject, the presence or absence of a genetic lesion characterized by at least one of an alteration affecting the integrity of a gene encoding a NOV-protein, or the misexpression of the NOV gene. For example, such genetic lesions can be detected by ascertaining the existence of at least one of: (i) a deletion of one or more nucleotides from a NOV gene; (ii) an addition of one or more nucleotides to a NOV gene; (iii) a substitution of one or more nucleotides of a NOV gene, (iv) a chromosomal rearrangement of a NOV gene; (v) an alteration in the level of a messenger RNA transcript of a NOV gene, (vi) aberrant modification of a NOV gene, such as of the methylation pattern of the genomic DNA, (vii) the presence of a non-wild-type splicing pattern of a messenger RNA transcript of a NOV gene, (viii) a non-wild-type level of a NOV protein, (ix) allelic loss of a NOV gene, and (x) inappropriate post-translational modification of a NOV protein. As described herein, there are a large number of assay techniques known in the art which can be used for detecting lesions in a NOV gene. A preferred biological sample is a peripheral blood leukocyte sample isolated by conventional means from a subject. However, any biological sample containing nucleated cells can be used, including, for example, buccal mucosal cells.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran, et al., 1988. Science 241: 1077–1080; and Nakazawa, et al., 1994. Proc. Natl. Acad. Sci. USA 91: 360–364), the latter of which can be particularly useful for detecting point mutations in the NOV-gene (see, Abravaya, et al., 1995. Nucl. Acids Res. 23: 675–682). This method can include the steps of collecting a sample of cells from a patient, isolating nucleic acid (e.g., genomic, mRNA or both) from the cells of the sample, contacting the nucleic acid sample with one or more primers that specifically hybridize to a NOV gene under conditions such that hybridization and amplification of the NOV gene (if present) occurs, and detecting the presence or absence of an amplification product, or detecting the size of the amplification product and comparing the length to a control sample. It is anticipated that PCR and/or LCR can be desirable to use as a preliminary amplification step in conjunction with any of the techniques used for detecting mutations described herein.

Alternative amplification methods include: self sustained sequence replication (see, Guatelli, et al., 1990. Proc. Natl. Acad. Sci. USA 87: 1874–1878), transcriptional amplification system (see, Kwoh, et al., 1989. Proc. Natl. Acad. Sci. USA 86: 1173–1177); Qβ Replicase (see, Lizardi, et al, 1988. BioTechnology 6: 1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a NOV gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,493,531) can be used to score for the presence of specific mutations by development or loss of a ribozyme cleavage site.

In other embodiments, genetic mutations in NOV can be identified by hybridizing a sample and control nucleic acids, e.g., DNA or RNA, to high-density arrays containing hundreds or thousands of oligonucleotides probes. See, e.g., Cronin, et al., 1996. Human Mutation 7: 244–255; Kozal, et al., 1996. Nat. Med. 2: 753–759. For example, genetic mutations in NOV can be identified in two dimensional arrays containing light-generated DNA probes as described in Cronin, et al., supra. Briefly, a first hybridization array of probes can be used to scan through long stretches of DNA in a sample and control to identify base changes between the sequences by making linear arrays of sequential overlapping probes. This step allows the identification of point mutations. This is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the NOV gene and detect mutations by comparing the sequence of the sample NOV with the corresponding wild-type (control) sequence. Examples of sequencing reactions include those based on techniques developed by Maxim and Gilbert, 1977. Proc. Natl. Acad. Sci. USA 74: 560 or Sanger, 1977. Proc. Natl. Acad. Sci. USA 74: 5463. It is also contemplated that any of a variety of automated sequencing procedures can be utilized when performing the diagnostic assays (see, e.g., Naeve, et al., 1995. Biotechniques 19: 448), including sequencing by mass spectrometry (see, e.g., PCT International Publication No. WO 94/16101; Cohen, et al., 1996. Adv. Chromatography 36: 127–162; and Griffin, et al., 1993. Appl. Biochem. Biotechnol. 38: 147–159).

Other methods for detecting mutations in the NOV gene include methods in which protection from cleavage agents is used to detect mismatched bases in RNA/RNA or RNA/DNA heteroduplexes. See, e.g., Myers, et al., 1985. Science 230: 1242. In general, the art technique of "mismatch cleavage" starts by providing heteroduplexes of formed by hybridizing (labeled) RNA or DNA containing the wild-type NOV sequence with potentially mutant RNA or DNA obtained from a tissue sample. The double-stranded duplexes are treated with an agent that cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton, et al., 1988. Proc. Natl. Acad. Sci. USA 85: 4397; Saleeba, et al., 1992. Methods Enzymol. 217: 286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in NOV cDNAs obtained from samples of cells. For example, the mutY enzyme of *E. coli* cleaves A at G/A mismatches and the thymidine DNA glycosylase from HeLa cells cleaves T at G/T mismatches. See, e.g., Hsu, et al., 1994. Carcinogenesis 15: 1657–1662. According to an exemplary embodiment, a probe based on a NOV sequence, e.g., a wild-type NOV sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in NOV genes. For example, single strand conformation polymorphism (SSCP) can be used to detect differences in electrophoretic mobility between mutant and wild type nucleic acids. See, e.g., Orita, et al., 1989. Proc. Natl. Acad. Sci. USA: 86: 2766; Cotton, 1993. Mutat. Res. 285: 125–144; Hayashi, 1992. Genet. Anal. Tech. Appl. 9: 73–79. Single-stranded DNA fragments of sample and control NOV nucleic acids will be denatured and allowed to renature. The secondary structure of single-stranded nucleic acids varies according to sequence, the resulting alteration in electrophoretic mobility enables the detection of even a single base change. The DNA fragments can be labeled or detected with labeled probes. The sensitivity of the assay can be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility. See, e.g., Keen, et al., 1991. Trends Genet. 7: 5.

In yet another embodiment, the movement of mutant or wild-type fragments in polyacrylamide gels containing a gradient of denaturant is assayed using denaturing gradient gel electrophoresis (DGGE). See, e.g., Myers, et al., 1985. Nature 313: 495. When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA. See, e.g., Rosenbaum and Reissner, 1987. Biophys. Chem. 265: 12753.

Examples of other techniques for detecting point mutations include, but are not limited to, selective oligonucleotide hybridization, selective amplification, or selective primer extension. For example, oligonucleotide primers can be prepared in which the known mutation is placed centrally and then hybridized to target DNA under conditions that permit hybridization only if a perfect match is found. See, e.g., Saiki, et al., 1986. Nature 324: 163; Saiki, et al., 1989. Proc. Natl. Acad. Sci. USA 86: 6230. Such allele specific oligonucleotides are hybridized to PCR amplified target DNA or a number of different mutations when the oligonucleotides are attached to the hybridizing membrane and hybridized with labeled target DNA.

Alternatively, allele specific amplification technology that depends on selective PCR amplification can be used in conjunction with the instant invention. Oligonucleotides used as primers for specific amplification may carry the mutation of interest in the center of the molecule (so that amplification depends on differential hybridization; see, e.g., Gibbs, et al., 1989. Nucl. Acids Res. 17: 2437–2448) or at the extreme 3'-terminus of one primer where, under appropriate conditions, mismatch can prevent, or reduce polymerase extension (see, e.g., Prossner, 1993. Tibtech. 11: 238). In addition it can be desirable to introduce a novel restriction site in the region of the mutation to create cleavage-based detection. See, e.g., Gasparini, et al., 1992. Mol. Cell Probes 6: 1. It is anticipated that in certain embodiments amplification may also be performed using Taq ligase for amplification. See, e.g., Barany, 1991. Proc. Natl. Acad. Sci. USA 88: 189. In such cases, ligation will occur only if there is a perfect match at the 3'-terminus of the 5' sequence, making it possible to detect the presence of a known mutation at a specific site by looking for the presence or absence of amplification.

The methods described herein can be performed, for example, by utilizing pre-packaged diagnostic kits comprising at least one probe nucleic acid or antibody reagent described herein, which can be conveniently used, e.g., in clinical settings to diagnose patients exhibiting symptoms or family history of a disease or illness involving a NOV gene. Furthermore, any cell type or tissue, preferably peripheral blood leukocytes, in which NOV is expressed can be utilized in the prognostic assays described herein. However, any biological sample containing nucleated cells can be used, including, for example, buccal mucosal cells.

Pharmacogenomics

Agents, or modulators that have a stimulatory or inhibitory effect on NOV activity (e.g., NOV gene expression), as identified by a screening assay described herein can be administered to individuals to treat (prophylactically or therapeutically) disorders (e.g., cancer or immune disorders associated with aberrant NOV activity. In conjunction with such treatment, the pharmacogenomics (i.e., the study of the relationship between an individual's genotype and that individual's response to a foreign compound or drug) of the individual can be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of NOV protein, expression of NOV nucleic acid, or mutation content of NOV genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See e.g., Eichelbaum, 1996. Clin. Exp. Pharmacol. Physiol., 23: 983–985; Linder, 1997. Clin. Chem., 43: 254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. At the other extreme are the so-called ultra-rapid metabolizers who do not respond to standard doses. Recently, the molecular basis of ultra-rapid metabolism has been identified to be due to CYP2D6 gene amplification.

Thus, the activity of NOV protein, expression of NOV nucleic acid, or mutation content of NOV genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a NOV modulator, such as a modulator identified by one of the exemplary screening assays described herein.

Monitoring of Effects During Clinical Trials

Monitoring the influence of agents (e.g., drugs, compounds) on the expression or activity of NOV (e.g., the ability to modulate aberrant cell proliferation and/or differentiation) can be applied not only in basic drug screening, but also in clinical trials. For example, the effectiveness of an agent determined by a screening assay as described herein to increase NOV gene expression, protein levels, or upregulate NOV activity, can be monitored in clinical trails of subjects exhibiting decreased NOV gene expression, protein levels, or downregulated NOV activity. Alternatively, the effectiveness of an agent determined by a screening assay to decrease NOV gene expression, protein levels, or downregulate NOV activity, can be monitored in clinical trails of subjects exhibiting increased NOV gene expression, protein levels, or upregulated NOV activity. In such clinical trials, the expression or activity of NOV and, preferably, other genes that have been implicated in, for example, a cellular proliferation or immune disorder can be used as a "read out" or markers of the immune responsiveness of a particular cell.

By way of example, and not of limitation, genes, including NOV, that are modulated in cells by treatment with an agent (e.g., compound, drug or small molecule) that modulates NOV activity (e.g., identified in a screening assay as described herein) can be identified. Thus, to study the effect of agents on cellular proliferation disorders, for example, in a clinical trial, cells can be isolated and RNA prepared and analyzed for the levels of expression of NOV and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of NOV or other genes. In this manner, the gene expression pattern can serve as a marker, indicative of the physiological response of the cells to the agent. Accordingly, this response state can be determined before, and at various points during, treatment of the individual with the agent.

In one embodiment, the invention provides a method for monitoring the effectiveness of treatment of a subject with an agent (e.g., an agonist, antagonist, protein, peptide, peptidomimetic, nucleic acid, small molecule, or other drug candidate identified by the screening assays described herein) comprising the steps of (i) obtaining a pre-administration sample from a subject prior to administration of the agent; (ii) detecting the level of expression of a NOV protein, mRNA, or genomic DNA in the preadministration sample; (iii) obtaining one or more post-administration samples from the subject; (iv) detecting the level of expression or activity of the NOV protein, mRNA, or genomic DNA in the post-administration samples; (v) comparing the level of expression or activity of the NOV protein, mRNA, or genomic DNA in the pre-administration sample with the NOV protein, mRNA, or genomic DNA in the post administration sample or samples; and (vi) altering the administration of the agent to the subject accordingly. For example, increased administration of the agent can be desirable to increase the expression or activity of NOV to higher levels than detected, i.e., to increase the effectiveness of the agent. Alternatively, decreased administration of the agent can be desirable to decrease expression or activity of NOV to lower levels than detected, i.e., to decrease the effectiveness of the agent.

Methods of Treatment

The invention provides for both prophylactic and therapeutic methods of treating a subject at risk of (or susceptible to) a disorder or having a disorder associated with aberrant NOV expression or activity. Such related diseases or disorders include for NOV1 for example, those involving development, differentiation, and activation of thymic immune cells; in pathologies related to spermatogenesis and male infertility; diagnosis of several human neoplasias; in diseases or pathologies of cells in blood circulation such as red blood cells and platelets; and small cell lung cancer NCI-H23; for NOV2 and NOV4, for example, neurological, cardiac and vascular pathologies; for NOV3 and NOV5, for example, rheumatoid arthritis; congenital muscular dystrophies; various muscle disorders; fixed deformities (arthrogryposis); prostate cancer; and abnormal white matter. These methods of treatment will be discussed more fully, below.

Disease and Disorders

Diseases and disorders that are characterized by increased (relative to a subject not suffering from the disease or disorder) levels or biological activity can be treated with Therapeutics that antagonize (i.e., reduce or inhibit) activity. Therapeutics that antagonize activity can be administered in a therapeutic or prophylactic manner. Therapeutics that can be utilized include, but are not limited to: (i) an aforementioned peptide, or analogs, derivatives, fragments or homologs thereof; (ii) antibodies to an aforementioned peptide; (iii) nucleic acids encoding an aforementioned peptide; (iv) administration of antisense nucleic acid and nucleic acids that are "dysfunctional" (i.e., due to a heterologous insertion within the coding sequences of coding sequences to an aforementioned peptide) that are utilized to "knockout" endogenous function of an aforementioned peptide by homologous recombination (see, e.g., Capecchi, 1989. Science 244: 1288–1292); or (v) modulators (i.e., inhibitors, agonists and antagonists, including additional peptide mimetic of the invention or antibodies specific to a peptide of the invention) that alter the interaction between an aforementioned peptide and its binding partner.

Diseases and disorders that are characterized by decreased (relative to a subject not suffering from the disease or disorder) levels or biological activity can be treated with Therapeutics that increase (i.e., are agonists to) activity. Therapeutics that upregulate activity can be administered in a therapeutic or prophylactic manner. Therapeutics that can be utilized include, but are not limited to, an aforementioned peptide, or analogs, derivatives, fragments or homologs thereof; or an agonist that increases bioavailability.

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of an aforementioned peptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, and the like).

Prophylactic Methods

In one aspect, the invention provides a method for preventing, in a subject, a disease or condition associated with an aberrant NOV expression or activity, by administering to the subject an agent that modulates NOV expression or at least one NOV activity. These conditions include for NOV1, for example, those involving development, differentiation, and activation of thymic immune cells; in pathologies related to spermatogenesis and male infertility; diagnosis of several human neoplasias; in diseases or pathologies of cells in blood circulation such as red blood cells and platelets; and small cell lung cancer NCI-H23; for NOV2 and NOV4, for example, neurological, cardiac and vascular pathologies; for NOV3 and NOV5, for example, rheumatoid arthritis; congenital muscular dystrophies; various muscle disorders; fixed deformities (arthrogryposis); prostate cancer; and abnormal white matter. Subjects at risk for a disease that is caused or contributed to by aberrant NOV expression or activity can be identified by, for example, any or a combination of diagnostic or prognostic assays as described herein. Administration of a prophylactic agent can occur prior to the manifestation of symptoms characteristic of the NOV aberrancy, such that a disease or disorder is prevented or, alternatively, delayed in its progression. Depending upon the type of NOV aberrancy, for example, a NOV agonist or NOV antagonist agent can be used for treating the subject. The appropriate agent can be determined based on screening assays described herein. The prophylactic methods of the invention are further discussed in the following subsections.

Therapeutic Methods

Another aspect of the invention pertains to methods of modulating NOV expression or activity for therapeutic purposes. The modulatory method of the invention involves contacting a cell with an agent that modulates one or more of the activities of NOV protein activity associated with the cell. An agent that modulates NOV protein activity can be an agent as described herein, such as a nucleic acid or a protein, a naturally-occurring cognate ligand of a NOV protein, a peptide, a NOV peptidomimetic, or other small molecule. In one embodiment, the agent stimulates one or more NOV protein activity. Examples of such stimulatory agents include active NOV protein and a nucleic acid molecule encoding NOV that has been introduced into the cell. In another embodiment, the agent inhibits one or more NOV protein activity. Examples of such inhibitory agents include antisense NOV nucleic acid molecules and anti-NOV antibodies. These modulatory methods can be performed in vitro (e.g., by culturing the cell with the agent) or, alternatively, in vivo (e.g., by administering the agent to a subject). As such, the invention provides methods of treating an individual afflicted with a disease or disorder characterized by aberrant expression or activity of a NOV protein or nucleic acid molecule. In one embodiment, the method involves administering an agent (e.g., an agent identified by a screening assay described herein), or combination of agents that modulates (e.g., up-regulates or down-regulates) NOV expression or activity. In another embodiment, the method involves administering a NOV protein or nucleic acid molecule as therapy to compensate for reduced or aberrant NOV expression or activity.

Stimulation of NOV activity is desirable in situations in which NOV is abnormally downregulated and/or in which increased NOV activity is likely to have a beneficial effect. One example of such a situation is where a subject has a disorder characterized by aberrant cell proliferation and/or differentiation (e.g., cancer or immune associated disorders). Another example of such a situation is where the subject has a gestational disease (e.g., preclampsia).

Determination of the Biological Effect of the Therapeutic

In various embodiments of the invention, suitable in vitro or in vivo assays are performed to determine the effect of a specific Therapeutic and whether its administration is indicated for treatment of the affected tissue.

In various specific embodiments, in vitro assays can be performed with representative cells of the type(s) involved in the patient's disorder, to determine if a given Therapeutic exerts the desired effect upon the cell type(s). Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects.

Prophylactic and Therapeutic Uses of the Compositions of the Invention

The NOV nucleic acids and proteins of the invention are useful in potential prophylactic and therapeutic applications implicated in a variety of disorders including, but not limited to: for NOV1 those involving development, differentiation, and activation of thymic immune cells; in pathologies related to spermatogenesis and male infertility; diagnosis of several human neoplasias; in diseases or pathologies of cells in blood circulation such as red blood cells and platelets; in blood circulation such as red blood cells and platelets; for NOV2 and NOV4 neurological, cardiac and vascular pathologies; for NOV3 and NOV5 rheumatoid arthritis; congenital muscular dystrophies; various muscle disorders; fixed deformities (arthrogryposis); and abnormal white matter.

As an example, a cDNA encoding the NOV protein of the invention can be useful in gene therapy, and the protein can be useful when administered to a subject in need thereof. By way of non-limiting example, the compositions of the invention will have efficacy for treatment of patients suffering from the above mentioned disorders.

Both the novel nucleic acid encoding the NOV protein, and the NOV protein of the invention, or fragments thereof, may also be useful in diagnostic applications, wherein the presence or amount of the nucleic acid or the protein are to be assessed. A further use could be as an anti-bacterial molecule (i.e., some peptides have been found to possess anti-bacterial properties). These materials are further useful in the generation of antibodies which immunospecifically-bind to the novel substances of the invention for use in therapeutic or diagnostic methods. Those involving development, differentiation, and activation of thymic immune cells; in pathologies related to spermatogenesis and male infertility; diagnosis of several human neoplasias; in diseases or pathologies of cells in blood circulation such as red blood cells and platelets; neurological, cardiac and vascular pathologies; rheumatoid arthritis; congenital muscular dystrophies; various muscle disorders; fixed deformities (arthrogryposis); and abnormal white matter

EXAMPLES

The following examples illustrate by way of non-limiting example various aspects of the invention.

Example 1

Quantitative Expression Analysis of NOV1, NOV2 and NOV3 in Various Cells and Tissues The quantitative expression of various clones was assessed in about 41 normal and about 55 tumor samples by real time quantitative PCR (TAQMAN®) performed on a Perkin-Elmer Biosystems ABI PRISMS® 7700 Sequence Detection System. In the following Tables 15–17, the following abbreviations are used:
ca.=carcinoma,
*=established from metastasis,
met=metastasis,
s cell var=small cell variant,
non-s=non-sm=non-small,
squam=squamous,
pl. eff=pl effusion=pleural effusion,
glio=glioma,
astro=astrocytoma, and
neuro=neuroblastoma
NAT=normal adjacent tissue.

First, up to 96 RNA samples were normalized to β-actin and GAPDH. RNA (~50 ng total or ~1 ng polyA+) was converted to cDNA using the TAQMAN® Reverse Transcription Reagents Kit (PE Biosystems, Foster City, Calif.; Catalog No. N808-0234) and random hexamers according to the manufacturer's protocol. Reactions were performed in 20 ul and incubated for 30 min. at 48° C. cDNA (5 ul) was then transferred to a separate plate for the TAQMAN® reaction using β-actin and GAPDH TAQMAN® Assay Reagents (PE Biosystems; Catalog Nos. 4310881E and 4310884E, respectively) and TAQMAN® universal PCR Master Mix (PE Biosystems; Catalog No. 4304447) according to the manufacturer's protocol. Reactions were performed in 25 ul using the following parameters: 2 min. at 50° C.; 10 min. at 95° C.; 15 sec. at 95° C./1 min. at 60° C. (40 cycles). Results were recorded as CT values (cycle at which a given sample crosses a threshold level of fluorescence) using a log scale, with the difference in RNA concentration between a given sample and the sample with the lowest CT value being represented as 2 to the power of delta CT. The percent relative expression is then obtained by taking the reciprocal of this RNA difference and multiplying by 100. The relative expression percent is in reference to the β-actin and GAPDH levels. Higher relative expression in a normal versus a cancerous tissues indicates an increased expression of gene in cancerous tissues and that the gene is a marker for a type of cancer. The average CT values obtained for β-actin and GAPDH were used to normalize RNA samples. The RNA sample generating the highest CT value required no further diluting, while all other samples were diluted relative to this sample according to their β-actin /GAPDH average CT values.

Normalized RNA (5 ul) was converted to cDNA and analyzed via TAQMAN® using One Step RT-PCR Master Mix Reagents (PE Biosystems; Catalog No. 4309169) and gene-specific primers according to the manufacturer's instructions. Probes and primers were designed for each assay according to Perkin Elmer Biosystem's *Primer Express* Software package (version I for Apple Computer's Macintosh Power PC) or a similar algorithm using the target sequence as input. Default settings were used for reaction conditions and the following parameters were set before selecting primers: primer concentration=250 nM, primer melting temperature ($T_m$) range=58°–60° C., primer optimal Tm=59° C., maximum primer difference=2° C., probe does not have 5' G, probe $T_m$ must be 10° C. greater than primer $T_m$, amplicon size 75 bp to 100 bp. The probes and primers selected (see below) were synthesized by Synthegen (Houston, Tex., USA). Probes were double purified by HPLC to remove uncoupled dye and evaluated by mass spectroscopy to verify coupling of reporter and quencher dyes to the 5' and 3' ends of the probe, respectively. Their final concentrations were: forward and reverse primers, 900 nM each, and probe, 200 nM.

PCR conditions: Normalized RNA from each tissue and each cell line was spotted in each well of a 96 well PCR plate (Perkin Elmer Biosystems). PCR cocktails including two probes (SEQX-specific and another gene-specific probe multiplexed with the SEQX probe) were set up using 1×TaqMan™ PCR Master Mix for the PE Biosystems 7700, with 5 mM MgCl2, dNTPs (dA, G, C, U at 1:1:1:2 ratios), 0.25 U/ml AmpliTaq Gold™ (PE Biosystems), and 0.4 U/□1 RNase inhibitor, and 0.25 U/□1 reverse transcriptase. Reverse transcription was performed at 48° C. for 30 minutes followed by amplification/PCR cycles as follows: 95° C. 10 min, then 40 cycles of 95° C. for 15 seconds, 60° C. for 1 minute.

A. NOV1

Probe Name: Ag190

| Primers | Sequences | Lenght | Start Position | SEQ ID NO: |
|---|---|---|---|---|
| Forward | 5'-TGGAGGAAGAATCACCACAAGA-3' | 22 | 243 | 8 |
| Probe | TET-5'-CAAGCCACAAACTGTGACGTGAACCTG-3'-TAMRA | 27 | 271 | 9 |
| Reverse | 5'-GTGGCATCAGCACGGAGTG-3' | 19 | 300 | 10 |

The results obtained for clone NOV1 using primer-probe set Ag190 are shown in Table 15.

TABLE 15

| Tissue_Name | Relative Expression % |
|---|---|
| Endothelial cells | 0.0 |
| Endothelial cells (treated) | 0.0 |
| Pancreas | 0.0 |
| Pancreatic ca. CAPAN 2 | 0.0 |
| Adrenal Gland (new lot*) | 92.0 |
| Thyroid | 0.0 |
| Salavary gland | 23.8 |
| Pituitary gland | 0.0 |
| Brain (fetal) | 0.0 |
| Brain (whole) | 0.0 |
| Brain (amygdala) | 0.0 |
| Brain (cerebellum) | 0.0 |
| Brain (hippocampus) | 0.0 |
| Brain (thalamus) | 0.0 |
| Cerebral Cortex | 1.2 |
| Spinal cord | 0.0 |
| CNS ca. (glio/astro) U87-MG | 2.5 |
| CNS ca. (glio/astro) U-118-MG | 0.0 |
| CNS ca. (astro) SW1783 | 0.0 |
| CNS ca.* (neuro; met) SK-N-AS | 7.8 |
| CNS ca. (astro) SF-539 | 0.0 |
| CNS ca. (astro) SNB-75 | 0.0 |
| CNS ca. (glio) SNB-19 | 2.1 |
| CNS ca. (glio) U251 | 0.0 |
| CNS ca. (glio) SF-295 | 0.3 |
| Heart | 0.0 |
| Skeletal Muscle (new lot*) | 0.0 |
| Bone marrow | 0.0 |
| Thymus | 0.0 |
| Spleen | 0.0 |
| Lymph node | 0.0 |
| Colorectal | 0.0 |
| Stomach | 0.0 |
| Small intestine | 7.3 |
| Colon ca. SW480 | 0.0 |
| Colon ca.* (SW480 met) SW620 | 0.4 |
| Colon ca. HT29 | 0.0 |
| Colon ca. HCT-116 | 14.6 |
| Colon ca. CaCo-2 | 14.5 |
| 83219 CC Well to Mod Diff (ODO3866) | 0.0 |
| Colon ca. HCC-2998 | 55.1 |
| Gastric ca.* (liver met) NCI-N87 | 0.0 |
| Bladder | 0.0 |
| Trachea | 0.0 |
| Kidney | 4.4 |
| Kidney (fetal) | 6.1 |
| Renal ca. 786-0 | 0.0 |
| Renal ca. A498 | 0.0 |
| Renal ca. RXF 393 | 0.0 |
| Renal ca. ACHN | 0.9 |
| Renal ca. UO-31 | 0.0 |
| Renal ca. TK-10 | 0.6 |
| Liver | 0.0 |
| Liver (fetal) | 0.0 |
| Liver ca. (hepatoblast) HepG2 | 32.1 |
| Lung | 0.0 |
| Lung (fetal) | 0.0 |
| Lung ca. (small cell) LX-1 | 0.0 |
| Lung ca. (small cell) NCI-H69 | 22.9 |
| Lung ca. (s.cell var.) SHP-77 | 0.0 |
| Lung ca. (large cell) NCI-H460 | 4.0 |
| Lung ca. (non-sm. cell) A549 | 8.4 |
| Lung ca. (non-s.cell) NCI-H23 | 100.0 |
| Lung ca (non-s.cell) HOP-62 | 0.8 |
| Lung ca. (non-s.cl) NCI-H522 | 15.4 |
| Lung ca. (squam.) SW 900 | 0.0 |
| Lung ca. (squam.) NCI-H596 | 42.3 |
| Mammary gland | 0.0 |
| Breast ca.* (pl. effusion) MCF-7 | 2.1 |
| Breast ca.* (pl.ef) MDA-MB-231 | 0.0 |
| Breast ca.* (pl. effusion) T47D | 21.0 |
| Breast ca. BT-549 | 0.0 |
| Breast ca. MDA-N | 16.5 |
| Ovary | 0.0 |

TABLE 15-continued

| Tissue_Name | Relative Expression % |
|---|---|
| Ovarian ca. OVCAR-3 | 1.0 |
| Ovarian ca. OVCAR-4 | 0.2 |
| Ovarian ca. OVCAR-5 | 1.8 |
| Ovarian ca. OVCAR-8 | 7.5 |
| Ovarian ca. IGROV-1 | 3.9 |
| Ovarian ca.* (ascites) SK-OV-3 | 0.5 |
| Uterus | 0.0 |
| Plancenta | 0.0 |
| Prostate | 2.1 |
| Prostate ca.* (bone met) PC-3 | 11.5 |
| Testis | 0.0 |
| Melanoma Hs688(A).T | 0.0 |
| Melanoma* (met) Hs688(B).T | 0.0 |
| Melanoma UACC-62 | 0.0 |
| Melanoma M14 | 0.0 |
| Melanoma LOX IMVI | 0.0 |
| Melanoma* (met) SK-MEL-5 | 0.0 |

TABLE 15.A

| Tissue Name | Rel. Expr., % 2dtm2376t_ag190 |
|---|---|
| Normal Colon GENPAK 061003 | 27 |
| 83219 CC Well to Mod Diff (ODO3866) | 8.9 |
| 83220 CC NAT (ODO3866) | 15.8 |
| 83221 CC Gr.2 rectosigmoid (ODO3868) | 5.1 |
| 83222 CC NAT (ODO3868) | 0 |
| 83235 CC Mod Diff (ODO3920) | 35.1 |
| 83236 CC NAT (ODO3920) | 7 |
| 83237 CC Gr.2 ascend colon (ODO3921) | 9 |
| 83238 CC NAT (ODO3921) | 0 |
| 83241 CC from Partial Hepatectomy (ODO4309) | 7.9 |
| 83242 Liver NAT (ODO4309) | 4.1 |
| 87472 Colon mets to lung (OD04451-01) | 37.9 |
| 87473 Lung NAT (OD04451-02) | 0 |
| Normal Prostate Clontech A+ 6546-1 | 23.7 |
| 84140 Prostate Cancer (OD04410) | 12.5 |
| 84141 Prostate NAT (OD04410) | 19.2 |
| 87073 Prostate Cancer (OD04720-01) | 35.6 |
| 87074 Prostate NAT (OD04720-02) | 4.5 |
| Normal Lung GENPAK 061010 | 3.6 |
| 83239 Lung Met to Muscle (ODO4286) | 0 |
| 83240 Muscle NAT (ODO4286) | 8.1 |
| 84136 Lung Malignant Cancer (OD03126) | 0 |
| 84137 Lung NAT (OD03126) | 4.6 |
| 84871 Lung Cancer (OD04404) | 0 |
| 84872 Lung NAT (OD04404) | 10.3 |
| 84875 Lung Cancer (OD04565) | 0 |
| 84876 Lung NAT (OD04565) | 0 |
| 85950 Lung Cancer (OD04237-01) | 70.2 |
| 85970 Lung NAT (OD04237-02) | 0 |
| 83255 Ocular Mel Met to Liver (ODO4310) | 9.3 |
| 83256 Liver NAT (ODO4310) | 0 |
| 84139 Melanoma Mets to Lung (OD04321) | 28.3 |
| 84138 Lung NAT (OD04321) | 0 |
| Normal Kidney GENPAK 061008 | 40.6 |
| 83786 Kidney Ca, Nuclear grade 2 (OD04338) | 0 |
| 83787 Kidney NAT (OD04338) | 17.8 |
| 83788 Kidney Ca Nuclear grade 1/2 (OD04339) | 0 |
| 83789 Kidney NAT (OD04339) | 4 |
| 83790 Kidney Ca, Clear cell type (OD04340) | 4.1 |
| 83791 Kidney NAT (OD04340) | 4.5 |
| 83792 Kidney Ca, Nuclear grade 3 (OD04348) | 0 |
| 83793 Kidney NAT (OD04348) | 4 |
| 87474 Kidney Cancer (OD04622-01) | 0 |
| 87475 Kidney NAT (OD04622-03) | 0 |
| 85973 Kidney Cancer (OD04450-01) | 4.9 |
| 85974 Kidney NAT (OD04450-03) | 10.5 |
| Kidney Cancer Clontech 8120607 | 0 |
| Kidney NAT Clontech 8120608 | 4.8 |
| Kidney Cancer Clontech 8120613 | 0 |
| Kidney NAT Clontech 8120614 | 4.1 |
| Kidney Cancer Clontech 9010320 | 4.2 |

TABLE 15.A-continued

| Tissue Name | Rel. Expr., %<br>2dtm2376t_ag190 |
|---|---|
| Kidney NAT Clontech 9010321 | 0 |
| Normal Uterus GENPAK 061018 | 4 |
| Uterus Cancer GENPAK 064011 | 33.2 |
| Normal Thyroid Clontech A+ 6570-1 | 100 |
| Thyroid Cancer GENPAK 064010 | 14.8 |
| Thyroid Cancer INVITROGEN A302152 | 4.3 |
| Thyroid NAT INVITROGEN A302153 | 34.2 |
| Normal Breast GENPAK 061019 | 39.8 |
| 84877 Breast Cancer (OD04566) | 4.9 |
| 85975 Breast Cancer (OD04590-01) | 0 |
| 85976 Breast Cancer Mets (OD04590-03) | 2.3 |
| 87070 Breast Cancer Metastasis (OD04655-05) | 19.1 |
| GENPAK Breast Cancer 064006 | 0 |
| Breast Cancer Res. Gen. 1024 | 8.2 |
| Breast Cancer Clontech 9100266 | 15.9 |
| Breast NAT Clontech 9100265 | 0 |
| Breast Cancer INVITROGEN A209073 | 22.1 |
| Breast NAT INVITROGEN A2090734 | 34.4 |
| Normal Liver GENPAK 061009 | 0 |
| Liver Cancer GENPAK 064003 | 13.4 |
| Liver Cancer Research Genetics RNA 1025 | 0 |
| Liver Cancer Research Genetics RNA 1026 | 0 |
| Paired Liver Cancer Tissue Research Genetics RNA 6004-T | 5.6 |
| Paired Liver Tissue Research Genetics RNA 6004-N | 30.6 |
| Paired Liver Cancer Tissue Research Genetics RNA 6005-T | 0 |
| Paired Liver Tissue Research Genetics RNA 6005-N | 0 |
| Normal Bladder GENPAK 061001 | 0 |
| Bladder Cancer Research Genetics RNA 1023 | 5.1 |
| Bladder Cancer INVITROGEN A302173 | 33.2 |
| 87071 Bladder Cancer (OD04718-01) | 3.8 |
| 87072 Bladder Normal Adjacent (OD04718-03) | 7.6 |
| Normal Ovary Res. Gen. | 4 |
| Ovarian Cancer GENPAK 064008 | 8.9 |
| 87492 Ovary Cancer (OD04768-07) | 29.9 |
| 87493 Ovary NAT (OD04768-08) | 4.4 |
| Normal Stomach GENPAK 061017 | 4.2 |
| Gastric Cancer Clontech 9060358 | 9.5 |
| NAT Stomach Clontech 9060359 | 0 |
| Gastric Cancer Clontech 9060395 | 0 |
| NAT Stomach Clontech 9060394 | 0 |
| Gastric Cancer Clontech 9060397 | 15.4 |
| NAT Stomach Clontech 9060396 | 0 |
| Gastric Cancer GENPAK 064005 | 5.4 |

TABLE 15.B

| Tissue Name | Rel. Expr., %<br>2Dtm2390t_ag190 |
|---|---|
| Normal Colon GENPAK 061003 | 63.7 |
| 83219 CC Well to Mod Diff (ODO3866) | 32.3 |
| 83220 CC NAT (ODO3866) | 13 |
| 83221 CC Gr.2 rectosigmoid (ODO3868) | 0 |
| 83222 CC NAT (ODO3868) | 3.1 |
| 83235 CC Mod Diff (ODO3920) | 42 |
| 83236 CC NAT (ODO3920) | 0 |
| 83237 CC Gr.2 ascend colon (ODO3921) | 8.1 |
| 83238 CC NAT (ODO3921) | 0 |
| 83241 CC from Partial Hepatectomy (ODO4309) | 7.1 |
| 83242 Liver NAT (ODO4309) | 0 |
| 87472 Colon mets to lung (OD04451-01) | 11.8 |
| 87473 Lung NAT (OD04451-02) | 0 |
| Normal Prostate Clontech A+ 6546-1 | 63.7 |
| 84140 Prostate Cancer (OD04410) | 35.4 |
| 84141 Prostate NAT (OD04410) | 8.7 |
| 87073 Prostate Cancer (OD04720-01) | 0 |
| 87074 Prostate NAT (OD04720-02) | 44.1 |
| Normal Lung GENPAK 061010 | 15.8 |
| 83239 Lung Met to Muscle (ODO4286) | 8.4 |
| 83240 Muscle NAT (ODO4286) | 0 |

TABLE 15.B-continued

| Tissue Name | Rel. Expr., %<br>2Dtm2390t_ag190 |
|---|---|
| 84136 Lung Malignant Cancer (OD03126) | 0 |
| 84137 Lung NAT (OD03126) | 0 |
| 84871 Lung Cancer (OD04404) | 0 |
| 84872 Lung NAT (OD04404) | 11.1 |
| 84875 Lung Cancer (OD04565) | 0 |
| 84876 Lung NAT (OD04565) | 0 |
| 85950 Lung Cancer (OD04237-01) | 83.5 |
| 85970 Lung NAT (OD04237-02) | 0 |
| 83255 Ocular Mel Met to Liver (ODO4310) | 0 |
| 83256 Liver NAT (ODO4310) | 0 |
| 84139 Melanoma Mets to Lung (OD04321) | 47 |
| 84138 Lung NAT (OD04321) | 0 |
| Normal Kidney GENPAK 061008 | 51.4 |
| 83786 Kidney Ca, Nuclear grade 2 (OD04338) | 0 |
| 83787 Kidney NAT (OD04338) | 5.6 |
| 83788 Kidney Ca Nuclear grade 1/2 (OD04339) | 0 |
| 83789 Kidney NAT (OD04339) | 0 |
| 83790 Kidney Ca, Clear cell type (OD04340) | 10.7 |
| 83791 Kidney NAT (OD04340) | 15.6 |
| 83792 Kidney Ca, Nuclear grade 3 (OD04348) | 0 |
| 83793 Kidney NAT (OD04348) | 0 |
| 87474 Kidney Cancer (OD04622-01) | 0 |
| 87475 Kidney NAT (OD04622-03) | 8.9 |
| 85973 Kidney Cancer (OD04450-01) | 3.6 |
| 85974 Kidney NAT (OD04450-03) | 4.3 |
| Kidney Cancer Clontech 8120607 | 0 |
| Kidney NAT Clontech 8120608 | 6.6 |
| Kidney Cancer Clontech 8120613 | 0 |
| Kidney NAT Clontech 8120614 | 9 |
| Kidney Cancer Clontech 9010320 | 0 |
| Kidney NAT Clontech 9010321 | 0 |
| Normal Uterus GENPAK 061018 | 13 |
| Uterus Cancer GENPAK 064011 | 11.7 |
| Normal Thyroid Clontech A+ 6570-1 | 100 |
| Thyroid Cancer GENPAK 064010 | 2.9 |
| Thyroid Cancer INVITROGEN A302152 | 8 |
| Thyroid NAT INVITROGEN A302153 | 29.7 |
| Normal Breast GENPAK 061019 | 24.3 |
| 84877 Breast Cancer (OD04566) | 0 |
| 85975 Breast Cancer (OD04590-01) | 0 |
| 85976 Breast Cancer Mets (OD04590-03) | 7.6 |
| 87070 Breast Cancer Metastasis (OD04655-05) | 6.3 |
| GENPAK Breast Cancer 064006 | 7.5 |
| Breast Cancer Res. Gen. 1024 | 12.1 |
| Breast Cancer Clontech 9100266 | 16.8 |
| Breast NAT Clontech 9100265 | 0 |
| Breast Cancer INVITROGEN A209073 | 8.5 |
| Breast NAT INVITROGEN A2090734 | 25.3 |
| Normal Liver GENPAK 061009 | 5.5 |
| Liver Cancer GENPAK 064003 | 13.5 |
| Liver Cancer Research Genetics RNA 1025 | 0 |
| Liver Cancer Research Genetics RNA 1026 | 0 |
| Paired Liver Cancer Tissue Research Genetics RNA 6004-T | 0 |
| Paired Liver Tissue Research Genetics RNA 6004-N | 0 |
| Paired Liver Cancer Tissue Research Genetics RNA 6005-T | 0 |
| Paired Liver Tissue Research Genetics RNA 6005-N | 0 |
| Normal Bladder GENPAK 061001 | 8.1 |
| Bladder Cancer Research Genetics RNA 1023 | 0 |
| Bladder Cancer INVITROGEN A302173 | 34.9 |
| 87071 Bladder Cancer (OD04718-01) | 0 |
| 87072 Bladder Normal Adjacent (OD04718-03) | 0 |
| Normal Ovary Res. Gen. | 4.3 |
| Ovarian Cancer GENPAK 064008 | 4.5 |
| 87492 Ovary Cancer (OD04768-07) | 28.1 |
| 87493 Ovary NAT (OD04768-08) | 0 |
| Normal Stomach GENPAK 061017 | 0 |
| Gastric Cancer Clontech 9060358 | 0 |
| NAT Stomach Clontech 9060359 | 0 |
| Gastric Cancer Clontech 9060395 | 0 |
| NAT Stomach Clontech 9060394 | 5.4 |
| Gastric Cancer Clontech 9060397 | 2.3 |
| NAT Stomach Clontech 9060396 | 0 |
| Gastric Cancer GENPAK 064005 | 0 |

TABLE 15.C

| Tissue Name | Rel. Expression % 1.3Dtm3336t_ag190 | Rel. Expression % 1.3dx4tm5422t_ag190_b1 |
|---|---|---|
| Liver adenocarcinoma | 34.9 | 17 |
| Pancreas | 9.3 | 7.4 |
| Pancreatic ca. CAPAN 2 | 9.9 | 6 |
| Adrenal gland | 66.4 | 34 |
| Thyroid | 28.5 | 29.8 |
| Salivary gland | 12.2 | 15.7 |
| Pituitary gland | 32.5 | 25.3 |
| Brain (fetal) | 6.1 | 45.8 |
| Brain (whole) | 19.8 | 50.8 |
| Brain (amygdala) | 16.7 | 31.1 |
| Brain (cerebellum) | 3.2 | 24.7 |
| Brain (hippocampus) | 56.6 | 9.4 |
| Brain (substantia nigra) | 20.4 | 10.7 |
| Brain (thalamus) | 27.9 | 18.6 |
| Cerebral Cortex | 13.2 | 0 |
| Spinal cord | 9 | 0 |
| CNS ca. (glio/astro) U87-MG | 8.1 | 22 |
| CNS ca. (glio/astro) U-118-MG | 58.6 | 100 |
| CNS ca. (astro) SW1783 | 34.9 | 0 |
| CNS ca.* (neuro; met) SK-N-AS | 32.1 | 24.1 |
| CNS ca. (astro) SF-539 | 14.8 | 9.1 |
| CNS ca. (astro) SNB-75 | 20 | 0 |
| CNS ca. (glio) SNB-19 | 23.8 | 22.4 |
| CNS ca. (glio) U251 | 0 | 20.6 |
| CNS ca. (glio) SF-295 | 7.9 | 7.8 |
| Heart (fetal) | 0 | 0 |
| Heart | 4.9 | 0 |
| Fetal Skeletal | 92.7 | 0 |
| Skeletal muscle | 0 | 0 |
| Bone marrow | 7.6 | 38.1 |
| Thymus | 21.3 | 8 |
| Spleen | 12.8 | 15.1 |
| Lymph node | 13 | 12.9 |
| Colorectal | 5 | 10.3 |
| Stomach | 9.7 | 0 |
| Small intestine | 13.5 | 20.1 |
| Colon ca. SW480 | 12.7 | 17.8 |
| Colon ca.* (SW480 met) SW620 | 53.2 | 6.6 |
| Colon ca. HT29 | 11.3 | 0 |
| Colon ca. HCT-116 | 9 | 0 |
| Colon ca. CaCo-2 | 48.6 | 24.3 |
| 83219 CC Well to Mod Diff (ODO3866) | 4 | 0 |
| Colon ca. HCC-2998 | 12.7 | 24.5 |
| Gastric ca.* (liver met) NCI-N87 | 0 | 0 |
| Bladder | 11 | 7.6 |
| Trachea | 3.5 | 0 |
| Kidney | 0 | 5.9 |
| Kidney (fetal) | 0 | 0 |
| Renal ca. 786-0 | 15.3 | 8.9 |
| Renal ca. A498 | 4.3 | 0 |
| Renal ca. RXF 393 | 0 | 24 |
| Renal ca. ACHN | 23 | 0 |
| Renal ca. UO-31 | 5.3 | 0 |
| Renal ca. TK-10 | 0 | 0 |
| Liver | 0 | 0 |
| Liver (fetal) | 18.2 | 17.9 |
| Liver ca. (hepatoblast) HepG2 | 30.8 | 18 |
| Lung | 0 | 0 |
| Lung (fetal) | 9.4 | 25.2 |
| Lung ca. (small cell) LX-1 | 0 | 11.5 |
| Lung ca. (small cell) NCI-H69 | 22.7 | 20.1 |
| Lung ca. (s.cell var.) SHP-77 | 0 | 0 |
| Lung ca. (large cell) NCI-H460 | 20.4 | 77.7 |
| Lung ca. (non-sm. cell) A549 | 17.1 | 45.3 |
| Lung ca. (non-s.cell) NCI-H23 | 100 | 26 |
| Lung ca (non-s.cell) HOP-62 | 0 | 0 |
| Lung ca. (non-s.cl) NCI-H522 | 33.7 | 28 |
| Lung ca. (squam.) SW 900 | 0 | 0 |
| Lung ca. (squam.) NCI-H596 | 29.9 | 56.2 |
| Mammary gland | 0 | 0 |
| Breast ca.* (pl. effusion) MCF-7 | 41.2 | 54.8 |
| Breast ca.* (pl.ef) MDA-MB-231 | 16.3 | 2.9 |
| Breast ca.* (pl. effusion) T47D | 35.6 | 34.7 |
| Breast ca. BT-549 | 33 | 70.1 |
| Breast ca. MDA-N | 32.5 | 0 |
| Ovary | 4.2 | 0 |

TABLE 15.C-continued

| Tissue Name | Rel. Expression % 1.3Dtm3336t_ag190 | Rel. Expression % 1.3dx4tm5422t_ag190_b1 |
|---|---|---|
| Ovarian ca. OVCAR-3 | 12.5 | 10 |
| Ovarian ca. OVCAR-4 | 4.4 | 35 |
| Ovarian ca. OVCAR-5 | 7.6 | 8.1 |
| Ovarian ca. OVCAR-8 | 22.8 | 37.9 |
| Ovarian ca. IGROV-1 | 2.6 | 0 |
| Ovarian ca.* (ascites) SK-OV-3 | 27.5 | 37.1 |
| Uterus | 18.2 | 34.2 |
| Placenta | 11.7 | 0 |
| Prostate | 19.8 | 9.5 |
| Prostate ca.* (bone met) PC-3 | 33.2 | 0 |
| Testis | 26.2 | 1.7 |
| Melanoma Hs688(A) .T | 0 | 0 |
| Melanoma* (met) Hs688(B) .T | 0 | 0 |
| Melanoma UACC-62 | 2.6 | 0 |
| Melanoma M14 | 4.3 | 8 |
| Melanoma LOX IMVI | 5.7 | 0 |
| Melanoma* (met) SK-MEL-5 | 10.4 | 5 |
| Adipose | 0 | 0 |

TABLE 15.D

| Tissue Name | Rel. Expr., % 1.2tm1980t_ag190 | Rel. Expr., % 1.2tm2173t_ag190 |
|---|---|---|
| Endothelial cells | 0 | 1.1 |
| Heart (fetal) | 0 | 0.4 |
| Pancreas | 0 | 0.6 |
| Pancreatic ca. CAPAN 2 | 0 | 0.6 |
| Adrenal Gland (new lot*) | 92 | 27.2 |
| Thyroid | 0 | 0.2 |
| Salavary gland | 23.8 | 10.4 |
| Pituitary gland | 0 | 0 |
| Brain (fetal) | 0 | 0.7 |
| Brain (whole) | 0 | 1 |
| Brain (amygdala) | 0 | 1.9 |
| Brain (cerebellum) | 0 | 0.7 |
| Brain (hippocampus) | 0 | 3.3 |
| Brain (thalamus) | 0 | 1.9 |
| Cerebral Cortex | 1.2 | 4.6 |
| Spinal cord | 0 | 0.2 |
| CNS ca. (glio/astro) U87-MG | 2.5 | 4.6 |
| CNS ca. (glio/astro) U-118-MG | 0 | 3.5 |
| CNS ca. (astro) SW1783 | 0 | 2 |
| CNS ca.* (neuro; met) SK-N-AS | 7.8 | 2.9 |
| CNS ca. (astro) SF-539 | 0 | 1.5 |
| CNS ca. (astro) SNB-75 | 0 | 1.2 |
| CNS ca. (glio) SNB-19 | 2.1 | 3.1 |
| CNS ca. (glio) U251 | 0 | 1.6 |
| CNS ca. (glio) SF-295 | 0.3 | 3.3 |
| Heart | 0 | 4.8 |
| Skeletal Muscle (new lot*) | 0 | 0.1 |
| Bone marrow | 0 | 3.3 |
| Thymus | 0 | 0.7 |
| Spleen | 0 | 0.9 |
| Lymph node | 0 | 0.3 |
| Colorectal | 0 | 1 |
| Stomach | 0 | 0.3 |
| Small intestine | 7.3 | 3.9 |
| Colon ca. SW480 | 0 | 1.8 |
| Colon ca.* (SW480 met) SW620 | 0.4 | 4.7 |
| Colon ca. HT29 | 0 | 2.1 |
| Colon ca. HCT-116 | 14.6 | 4.9 |
| Colon ca. CaCo-2 | 14.5 | 6.2 |
| 83219 CC Well to Mod Diff (ODO3866) | 0 | 0.7 |
| Colon ca. HCC-2998 | 55.1 | 12.2 |
| Gastric ca.* (liver met) NCI-N87 | 0 | 0 |
| Bladder | 0 | 4.4 |
| Trachea | 0 | 0.2 |
| Kidney | 4.4 | 6.2 |
| Kidney (fetal) | 6.1 | 1.5 |
| Renal ca. 786-0 | 0 | 1 |
| Renal ca. A498 | 0 | 0.7 |
| Renal ca. RXF 393 | 0 | 0.1 |

TABLE 15.D-continued

| Tissue Name | Rel. Expr., % 1.2tm1980t_ag190 | Rel. Expr., % 1.2tm2173t_ag190 |
|---|---|---|
| Renal ca. ACHN | 0.9 | 5.6 |
| Renal ca. UO-31 | 0 | 0.5 |
| Renal ca. TK-10 | 0.6 | 2 |
| Liver | 0 | 1.1 |
| Liver (fetal) | 0 | 2.8 |
| Liver ca. (hepatoblast) HepG2 | 32.1 | 7.7 |
| Lung | 0 | 0.1 |
| Lung (fetal) | 0 | 0.2 |
| Lung ca. (small cell) LX-1 | 0 | 0.6 |
| Lung ca. (small cell) NCI-H69 | 22.8 | 8.9 |
| Lung ca. (s.cell var.) SHP-77 | 0 | 0 |
| Lung ca. (large cell) NCI-H460 | 4 | 14.8 |
| Lung ca. (non-sm. cell) A549 | 8.4 | 5.1 |
| Lung ca. (non-s.cell) NCI-H23 | 100 | 15.3 |
| Lung ca (non-s.cell) HOP-62 | 0.8 | 2.5 |
| Lung ca. (non-s.cl) NCI-H522 | 15.4 | 37.6 |
| Lung ca. (squam.) SW 900 | 0 | 2.8 |
| Lung ca. (squam.) NCI-H596 | 42.3 | 18.6 |
| Mammary gland | 0 | 0.7 |
| Breast ca.* (pl. effusion) MCF-7 | 2.1 | 3.6 |
| Breast ca.* (pl.ef) MDA-MB-231 | 0 | 0.5 |
| Breast ca.* (pl. effusion) T47D | 21 | 9.6 |
| Breast ca. BT-549 | 0 | 2.2 |
| Breast ca. MDA-N | 16.5 | 9.2 |
| Ovary | 0 | 1.5 |
| Ovarian ca. OVCAR-3 | 1 | 4.9 |
| Ovarian ca. OVCAR-4 | 0.2 | 6 |
| Ovarian ca. OVCAR-5 | 1.8 | 4.5 |
| Ovarian ca. OVCAR-8 | 7.5 | 6.4 |
| Ovarian ca. IGROV-1 | 3.9 | 3.3 |
| Ovarian ca.* (ascites) SK-OV-3 | 0.5 | 11.3 |
| Uterus | 0 | 1.6 |
| Placenta | 0 | 0.5 |
| Prostate | 2.1 | 4 |
| Prostate ca.* (bone met) PC-3 | 11.5 | 5.3 |
| Testis | 0 | 1 |
| Melanoma Hs688(A) .T | 0 | 0.4 |
| Melanoma* (met) Hs688(B) .T | 0 | 0.4 |
| Melanoma UACC-62 | 0 | 0.7 |
| Melanoma M14 | 0 | 2.7 |
| Melanoma LOX IMVI | 0 | 1.1 |
| Melanoma* (met) SK-MEL-5 | 0 | 4.5 |
| Adipose | 94.6 | 100 |

TABLE 15.E

| Tissue Name | Rel. Expr., % 4Dtm3337t_ag190 |
|---|---|
| 93768_Secondary Th1_anti-CD28/anti-CD3 | 4 |
| 93769_Secondary Th2_anti-CD28/anti-CD3 | 20 |
| 93770_Secondary Tr1_anti-CD28/anti-CD3 | 9.7 |
| 93573_Secondary Th1_resting day 4–6 in IL-2 | 0 |
| 93572_Secondary Th2_resting day 4–6 in IL-2 | 2.8 |
| 93571_Secondary Tr1_resting day 4–6 in IL-2 | 0 |
| 93568_primary Th1_anti-CD28/anti-CD3 | 19.8 |
| 93569_primary Th2_anti-CD28/anti-CD3 | 8.5 |
| 93570_primary Tr1_anti-CD28/anti-CD3 | 24.5 |
| 93565_primary Th1_resting dy 4–6 in IL-2 | 8.8 |
| 93566_primary Th2_resting dy 4–6 in IL-2 | 0 |
| 93567_primary Tr1_resting dy 4–6 in IL-2 | 5.5 |
| 93351_CD45RA CD4 lymphocyte_anti-CD28/anti-CD3 | 6.5 |
| 93352_CD45RO CD4 lymphocyte_anti-CD28/anti-CD3 | 9.9 |
| 93251_CD8 Lymphocytes_anti-CD28/anti-CD3 | 9 |
| 93353_chronic CD8 Lymphocytes 2ry_resting dy 4–6 in IL-2 | 3.8 |
| 93574_chronic CD8 Lymphocytes 2ry_activated CD3/CD28 | 0 |
| 93354_CD4_none | 1.9 |
| 93252_Secondary Th1/Th2/Tr1_anti-CD95 CH11 | 0 |
| 93103_LAK cells_resting | 0 |
| 93788_LAK cells_IL-2 | 8 |
| 93787_LAK cells_IL-2 + IL-12 | 1.8 |
| 93789_LAK cells_IL-2 + IFN gamma | 1.9 |
| 93790_LAK cells_IL-2 + IL-18 | 17.2 |
| 93104_LAK cells_PMA/ionomycin and IL-18 | 0 |

TABLE 15.E-continued

| Tissue Name | Rel. Expr., % 4Dtm3337t_ag190 |
|---|---|
| 93578_NK Cells IL-2_resting | 11.6 |
| 93109_Mixed Lymphocyte Reaction_Two Way MLR | 3 |
| 93110_Mixed Lymphocyte Reaction_Two Way MLR | 0 |
| 93111_Mixed Lymphocyte Reaction_Two Way MLR | 0 |
| 93112_Mononuclear Cells (PBMCs)_resting | 1.8 |
| 93113_Mononuclear Cells (PBMCs)_PWM | 11.9 |
| 93114_Mononuclear Cells (PBMCs)_PHA-L | 3.8 |
| 93249_Ramos (B cell)_none | 74.2 |
| 93250_Ramos (B cell)_ionomycin | 100 |
| 93349_B lymphocytes_PWM | 2.8 |
| 93350_B lymphoytes_CD40L and IL-4 | 3.6 |
| 92665_EOL-1 (Eosinophil)_dbcAMP differentiated | 16.2 |
| 93248_EOL-1 (Eosinophil)_dbcAMP/PMAionomycin | 12.9 |
| 93356_Dendritic Cells_none | 1.9 |
| 93355_Dendritic Cells_LPS 100 ng/ml | 0 |
| 93775_Dendritic Cells_anti-CD40 | 0 |
| 93774_Monocytes_resting | 3.1 |
| 93776_Monocytes_LPS 50 ng/ml | 0 |
| 93581_Macrophages_resting | 0 |
| 93582_Macrophages_LPS 100 ng/ml | 2 |
| 93098_HUVEC (Endothelial)_none | 1.9 |
| 93099_HUVEC (Endothelial)_starved | 7.1 |
| 93100_HUVEC (Endothelial)_IL-1b | 0 |
| 93779_HUVEC (Endothelial)_IFN gamma | 3.9 |
| 93102_HUVEC (Endothelial)_TNF alpha + IFN gamma | 1.9 |
| 93101_HUVEC (Endothelial)_TNF alpha + IL4 | 1.8 |
| 93781_HUVEC (Endothelial)_IL-11 | 0 |
| 93583_Lung Microvascular Endothelial Cells_none | 3.6 |
| 93584_Lung Microvascular Endothelial Cells_TNFa (4 ng/ml) and IL1b (1 ng/ml) | 3.9 |
| 92662_Microvascular Dermal endothelium_none | 2 |
| 92663_Microsvascular Dermal endothelium_TNFa (4 ng/ml) and IL1b (1 ng/ml) | 3.6 |
| 93773_Bronchial epithelium_TNFa (4 ng/ml) and IL1b (1 ng/ml)** | 0 |
| 93347_Small Airway Epithelium_none | 0 |
| 93348_Small Airway Epithelium_TNFa (4 ng/ml) and IL1b (1 ng/ml) | 3.8 |
| 92668_Coronery Artery SMC_resting | 1.5 |
| 92669_Coronery Artery SMC_TNFa (4 ng/ml) and IL1b (1 ng/ml) | 0 |
| 93107_astrocytes_resting | 0 |
| 93108_astrocytes_TNFa (4 ng/ml) and IL1b (1 ng/ml) | 0 |
| 92666_KU-812 (Basophil)_resting | 13.9 |
| 92667_KU-812 (Basophil)_PMA/ionoycin | 44.1 |
| 93579_CCD1106 (Keratinocytes)_none | 5.3 |
| 93580_CCD1106 (Keratinocytes)_TNFa and IFNg** | 0 |
| 93791_Liver Cirrhosis | 8.3 |
| 93792_Lupus Kidney | 0 |
| 93577_NCI-H292 | 0 |
| 93358_NCI-H292_IL-4 | 0 |
| 93360_NCI-H292_IL-9 | 0 |
| 93359_NCI-H292_IL-13 | 0 |
| 93357_NCI-H292_IFN gamma | 0 |
| 93777_HPAEC_- | 0 |
| 93778_HPAEC_IL-1 beta/TNA alpha | 2.1 |
| 93254_Normal Human Lung Fibroblast_none | 7.8 |
| 93253_Normal Human Lung Fibroblast_TNFa (4 ng/ml) and IL-1b (1 ng/ml) | 8 |
| 93257_Normal Human Lung Fibroblast_IL-4 | 0 |
| 93256_Normal Human Lung Fibroblast_IL-9 | 2.1 |
| 93255_Normal Human Lung Fibroblast_IL-13 | 2.1 |
| 93258_Normal Human Lung Fibroblast_IFN gamma | 5.8 |
| 93106_Dermal Fibroblasts CCD1070_resting | 14 |
| 93361_Dermal Fibroblasts CCD1070_TNF alpha 4 ng/ml | 18.4 |
| 93105_Dermal Fibroblasts CCD1070_IL-1 beta 1 ng/ml | 7.4 |
| 93772_dermal fibroblast_IFN gamma | 6.1 |
| 93771_dermal fibroblast_IL-4 | 10.2 |
| 93259_IBD Colitis 1** | 0 |
| 93260_IBD Colitis 2 | 1.7 |
| 93261_IBD Crohns | 1.8 |
| 735010_Colon_normal | 7.9 |
| 735019_Lung_none | 3.9 |
| 640281_Thymus_none | 15.7 |
| 64030-1_Kidney_none | 17.1 |

It is seen that clone NOV1 expression is enhanced in certain cancer cell lines, especially non-small cell lung cancer NCI-H23, breast cancer, and colon cancer, but not in cell lines from the corresponding normal tissue. For example, Table 15 shows greatest relative % expression for lung carcinoma (100% and 42.3%), normal adrenal (92%) and colon cancer (55.1%) cell lines. Table 15. A. shows significant relative expression levels for lung cancer (83.5% and 70.2%), prostate (35.6%) and colon cancer metastatic to lung (37.9%). Thus, Table 15. A. provides support for the results found in Table 15.

Similarly, Table 15. B. shows high % expression levels for lung cancer (83.5%), normal colon (63.7%) and normal prostate (63.7%); Table 15. C. indicates high % expression levels for glial/astrocytomal carcinoma (58.6% and 100%), fetal skeletal (92.7%), large cell lung (77.7%) and breast (70.1%) cancers; Table 15. D. shows overall lower % expression levels but still 55.1% for colon carcinoma, 42.3% for lung squamous cell carcinoma, and 94.6% and 100% for adipose tissue; and Table 15. E. shows 74.2% for Ramos (B cell) and 100% for Ramos (B cell)-ionomycin cell lines.

All these results are consistent with a showing that NOV1 can be used as a cancer-specific marker in such tissues. Moreover, the differences in levels of expression may be used to distinguish between fetal and adult same-type tissues.

B. NOV2

```
                              Probe Name: Ag087

Start
Primers  Sequences                 Length Position  SEQ ID NO:

Forward  5'-CGCAGTTTCACTCGGGAGAT-3'   20   1870      11

Probe    TET-5'-                       31   1895      12
         CCTCTAGGATCCACATCGAGAAAATCATCGG-3'-
         TAMRA Reverse  5'-AGCAGACTTCCCCGGAGTCT-3'   20   1932      13
```

The results obtained on a panel of cell lines for clone NOV2 using primer-probe set Ag087 are shown in Table 16, and those obtained on a second panel of surgical tissue samples are shown in Table 17. In Table 17, "NAT" designates surgical tissues deemed not cancerous obtained by the surgeon from the region immediately adjacent to a tumor or cancer.

TABLE 16

| Tissue_Name | Relative Expression % |
|---|---|
| Endothelial cells | 0.3 |
| Endothelial cells (treated) | 0.6 |
| Pancreas | 1.0 |
| Pancreatic ca. CAPAN 2 | 2.5 |
| Adipose | 1.8 |
| Adrenal gland | 0.2 |
| Thyroid | 0.1 |
| Salavary gland | 0.2 |
| Pituitary gland | 0.2 |
| Brain (fetal) | 0.9 |
| Brain (whole) | 3.0 |
| Brain (amygdala) | 0.7 |
| Brain (cerebellum) | 7.1 |
| Brain (hippocampus) | 2.8 |
| Brain (substantia nigra) | 2.7 |

TABLE 16-continued

| Tissue_Name | Relative Expression % |
|---|---|
| Brain (thalamus) | 2.5 |
| Brain (hypothalamus) | 0.3 |
| Spinal cord | 2.1 |
| CNS ca. (glio/astro) U87-MG | 0.4 |
| CNS ca. (glio/astro) U-118-MG | 0.3 |
| CNS ca. (astro) SW1783 | 0.3 |
| CNS ca.* (neuro; met) SK-N-AS | 1.1 |
| CNS ca. (astro) SF-539 | 0.0 |
| CNS ca. (astro) SNB-75 | 2.2 |
| CNS ca. (glio) SNB-19 | 2.0 |
| CNS ca. (glio) U251 | 0.9 |
| CNS ca. (glio) SF-295 | 0.0 |
| Heart | 0.4 |
| Skeletal muscle | 0.1 |
| Bone marrow | 0.1 |
| Thymus | 3.5 |
| Spleen | 0.4 |
| Lymph node | 0.4 |
| Colon (ascending) | 0.6 |
| Stomach | 1.3 |
| Small intestine | 0.5 |
| Colon ca. SW480 | 0.3 |
| Colon ca.* (SW480 met) SW620 | 0.2 |
| Colon ca. HT29 | 2.8 |
| Colon ca. HCT-116 | 8.0 |

TABLE 16-continued

| Tissue_Name | Relative Expression % |
|---|---|
| Colon ca. CaCo-2 | 1.2 |
| Colon ca. HCT-15 | 0.9 |
| Colon ca. HCC-2998 | 1.5 |
| Gastric ca.* (liver met) NCI-N87 | 2.8 |
| Bladder | 0.4 |
| Trachea | 1.3 |
| Kidney | 1.7 |
| Kidney (fetal) | 1.0 |
| Renal ca. 786-0 | 0.6 |
| Renal ca. A498 | 0.3 |
| Renal ca. RXF 393 | 0.2 |
| Renal ca. ACHN | 0.4 |
| Renal ca. UO-31 | 0.3 |
| Renal ca. TK-10 | 1.3 |
| Liver | 0.3 |
| Liver (fetal) | 0.1 |
| Liver ca. (hepatoblast) HepG2 | 1.0 |
| Lung | 0.2 |
| Lung (fetal) | 0.8 |
| Lung ca. (small cell) LX-1 | 0.3 |
| Lung ca. (small cell) NCI-H69 | 0.7 |
| Lung ca. (s.cell var.) SHP-77 | 25.9 |
| Lung ca. (large cell) NCI-H460 | 0.7 |

TABLE 16-continued

| Tissue_Name | Relative Expression % |
|---|---|
| Lung ca. (non-sm. cell) A549 | 1.1 |
| Lung ca. (non-s.cell) NCI-H23 | 0.6 |
| Lung ca (non-s.cell) HOP-62 | 1.0 |
| Lung ca. (non-s.cl) NCI-H522 | 0.3 |
| Lung ca. (squam.) SW 900 | 11.5 |
| Lung ca. (squam.) NCI-H596 | 0.8 |
| Mammary gland | 1.8 |
| Breast ca.* (pl. effusion) MCF-7 | 0.3 |
| Breast ca.* (pl.ef) MDA-MB-231 | 1.6 |
| Breast ca.* (pl. effusion) T47D | 0.5 |
| Breast ca. BT-549 | 4.7 |
| Breast ca. MDA-N | 1.6 |
| Ovary | 0.6 |
| Ovarian ca. OVCAR-3 | 0.6 |
| Ovarian ca. OVCAR-4 | 0.5 |
| Ovarian ca. OVCAR-5 | 4.6 |
| Ovarian ca. OVCAR-8 | 0.3 |
| Ovarian ca. IGROV-1 | 0.6 |
| Ovarian ca.* (ascites) SK-OV-3 | 1.0 |
| Uterus | 1.8 |
| Placenta | 1.5 |
| Prostate | 0.5 |
| Prostate ca.* (bone met) PC-3 | 100.0 |
| Testis | 4.6 |
| Melanoma Hs688(A).T | 0.1 |
| Melanoma* (met) Hs688(B).T | 0.1 |
| Melanoma UACC-62 | 0.8 |
| Melanoma M14 | 0.3 |
| Melanoma LOX IMVI | 0.7 |
| Melanoma* (met) SK-MEL-5 | 0.2 |
| Melanoma SK-MEL-28 | 0.3 |

TABLE 16.A

| Tissue Name | Rel. Expr., % tm254t | Rel. Expr., % tm252t_ag087 |
|---|---|---|
| Endothelial cells | 0.3 | 0.3 |
| Endothelial cells (treated) | 0.1 | 0.6 |
| Pancreas | 10.2 | 1 |
| Pancreatic ca. CAPAN 2 | 2.6 | 2.5 |
| Adipose | 2 | 1.8 |
| Adrenal gland | 11.5 | 0.2 |
| Thyroid | 3.1 | 0.1 |
| Salavary gland | 3 | 0.2 |
| Pituitary gland | 7.3 | 0.2 |
| Brain (fetal) | 4.6 | 0.9 |
| Brain (whole) | 15.9 | 3 |
| Brain (amygdala) | 21 | 0.7 |
| Brain (cerebellum) | 98.6 | 7.1 |
| Brain (hippocampus) | 22.1 | 2.8 |
| Brain (substantia nigra) | 24.1 | 2.7 |
| Brain (thalamus) | 62.4 | 2.5 |
| Brain (hypothalamus) | 11.3 | 0.3 |
| Spinal cord | 4 | 2.1 |
| CNS ca. (glio/astro) U87-MG | 0.2 | 0.4 |
| CNS ca. (glio/astro) U-118-MG | 0.6 | 0.3 |
| CNS ca. (astro) SW1783 | 1.1 | 0.3 |
| CNS ca.* (neuro; met) SK-N-AS | 2.2 | 1.1 |
| CNS ca. (astro) SF-539 | 0.5 | 0 |
| CNS ca. (astro) SNB-75 | 0.5 | 2.2 |
| CNS ca. (glio) SNB-19 | 2.8 | 2 |
| CNS ca. (glio) U251 | 0 | 0.9 |
| CNS ca. (glio) SF-295 | 3.5 | 0 |
| Heart | 6 | 0.4 |
| Skeletal muscle | 1.8 | 0 |
| Bone marrow | 0.8 | 0 |
| Thymus | 2.8 | 3.5 |
| Spleen | 10.8 | 0.4 |
| Lymph node | 1.8 | 0.4 |
| Colon (ascending) | 0.4 | 0.6 |
| Stomach | 1.1 | 1.3 |
| Small intestine | 2.8 | 0.5 |

TABLE 16.A-continued

| Tissue Name | Rel. Expr., % tm254t | Rel. Expr., % tm252t_ag087 |
|---|---|---|
| Colon ca. SW480 | 0.6 | 0.3 |
| Colon ca.* (SW480 met) SW620 | 0.2 | 0.2 |
| Colon ca. HT29 | 0.4 | 2.8 |
| Colon ca. HCT-116 | 0 | 8 |
| Colon ca. CaCo-2 | 0.3 | 1.2 |
| Colon ca. HCT-15 | 0.6 | 0.8 |
| Colon ca. HCC-2998 | 1.3 | 1.5 |
| Gastric ca.* (liver met) NCI-N87 | 1.1 | 2.8 |
| Bladder | 0.2 | 0.4 |
| Trachea | 0 | 1.3 |
| Kidney | 2.8 | 1.7 |
| Kidney (fetal) | 11.3 | 1 |
| Renal ca. 786-0 | 0.4 | 0.6 |
| Renal ca. A498 | 0.3 | 0.3 |
| Renal ca. RXF 393 | 0.2 | 0.2 |
| Renal ca. ACHN | 0 | 0.4 |
| Renal ca. UO-31 | 0.4 | 0.3 |
| Renal ca. TK-10 | 0.3 | 1.3 |
| Liver | 4.5 | 0.3 |
| Liver (fetal) | 2.6 | 0.1 |
| Liver ca. (hepatoblast) HepG2 | 0.3 | 1 |
| Lung | 0.1 | 0.2 |
| Lung (fetal) | 4.9 | 0.8 |
| Lung ca. (small cell) LX-1 | 0 | 0.3 |
| Lung ca. (small cell) NCI-H69 | 1.7 | 0.7 |
| Lung ca. (s.cell var.) SHP-77 | 0 | 25.9 |
| Lung ca. (large cell) NCI-H460 | 0 | 0.7 |
| Lung ca. (non-sm. cell) A549 | 0.5 | 1.1 |
| Lung ca. (non-s. cell) NCI-H23 | 1.4 | 0.6 |
| Lung ca (non-s. cell) HOP-62 | 0.6 | 1 |
| Lung ca. (non-s. cl) NCI-H522 | 7.7 | 0.3 |
| Lung ca. (squam.) SW 900 | 0.6 | 11.5 |
| Lung ca. (squam.) NCI-H596 | 2.7 | 0.8 |
| Mammary gland | 3.8 | 1.8 |
| Breast ca.* (pl. effusion) MCF-7 | 1.6 | 0.3 |
| Breast ca.* (pl. ef) MDA-MB-231 | 0.3 | 1.6 |
| Breast ca.* (pl. effusion) T47D | 11 | 0.5 |
| Breast ca. BT-549 | 0 | 4.7 |
| Breast ca. MDA-N | 3.1 | 1.6 |
| Ovary | 4.4 | 0.6 |
| Ovarian ca. OVCAR-3 | 0.2 | 0.6 |
| Ovarian ca. OVCAR-4 | 0 | 0.5 |
| Ovarian ca. OVCAR-5 | 1 | 4.6 |
| Ovarian ca. OVCAR-8 | 2 | 0.2 |
| Ovarian ca. IGROV-1 | 0.6 | 0.6 |
| Ovarian ca.* (ascites) SK-OV-3 | 1.2 | 1 |
| Uterus | 4.8 | 1.8 |
| Placenta | 2.9 | 1.5 |
| Prostate | 3.4 | 0.5 |
| Prostate ca.* (bone met) PC-3 | 0 | 100 |
| Testis | 100 | 4.6 |
| Melanoma Hs688(A).T | 1.3 | 0.1 |
| Melanoma* (met) Hs688(B).T | 0.4 | 0 |
| Melanoma UACC-62 | 0.2 | 0.8 |
| Melanoma M14 | 2.4 | 0.3 |
| Melanoma LOX IMVI | 4.5 | 0.7 |
| Melanoma* (met) SK-MEL-5 | 2.3 | 0.2 |
| Melanoma SK-MEL-28 | 4.7 | 0.3 |

TABLE 16.B

| Tissue Name | Rel. Expr., % 1.2tm2217t_ag87% |
|---|---|
| Endothelial cells | 0 |
| Heart (fetal) | 0 |
| Pancreas | 97.3 |
| Pancreatic ca. CAPAN 2 | 0 |
| Adrenal Gland (new lot*) | 22.5 |
| Thyroid | 0 |
| Salavary gland | 0 |
| Pituitary gland | 0 |
| Brain (fetal) | 3.4 |

TABLE 16.B-continued

| Tissue Name | Rel. Expr., % 1.2tm2217t_ag87% |
|---|---|
| Brain (whole) | 8 |
| Brain (amygdala) | 24.8 |
| Brain (cerebellum) | 8.3 |
| Brain (hippocampus) | 20.7 |
| Brain (thalamus) | 100 |
| Cerebral Cortex | 63.7 |
| Spinal cord | 0 |
| CNS ca. (glio/astro) U87-MG | 0 |
| CNS ca. (glio/astro) U-118-MG | 0 |
| CNS ca. (astro) SW1783 | 0 |
| CNS ca.* (neuro; met) SK-N-AS | 21.9 |
| CNS ca. (astro) SF-539 | 0 |
| CNS ca. (astro) SNB-75 | 0 |
| CNS ca. (glio) SNB-19 | 0 |
| CNS ca. (glio) U251 | 0 |
| CNS ca. (glio) SF-295 | 0 |
| Heart | 0 |
| Skeletal Muscle (new lot*) | 4.2 |
| Bone marrow | 0 |
| Thymus | 0 |
| Spleen | 12.2 |
| Lymph node | 0 |
| Colorectal | 0 |
| Stomach | 0 |
| Small intestine | 0 |
| Colon ca. SW480 | 0 |
| Colon ca.* (SW480 met) SW620 | 0 |
| Colon ca. HT29 | 0 |
| Colon ca. HCT-116 | 0 |
| Colon ca. CaCo-2 | 0 |
| 83219 CC Well to Mod Diff (ODO3866) | 0 |
| Colon ca. HCC-2998 | 5.5 |
| Gastric ca.* (liver met) NCI-N87 | 0 |
| Bladder | 2.9 |
| Trachea | 0 |
| Kidney | 0 |
| Kidney (fetal) | 0 |
| Renal ca. 786-0 | 0 |
| Renal ca. A498 | 0 |
| Renal ca. RXF 393 | 0 |
| Renal ca. ACHN | 0 |
| Renal ca. UO-31 | 0 |
| Renal ca. TK-10 | 0 |
| Liver | 0 |
| Liver (fetal) | 0 |
| Liver ca. (hepatoblast) HepG2 | 0 |
| Lung | 0 |
| Lung (fetal) | 0 |
| Lung ca. (small cell) LX-1 | 0 |
| Lung ca. (small cell) NCI-H69 | 33 |
| Lung ca. (s.cell var.) SHP-77 | 3.3 |
| Lung ca. (large cell) NCI-H460 | 0 |
| Lung ca. (non-sm.cell) A549 | 0 |
| Lung ca. (non-s.cell) NCI-H23 | 1.7 |
| Lung ca (non-s.cell) HOP-62 | 0 |
| Lung ca. (non-s.cl) NCI-H522 | 17.1 |
| Lung ca.(squam.) SW 900 | 0 |
| Lung ca. (squam.) NCI-H596 | 55.5 |
| Mammary gland | 0 |
| Breast ca.* (pl. effusion) MCF-7 | 0 |
| Breast ca.* (pl. ef) MDA-MB-231 | 0 |
| Breast ca.* (pl. effusion) T47D | 26.6 |
| Breast ca. BT-549 | 0 |
| Breast ca. MDA-N | 0 |
| Ovary | 8.2 |
| Ovarian ca. OVCAR-3 | 0 |
| Ovarian ca. OVCAR-4 | 0 |
| Ovarian ca. OVCAR-5 | 0 |
| Ovarian ca. OVCAR-8 | 0 |
| Ovarian ca. IGROV-1 | 6.6 |
| Ovarian ca.* (ascites) SK-OV-3 | 0 |
| Uterus | 0 |
| Placenta | 0 |
| Prostate | 0 |
| Prostate ca.* (bone met) PC-3 | 0 |
| Testis | 41.5 |

TABLE 16.B-continued

| Tissue Name | Rel. Expr., % 1.2tm2217t_ag87% |
|---|---|
| Melanoma Hs688(A).T | 0 |
| Melanoma* (met) Hs688(B).T | 0 |
| Melanoma UACC-62 | 0 |
| Melanoma M14 | 0 |
| Melanoma LOX IMVI | 0 |
| Melanoma* (met) SK-MEL-5 | 0 |
| Adipose | 24.3 |

TABLE 16.C

| Tissue Name | Rel. Expr., % 1.3dtm4681t_ag87 |
|---|---|
| Liver adenocarcinoma | 0 |
| Pancreas | 4.8 |
| Pancreatic ca. CAPAN 2 | 0 |
| Adrenal gland | 0 |
| Thyroid | 0 |
| Salivary gland | 0 |
| Pituitary gland | 7.8 |
| Brain (fetal) | 15.2 |
| Brain (whole) | 0 |
| Brain (amygdala) | 15 |
| Brain (cerebellum) | 52.5 |
| Brain (hippocampus) | 33 |
| Brain (substantia nigra) | 19.9 |
| Brain (thalamus) | 88.9 |
| Cerebral Cortex | 8.1 |
| Spinal cord | 9 |
| CNS ca. (glio/astro) U87-MG | 0 |
| CNS ca. (glio/astro) U-118-MG | 0 |
| CNS ca. (astro) SW1783 | 0 |
| CNS ca.* (neuro; met) SK-N-AS | 0 |
| CNS ca. (astro) SF-539 | 0 |
| CNS ca. (astro) SNB-75 | 0 |
| CNS ca. (glio) SNB-19 | 0 |
| CNS ca. (glio) U251 | 0 |
| CNS ca. (glio) SF-295 | 0 |
| Heart (fetal) | 0 |
| Heart | 0 |
| Fetal Skeletal | 9 |
| Skeletal muscle | 0 |
| Bone marrow | 0 |
| Thymus | 0 |
| Spleen | 34.2 |
| Lymph node | 0 |
| Colorectal | 0 |
| Stomach | 0 |
| Small intestine | 0 |
| Colon ca. SW480 | 0 |
| Colon ca.* (SW480 met) SW620 | 0 |
| Colon ca. HT29 | 0 |
| Colon ca. HCT-116 | 0 |
| Colon ca. CaCo-2 | 0 |
| 83219 CC Well to Mod Diff (ODO3866) | 0 |
| Colon ca. HCC-2998 | 0 |
| Gastric ca.* (liver met) NCI-N87 | 13.5 |
| Bladder | 11.7 |
| Trachea | 0 |
| Kidney | 0 |
| Kidney (fetal) | 0 |
| Renal ca. 786-0 | 0 |
| Renal ca. A498 | 0 |
| Renal ca. RXF 393 | 0 |
| Renal ca. ACHN | 0 |
| Renal ca. UO-31 | 0 |
| Renal ca. TK-10 | 0 |
| Liver | 0 |
| Liver (fetal) | 0 |
| Liver ca. (hepatoblast) HepG2 | 0 |
| Lung | 0 |
| Lung (fetal) | 0 |
| Lung ca. (small cell) LX-1 | 0 |

TABLE 16.C-continued

| Tissue Name | Rel. Expr., % 1.3dtm4681t_ag87 |
|---|---|
| Lung ca. (small cell) NCI-H69 | 0 |
| Lung ca. (s.cell var.) SHP-77 | 0 |
| Lung ca. (large cell) NCI-H460 | 0 |
| Lung ca. (non-sm. cell) A549 | 0 |
| Lung ca. (non-s. cell) NCI-H23 | 0 |
| Lung ca (non-s. cell) HOP-62 | 0 |
| Lung ca. (non-scl) NCI-H522 | 0 |
| Lung ca. (squam.) SW 900 | 0 |
| Lung ca. (squam.) NCI-H596 | 0 |
| Mammary gland | 0 |
| Breast ca.* (pl. effusion) MCF-7 | 0 |
| Breast ca.* (pl. ef) MDA-MB-231 | 0 |
| Breast ca.* (pl. effusion) T47D | 14.9 |
| Breast ca. BT-549 | 0 |
| Breast ca. MDA-N | 0 |
| Ovary | 0 |
| Ovarian ca. OVCAR-3 | 0 |
| Ovarian ca. OVCAR-4 | 0 |
| Ovarian ca. OVCAR-5 | 0 |
| Ovarian ca. OVCAR-8 | 0 |
| Ovarian ca. IGROV-1 | 0 |
| Ovarian ca.* (ascites) SK-OV-3 | 0 |
| Uterus | 0 |
| Placenta | 0 |
| Prostate | 0 |
| Prostate ca.* (bone met) PC-3 | 0 |
| Testis | 100 |
| Melanoma Hs688(A) .T | 0 |
| Melanoma* (met) Hs688(B) .T | 0 |
| Melanoma UACC-62 | 9.8 |
| Melanoma M14 | 0 |
| Melanoma LOX IMVI | 0 |
| Melanoma* (met) SK-MEL-5 | 0 |
| Adipose | 0 |

TABLE 17

| Tissue_Name/Run_Name | Relative Expr. % | |
|---|---|---|
| | 2tm723t | 2tm819t |
| Normal Colon GENPAK 061003 | 0.0 | 0.0 |
| 83219 CC Well to Mod Diff (ODO3866) | 0.0 | 0.0 |
| 83220 CC NAT (ODO3866) | 0.0 | 0.0 |
| 83221 CC Gr.2 rectosigmoid (ODO3868) | 0.0 | 0.0 |
| 83222 CC NAT (ODO3868) | 0.0 | 0.0 |
| 83235 CC Mod Diff (ODO3920) | 0.0 | 0.0 |
| 83236 CC NAT (ODO3920) | 0.0 | 0.0 |
| 83237 CC Gr.2 ascend colon (ODO3921) | 0.0 | 0.0 |
| 83238 CC NAT (ODO3921) | 0.0 | 0.0 |
| 83241 CC from Partial Hepatectomy (ODO4309) | 0.0 | 0.0 |
| 83242 Liver NAT (ODO4309) | 27.0 | 3.0 |
| 87472 Colon mets to lung (OD04451-01) | 0.0 | 0.0 |
| 87473 Lung NAT (OD04451-02) | 0.0 | 0.0 |
| Normal Prostate Clontech A+ 6546-1 | 0.0 | 0.0 |
| 84140 Prostate Cancer (OD04410) | 5.6 | 6.8 |
| 84141 Prostate NAT (OD04410) | 0.0 | 0.0 |
| 87073 Prostate Cancer (OD04720-01) | 100.0 | 100.0 |
| 87074 Prostate NAT (OD04720-02) | 0.6 | 0.0 |
| Normal Lung GENPAK 061010 | 0.0 | 0.0 |
| 83239 Lung Met to Muscle (ODO4286) | 0.0 | 0.0 |
| 83240 Muscle NAT (ODO4286) | 0.4 | 0.0 |
| 84136 Lung Malignant Cancer (OD03126) | 1.2 | 0.0 |
| 84137 Lung NAT (OD03126) | 0.0 | 0.0 |
| 84871 Lung Cancer (OD04404) | 1.7 | 0.0 |
| 84872 Lung NAT (OD04404) | 0.0 | 0.0 |
| 84875 Lung Cancer (OD04565) | 0.0 | 0.4 |
| 85950 Lung Cancer (OD04237-01) | 0.0 | 0.0 |
| 85970 Lung NAT (OD04237-02) | 0.0 | 0.0 |
| 83255 Ocular Mel Met to Liver (ODO4310) | 1.6 | 0.8 |
| 83256 Liver NAT (ODO4310) | 48.6 | 1.8 |
| 84139 Melanoma Mets to Lung (OD04321) | 0.0 | 0.0 |
| 84138 Lung NAT (OD04321) | 0.0 | 0.0 |

TABLE 17-continued

| Tissue_Name/Run_Name | Relative Expr. % | |
|---|---|---|
| | 2tm723t | 2tm819t |
| Normal Kidney GENPAK 061008 | 0.0 | 0.0 |
| 83786 Kidney Ca, Nuclear grade 2 (OD04338) | 0.0 | 0.0 |
| 83787 Kidney NAT (OD04338) | 0.0 | 0.0 |
| 83788 Kidney Ca Nuclear grade 1/2 (OD04339) | 0.0 | 0.0 |
| 83789 Kidney NAT (OD04339) | 0.9 | 0.6 |
| 83790 Kidney Ca, Clear cell type (OD04340) | 0.0 | 0.0 |
| 83791 Kidney NAT (OD04340) | 0.0 | 0.0 |
| 83792 Kidney Ca, Nuclear grade 3 (OD04348) | 0.0 | 0.0 |
| 83793 Kidney NAT (OD04348) | 0.0 | 0.0 |
| 87474 Kidney Cancer (OD04622-01) | 0.0 | 0.0 |
| 87475 Kidney NAT (OD04622-03) | 0.0 | 0.0 |
| 85973 Kidney Cancer (OD04450-01) | 0.0 | 0.0 |
| 85974 Kidney NAT (OD04450-03) | 0.0 | 0.0 |
| Kidney Cancer Clontech 8120607 | 0.0 | 0.0 |
| Kidney NAT Clontech 8120608 | 0.0 | 0.0 |
| Kidney Cancer Clontech 8120613 | 0.0 | 0.0 |
| Kidney NAT Clontech 8120614 | 0.0 | 0.0 |
| Kidney Cancer Clontech 9010320 | 0.0 | 0.0 |
| Kidney NAT Clontech 9010321 | 0.0 | 0.0 |
| Normal Uterus GENPAK 061018 | 0.0 | 0.0 |
| Uterus Cancer GENPAK 064011 | 4.2 | 0.0 |
| Normal Thyroid Clontech A+ 6570-1** | 0.0 | 0.0 |
| Thyroid Cancer GENPAK 064010 | 0.0 | 0.0 |
| Thyroid Cancer INVITROGEN A302152 | 3.3 | 1.3 |
| Thyroid NAT INVITROGEN A302153 | 0.0 | 0.0 |
| Normal Breast GENPAK 061019 | 3.8 | 2.9 |
| 84877 Breast Cancer (OD04566) | 42.6 | 56.6 |
| 85975 Breast Cancer (OD04590-01) | 7.6 | 6.0 |
| 85976 Breast Cancer Mets (OD04590-03) | 39.2 | 38.4 |
| 87070 Breast Cancer Metastasis (OD04655-05) | 35.4 | 45.7 |
| GENPAK Breast Cancer 064006 | 50.7 | 55.1 |
| Breast Cancer Clontech 9100266 | 46.0 | 28.5 |
| Breast NAT Clontech 9100265 | 2.1 | 0.0 |
| Breast Cancer INVITROGEN A209073 | 8.5 | 0.0 |
| Breast NAT INVITROGEN A2090734 | 4.2 | 1.3 |
| Normal Liver GENPAK 061009 | 0.6 | 0.0 |
| Liver Cancer GENPAK 064003 | 0.0 | 0.0 |
| Liver Cancer Research Genetics RNA 1025 | 0.5 | 0.0 |
| Liver Cancer Research Genetics RNA 1026 | 0.0 | 0.0 |
| Paired Liver Cancer Tissue Research Genetics RNA 6004-T | 0.0 | 0.0 |
| Paired Liver Tissue Research Genetics RNA 6004-N | 0.0 | 0.0 |
| Paired Liver Cancer Tissue Research Genetics RNA 6005-T | 0.9 | 0.0 |
| Paired Liver Tissue Research Genetics RNA 6005-N | 2.7 | 0.0 |
| Normal Bladder GENPAK 061001 | 1.4 | 0.0 |
| Bladder Cancer Research Genetics RNA 1023 | 0.0 | 0.0 |
| Bladder Cancer INVITROGEN A302173 | 0.0 | 0.0 |
| 87071 Bladder Cancer (OD04718-01) | 6.0 | 1.0 |
| 87072 Bladder Normal Adjacent (OD04718-03) | 2.7 | 0.0 |
| Normal Ovary Res. Gen. | 6.5 | 0.0 |
| Ovarian Cancer GENPAK 064008 | 0.0 | 0.0 |
| 87492 Ovary Cancer (OD04768-07) | 25.9 | 11.7 |
| 87493 Ovary NAT (OD04768-08) | 0.0 | 0.0 |
| Normal Stomach GENPAK 061017 | 0.0 | 0.0 |
| NAT Stomach Clontech 9060359 | 0.0 | 0.0 |
| Gastric Cancer Clontech 9060395 | 20.7 | 27.9 |
| NAT Stomach Clontech 9060394 | 1.7 | 0.0 |
| Gastric Cancer Clontech 9060397 | 0.0 | 0.0 |
| NAT Stomach Clontech 9060396 | 0.0 | 0.0 |
| Gastric Cancer GENPAK 064005 | 0.0 | 0.0 |

TABLE 17.A

| Tissue Name | Rel. Expr., % 2Dtm2323t_ag87 | Rel. Expr., % 2Dtm2361t_ag087 |
|---|---|---|
| Normal Colon GENPAK 061003 | 0 | 0 |
| 83219 CC Well to Mod Diff (ODO3866) | 0 | 0 |
| 83220 CC NAT (ODO3866) | 0 | 0 |
| 83221 CC Gr.2 rectosigmoid (ODO3868) | 0 | 0 |
| 83222 CC NAT (ODO3868) | 0 | 0 |
| 83235 CC Mod Diff (ODO3920) | 0 | 0 |
| 83236 CC NAT (ODO3920) | 0 | 0 |
| 83237 CC Gr.2 ascend colon (ODO3921) | 0 | 0 |
| 83238 CC NAT (ODO3921) | 0 | 0 |
| 83241 CC from Partial Hepatectomy (ODO4309) | 0 | 0 |
| 83242 Liver NAT (ODO4309) | 0 | 0 |
| 87472 Colon mets to lung (OD04451-01) | 0 | 0 |
| 87473 Lung NAT (OD04451-02) | 0 | 0 |
| Normal Prostate Clontech A+ 6546-1 | 0 | 19.8 |
| 84140 Prostate Cancer (OD04410) | 0 | 0 |
| 84141 Prostate NAT (OD04410) | 0 | 0 |
| 87073 Prostate Cancer (OD04720-01) | 0 | 0 |
| 87074 Prostate NAT (OD04720-02) | 0 | 0 |
| Normal Lung GENPAK 061010 | 0 | 0 |
| 83239 Lung Met to Muscle (ODO4286) | 0 | 0 |
| 83240 Muscle NAT (ODO4286) | 0 | 0 |
| 84136 Lung Malignant Cancer (OD03126) | 0 | 0 |
| 84137 Lung NAT (OD03126) | 0 | 0 |
| 84871 Lung Cancer (OD04404) | 0 | 0 |
| 84872 Lung NAT (OD04404) | 0 | 0 |
| 84875 Lung Cancer (OD04565) | 0 | 0 |
| 84876 Lung NAT (OD04565) | 0 | 0 |
| 85950 Lung Cancer (OD04237-01) | 0 | 0 |
| 85970 Lung NAT (OD04237-02) | 0 | 0 |
| 83255 Ocular Mel Met to Liver (ODO4310) | 0 | 0 |
| 83256 Liver NAT (ODO4310) | 0 | 0 |
| 84139 Melanoma Mets to Lung (OD04321) | 0 | 0 |
| 84138 Lung NAT (OD04321) | 0 | 0 |
| Normal Kidney GENPAK 061008 | 0 | 0 |
| 83786 Kidney Ca, Nuclear grade 2 (OD04338) | 0 | 0 |
| 83787 Kidney NAT (OD04338) | 0 | 0 |
| 83788 Kidney Ca Nuclear grade 1/2 (OD04339) | 0 | 0 |
| 83789 Kidney NAT (OD04339) | 0 | 18.7 |
| 83790 Kidney Ca, Clear cell type (OD04340) | 0 | 0 |
| 83791 Kidney NAT (OD04340) | 0 | 0 |
| 83792 Kidney Ca, Nuclear grade 3 (OD04348) | 0 | 0 |
| 83793 Kidney NAT (OD04348) | 0 | 0 |
| 87474 Kidney Cancer (OD04622-01) | 0 | 0 |
| 87475 Kidney NAT (OD04622-03) | 0 | 0 |
| 85973 Kidney Cancer (OD04450-01) | 0 | 0 |
| 85974 Kidney NAT (OD04450-03) | 0 | 0 |
| Kidney Cancer Clontech 8120607 | 0 | 0 |
| Kidney NAT Clontech 8120608 | 0 | 0 |
| Kidney Cancer Clontech 8120613 | 0 | 0 |
| Kidney NAT Clontech 8120614 | 0 | 0 |
| Kidney Cancer Clontech 9010320 | 0 | 0 |
| Kidney NAT Clontech 9010321 | 0 | 0 |
| Normal Uterus GENPAK 061018 | 0 | 0 |
| Uterus Cancer GENPAK 064011 | 0 | 0 |
| Normal Thyroid Clontech A+ 6570-1 | 0 | 0 |
| Thyroid Cancer GENPAK 064010 | 0 | 0 |
| Thyroid Cancer INVITROGEN A302152 | 0 | 0 |
| Thyroid NAT INVITROGEN A302153 | 0 | 0 |
| Normal Breast GENPAK 061019 | 0 | 0 |
| 84877 Breast Cancer (OD04566) | 0 | 0 |
| 85975 Breast Cancer (OD04590-01) | 0 | 0 |
| 85976 Breast Cancer Mets (OD04590-03) | 46.7 | 100 |
| 87070 Breast Cancer Metastasis (OD04655-05) | 30.1 | 0 |
| GENPAK Breast Cancer 064006 | 0 | 0 |
| Breast Cancer Res. Gen. 1024 | 100 | 90.8 |
| Breast Cancer Clontech 9100266 | 0 | 35.8 |
| Breast NAT Clontech 9100265 | 0 | 0 |
| Breast Cancer INVITROGEN A209073 | 0 | 0 |
| Breast NAT INVITROGEN A2090734 | 21.5 | 0 |
| Normal Liver GENPAK 061009 | 0 | 0 |
| Liver Cancer GENPAK 064003 | 0 | 0 |
| Liver Cancer Research Genetics RNA 1025 | 0 | 0 |
| Liver Cancer Research Genetics RNA 1026 | 0 | 0 |
| Paired Liver Cancer Tissue Research Genetics RNA 6004-T | 0 | 0 |
| Paired Liver Tissue Research Genetics RNA 6004-N | 0 | 0 |

TABLE 17.A-continued

| Tissue Name | Rel. Expr., % 2Dtm2323t_ ag87 | Rel. Expr., % 2Dtm2361t_ ag087 |
|---|---|---|
| Paired Liver Cancer Tissue Research Genetics RNA 6005-T | 0 | 0 |
| Paired Liver Tissue Research Genetics RNA 6005-N | 0 | 0 |
| Normal Bladder GENPAK 061001 | 13.6 | 0 |
| Bladder Cancer Research Genetics RNA 1023 | 0 | 0 |
| Bladder Cancer INVITROGEN A302173 | 0 | 0 |
| 87071 Bladder Cancer (OD04718-01) | 0 | 0 |
| 87072 Bladder Normal Adjacent (OD04718-03) | 0 | 0 |
| Normal Ovary Res. Gen. | 0 | 0 |
| Ovarian Cancer GENPAK 064008 | 0 | 0 |
| 87492 Ovary Cancer (OD04768-07) | 0 | 0 |
| 87493 Ovary NAT (OD04768-08) | 0 | 0 |
| Normal Stomach GENPAK 061017 | 0 | 0 |
| Gastric Cancer Clontech 9060358 | 0 | 0 |
| NAT Stomach Clontech 9060359 | 0 | 0 |
| Gastric Cancer Clontech 9060395 | 15.3 | 0 |
| NAT Stomach Clontech 9060394 | 0 | 0 |
| Gastric Cancer Clontech 9060397 | 0 | 0 |
| NAT Stomach Clontech 9060396 | 0 | 0 |
| Gastric Cancer GENPAK 064005 | 0 | 0 |

The results in Tables 16 and 17 demonstrate that clone NOV2 is highly expressed in certain tumors, especially prostate cancer metastasis, but not in corresponding normal cell lines, and that this clone is highly expressed in many surgical tumor samples, especially prostate cancer, but minimally or not detectably in the immediate normal adjacent tissue. For example, Table 16 shows 100% relative expression levels for prostate cancer and 25.9% for lung carcinoma; Table 16. A. shows expression levels of 98.6% and 62.4% for brain cerebellum and thalamus respectively, and 25.9% for lung carcinoma. Table 16. B. shows expression levels of 97.3% for pancreas, 100% for brain thalamus, 55.5% for lung carcinoma and 41.5% for normal testis, while Table 16C resulted in expression levels of 52.5% and 88.9% for brain cerebellum and thalamus respectively, and 100% for normal testis tissue. The results in Tables 16–16C are substantiated by the results in Tables 17–17A where expression levels were 100% for prostate and breast cancers, 48.6% for normal liver, and 46.7% and 100% for metastatic breast cancer. These results indicate that clone NOV2 may be used as a marker for certain cancers, especially prostate cancer.

NOV3

The results obtained on a panel of cell lines for clone NOV3 using primer-probe set Ag148 are shown in Table 18.

TABLE 18

| Tissue Name | Rel. Expr., % 1.2tm1981f_ag148 |
|---|---|
| Endothelial cells | 1.4 |
| Heart (fetal) | 1.7 |
| Pancreas | 1.6 |
| Pancreatic ca. CAPAN 2 | 0.8 |
| Adrenal Gland (new lot*) | 14.1 |
| Thyroid | 2 |
| Salavary gland | 7.8 |
| Pituitary gland | 0.6 |
| Brain (fetal) | 2.9 |
| Brain (whole) | 6.7 |
| Brain (amygdala) | 10.7 |
| Brain (cerebellum) | 3 |
| Brain (hippocampus) | 42.9 |
| Brain (thalamus) | 29.9 |
| Cerebral Cortex | 81.8 |
| Spinal cord | 3.1 |
| CNS ca. (glio/astro) U87-MG | 3.1 |
| CNS ca. (glio/astro) U-118-MG | 2.9 |
| CNS ca. (astro) SW1783 | 0.7 |
| CNS ca.* (neuro; met) SK-N-AS | 4.8 |
| CNS ca. (astro) SF-539 | 2 |

Probe Name: Ag148

| Primers | Sequences | Length | Start Position | SEQ ID NO: |
|---|---|---|---|---|
| Forward | 5'-CGCAGTTTCACTCGGGAGAT-3' | 20 | 1870 | 11 |
| Probe | TET-5'-CCTCTAGGATCCACATCGAGAAAATCATCGG-3'-TAMRA | 31 | 1895 | 12 |
| Reverse | 5'-AGCAGACTTCCCCGGAGTCT-3' | 20 | 1932 | 13 |

TABLE 18-continued

| Tissue Name | Rel. Expr., %<br>1.2tm1981f_ag148 |
|---|---|
| CNS ca. (astro) SNB-75 | 10.5 |
| CNS ca. (glio) SNB-19 | 8.9 |
| CNS ca. (glio) U251 | 3.9 |
| CNS ca. (glio) SF-295 | 7.9 |
| Heart | 17.8 |
| Skeletal Muscle (new lot*) | 12.7 |
| Bone marrow | 1.3 |
| Thymus | 0.6 |
| Spleen | 0.6 |
| Lymph node | 0.1 |
| Colorectal | 1.2 |
| Stomach | 2.6 |
| Small intestine | 12.8 |
| Colon ca. SW480 | 2.2 |
| Colon ca.* (SW480 met) SW620 | 6.2 |
| Colon ca. HT29 | 7.5 |
| Colon ca. HCT-116 | 3.9 |
| Colon ca. CaCo-2 | 5.5 |
| 83219 CC Well to Mod Diff (ODO3866) | 1.1 |
| Colon ca. HCC-2998 | 13 |
| Gastric ca.* (liver met) NCI-N87 | 9.2 |
| Bladder | 4.9 |
| Trachea | 0.2 |
| Kidney | 64.6 |
| Kidney (fetal) | 4.8 |
| Renal ca. 786-0 | 0.4 |
| Renal ca. A498 | 4.4 |
| Renal ca. RXF 393 | 1.6 |
| Renal ca. ACHN | 1.6 |
| Renal ca. UO-31 | 1.6 |
| Renal ca. TK-10 | 6.1 |
| Liver | 2.4 |
| Liver (fetal) | 1.3 |
| Liver ca. (hepatoblast) HepG2 | 3.7 |
| Lung | 0.3 |
| Lung (fetal) | 0.6 |
| Lung ca. (small cell) LX-1 | 9.8 |
| Lung ca. (small cell) NCI-H69 | 21.2 |
| Lung ca. (s.cell var.) SHP-77 | 2 |
| Lung ca. (large cell) NCI-H460 | 10.3 |
| Lung ca. (non-sm. cell) A549 | 6.4 |
| Lung ca. (non-s.cell) NCI-H23 | 9.1 |
| Lung ca. (non-s.cell) HOP-62 | 5.6 |
| Lung ca. (non-s.cl) NCI-H522 | 12.5 |
| Lung ca. (squam.) SW 900 | 3.6 |
| Lung ca. (squam.) NCI-H596 | 21.8 |
| Mammary gland | 3.5 |
| Breast ca.* (pl. effusion) MCF-7 | 8.1 |
| Breast ca.* (pl.ef) MDA-MB-231 | 1.4 |
| Breast ca.* (pl. effusion) T47D | 10.4 |
| Breast ca. BT-549 | 2.6 |
| Breast ca. MDA-N | 25.5 |
| Ovary | 1.6 |
| Ovarian ca. OVCAR-3 | 8.7 |
| Ovarian ca. OVCAR-4 | 5.3 |
| Ovarian ca. OVCAR-5 | 12.6 |
| Ovarian ca. OVCAR-8 | 5.2 |
| Ovarian ca. IGROV-1 | 4.4 |
| Ovarian ca.* (ascites) SK-OV-3 | 6.3 |
| Uterus | 1.7 |
| Placenta | 0.4 |
| Prostate | 8.2 |
| Prostate ca.* (bone met) PC-3 | 5.4 |
| Testis | 0.1 |
| Melanoma Hs688(A).T | 0.7 |
| Melanoma* (met) Hs688(B).T | 1 |
| Melanoma UACC-62 | 1.3 |
| Melanoma M14 | 2 |
| Melanoma LOX IMVI | 1.3 |
| Melanoma* (met) SK-MEL-5 | 2.4 |
| Adipose | 100 |

TABLE 18.A

| Tissue Name | Rel. Expr., %<br>2dtm2779<br>f_ag148 | Rel. Expr., %<br>2Dtm3038<br>f_ag148 |
|---|---|---|
| Normal Colon GENPAK 061003 | 40.1 | 59.9 |
| 83219 CC Well to Mod Diff (ODO3866) | 16.2 | 11.6 |
| 83220 CC NAT (ODO3866) | 14.8 | 25.9 |
| 83221 CC Gr.2 rectosigmoid (ODO3868) | 2.3 | 6.4 |
| 83222 CC NAT (ODO3868) | 14.3 | 16.8 |
| 83235 CC Mod Diff (ODO3920) | 11.5 | 42 |
| 83236 CC NAT (ODO3920) | 13.3 | 25.5 |
| 83237 CC Gr.2 ascend colon (ODO3921) | 6.7 | 30.6 |
| 83238 CC NAT (ODO3921) | 7.6 | 17.4 |
| 83241 CC from Partial Hepatectomy (ODO4309) | 2.4 | 15.8 |
| 83242 Liver NAT (ODO4309) | 0.3 | 2 |
| 87472 Colon mets to lung (OD04451-01) | 2 | 0 |
| 87473 Lung NAT (OD04451-02) | 1 | 3.7 |
| Normal Prostate Clontech A+ 6546-1 | 20.3 | 44.1 |
| 84140 Prostate Cancer (OD04410) | 18.7 | 47.6 |
| 84141 Prostate NAT (OD04410) | 9.8 | 25.2 |
| 87073 Prostate Cancer (OD04720-01) | 21 | 35.6 |
| 87074 Prostate NAT (OD04720-02) | 10.4 | 23 |
| Normal Lung GENPAK 061010 | 9.6 | 27.2 |
| 83239 Lung Met to Muscle (ODO4286) | 14 | 17.6 |
| 83240 Muscle NAT (ODO4286) | 9.5 | 21.2 |
| 84136 Lung Malignant Cancer (OD03126) | 0.3 | 5.8 |
| 84137 Lung NAT (OD03126) | 1.2 | 6.2 |
| 84871 Lung Cancer (OD04404) | 1.2 | 1.5 |
| 84872 Lung NAT (OD04404) | 4.5 | 5.5 |
| 84875 Lung Cancer (OD04565) | 1.6 | 3 |
| 84876 Lung NAT (OD04565) | 1.9 | 2.9 |
| 85950 Lung Cancer (OD04237-01) | 5.6 | 16.6 |
| 85970 Lung NAT (OD04237-02) | 0.8 | 3.1 |
| 83255 Ocular Mel Met to Liver (ODO4310) | 8 | 7.1 |
| 83256 Liver NAT (ODO4310) | 2.6 | 3.1 |
| 84139 Melanoma Mets to Lung (OD04321) | 10 | 18.6 |
| 84138 Lung NAT (OD04321) | 0.3 | 5.6 |
| Normal Kidney GENPAK 061008 | 29.3 | 75.3 |
| 83786 Kidney Ca, Nuclear grade 2 (OD04338) | 2.7 | 7 |
| 83787 Kidney NAT (OD04338) | 39 | 44.4 |
| 83788 Kidney Ca Nuclear grade 1/2 (OD04339) | 6.3 | 9.2 |
| 83789 Kidney NAT (OD04339) | 28.9 | 51 |
| 83790 Kidney Ca, Clear cell type (OD04340) | 11.4 | 9.2 |
| 83791 Kidney NAT (OD04340) | 73.2 | 90.1 |
| 83792 Kidney Ca, Nuclear grade 3 (OD04348) | 3.7 | 4.3 |
| 83793 Kidney NAT (OD04348) | 25.5 | 63.7 |
| 87474 Kidney Cancer (OD04622-01) | 0.5 | 3 |
| 87475 Kidney NAT (OD04622-03) | 19.2 | 21 |
| 85973 Kidney Cancer (OD04450-01) | 1.8 | 3.3 |
| 85974 Kidney NAT (OD04450-03) | 34.6 | 46.7 |
| Kidney Cancer Clontech 8120607 | 0.8 | 2.6 |
| Kidney NAT Clontech 8120608 | 23.8 | 25.2 |
| Kidney Cancer Clontech 8120613 | 7 | 25.9 |
| Kidney NAT Clontech 8120614 | 12.4 | 39 |
| Kidney Cancer Clontech 9010320 | 2 | 4.4 |
| Kidney NAT Clontech 9010321 | 26.4 | 26.1 |
| Normal Uterus GENPAK 061018 | 3 | 7.7 |
| Uterus Cancer GENPAK 064011 | 8.3 | 16.3 |
| Normal Thyroid Clontech A+ 6570-1 | 68.3 | 100 |
| Thyroid Cancer GENPAK 064010 | 1.4 | 8.8 |
| Thyroid Cancer INVITROGEN A302152 | 6 | 7.4 |
| Thyroid NAT INVITROGEN A302153 | 15.2 | 36.6 |
| Normal Breast GENPAK 061019 | 8.3 | 23.7 |
| 84877 Breast Cancer (OD04566) | 4.1 | 5.6 |
| 85975 Breast Cancer (OD04590-01) | 17.2 | 13.6 |
| 85976 Breast Cancer Mets (OD04590-03) | 20 | 26.8 |
| 87070 Breast Cancer Metastasis (OD04655-05) | 18.9 | 7.7 |
| GENPAK Breast Cancer 064006 | 8.1 | 14.7 |
| Breast Cancer Res. Gen. 1024 | 100 | 100 |
| Breast Cancer Clontech 9100266 | 8.7 | 17.9 |
| Breast NAT Clontech 9100265 | 4.3 | 16 |
| Breast Cancer INVITROGEN A209073 | 4 | 20.2 |
| Breast NAT INVITROGEN A2090734 | 4.1 | 18 |
| Normal Liver GENPAK 061009 | 4.4 | 10.3 |
| Liver Cancer GENPAK 064003 | 3.9 | 1.6 |
| Liver Cancer Research Genetics RNA 1025 | 5.1 | 10.6 |
| Liver Cancer Research Genetics RNA 1026 | 0 | 0.3 |

TABLE 18.A-continued

| Tissue Name | Rel. Expr., % 2dtm2779 f_ag148 | Rel. Expr., % 2Dtm3038 f_ag148 |
|---|---|---|
| Paired Liver Cancer Tissue Research Genetics RNA 6004-T | 4.9 | 11 |
| Paired Liver Tissue Research Genetics RNA 6004-N | 24.5 | 26.4 |
| Paired Liver Cancer Tissue Research Genetics RNA 6005-T | 2.9 | 3.1 |
| Paired Liver Tissue Research Genetics RNA 6005-N | 0 | 2 |
| Normal Bladder GENPAK 061001 | 4.7 | 19.1 |
| Bladder Cancer Research Genetics RNA 1023 | 1.9 | 9.1 |
| Bladder Cancer INVITROGEN A302173 | 0.3 | 13.6 |

TABLE 18.B

| Tissue Name | Rel. Expr., % 1.3Dtm3037f_ag148 |
|---|---|
| Liver adenocarcinoma | 3.7 |
| Pancreas | 2.4 |
| Pancreatic ca. CAPAN 2 | 4.7 |
| Adrenal gland | 4.8 |
| Thyroid | 20.6 |
| Salivary gland | 1.0 |
| Pituitary gland | 4.5 |
| Brain (fetal) | 8.4 |
| Brain (whole) | 28.5 |
| Brain (amygdala) | 48.3 |
| Brain (cerebellum) | 7.5 |
| Brain (hippocampus) | 97.9 |
| Brain (substantia nigra) | 5.8 |
| Brain (thalamus) | 30.4 |
| Cerebral Cortex | 33.4 |
| Spinal cord | 6.4 |
| CNS ca. (glio/astro) U87-MG | 0.9 |
| CNS ca. (glio/astro) U-118-MG | 1.5 |
| CNS ca. (astro) SW1783 | 1.0 |
| CNS ca.* (neuro; met) SK-N-AS | 4.9 |
| CNS ca. (astro) SF-539 | 3.4 |
| CNS ca. (astro) SNB-75 | 5.8 |
| CNS ca. (glio) SNB-19 | 3.4 |
| CNS ca. (glio) U251 | 3.3 |
| CNS ca. (glio) SF-295 | 9.3 |
| Heart (fetal) | 2.5 |
| Heart | 0.8 |
| Fetal Skeletal | 100.0 |
| Skeletal muscle | 0.3 |
| Bone marrow | 1.2 |
| Thymus | 3.9 |
| Spleen | 0.9 |
| Lymph node | 1.5 |
| Colorectal | 4.8 |
| Stomach | 4.7 |
| Small intestine | 5.8 |
| Colon ca. SW480 | 7.7 |
| Colon ca.* (SW480 met) SW620 | 3.3 |
| Colon ca. HT29 | 0.6 |
| Colon ca. HCT-116 | 2.7 |
| Colon ca. CaCo-2 | 3.2 |
| 83219 CC Well to Mod Diff (ODO3866) | 0.5 |
| Colon ca. HCC-2998 | 2.4 |
| Gastric ca.* (liver met) NCI-N87 | 3.4 |
| Bladder | 1.8 |
| Trachea | 1.4 |
| Kidney | 2.8 |
| Kidney (fetal) | 4.6 |
| Renal ca. 786-0 | 1.5 |
| Renal ca. A498 | 7.3 |
| Renal ca. RXF 393 | 0.4 |
| Renal ca. ACHN | 0.9 |
| Renal ca. UO-31 | 2.0 |
| Renal ca. TK-10 | 3.3 |

TABLE 18.B-continued

| Tissue Name | Rel. Expr., % 1.3Dtm3037f_ag148 |
|---|---|
| Liver | 0.9 |
| Liver (fetal) | 0.7 |
| Liver ca. (hepatoblast) HepG2 | 4.0 |
| Lung | 0.6 |
| Lung (fetal) | 0.7 |
| Lung ca. (small cell) LX-1 | 4.5 |
| Lung ca. (small cell) NCI-H69 | 19.1 |
| Lung ca. (s.cell var.) SHP-77 | 3.0 |
| Lung ca. (large cell) NCI-H460 | 3.6 |
| Lung ca. (non-sm. cell) A549 | 1.7 |
| Lung ca. (non-s.cell) NCI-H23 | 6.7 |
| Lung ca (non-s.cell) HOP-62 | 5.4 |
| Lung ca. (non-s.cl) NCI-H522 | 4.8 |
| Lung ca. (squam.) SW 900 | 1.0 |
| Lung ca. (squam.) NCI-H596 | 4.6 |
| Mammary gland | 2.2 |
| Breast ca.* (pl. effusion) MCF-7 | 3.1 |
| Breast ca.* (pl.ef) MDA-MB-231 | 1.8 |
| Breast ca.* (pl. effusion) T47D | 1.6 |
| Breast ca. BT-549 | 1.7 |
| Breast ca. MDA-N | 4.4 |
| Ovary | 2.8 |
| Ovarian ca. OVCAR-3 | 0.7 |
| Ovarian ca. OVCAR-4 | 0.3 |
| Ovarian ca. OVCAR-5 | 4.1 |
| Ovarian ca. OVCAR-8 | 4.0 |
| Ovarian ca. IGROV-1 | 0.6 |
| Ovarian ca.* (ascites) SK-OV-3 | 1.6 |
| Uterus | 4.2 |
| Placenta | 3.5 |
| Prostate | 4.7 |
| Prostate ca.* (bone met)PC-3 | 1.8 |
| Testis | 1.8 |
| Melanoma Hs688(A).T | 1.5 |
| Melanoma* (met) Hs688(B).T | 4.9 |
| Melanoma UACC-62 | 1.4 |
| Melanoma M14 | 0.4 |
| Melanoma LOX IMVI | 1.4 |
| Melanoma* (met) SK-MEL-5 | 1.8 |
| Adipose | 0.0 |

TABLE 18.C

| Tissue Name | Rel. Expr., % 4Dtm 3075 f_ag148 |
|---|---|
| 93768_Secondary Th1_anti-CD28/anti-CD3 | 9.3 |
| 93769_Secondary Th2_anti-CD28/anti-CD3 | 12.5 |
| 93770_Secondary Tr1_anti-CD28/anti-CD3 | 16.7 |
| 93573_Secondary Th1_resting day 4–6 in IL-2 | 8.9 |
| 93572_Secondary Th2_resting day 4–6 in IL-2 | 6.7 |
| 93571_Secondary Tr1_resting day 4–6 in IL-2 | 10.5 |
| 93568_primary Th1_anti-CD28/anti-CD3 | 26.8 |
| 93569_primary Th2_anti-CD28/anti-CD3 | 17.2 |
| 93570_primary Tr1_anti-CD28/anti-CD3 | 32.8 |
| 93565_primary Th1_resting dy 4–6 in IL-2 | 17.7 |
| 93566_primary Th2_resting dy 4–6 in IL-2 | 8.8 |
| 93567_primary Tr1_resting dy 4–6 in IL-2 | 22.8 |
| 93351_CD45RA CD4 lymphocyte_anti-CD28/anti-CD3 | 7.9 |
| 93352_CD45RO CD4 lymphocyte_anti-CD28/anti-CD3 | 15.5 |
| 93251_CD8 Lymphocytes_anti-CD28/anti-CD3 | 22.5 |
| 93353_chronic CD8 Lymphocytes 2ry_resting dy 4–6 in IL-2 | 8.7 |
| 93574_chronic CD8 Lymphocytes 2ry_activated CD3/CD28 | 4.9 |
| 93354_CD4_none | 3.7 |
| 93252_Secondary Th1/Th2/Tr1_anti-CD95 CH11 | 3.3 |
| 93103_LAK cells_resting | 9.0 |
| 93788_LAK cells_IL-2 | 8.4 |
| 93787_LAK cells_IL-2 + IL-12 | 10.0 |
| 93789_LAK cells_IL-2 + IFN gamma | 6.3 |

TABLE 18.C-continued

| Tissue Name | Rel. Expr., % 4Dtm 3075 f_ag148 |
|---|---|
| 93790_LAK cells_IL-2 + IL-18 | 11.3 |
| 93104_LAK cells_PMA/ionomycin and IL-18 | 0.0 |
| 93578_NK Cells IL-2_resting | 2.0 |
| 93109_Mixed Lymphocyte Reaction_Two Way MLR | 12.4 |
| 93110_Mixed Lymphocyte Reaction_Two Way MLR | 2.0 |
| 93111_Mixed Lymphocyte Reaction_Two Way MLR | 1.8 |
| 93112_Mononuclear Cells (PBMCs)_resting | 1.8 |
| 93113_Mononuclear Cells (PBMCs)_PWM | 32.3 |
| 93114_Mononuclear Cells (PBMCs)_PHA-L | 8.2 |
| 93249_Ramos (B cell)_none | 12.6 |
| 93250_Ramos (B cell)_ionomycin | 59.0 |
| 93349_B lymphocytes_PWM | 18.2 |
| 93350_B lymphoytes_CD40L and IL-4 | 11.5 |
| 92665_EOL-1 (Eosinophil)_dbcAMP differentiated | 46.3 |
| 93248_EOL-1 (Eosinophil)_dbcAMP/PMAionomycin | 5.6 |
| 93356_Dendritic Cells_none | 2.0 |
| 93355_Dendritic Cells_LPS 100 ng/ml | 0.0 |
| 93775_Dendritic Cells_anti-CD40 | 1.5 |
| 93774_Monocytes_resting | 0.0 |
| 93776_Monocytes_LPS 50 ng/ml | 0.0 |
| 93581_Macrophages_resting | 7.2 |
| 93582_Macrophages_LPS 100 ng/ml | 0.0 |
| 93098_HUVEC (Endothelial)_none | 18.2 |
| 93099_HUVEC (Endothelial)_starved | 17.4 |
| 93100_HUVEC (Endothelial)_IL-1b | 7.2 |
| 93779_HUVEC (Endothelial)_IFN gamma | 7.7 |
| 93102_HUVEC (Endothelial)_TNF alpha + IFN gamma | 5.3 |
| 93101_HUVEC (Endothelial)_TNF alpha + IL4 | 15.0 |
| 93781_HUVEC (Endothelial)_IL-11 | 5.6 |
| 93583_Lung Microvascular Endothelial Cells_none | 16.0 |
| 93584_Lung Microvascular Endothelial Cells_TNFa (4 ng/ml) and IL1b (1 ng/ml) | 12.9 |
| 92662_Microvascular Dermal endothelium_none | 7.0 |
| 92663_Microsvascular Dermal endothelium _TNFa (4 ng/ml) and IL1b (1 ng/ml) | 1.0 |
| 93773_Bronchial epithelium_TNFa (4 ng/ml) and IL1b (1 ng/ml)** | 10.3 |
| 93347_Small Airway Epithelium_none | 4.6 |
| 93348_Small Airway Epithelium_TNFa (4 ng/ml) and IL1b (1 ng/ml) | 8.1 |
| 92668_Coronery Artery SMC_resting | 0.0 |
| 92669_Coronery Artery SMC_TNFa (4 ng/ml) and IL1b (1 ng/ml) | 2.3 |
| 93107_astrocytes_resting | 7.6 |
| 93108_astrocytes_TNFa (4 ng/ml) and IL1b (1 ng/ml) | 4.0 |
| 92666_KU-812 (Basophil)_resting | 68.8 |
| 92667_KU-812 (Basophil)_PMA/ionoycin | 47.6 |
| 93579_CCD1106 (Keratinocytes)_none | 16.2 |
| 93580_CCD1106 (Keratinocytes)_TNFa and IFNg** | 3.4 |
| 93791_Liver Cirrhosis | 4.3 |
| 93792_Lupus Kidney | 11.3 |
| 93577_NCI-H292 | 43.8 |
| 93358_NCI-H292_IL-4 | 95.3 |
| 93360_NCI-H292_IL-9 | 95.9 |
| 93359_NCI-H292_IL-13 | 41.8 |
| 93357_NCI-H292_IFN gamma | 52.5 |
| 93777_HPAEC_- | 9.5 |
| 93778_HPAEC_IL-1 beta/TNA alpha | 12.0 |
| 93254_Normal Human Lung Fibroblast_none | 4.0 |
| 93253_Normal Human Lung Fibroblast_TNFa (4 ng/ml) and IL-1b (1 ng/ml) | 1.7 |
| 93257_Normal Human Lung Fibroblast_IL-4 | 14.0 |
| 93256_Normal Human Lung Fibroblast_IL-9 | 12.6 |
| 93255_Normal Human Lung Fibroblast_IL-13 | 4.3 |
| 93258_Normal Human Lung Fibroblast_IFN gamma | 8.2 |
| 93106_Dermal Fibroblasts CCD1070_resting | 25.0 |
| 93361_Dermal Fibroblasts CCD1070_TNF alpha 4 ng/ml | 44.4 |
| 93105_Dermal Fibroblasts CCD1070_IL-1 beta 1 ng/ml | 5.8 |
| 93772_dermal fibroblast_IFN gamma | 11.3 |
| 93771_dermal fibroblast_IL-4 | 5.7 |
| 93259_IBD Colitis 1** | 13.8 |
| 93260_IBD Colitis 2 | 0.0 |
| 93261_IBD Crohns | 1.9 |
| 735010_Colon_normal | 40.6 |
| 735019_Lung_none | 9.0 |
| 64028-1_Thymus_none | 100.0 |
| 64030-1_Kidney_none | 9.7 |

TABLE 18.D

| Tissue Name | Rel. Expr., % 4dtm 3351 f_ag148 |
|---|---|
| 93768_Secondary Th1_anti-CD28/anti-CD3 | 20.2 |
| 93769_Secondary Th2_anti-CD28/anti-CD3 | 12.2 |
| 93770_Secondary Tr1_anti-CD28/anti-CD3 | 11.4 |
| 93573_Secondary Th1_resting day 4–6 in IL-2 | 3.5 |
| 93572_Secondary Th2_resting day 4–6 in IL-2 | 3.5 |
| 93571_Secondary Tr1_resting day 4–6 in IL-2 | 6.6 |
| 93568_primary Th1_anti-CD28/anti-CD3 | 11.7 |
| 93569_primary Th2_anti-CD28/anti-CD3 | 5.6 |
| 93570_primary Tr1_anti-CD28/anti-CD3 | 7.6 |
| 93565_primary Th1_resting dy 4–6 in IL-2 | 5.8 |
| 93566_primary Th2_resting dy 4–6 in IL-2 | 1.8 |
| 93567_primary Tr1_resting dy 4–6 in IL-2 | 5.6 |
| 93351_CD45RA CD4 lymphocyte_anti-CD28/anti-CD3 | 5.8 |
| 93352_CD45RO CD4 lymphocyte_anti-CD28/anti-CD3 | 24.3 |
| 93251_CD8 Lymphocytes_anti-CD28/anti-CD3 | 9.1 |
| 93353_chronic CD8 Lymphocytes 2ry_resting dy 4–6 in IL-2 | 16.0 |
| 93574_chronic CD8 Lymphocytes 2ry_activated CD3/CD28 | 1.6 |
| 93354_CD4_none | 0.0 |
| 93252_Secondary Th1/Th2/Tr1_anti-CD95 CH11 | 2.7 |
| 93103_LAK cells_resting | 4.9 |
| 93788_LAK cells_IL-2 | 2.4 |
| 93787_LAK cells_IL-2 + IL-12 | 6.3 |
| 93789_LAK cells_IL-2 + IFN gamma | 7.0 |
| 93790_LAK cells_IL-2 + IL-18 | 10.3 |
| 93104_LAK cells_PMA/ionomycin and IL-18 | 7.7 |
| 93578_NK Cells IL-2_resting | 2.1 |
| 93109_Mixed Lymphocyte Reaction_Two Way MLR | 17.3 |
| 93110_Mixed Lymphocyte Reaction_Two Way MLR | 7.6 |
| 93111_Mixed Lymphocyte Reaction_Two Way MLR | 1.5 |
| 93112_Mononuclear Cells (PBMCs)_resting | 1.3 |
| 93113_Mononuclear Cells (PBMCs)_PWM | 12.6 |
| 93114_Mononuclear Cells (PBMCs)_PHA-L | 1.6 |
| 93249_Ramos (B cell)_none | 10.8 |
| 93250_Ramos (B cell)_ionomycin | 13.7 |
| 93349_B lymphocytes_PWM | 5.6 |
| 93350_B lymphoytes_CD40L and IL-4 | 6.2 |
| 92665_EOL-1 (Eosinophil)_dbcAMP differentiated | 58.6 |
| 93248_EOL-1 (Eosinophil)_dbcAMP/PMAionomycin | 14.7 |
| 93356_Dendritic Cells_none | 4.0 |
| 93355_Dendritic Cells_LPS 100 ng/ml | 5.4 |
| 93775_Dendritic Cells_anti-CD40 | 7.1 |
| 93774_Monocytes_resting | 0.0 |
| 93776_Monocytes_LPS 50 ng/ml | 3.2 |
| 93581_Macrophages_resting | 1.8 |
| 93582_Macrophages_LPS 100 ng/ml | 4.4 |
| 93098_HUVEC (Endothelial)_none | 17.3 |
| 93099_HUVEC (Endothelial)_starved | 0.4 |
| 93100_HUVEC (Endothelial)_IL-1b | 1.3 |
| 93779_HUVEC (Endothelial)_IFN gamma | 9.1 |
| 93102_HUVEC (Endothelial)_TNF alpha + IFN gamma | 2.8 |
| 93101_HUVEC (Endothelial)_TNF alpha + IL4 | 14.2 |
| 93781_HUVEC (Endothelial)_IL-11 | 7.1 |
| 93583_Lung Microvascular Endothelial Cells_none | 11.3 |
| 93584_Lung Microvascular Endothelial Cells_TNFa (4 ng/ml) and IL1b (1 ng/ml) | 9.8 |
| 92662_Microvascular Dermal endothelium_none | 5.8 |

TABLE 18.D-continued

| Tissue Name | Rel. Expr., % 4dtm3351f_ag148 |
|---|---|
| 92663_Microsvasular Dermal endothelium_TNFa (4 ng/ml) and IL1b (1 ng/ml) | 8.8 |
| 93773_Bronchial epithelium_TNFa (4 ng/ml) and IL1b (1 ng/ml)** | 0.2 |
| 93347_Small Airway Epithelium_none | 3.8 |
| 93348_Small Airway Epithelium_TNFa (4 ng/ml) and IL1b (1 ng/ml) | 4.2 |
| 92668_Coronery Artery SMC_resting | 1.1 |
| 92669_Coronery Artery SMC_TNFa (4 ng/ml) and IL1b (1 ng/ml) | 1.4 |
| 93107_astrocytes_resting | 7.3 |
| 93108_astrocytes_TNFa (4 ng/ml) and IL1b (1 ng/ml) | 13.2 |
| 92666_KU-812 (Basophil)_resting | 63.7 |
| 92667_KU-812 (Basophil)_PMA/ionoycin | 55.1 |
| 93579_CCD1106 (Keratinocytes)_none | 11.3 |
| 93580_CCD1106 (Keratinocytes)_TNFa and IFNg** | 0.0 |
| 93791_Liver Cirrhosis | 9.5 |
| 93792_Lupus Kidney | 1.6 |
| 93577_NCI-H292 | 16.0 |
| 93358_NCI-H292_IL-4 | 28.5 |
| 93360_NCI-H292_IL-9 | 23.2 |
| 93359_NCI-H292_IL-13 | 100.0 |
| 93357_NCI-H292_IFN gamma | 52.5 |
| 93777_HPAEC_- | 8.9 |
| 93778_HPAEC_IL-1 beta/TNA alpha | 12.9 |
| 93254_Normal Human Lung Fibroblast_none | 8.9 |
| 93253_Normal Human Lung Fibroblast_TNFa (4 ng/ml) and IL-1b (1 ng/ml) | 1.0 |
| 93257_Normal Human Lung Fibroblast_IL-4 | 5.2 |
| 93256_Normal Human Lung Fibroblast_IL-9 | 7.9 |
| 93255_Normal Human Lung Fibroblast_IL-13 | 5.3 |
| 93258_Normal Human Lung Fibroblast_IFN gamma | 4.0 |
| 93106_Dermal Fibroblasts CCD1070_resting | 7.5 |
| 93361_Dermal Fibroblasts CCD1070_TNF alpha 4 ng/ml | 2.5 |
| 93105_Dermal Fibroblasts CCD1070_IL-1 beta 1 ng/ml | 20.6 |
| 93772_dermal fibroblast_lFN gamma | 10.2 |
| 93771_dermal fibroblast_IL-4 | 6.7 |
| 93259_IBD Colitis 1** | 5.8 |
| 93260_IBD Colitis 2 | 1.3 |
| 93261_IBD Crohns | 0.0 |
| 735010_Colon_normal | 26.2 |
| 735019_Lung_none | 9.1 |
| 64028-1_Thymus_none | 55.9 |
| 64030-1_Kidney_none | 8.7 |

TABLE 18.E

| Tissue Name | Rel. Expr., % cns_1x4tm6548f_ag148_a1 |
|---|---|
| 102633_BA4 Control | 93.8 |
| 102634_BA7 Control | 60.7 |
| 102632_BA9 Control | 42.7 |
| 102635_BA17 Control | 58.2 |
| 102636_Glob Palladus Control | 14.7 |
| 102637_Sub Nigra Control | 53.4 |
| 102638_Temp Pole Control | 9.2 |
| 102639_Cing Gyr Control | 49.1 |
| 102641_BA4 Control2 | 67.7 |
| 102642_BA7 Control2 | 79.8 |
| 102640_BA9 Control2 | 73.8 |
| 102643_BA17 Control2 | 61.4 |
| 102644_Glob Palladus Control2 | 34.6 |
| 102645_Sub Nigra Control2 | 25.6 |
| 102646_Temp Pole Control2 | 94.8 |
| 102647_Cing Gyr Control2 | 83.8 |
| 102617_BA9 Alzheimer's | 6.5 |
| 102620_Glob Palladus Alzheimer's | 18.8 |
| 102622_Temp Pole Alzheimer's | 6.8 |
| 102623_Cing Gyr Alzheimer's | 32.2 |

TABLE 18.E-continued

| Tissue Name | Rel. Expr., % cns_1x4tm6548f_ag148_a1 |
|---|---|
| 102625_BA4 Alzheimer's2 | 11.5 |
| 102626_BA7 Alzheimer's2 | 15.1 |
| 102624_BA9 Alzheimer's2 | 21.3 |
| 102627_BA17 Alzheimer's2 | 11.5 |
| 102628_Glob Palladus Alzheimer's2 | 13.1 |
| 102629_Sub Nigra Alzheimer's2 | 22.4 |
| 102630_Temp Pole Alzheimer's2 | 12.9 |
| 102631_Cing Gyr Alzheimer's2 | 26.0 |
| 102649_BA4 Parkinson's | 47.5 |
| 102650_BA7 Parkinson's | 19.4 |
| 102648_BA9 Parkinson's | 19.5 |
| 102651_BA17 Parkinson's | 57.0 |
| 102652_Glob Palladus Parkinson's | 100.0 |
| 102653_Temp Pole Parkinson's | 20.7 |
| 102654_Cing Gyr Parkinson's | 37.0 |
| 102656_BA4 Parkinson's2 | 55.0 |
| 102657_BA7 Parkinson's2 | 17.0 |
| 102655_BA9 Parkinson's2 | 49.6 |
| 102658_BA17 Parkinson's2 | 56.1 |
| 102659_Glob Palladus Parkinson's2 | 41.9 |
| 102660_Sub Nigra Parkinson's2 | 30.8 |
| 102661_Temp Pole Parkinson's2 | 36.4 |
| 102662_Cing Gyr Parkinson's2 | 44.2 |
| 102664_BA4 Huntington's | 24.2 |
| 102665_BA7 Huntington's | 33.0 |
| 102663_BA9 Huntington's | 37.8 |
| 102666_BA17 Huntington's | 46.4 |
| 102667_Sub Nigra Huntington's | 47.8 |
| 102668_Temp Pole Huntington's | 58.8 |
| 102669_Cing Gyr Huntington's | 71.2 |
| 102671_BA4 Huntington's2 | 13.6 |
| 102672_BA7 Huntington's2 | 34.0 |
| 102670_BA9 Huntington's2 | 19.8 |
| 102673_BA17 Huntington's2 | 18.6 |
| 102674_Sub Nigra Huntington's2 | 20.2 |
| 102676_Cing Gyr Huntington's2 | 41.0 |
| 102603_BA4 PSP | 13.3 |
| 102604_BA7 PSP | 27.1 |
| 102602_BA9 PSP | 24.1 |
| 102605_BA17 PSP | 23.2 |
| 102606_Glob Palladus PSP | 16.6 |
| 102607_Temp Pole PSP | 7.1 |
| 102608_Cing Gyr PSP | 23.9 |
| 102610_BA4 PSP2 | 37.4 |
| 102611_BA7 PSP2 | 24.1 |
| 102609_BA9 PSP2 | 9.3 |
| 102612_BA17 PSP2 | 8.6 |
| 102613_Glob Palladus PSP2 | 15.7 |
| 102614_Sub Nigra PSP2 | 11.2 |
| 102615_Temp Pole PSP2 | 3.9 |
| 102616_Cing Gyr PSP2 | 15.6 |
| 102588_BA4 Depression | 28.8 |
| 102589_BA7 Depression | 9.3 |
| 102587_BA9 Depression | 26.0 |
| 102590_BA17 Depression | 24.3 |
| 102591_Glob Palladus Depression | 12.0 |
| 102592_Sub Nigra Depression | 32.3 |
| 102594_Cing Gyr Depression | 49.9 |
| 102596_BA4 Depression2 | 21.5 |
| 102595_BA9 Depression2 | 23.7 |
| 102597_BA17 Depression2 | 48.6 |
| 102599_Sub Nigra Depression2 | 22.0 |
| 102600_Temp Pole Depression2 | 26.1 |
| 102601_Cing Gyr Depression2 | 30.7 |

The results in Tables 18–18. E. demonstrate that clone NOV3 is highly expressed in normal brain, kidney, fetal skeletal, colon, thyroid and adipose tissues (Tables 18, 18. A, and 18. B); in certain tumors, especially breast cancer (Table 18. A); in IL-13 (Table 18. C); and in numerous areas of the central nervous system (Table 18. E), but not in corresponding normal cell lines. These results indicate that clone NOV3 may be used as a marker for certain cancers, especially breast cancer.

Example 2

Radiation Hybrid Mapping Provides the Chromosomal Location of NOV2 and NOV3

Radiation hybrid mapping using human chromosome markers was carried out for NOV2 and NOV3 in the present invention. The procedure used to obtain these results is analogous to that described in Steen, R G et al. (A High-Density Integrated Genetic Linkage and Radiation Hybrid Map of the Laboratory Rat, Genome Research 1999 (Published Online on May 21, 1999) Vol. 9, AP1–AP8, 1999). A panel of 93 cell clones containing randomized radiation-induced human chromosomal fragments was screened in 96 well plates using PCR primers designed to identify the sought clones in a unique fashion. Table 19 provides the results obtained for two of the three clones of the present invention, showing the markers straddling the gene of the invention, and the distance in cR separating them.

TABLE 19

| Clone | Chromosome | Distance from Marker, cR |
|---|---|---|
| NOV2 | 1 | AFMA129ZB5, 0.0 |
| NOV3 | 11 | D11S913, 5.5 |
| NOV3 | 11 | WI-1409, 4.7 |

Example 3

Molecular Cloning of NOV2

The open reading frame of clone NOV2 codes for a Type I membrane protein with a transmembrane domain, predicted by PSORT, to be between residues 540–566. In addition, SIGNALP predicts that a signal peptidase cleavage site occurs between residues 27 and 28. Accordingly the mature form of the predicted extracellular domain of clone NOV2 was targeted for cloning, from residue 28 to 538. Oligonucleotide primers were designed to PCR amplify a DNA segment coding for this mature domain of NOV2. The forward primer includes an in frame BamHI site. The reverse primer contains an in frame XhoI restriction site. The sequences of the primers are the following:

```
NOV2 Forward:
GGATCCGCGCGCGGCGAAGTGAATTTGCTGG   (SEQ ID NO:14)

and
NOV2 Reverse:
CTCGAGGGTCCTGGTGTCATAGCGGGCC.     (SEQ ID NO:15)
```

PCR reactions were set up using 5 ng human hypothalamus cDNA as a template, 1 microM of each of the NOV2 Forward and NOV2 Reverse primers, 5 micromoles dNTP (Clontech Laboratories, Palo Alto Calif.) and 1 microliter of 50xAdvantage-HF 2 polymerase (Clontech Laboratories, Palo Alto Calif.) in 50 microliter volume. The following reaction conditions were used:

a) 96° C. 3 minutes
b) 96° C. 30 seconds denaturation
c) 70° C. 30 seconds, primer annealing. This temperature was gradually decreased by 1° C./cycle
d) 72° C. 3 minutes extension.
Repeat steps b–d 10 times
e) 96° C. 30 seconds denaturation
f) 60° C. 30 seconds annealing
g) 72° C. 3 minutes extension
Repeat steps e–g 25 times
h) 72° C. 5 minutes final extension A single amplified product having a size of approximately 1500 bp was detected by agarose gel electrophoresis. The product was isolated and ligated into the pCR2.1 vector (Invitrogen Corp, Carlsbad Calif.).

The construct was sequenced using the following gene-specific primers:

```
NOV2 S1: TACCTGGAGTCGGACCGC,         (SEQ ID NO: 16)
NOV2 S2: GCGGTCCGACTCCAGGTA,         (SEQ ID NO: 17)
NOV2 S3: CAGTGCGTGCGGCACTCAG,        (SEQ ID NO: 18)
NOV2 S4: TGAGTGCCGCACGCACTGG,        (SEQ ID NO: 19)
NOV2 S5: CTGGACCCAGGTGGCCGC,         (SEQ ID NO: 20)
NOV2 S6: GCGGCCACCTGGGTCCAG,         (SEQ ID NO: 21)
NOV2 S7: CCCGAGCAGCCGAACGGC, and     (SEQ ID NO: 22)
NOV2 S8: GCCGTTCGGCTGCTCGGG.         (SEQ ID NO: 23)
```

The cloned insert was verified to be 100% identical to the nucleotide sequence of clone NOV2 (SEQ ID NO: 4) from residues 28 to 538. The construct is called pCR2.1-cgNOV2-S340-1C.

Example 4

Molecular Cloning of NOV3

The open reading frame of clone NOV3 codes for a Type I membrane protein with a transmembrane domain, predicted by PSORT, between residues 547–580. SIGNALP predicted the signal peptidase cleavage site between residues 51 and 52. For these reasons the mature form of the extracellular domain was targeted for cloning, from residues 52 to 546. Oligonucleotide primers were designed to PCR amplify a DNA segment coding for this mature extracellular domain. The forward primer includes an in frame BamHI site. The reverse primer contains an in frame XhoI restriction site. The sequences of the primers are the following:

```
NOV3Forw:
GGATCCACCACCTGCCCCTCGGTGTGC and      (SEQ ID NO:24)

NOV3Rev:
CTCGAGGCCAGCGTTCTGCTCCTGGTTGAGTGTGG. (SEQ ID NO:25)
```

PCR reactions were set up using 5 ng human fetal brain cDNA template, 1 microM of each of the NOV3Forw and NOV3Rev primers, 5 micromoles dNTP (Clontech Laboratories, Palo Alto Calif.) and 1 microliter of 50xAdvantage-HF 2 polymerase (Clontech Laboratories, Palo Alto Calif.) in 50 microliter volume. The reaction conditions used were the same as described in Example A.

A single amplified product having a size of approximately 1500 bp was detected by agarose gel electrophoresis. The product was isolated and ligated into the pCR2.1 vector (Invitrogen Corp, Carlsbad Calif.).

The construct was sequenced using the following gene-specific primers:

```
NOV3S1: CGCACCATTGCCAGGGAC,        (SEQ ID NO: 26)
NOV3S2: GTCCCTGGCAATGGTGCG,        (SEQ ID NO: 27)
NOV3S3: CTGGTGCGCAATTCGCTGGCC,     (SEQ ID NO: 28)
NOV3S4: GGCCAGCGAATTGCGCACCAG,     (SEQ ID NO: 29)
NOV3S5: CACGCCTCTGCCACCACG, and    (SEQ ID NO: 30)
NOV3S6; CGTGGTGGCAGAGGCGTG.        (SEQ ID NO: 31)
```

```
pSec-V5-His Forward:  CTCGTCCTCGAGGGTAAGCCTATCCCTAAC and  (SEQ ID NO:32)
pSec-V5-His Reverse:  CTCGTCGGGCCCCTGATCAGCGGGTTTAAAC,    (SEQ ID NO:33)
``` were designed to amplify a fragment from the pcDNA3.1-V5His (Invitrogen, Carlsbad, Calif.) expression vector that includes V5 and His6. The PCR product was digested with XhoI and ApaI and ligated into the XhoI/ApaI digested pSecTag2 B vector harboring an Ig kappa leader sequence (Invitrogen, Carlsbad Calif.). The correct structure of the resulting vector, pSecV5His, including an in-frame Ig-kappa leader and V5-His6 was verified by DNA sequence analysis. The vector pSecV5His was digested with PmeI and NheI to provide a fragment retaining the above elements in the correct frame. The PmeI-NheI fragment was ligated into the BamHI/Klenow and NheI treated vector pCEP4 (Invitrogen, Carlsbad, Calif.). The resulting vector was named pCEP4/Sec and includes an in-frame Ig kappa leader, a site for insertion of a clone of interest, V5 and His6 under control of the PCMV and/or the PT7 promoter. pCEP4/Sec is an expression vector that allows heterologous protein expression and secretion by fusing any protein to the Ig Kappa chain signal peptide. Detection and purification of the expressed protein are aided by the presence of the V5 epitope tag and 6xHis tag at the C-terminus (Invitrogen, Carlsbad, Calif.).

Example 6

Expression of NOV2 in Human Embryonic Kidney (HEK) 293 Cells

The BamHI-XhoI fragment containing the NOV2 sequence was isolated from pCR2.1-cgNOV2-S340-1C (Example 3) and subcloned into the vector pCEP4/Sec (Example 5) to generate expression vector pCEP4/Sec-NOV2. The pCEP4/Sec-NOV2 vector was transfected into HEK293 cells using the LipofectaminePlus reagent following the manufacturer's instructions (Gibco/BRL/Life Technologies, Rockville, Md.). The cell pellet and supernatant were harvested 72 hours after transfection and examined for NOV2 expression by Western blotting, after SDS-PAGE run under reducing conditions, with an anti-V5 antibody. FIG. 1 shows that NOV2 is highly expressed in the supernatant medium as a polypeptide having an apparent molecular weight of approximately 64 kDa protein that is secreted by the transfected 293 cells. The molecular weight standard used was SeeBlue Marker (Invitrogen, Carlsbad, Calif.). This result is in reasonable agreement with the predicted molecular weight of 56842.5 Da. The program PROSITE predicts that there are three N-glycosylation sites in this polypeptide. Glycosylation of the polypeptide expressed in the transfected cells may be responsible for the difference between the predicted and observed molecular weights.

The cloned insert was verified as being 100% identical to clone NOV3 (SEQ ID NO: 6) from residues 52 to 546. The construct is called pCR2.1-cgNOV3-S331-3A.

Example 5

Preparation of Mammalian Expression Vector pCEP4/Sec

The oligonucleotide primers,

Example 7

Expression of NOV3 in Human Embryonic Kidney 293 Cells

The BamHI-XhoI fragment containing the NOV3 sequence was isolated from pCR2.1-cgNOV3-S331-3A (Example 4) and subcloned into the vector pCEP4/Sec (Example 5) to generate expression vector pCEP4/Sec-NOV3. The pCEP4/Sec-NOV3 vector was transfected into HEK293 cells using the LipofectaminePlus reagent following the manufacturer's instructions (Gibco/BRL/Life Technologies). The cell pellet and supernatant were harvested 72 hours after transfection and examined for NOV3 expression by Western blotting, after SDS-PAGE run under reducing conditions, with an anti-V5 antibody. FIG. 2 shows that NOV3 is highly expressed in the supernatant as a polypeptide with an apparent molecular weight of approximately 70 kDa, secreted by the transfected 293 cells. The molecular weight standard used was SeeBlue Marker (Invitrogen, Carlsbad, Calif.). This result is in reasonable agreement with the predicted molecular weight of 54572.3 Da. The program PROSITE predicts that there are three N-glycosylation sites in this polypeptide. Glycosylation of the polypeptide produced in the transfected cells may be responsible for the difference in the molecular weights. The program PROSITE predicts that there are two N-glycosylation sites in this polypeptide. Glycosylation of the polypeptide expressed in the transfected cells may be responsible for the difference between the predicted and observed molecular weights.

Example 8

Quantitative Expression Analysis of NOV4 in Various Cells and Tissues

TAQMAN® Reverse Transcription Reagents Kit was used as given above in Example 1. NOV4 exhibited highest levels of expression in testis (100%), 85976 Breast Cancer Mets (100%), breast cancer Res. Gen. (90%), 94909-XF-498-CNS-ssDNA (100%) and dermal fibroblast-IL-4 (100%), and lower but consistent levels of expression in breast cancer (pl. effusion) T47D cells (15%), melanoma UACC-62 (10%), breast cancer Clontech 9100266 (38%), 94925-NCI-H1155-large cell lung cancer/neuroendocrine-ss cDNA (21%), 94923-NCI-H82-small cell lung cancer/neuroendocrine-ss cDNA (18%), 94918-DMS-79-small cell lung cancer/neuroendocrine-ss cDNA (19%) and normal prostate clontech A+ 6546-1 (20%). These results differ to some degree from the parent clone, NOV2, which did not exhibit such high levels of expression in central nervous system tissue, testis and fibroblast tissue, but did exhibit positive levels of expression in cancer cell lines. Such differences in expression reflect the distinction among variants. It is noteworthy that clone NOV4 is minimally or not detectably found in the immediate normal tissue adjacent to breast and lung tissue. Thus, clones of NOV4 may be used as markers for certain types of cancers, especially breast and lung cancer.

Probe Name: Ag087

| Primers | Sequences | Length | Start Position | SEQ ID NO: |
|---|---|---|---|---|
| Forward | 5'-CGCAGTTTCACTCGGGAGAT-3' | 20 | 1870 | 11 |
| Probe | TET-5'-CCTCTAGGATCCACATCGAGAAAATCATCGG-3'-TAMRA | 31 | 1895 | 12 |
| Reverse | 5'-AGCAGACTTCCCCGGAGTCT-3' | 20 | 1932 | 13 |

The results obtained for clone NOV4 using primer-probe set Ag87 are shown in Tables 20. A.–20. E.

TABLE 20.A

TAQMAN® Results for clone NOV4.

| Tissue Name | Rel. Expr., % tm252t_ag087 |
|---|---|
| Endothelial cells | 0.3 |
| Endothelial cells (treated) | 0.6 |
| Pancreas | 1 |
| Pancreatic ca. CAPAN 2 | 2.5 |
| Adipose | 1.8 |
| Adrenal gland | 0.2 |
| Thyroid | 0.1 |
| Salavary gland | 0.2 |
| Pituitary gland | 0.2 |
| Brain (fetal) | 0.9 |
| Brain (whole) | 3 |
| Brain (amygdala) | 0.7 |
| Brain (cerebellum) | 7.1 |
| Brain (hippocampus) | 2.8 |
| Brain (substantia nigra) | 2.7 |
| Brain (thalamus) | 2.5 |
| Brain (hypothalamus) | 0.3 |
| Spinal cord | 2.1 |
| CNS ca. (glio/astro) U87-MG | 0.4 |
| CNS ca. (glio/astro) U-118-MG | 0.3 |
| CNS ca. (astro) SW1783 | 0.3 |
| CNS ca.* (neuro; met) SK-N-AS | 1.1 |
| CNS ca. (astro) SF-539 | 0 |
| CNS ca. (astro) SNB-75 | 2.2 |
| CNS ca. (glio) SNB-19 | 2 |
| CNS ca. (glio) U251 | 0.9 |
| CNS ca. (glio) SF-295 | 0 |
| Heart | 0.4 |
| Skeletal muscle | 0 |
| Bone marrow | 0 |
| Thymus | 3.5 |
| Spleen | 0.4 |
| Lymph node | 0.4 |
| Colon (ascending) | 0.6 |
| Stomach | 1.3 |
| Small intestine | 0.5 |
| Colon ca. SW480 | 0.3 |
| Colon ca.* (SW480 met) SW620 | 0.2 |
| Colon ca. HT29 | 2.8 |
| Colon ca. HCT-116 | 8 |
| Colon ca. CaCo-2 | 1.2 |
| Colon ca. HCT-15 | 0.8 |
| Colon ca. HCC-2998 | 1.5 |
| Gastric ca.* (liver met) NCI-N87 | 2.8 |
| Bladder | 0.4 |
| Trachea | 1.3 |
| Kidney | 1.7 |
| Kidney (fetal) | 1 |
| Renal ca. 786-0 | 0.6 |
| Renal ca. A498 | 0.3 |
| Renal ca. RXF 393 | 0.2 |
| Renal ca. ACHN | 0.4 |
| Renal ca. UO-31 | 0.3 |
| Renal ca. TK-10 | 1.3 |
| Liver | 0.3 |
| Liver (fetal) | 0.1 |
| Liver ca. (hepatoblast) HepG2 | 1 |
| Lung | 0.2 |
| Lung (fetal) | 0.8 |
| Lung ca. (small cell) LX-1 | 0.3 |
| Lung ca. (small cell) NCI-H69 | 0.7 |
| Lung ca. (s.cell var.) SHP-77 | 25.9 |
| Lung ca. (large cell) NCI-H460 | 0.7 |
| Lung ca. (non-sm. cell) A549 | 1.1 |
| Lung ca. (non-s.cell) NCI-H23 | 0.6 |
| Lung ca (non-s.cell) HOP-62 | 1 |
| Lung ca. (non-s.cl) NCI-H522 | 0.3 |
| Lung ca. (squam.) SW 900 | 11.5 |
| Lung ca. (squam.) NCI-H596 | 0.8 |
| Mammary gland | 1.8 |
| Breast ca.* (pl. effusion) MCF-7 | 0.3 |
| Breast ca.* (pl.ef) MDA-MB-231 | 1.6 |
| Breast ca.* (pl.effusion) T47D | 0.5 |
| Breast ca. BT-549 | 4.7 |
| Breast ca. MDA-N | 1.6 |
| Ovary | 0.6 |
| Ovarian ca. OVCAR-3 | 0.6 |
| Ovarian ca. OVCAR-4 | 0.5 |
| Ovarian ca. OVCAR-5 | 4.6 |
| Ovarian ca. OVCAR-8 | 0.2 |
| Ovarian ca. IGROV-1 | 0.6 |

TABLE 20.A-continued

TAQMAN® Results for clone NOV4.

| Tissue Name | Rel. Expr., % tm252t_ag087 |
|---|---|
| Ovarian ca.* (ascites) SK-OV-3 | 1 |
| Uterus | 1.8 |
| Placenta | 1.5 |
| Prostate | 0.5 |
| Prostate ca.* (bone met) PC-3 | 100 |
| Testis | 4.6 |
| Melanoma Hs688(A).T | 0.1 |
| Melanoma* (met) Hs688(B).T | 0 |
| Melanoma UACC-62 | 0.8 |
| Melanoma M14 | 0.3 |
| Melanoma LOX IMVI | 0.7 |
| Melanoma* (met) SK-MEL-5 | 0.2 |
| Melanoma SK-MEL-28 | 0.3 |

TABLE 20.B.

TAQMAN® Results for clone NOV4.

| Tissue Name | Rel. Expr., % 1.2tm2217t_ag87 |
|---|---|
| Endothelial cells | 0 |
| Heart (fetal) | 0 |
| Pancreas | 97.3 |
| Pancreatic ca. CAPAN 2 | 0 |
| Adrenal Gland (new lot*) | 22.5 |
| Thyroid | 0 |
| Salavary gland | 0 |
| Pituitary gland | 0 |
| Brain (fetal) | 3.4 |
| Brain (whole) | 8 |
| Brain (amygdala) | 24.8 |
| Brain (cerebellum) | 8.3 |
| Brain (hippocampus) | 20.7 |
| Brain (thalamus) | 100 |
| Cerebral Cortex | 63.7 |
| Spinal cord | 0 |
| CNS ca. (glio/astro) U87-MG | 0 |
| CNS ca. (glio/astro) U-118-MG | 0 |
| CNS ca. (astro) SW1783 | 0 |
| CNS ca.* (neuro; met) SK-N-AS | 21.9 |
| CNS ca. (astro) SF-539 | 0 |
| CNS ca. (astro) SNB-75 | 0 |
| CNS ca. (glio) SNB-19 | 0 |
| CNS ca. (glio) U251 | 0 |
| CNS ca. (glio) SF-295 | 0 |
| Heart | 0 |
| Skeletal Muscle (new lot*) | 4.2 |
| Bone marrow | 0 |
| Thymus | 0 |
| Spleen | 12.2 |
| Lymph node | 0 |
| Colorectal | 0 |
| Stomach | 0 |
| Small intestine | 0 |
| Colon ca. SW480 | 0 |
| Colon ca.* (SW480 met)SW620 | 0 |
| Colon ca. HT29 | 0 |
| Colon ca. HCT-116 | 0 |
| Colon ca. CaCo-2 | 0 |
| 83219 CC Well to Mod Diff (ODO3866) | 0 |
| Colon ca. HCC-2998 | 5.5 |
| Gastric ca.* (liver met) NCI-N87 | 0 |
| Bladder | 2.9 |
| Trachea | 0 |
| Kidney | 0 |
| Kidney (fetal) | 0 |
| Renal ca. 786-0 | 0 |
| Renal ca. A498 | 0 |
| Renal ca. RXF 393 | 0 |
| Renal ca. ACHN | 0 |
| Renal ca. UO-31 | 0 |

TABLE 20.B.-continued

TAQMAN® Results for clone NOV4.

| Tissue Name | Rel. Expr., % 1.2tm2217t_ag87 |
|---|---|
| Renal ca. TK-10 | 0 |
| Liver | 0 |
| Liver (fetal) | 0 |
| Liver ca. (hepatoblast) HepG2 | 0 |
| Lung | 0 |
| Lung (fetal) | 0 |
| Lung ca. (small cell) LX-1 | 0 |
| Lung ca. (small cell) NCI-H69 | 33 |
| Lung ca. (s.cell var.) SHP-77 | 3.3 |
| Lung ca. (large cell) NCI-H460 | 0 |
| Lung ca. (non-sm. cell) A549 | 0 |
| Lung ca. (non-s.cell) NCI-H23 | 1.7 |
| Lung ca (non-s.cell) HOP-62 | 0 |
| Lung ca. (non-s.cl) NCI-H522 | 17.1 |
| Lung ca. (squam.) SW 900 | 0 |
| Lung ca. (squam.) NCI-H596 | 55.5 |
| Mammary gland | 0 |
| Breast ca.* (pl. effusion) MCF-7 | 0 |
| Breast ca.* (pl.ef) MDA-MB-231 | 0 |
| Breast ca.* (pl. effusion) T47D | 26.6 |
| Breast ca. BT-549 | 0 |
| Breast ca. MDA-N | 0 |
| Ovary | 8.2 |
| Ovarian ca. OVCAR-3 | 0 |
| Ovarian ca. OVCAR-4 | 0 |
| Ovarian ca. OVCAR-5 | 0 |
| Ovarian ca. OVCAR-8 | 0 |
| Ovarian ca. IGROV-1 | 6.6 |
| Ovarian ca.* (ascites) SK-OV-3 | 0 |
| Uterus | 0 |
| Placenta | 0 |
| Prostate | 0 |
| Prostate ca.* (bone met)PC-3 | 0 |
| Testis | 41.5 |
| Melanoma Hs688(A).T | 0 |
| Melanoma* (met) Hs688(B).T | 0 |
| Melanoma UACC-62 | 0 |
| Melanoma M14 | 0 |
| Melanoma LOX IMVI | 0 |
| Melanoma* (met) SK-MEL-5 | 0 |
| Adipose | 24.3 |

TABLE 20.C.

TAQMAN® Results for clone NOV4.

| Tissue Name | Rel. Expr., % 1.3dtm4681t_ag87 |
|---|---|
| Liver adenocarcinoma | 0.0 |
| Pancreas | 4.8 |
| Pancreatic ca. CAPAN 2 | 0.0 |
| Adrenal gland | 0.0 |
| Thyroid | 0.0 |
| Salivary gland | 0.0 |
| Pituitary gland | 7.8 |
| Brain (fetal) | 15.2 |
| Brain (whole) | 0.0 |
| Brain (amygdala) | 15.0 |
| Brain (cerebellum) | 52.5 |
| Brain (hippocampus) | 33.0 |
| Brain (substantia nigra) | 19.9 |
| Brain (thalamus) | 88.9 |
| Cerebral Cortex | 8.1 |
| Spinal cord | 9.0 |
| CNS ca. (glio/astro) U87-MG | 0.0 |
| CNS ca. (glio/astro) U-118-MG | 0.0 |
| CNS ca. (astro) SW1783 | 0.0 |
| CNS ca.* (neuro; met ) SK-N-AS | 0.0 |
| CNS ca. (astro) SF-539 | 0.0 |
| CNS ca. (astro) SNB-75 | 0.0 |
| CNS ca. (glio) SNB-19 | 0.0 |

TABLE 20.C.-continued

TAQMAN® Results for clone NOV4.

| Tissue Name | Rel. Expr., % 1.3dtm4681t_ag87 |
|---|---|
| CNS ca. (glio) U251 | 0.0 |
| CNS ca. (glio) SF-295 | 0.0 |
| Heart (fetal) | 0.0 |
| Heart | 0.0 |
| Fetal Skeletal | 9.0 |
| Skeletal muscle | 0.0 |
| Bone marrow | 0.0 |
| Thymus | 0.0 |
| Spleen | 34.2 |
| Lymph node | 0.0 |
| Colorectal | 0.0 |
| Stomach | 0.0 |
| Small intestine | 0.0 |
| Colon ca. SW480 | 0.0 |
| Colon ca.* (SW480 met)SW620 | 0.0 |
| Colon ca. HT29 | 0.0 |
| Colon ca. HCT-116 | 0.0 |
| Colon ca. CaCo-2 | 0.0 |
| 83219 CC Well to Mod Diff (ODO3866) | 0.0 |
| Colon ca. HCC-2998 | 0.0 |
| Gastric ca.* (liver met) NCI-N87 | 13.5 |
| Bladder | 11.7 |
| Trachea | 0.0 |
| Kidney | 0.0 |
| Kidney (fetal) | 0.0 |
| Renal ca. 786-0 | 0.0 |
| Renal ca. A498 | 0.0 |
| Renal ca. RXF393 | 0.0 |
| Renal ca. ACHN | 0.0 |
| Renal ca. UO-31 | 0.0 |
| Renal ca. TK-10 | 0.0 |
| Liver | 0.0 |
| Liver (fetal) | 0.0 |
| Liver ca. (hepatoblast) HepG2 | 0.0 |
| Lung | 0.0 |
| Lung (fetal) | 0.0 |
| Lung ca. (small cell) LX-1 | 0.0 |
| Lung ca. (small cell) NCI-H69 | 0.0 |
| Lung ca. (s.cell var.) SHP-77 | 0.0 |
| Lung ca. (large cell)NCI-H460 | 0.0 |
| Lung ca. (non-sm. cell) A549 | 0.0 |
| Lung ca. (non-s.cell) NCI-H23 | 0.0 |
| Lung ca (non-s.cell) HOP-62 | 0.0 |
| Lung ca. (non-s.cl) NCI-H522 | 0.0 |
| Lung ca. (squam.) SW 900 | 0.0 |
| Lung ca. (squam.) NCI-H596 | 0.0 |
| Mammary gland | 0.0 |
| Breast ca.* (pl. effusion) MCF-7 | 0.0 |
| Breast ca.* (pl.ef) MDA-MB-231 | 0.0 |
| Breast ca.* (pl. effusion) T47D | 14.9 |
| Breast ca. BT-549 | 0.0 |
| Breast ca. MDA-N | 0.0 |
| Ovary | 0.0 |
| Ovarian ca. OVCAR-3 | 0.0 |
| Ovarian ca. OVCAR-4 | 0.0 |
| Ovarian ca. OVCAR-5 | 0.0 |
| Ovarian ca. OVCAR-8 | 0.0 |
| Ovarian ca. IGROV-1 | 0.0 |
| Ovarian ca.* (ascites) SK-OV-3 | 0.0 |
| Uterus | 0.0 |
| Placenta | 0.0 |
| Prostate | 0.0 |
| Prostate ca.* (bone met)PC-3 | 0.0 |
| Testis | 100.0 |
| Melanoma Hs688(A).T | 0.0 |
| Melanoma* (met) Hs688(B).T | 0.0 |
| Melanoma UACC-62 | 9.8 |
| Melanoma M14 | 0.0 |
| Melanoma LOX IMVI | 0.0 |
| Melanoma* (met) SK-MEL-5 | 0.0 |
| Adipose | 0.0 |

TABLE 20.D.

TAQMAN® Results for clone NOV4.

| Tissue Name | Rel. Expr., % 2Dtm2323t_ag87 |
|---|---|
| Normal Colon GENPAK 061003 | 0 |
| 83219 CC Well to Mod Diff (ODO3866) | 0 |
| 83220 CC NAT (ODO3866) | 0 |
| 83221 CC Gr.2 rectosigmoid (ODO3868) | 0 |
| 83222 CC NAT (ODO3868) | 0 |
| 83235 CC Mod Duff (ODO3920) | 0 |
| 83236 CC NAT (ODO3920) | 0 |
| 83237 CC Gr.2 ascend colon (ODO3921) | 0 |
| 83238 CC NAT (ODO3921) | 0 |
| 83241 CC from Partial Hepatectomy (ODO4309) | 0 |
| 83242 Liver NAT (ODO4309) | 0 |
| 87472 Colon mets to lung (ODO4451-01) | 0 |
| 87473 Lung NAT (ODO4451-02) | 0 |
| Normal Prostate Clontech A+ 6546-1 | 0 |
| 84140 Prostate Cancer (ODO4410) | 0 |
| 84141 Prostate NAT (ODO4410) | 0 |
| 87073 Prostate Cancer (ODO4720-01) | 0 |
| 87074 Prostate NAT (ODO4720-02) | 0 |
| Normal Lung GENPAK 061010 | 0 |
| 83239 Lung Met to Muscle (ODO4286) | 0 |
| 83240 Muscle NAT (ODO4286) | 0 |
| 84136 Lung Malignant Cancer (OD03126) | 0 |
| 84137 Lung NAT (OD03126) | 0 |
| 84871 Lung Cancer (OD04404) | 0 |
| 84872 Lung NAT (OD04404) | 0 |
| 84875 Lung Cancer (OD04565) | 0 |
| 84876 Lung NAT (OD04565) | 0 |
| 85950 Lung Cancer (OD04237-01) | 0 |
| 85970 Lung NAT (OD04237-02) | 0 |
| 83255 Ocular Mel Met to Liver (OD04310) | 0 |
| 83256 Liver NAT (OD04310) | 0 |
| 84139 Melanoma Mets to Lung (OD04321) | 0 |
| 84138 Lung NAT (OD04321) | 0 |
| Normal Kidney GENPAK 061008 | 0 |
| 83786 Kidney Ca, Nuclear grade 2 (OD04338) | 0 |
| 83787 Kidney NAT (OD04338) | 0 |
| 83788 Kidney Ca Nuclear grade 1/2 (OD04339) | 0 |
| 83789 Kidney NAT (OD04339) | 0 |
| 83790 Kidney Ca, Clear cell type (OD04340) | 0 |
| 83791 Kidney NAT (OD04340) | 0 |
| 83792 Kidney Ca, Nuclear grade 3 (OD04348) | 0 |
| 83793 Kidney NAT (OD04348) | 0 |
| 87474 Kidney Cancer (OD04622-01) | 0 |
| 87475 Kidney NAT (OD04622-03) | 0 |
| 85973 Kidney Cancer (OD04450-01) | 0 |
| 85974 Kidney NAT (OD04450-03) | 0 |
| Kidney Cancer Clontech 8120607 | 0 |
| Kidney NAT Clontech 8120608 | 0 |
| Kidney Cancer Clontech 8120613 | 0 |
| Kidney NAT Clontech 8120614 | 0 |
| Kidney Cancer Clontech 9010320 | 0 |
| Kidney NAT Clontech 9010321 | 0 |
| Normal Uterus GENPAK 061018 | 0 |
| Uterus Cancer GENPAK 064011 | 0 |
| Normal Thyroid Clontech A+ 6570-1 | 0 |
| Thyroid Cancer GENPAK 064010 | 0 |
| Thyroid Cancer INVITROGEN A302152 | 0 |
| Thyroid NAT INVITROGEN A302153 | 0 |
| Normal Breast GENPAK 061019 | 0 |
| 84877 Breast Cancer (OD04566) | 0 |
| 85975 Breast Cancer (OD04590-01) | 0 |
| 85976 Breast Cancer Mets (OD04590-03) | 46.7 |
| 87070 Breast Cancer Metastasis (OD04655-05) | 30.1 |
| GENPAK Breast Cancer 064006 | 0 |
| Breast Cancer Res. Gen. 1024 | 100 |
| Breast Cancer Clontech 9100266 | 0 |
| Breast NAT Clontech 9100265 | 0 |
| Breast Cancer INVITROGEN A209073 | 0 |
| Breast NAT INVITROGEN A2090734 | 21.5 |
| Normal Liver GENPAK 061009 | 0 |
| Liver Cancer GENPAK 064003 | 0 |
| Liver Cancer Research Genetics RNA 1025 | 0 |
| Liver Cancer Research Genetics RNA 1026 | 0 |
| Paired Liver Cancer Tissue Research Genetics | 0 |

TABLE 20.D.-continued

TAQMAN ® Results for clone NOV4.

| Tissue Name | Rel. Expr., %<br>2Dtm2323t_ag87 |
|---|---|
| RNA 6004-T | |
| Paired Liver Tissue Research Genetics RNA 6004-N | 0 |
| Paired Liver Cancer Tissue Research Genetics RNA 6005-T | 0 |
| Paired Liver Tissue Research Genetics RNA 6005-N | 0 |
| Normal Bladder GENPAK 061001 | 13.6 |
| Bladder Cancer Research Genetics RNA 1023 | 0 |
| Bladder Cancer INVITROGEN A302173 | 0 |
| 87071 Bladder Cancer (OD04718-01) | 0 |
| 87072 Bladder Normal Adjacent (OD04718-03) | 0 |
| Normal Ovary Res. Gen. | 0 |
| Ovarian Cancer GENPAK 064008 | 0 |
| 87492 Ovary Cancer (OD04768-07) | 0 |
| 87493 Ovary NAT (OD04768-08) | 0 |
| Normal Stomach GENPAK 061017 | 0 |
| Gastric Cancer Clontech 9060358 | 0 |
| NAT Stomach Clontech 9060359 | 0 |
| Gastric Cancer Clontech 9060395 | 15.3 |
| NAT Stomach Clontech 9060394 | 0 |
| Gastric Cancer Clontech 9060397 | 0 |
| NAT Stomach Clontech 9060396 | 0 |
| Gastric Cancer GENPAK 064005 | 0 |

TABLE 20.E.

TAQMAN ® Results for clone NOV4.

| Tissue Name | Rel. Expr., %<br>2Dtm2361t_ag087 |
|---|---|
| Normal Colon GENPAK 061003 | 0.0 |
| 83219 CC Well to Mod Duff (ODO3866) | 0.0 |
| 83220 CC NAT (ODO3866) | 0.0 |
| 83221 CC Gr.2 rectosigmoid (ODO3868) | 0.0 |
| 83222 CC NAT (ODO3868) | 0.0 |
| 83235 CC Mod Diff (ODO3920) | 0.0 |
| 83236 CC NAT (ODO3920) | 0.0 |
| 83237 CC Gr.2 ascend colon (ODO3921) | 0.0 |
| 83238 CC NAT (ODO3921) | 0.0 |
| 83241 CC from Partial Hepatectomy (ODO4309) | 0.0 |
| 83242 Liver NAT (OD04309) | 0.0 |
| 87472 Colon mets to lung (OD04451-01) | 0.0 |
| 87473 Lung NAT (OD04451-02) | 0.0 |
| Normal Prostate Clontech A+ 6546-1 | 19.8 |
| 84140 Prostate Cancer (OD04410) | 0.0 |
| 84141 Prostate NAT (OD04410) | 0.0 |
| 87073 Prostate Cancer (OD04720-01) | 0.0 |
| 87074 Prostate NAT (OD04720-02) | 0.0 |
| Normal Lung GENPAK 061010 | 0.0 |
| 83239 Lung Met to Muscle (ODO4286) | 0.0 |
| 83240 Muscle NAT (ODO4286) | 0.0 |
| 84136 Lung Malignant Cancer (OD03126) | 0.0 |
| 84137 Lung NAT (OD03126) | 0.0 |
| 84871 Lung Cancer (OD04404) | 0.0 |
| 84872 Lung NAT (OD04404) | 0.0 |
| 84875 Lung Cancer (OD04565) | 0.0 |
| 84876 Lung NAT (OD04565) | 0.0 |
| 85950 Lung Cancer (OD04237-01) | 0.0 |
| 85970 Lung NAT (OD04237-02) | 0.0 |
| 83255 Ocular Mel Met to Liver (OD04310) | 0.0 |
| 83256 Liver NAT (OD04310) | 0.0 |
| 84139 Melanoma Mets to Lung (OD04321) | 0.0 |
| 84138 Lung NAT (OD04321) | 0.0 |
| Normal Kidney GENPAK 061008 | 0.0 |
| 83786 Kidney Ca, Nuclear grade 2 (OD04338) | 0.0 |
| 83787 Kidney NAT (OD04338) | 0.0 |
| 83788 Kidney Ca Nuclear grade 1/2 (OD04339) | 0.0 |
| 83789 Kidney NAT (OD04339) | 18.7 |
| 83790 Kidney Ca, Clear cell type (OD04340) | 0.0 |
| 83791 Kidney NAT (OD04340) | 0.0 |
| 83792 Kidney Ca, Nuclear grade 3 (OD04348) | 0.0 |

TABLE 20.E.-continued

TAQMAN ® Results for clone NOV4.

| Tissue Name | Rel. Expr., %<br>2Dtm2361t_ag087 |
|---|---|
| 83793 Kidney NAT (OD04348) | 0.0 |
| 87474 Kidney Cancer (OD04622-01) | 0.0 |
| 87475 Kidney NAT (OD04622-03) | 0.0 |
| 85973 Kidney Cancer (OD04450-01) | 0.0 |
| 85974 Kidney NAT (OD04450-03) | 0.0 |
| Kidney Cancer Clontech 8120607 | 0.0 |
| Kidney NAT Clontech 8120608 | 0.0 |
| Kidney Cancer Clontech 8120613 | 0.0 |
| Kidney NAT Clontech 8120614 | 0.0 |
| Kidney Cancer Clontech 9010320 | 0.0 |
| Kidney NAT Clontech 9010321 | 0.0 |
| Normal Uterus GENPAK 061018 | 0.0 |
| Uterus Cancer GENPAK 064011 | 0.0 |
| Normal Thyroid Clontech A+ 6570-1 | 0.0 |
| Thyroid Cancer GENPAK 064010 | 0.0 |
| Thyroid Cancer INVITROGEN A302152 | 0.0 |
| Thyroid NAT INVITROGEN A302153 | 0.0 |
| Normal Breast GENPAK 061019 | 0.0 |
| 84877 Breast Cancer (OD04566) | 0.0 |
| 85975 Breast Cancer (OD04590-01) | 0.0 |
| 85976 Breast Cancer Mets (OD04590-03) | 100.0 |
| 87070 Breast Cancer Metastasis (OD04655-05) | 0.0 |
| GENPAK Breast Cancer 064006 | 0.0 |
| Breast Cancer Res. Gen. 1024 | 90.8 |
| Breast Cancer Clontech 9100266 | 35.8 |
| Breast NAT Clontech 9100265 | 0.0 |
| Breast Cancer INVITROGEN A209073 | 0.0 |
| Breast NAT INVITROGEN A2090734 | 0.0 |
| Normal Liver GENPAK 061009 | 0.0 |
| Liver Cancer GENPAK 064003 | 0.0 |
| Liver Cancer Research Genetics RNA 1025 | 0.0 |
| Liver Cancer Research Genetics RNA 1026 | 0.0 |
| Paired Liver Cancer Tissue Research Genetics RNA 6004-T | 0.0 |
| Paired Liver Tissue Research Genetics RNA 6004-N | 0.0 |
| Paired Liver Cancer Tissue Research Genetics RNA 6005-T | 0.0 |
| Paired Liver Tissue Research Genetics RNA 6005-N | 0.0 |
| Normal Bladder GENPAK 061001 | 0.0 |
| Bladder Cancer Research Genetics RNA 1023 | 0.0 |
| Bladder Cancer INVITROGEN A302173 | 0.0 |
| 87071 Bladder Cancer (OD04718-01) | 0.0 |
| 87072 Bladder Normal Adjacent (OD04718-03) | 0.0 |
| Normal Ovary Res. Gen. | 0.0 |
| Ovarian Cancer GENPAK 064008 | 0.0 |
| 87492 Ovary Cancer (OD04768-07) | 0.0 |
| 87493 Ovary NAT (OD04768-08) | 0.0 |
| Normal Stomach GENPAK 061017 | 0.0 |
| Gastric Cancer Clontech 9060358 | 0.0 |
| NAT Stomach Clontech 9060359 | 0.0 |
| Gastric Cancer Clontech 9060395 | 0.0 |
| NAT Stomach Clontech 9060394 | 0.0 |
| Gastric Cancer Clontech 9060397 | 0.0 |
| NAT Stomach Clontech 9060396 | 0.0 |
| Gastric Cancer GENPAK 064005 | 0.0 |

Tables 20. A–20. E show expressions levels of NOV4 for various tissues with highest levels of expression found for lung carcinoma (25.9%) and prostate cancer (100%) in Table 20. A; normal pancreas (97.3%), cerebral cortex (63.7%), testis (41.5%) and lung carcinoma (55.5%) in Table 20. B; brain cerebellum (52.5%), brain thalamus (88.9%), and testis (100%) in Table 20. C; and metastatic breast cancer (46.7%, 30.1%, 100% and 90.8%) in Tables 20. D and 20. E. The results observed in these tables support one another and are further evidence that clones of NOV4 may be used as markers for certain types of cancers, notably breast cancer.

TABLE 21

Epitope Mapping for NOV4

| Epitope Type | | |
|---|---|---|
| I | II | III |
| 3.10 | 3.11 | 3.14 |
| 3.11 | | |
| 3.13 | | |
| 3.15 | | |

Table 21 shows the results from an enzyme-linked immunosorbent assay (ELISA) for the NOV4 clone. Here, monoclonal antibodies specific to a particular domain of the NOV4 protein are generated that can bind to a fragment of the NOV4 protein having that domain. Detection is facilitated by the use of a luminescent material in the assay ("Luminex Multiplexing Monoclonal Antibody Assay"). The assay comprises incubating monoclonal antibodies prepared against the NOV4 clone with the NOV4 clone to effect immunospecific binding of the monoclonal antibodies to the NOV4 clone, and then incubating the monoclonal antibody-NOV4 clone complexes with an additional, luminescent-labeled monoclonal antibody directed against the monoclonal antibody within the complex. Binding of the labeled monoclonal antibodies to the monoclonal antibody-NOV4 complexes results in luminescence and indicates the presence and location of epitopes (antigenic determinants) within the complexes.

Competition among detecting monoclonal antibodies 3.10, 3.11, 3.13 and 3.15 for the single epitope I is indicative of the specificity of the assay, while the detection of more than one epitope, here 3, shows the selectivity of the assay.

As seen in FIG. 3, proliferative activity is measured by treatment of serum-starved cultured cells with a given stimulating agent, and measurement of bromodeoxyuridine incorporation during DNA synthesis is measured. Here, breast epithelial T47D cells (ATTC; Catalog No. HTB-133; Manassas, Va.) were cultured in DMEM supplemented with 10% fetal bovine serum, and the cells grown to confluence at 37° C. in 10% $CO_2$/air. Cells were then starved in DMEM for 48 hours. Monoclonal antibodies at the indicated concentrations of 500 ng and 1 microgram were added and incubated for 18 hours. Finally, BrdU (deoxybromouridine) was added to obtain a 10 microgram final concentration in the culture, and the culture was incubated for 5 hours. BrdU incorporation then was assayed according to the manufacturer's (Boehringer Mannheim, Indianapolis, Ind.) specifications.

The results in FIG. 3 indicate that stimulation with Cura 10 3.10.3 monoclonal antibody results in DNA proliferation nearly as great as that in complete medium, while monoclonal antibodies Cura 10.3.11.7 and Cura 10 3.13.1 as well as the Cura 10 control, all produce DNA proliferation comparable to that of the serum-starved cells in culture. Additional studies carried out with NIH3T3 murine fibroblast cells and CCD1070 dermal fibroblast cells indicate that these cells exhibit no increase in DNA activity upon exposure to the same monoclonal antibodies and controls at identical concentrations as indicated in FIG. 3.

These results suggest that the CCD1070 and NIH 3T3 fibroblast cell lines do not express receptor activity for the monoclonal antibodies to NOV4 tested. However, the Cura 10 3.10.3 monoclonal antibody appears to trigger the receptors in T47D cells. Thus, this particular monoclonal antibody may play a role in targeting NOV4 receptor types in breast cancers and may have utility as an adjunct with chemotherapy to induce cell death.

Example 9
Method of Identifying the Nucleic Acid Encoding a Fibromodulin-like Protein The sequence of Acc. No. CG554254-02 was derived by laboratory cloning of cDNA fragments through in silico prediction of the sequence. cDNA fragments covering either the full length of the DNA sequence, or part of the sequence, or both, were cloned. In silico prediction was based on sequences available in Curagen's proprietary sequence databases or in the public human sequence databases, and provided either the full length DNA sequence, or some portion thereof.

Exon Linking: The cDNA coding for the CG554254-02 sequence was cloned by the polymerase chain reaction (PCR) using the primers: CAACGTGCAGGTCATCTAC-CTATACG (SEQ ID NO: 69) and GCCCGTCTCAAAA-CACTCTCCATCT (SEQ ID NO: 70). Primers were designed based on in silico predictions of the full length or some portion (one or more exons) of the cDNA/protein sequence of the invention. These primers were used to amplify a cDNA from a pool containing expressed human sequences derived from the following tissues: adrenal gland, bone marrow, brain—amygdala, brain—cerebellum, brain—hippocampus, brain—substantia nigra, brain—thalamus, brain—whole, fetal brain, fetal kidney, fetal liver, fetal lung, heart, kidney, lymphoma—Raji, mammary gland, pancreas, pituitary gland, placenta, prostate, salivary gland, skeletal muscle, small intestine, spinal cord, spleen, stomach, testis, thyroid, trachea and uterus.

Multiple clones were sequenced and these fragments were assembled together, sometimes including public human sequences, using bioinformatic programs to produce a consensus sequence for each assembly. Each assembly is included in CuraGen Corporation's database. Sequences were included as components for assembly when the extent of identity with another component was at least 95% over 50 bp. Each assembly represents a gene or portion thereof and includes information on variants, such as splice forms single nucleotide polymorphisms (SNPs), insertions, deletions and other sequence variations.

Variant sequences are also included in this application. A variant sequence can include a single nucleotide polymorphism (SNP). A SNP can, in some instances, be referred to as a "cSNP" to denote that the nucleotide sequence containing the SNP originates as a cDNA. A SNP can arise in several ways. For example, a SNP may be due to a substitution of one nucleotide for another at the polymorphic site. Such a substitution can be either a transition or a transversion. A SNP can also arise from a deletion of a nucleotide or an insertion of a nucleotide, relative to a reference allele. In this case, the polymorphic site is a site at which one allele bears a gap with respect to a particular nucleotide in another allele. SNPs occurring within genes may result in an alteration of the amino acid encoded by the gene at the position of the SNP. Intragenic SNPs may also be silent, when a codon including a SNP encodes the same amino acid as a result of the redundancy of the genetic code. SNPs occurring outside the region of a gene, or in an intron within a gene, do not result in changes in any amino acid sequence of a protein but may result in altered regulation of the expression pattern. Examples include alteration in temporal expression, physiological response regulation, cell type expression regulation, intensity of expression, and stability of transcribed message.

SeqCalling assemblies produced by the exon linking process were selected and extended using the following criteria. Genomic clones having regions with 98% identity to all or part of the initial or extended sequence were identified by BLASTN searches using the relevant sequence to query human genomic databases. The genomic clones that resulted were selected for further analysis because this identity indicates that these clones contain the genomic locus for these SeqCalling assemblies. These sequences were analyzed for putative coding regions as well as for similarity to the known DNA and protein sequences. Programs used for these analyses include Grail, Genscan, BLAST, HMMER, FASTA, Hybrid and other relevant programs.

Some additional genomic regions may have also been identified because selected SeqCalling assemblies map to those regions. Such SeqCalling sequences may have overlapped with regions defined by homology or exon prediction. They may also be included because the location of the fragment was in the vicinity of genomic regions identified by similarity or exon A prediction that had been included in the original predicted sequence. The sequence so identified was manually assembled and then may have been extended using one or more additional sequences taken from CuraGen Corporation's human SeqCalling database. SeqCalling fragments suitable for inclusion were identified by the CuraTools™ program SeqExtend or by identifying SeqCalling fragments mapping to the appropriate regions of the genomic clones analyzed. Such sequences were included in the derivation of Acc. No. CG554254-02 only when the extent of identity in the overlap region with one or more SeqCalling assemblies 148471786 146315781 was high.

The extent of identity may be, for example, about 90% or higher, preferably about 95% or higher, and even more preferably close to or equal to 100%. When necessary, the process to identify and analyze SeqCalling fragments and genomic clones was reiterated to derive the full length sequence.

The regions defined by the procedures described above were then manually integrated and corrected for apparent inconsistencies that may have arisen, for example, from miscalled bases in the original fragments or from discrepancies between predicted exon junctions, EST locations and regions of sequence similarity, to derive the final sequence disclosed herein. When necessary, the process to identify and analyze SeqCalling assemblies and genomic clones was reiterated to derive the full length sequence. The following public components were thus included in the invention: gb: AC0789107. In addition, the following Curagen Corporation SeqCalling Assembly ID's were also included in the invention: 148471786 146315781.

The DNA and protein sequences for the novel Fibromodulin-like gene are reported here as NOV5.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated polypeptide comprising the amino acid sequence of SEQ ID NO: 66.

2. A composition comprising the polypeptide of claim 1 and a carrier.

3. A kit comprising in one or more containers, the composition of claim 2.

4. An isolated polypeptide comprising the amino acid sequence encoded by a polynucleotide that is at least 98% identical to the coding sequence of SEQ ID NO: 65, wherein said polypeptide has kinase activity.

* * * * *